(12) United States Patent
Cagulada et al.

(10) Patent No.: US 9,440,991 B2
(45) Date of Patent: Sep. 13, 2016

(54) SYNTHESIS OF AN ANTIVIRAL COMPOUND

(71) Applicant: GILEAD SCIENCES, INC., Foster City, CA (US)

(72) Inventors: Amy Cagulada, San Francisco, CA (US); Johann Chan, San Mateo, CA (US); Lina Chan, Foster City, CA (US); Denise A. Colby, San Francisco, CA (US); Kapil Kumar Karki, Foster City, CA (US); Darryl Kato, San Francisco, CA (US); Katie Ann Keaton, Burlingame, CA (US); Sudha Kondapally, Foster City, CA (US); Chris Levins, San Mateo, CA (US); Adam Littke, Oakland, CA (US); Ruben Martinez, San Diego, CA (US); Dominika Pcion, San Francisco, CA (US); Troy Reynolds, San Francisco, CA (US); Bruce Ross, El Granada, CA (US); Michael Sangi, San Mateo, CA (US); Adam J. Schrier, Redwood City, CA (US); Pamela Seng, San Francisco, CA (US); Dustin Siegel, San Carlos, CA (US); Nathan Shapiro, Belmont, CA (US); Donald Tang, Millbrae, CA (US); James G. Taylor, San Mateo, CA (US); Jonathan Tripp, Foster City, CA (US); Andrew W. Waltman, San Francisco, CA (US); Lawrence Yu, Foster City, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 14/576,143

(22) Filed: Dec. 18, 2014

(65) Prior Publication Data
US 2015/0175626 A1   Jun. 25, 2015

Related U.S. Application Data

(60) Provisional application No. 61/920,446, filed on Dec. 23, 2013.

(51) Int. Cl.
| C07D 403/12 | (2006.01) |
| C07D 413/14 | (2006.01) |
| C07D 498/16 | (2006.01) |
| C07C 227/02 | (2006.01) |
| C07D 453/02 | (2006.01) |
| C07C 209/00 | (2006.01) |
| C07C 51/09  | (2006.01) |
| C07K 5/083  | (2006.01) |

(52) U.S. Cl.
CPC ............. *C07D 498/16* (2013.01); *C07C 51/09* (2013.01); *C07C 209/00* (2013.01); *C07C 227/02* (2013.01); *C07D 403/12* (2013.01); *C07D 453/02* (2013.01); *C07K 5/0808* (2013.01)

(58) Field of Classification Search
CPC ........................... C07D 403/12; C07D 413/14
See application file for complete search history.

(56) References Cited

U.S. PATENT DOCUMENTS

| 2012/0070416 A1 | 3/2012 | Or et al. |
| 2014/0017198 A1 | 1/2014 | Bjornson et al. |
| 2015/0175625 A1 | 6/2015 | Bringley et al. |

FOREIGN PATENT DOCUMENTS

| WO | WO-2009/064975 A1 | 5/2009 |
| WO | WO-2010/011566 A1 | 1/2010 |
| WO | WO-2012/040040 A1 | 3/2012 |
| WO | WO-2014/008285 A1 | 1/2014 |

*Primary Examiner* — Bruck Kifle

(57) ABSTRACT

The present disclosure provides processes for the preparation of a compound of formula I:

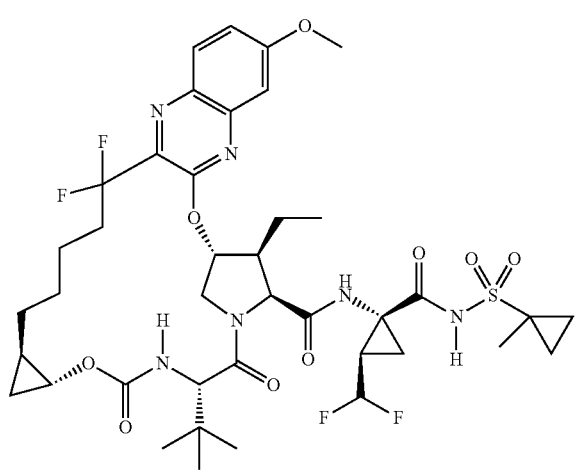

which is useful as an antiviral agent. The disclosure also provides compounds and processes for the preparation of the compounds that are synthetic intermediates to the compound of formula I.

6 Claims, No Drawings

SYNTHESIS OF AN ANTIVIRAL COMPOUND

This application claims priority under 35 U.S.C. §119(e) to U.S. Provisional Application Ser. No. 61/920,446 filed on Dec. 23, 2013, the entirety of which is incorporated herein by reference.

BACKGROUND

The present disclosure relates generally to the field of organic synthetic methodology for the preparation of Flaviviridae virus inhibitor compounds and their synthetic intermediates.

The hepatitis C virus (HCV), a member of the hepacivirus genera within the Flaviviridae family, is the leading cause of chronic liver disease worldwide (Boyer, N. et al. J Hepatol. 2000, 32, 98-112). Consequently, a significant focus of current antiviral research is directed toward the development of improved methods for the treatment of chronic HCV infections in humans (Ciesek, S., von Hahn T., and Manns, M P., Clin. Liver Dis., 2011, 15, 597-609; Soriano, V. et al, J. Antimicrob. Chemother., 2011, 66, 1573-1686; Brody, H., Nature Outlook, 2011, 474, S1-S7; Gordon, C. P., et al., J. Med. Chem. 2005, 48, 1-20; Maradpour, D., et al., Nat. Rev. Micro. 2007, 5, 453-463).

Virologic cures of patients with chronic HCV infection are difficult to achieve because of the prodigious amount of daily virus production in chronically infected patients and the high spontaneous mutability of HCV (Neumann, et al., Science 1998, 282, 103-7; Fukimoto, et al., Hepatology, 1996, 24, 1351-4; Domingo, et al., Gene 1985, 40, 1-8; Martell, et al., J. Virol. 1992, 66, 3225-9). HCV treatment is further complicated by the fact that HCV is genetically diverse and expressed as several different genotypes and numerous subtypes. For example, HCV is currently classified into six major genotypes (designated 1-6), many subtypes (designated a, b, c, and so on), and about 100 different strains (numbered 1, 2, 3, and so on).

HCV is distributed worldwide with genotypes 1, 2, and 3 predominate within the United States, Europe, Australia, and East Asia (Japan, Taiwan, Thailand, and China). Genotype 4 is largely found in the Middle East, Egypt and central Africa while genotype 5 and 6 are found predominantly in South Africa and South East Asia respectively (Simmonds, P. et al. J Virol. 84: 4597-4610, 2010).

There remains a need to develop effective treatments for HCV infections. Suitable compounds for the treatment of HCV infections are disclosed in U.S. Publication No. 2014-0017198, titled "Inhibitors of Hepatitis C Virus" filed on Jul. 2, 2013 including the compound of formula I:

SUMMARY

Presented herewith is an improved process for making a compound of formula I which provides several advantages over known synthesis. Specifically, route I disclosed herein uses a ring closing metathesis step at a different position than that disclosed previously. This leads to several advantages over the disclosed synthesis such as higher efficiency and higher overall yield. Further, routes II and III offer new synthetic routes for the compound of formula I.

The present disclosure provides in one embodiment a process for making a compound of formula I, named (1aR, 5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide:

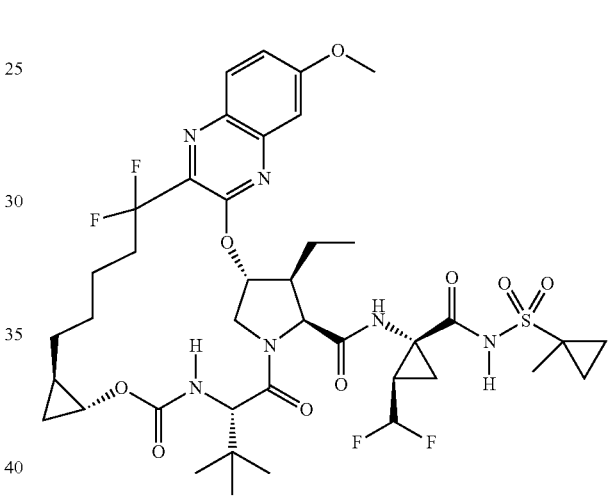

or a co-crystal, or a salt thereof.

In another embodiment, this disclosure provides a process for preparation of a compound of formula V:

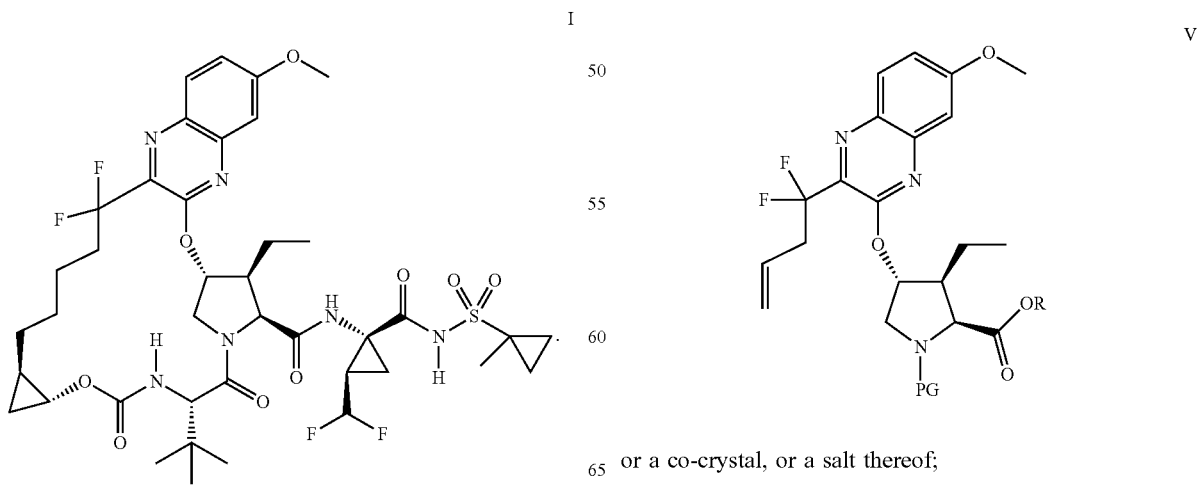

or a co-crystal, or a salt thereof;

comprising contacting a compound of formula III or a co-crystal, or a salt thereof, with a compound of formula IV:

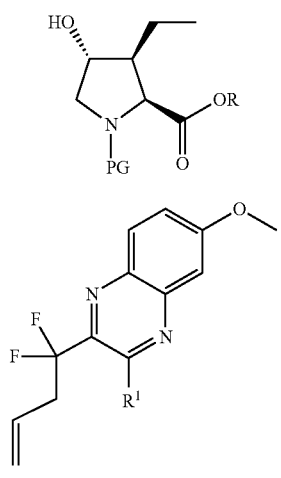

III

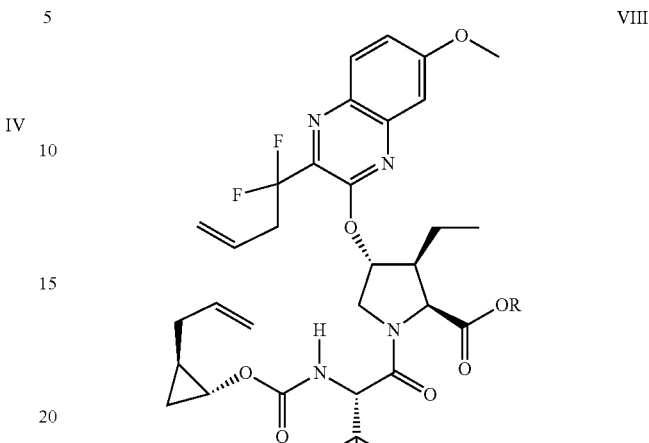

IV under O-arylation conditions to provide the compound of formula V or a co-crystal, or a salt thereof, wherein R is $C_{1-6}$ alkyl, PG is a protective group, and $R^1$ is a leaving group.

In another embodiment, this disclosure provides a process for preparation of a compound of formula VI:

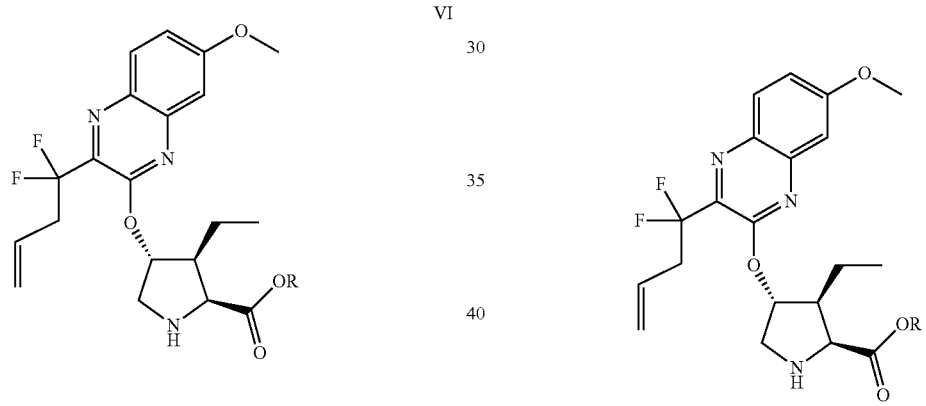

VI or a co-crystal, or a salt thereof;
comprising subjecting a compound of formula V:

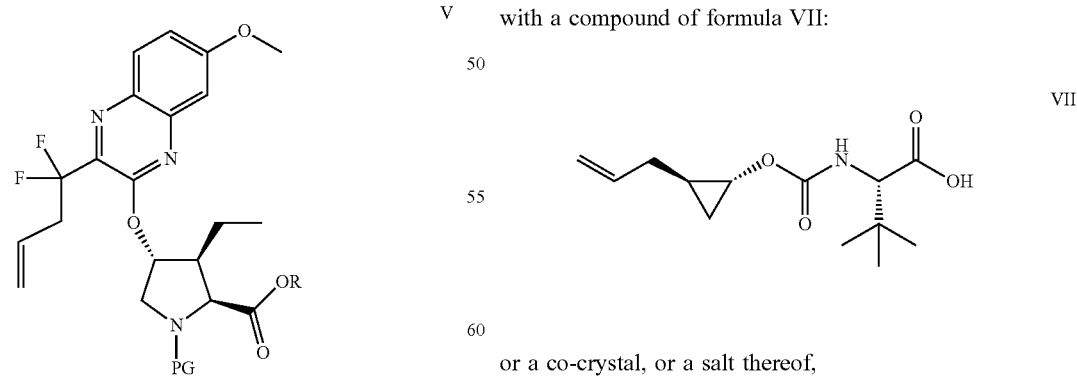

V or a co-crystal, or a salt thereof to N-deprotection conditions to provide the compound of formula VI or a co-crystal, or a salt thereof, wherein R is $C_{1-6}$ alkyl and PG is a protective group.

In another embodiment, this disclosure provides a process for preparation of a compound of formula VIII:

VIII or a co-crystal, or a salt thereof;
comprising contacting a compound of formula VI:

VI or a co-crystal, or a salt thereof;
with a compound of formula VII:

VII or a co-crystal, or a salt thereof,
under amide coupling conditions to provide the compound of formula VIII or a co-crystal, or a salt thereof, wherein R is $C_{1-6}$ alkyl.

In another embodiment, this disclosure provides a process for preparation of a compound of formula IX:

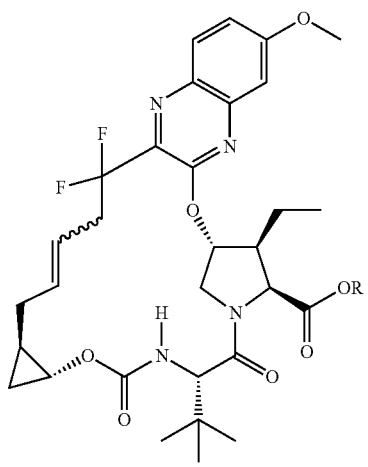

IX or a co-crystal, or a salt thereof;

comprising performing ring closing metathesis of a compound of formula VIII:

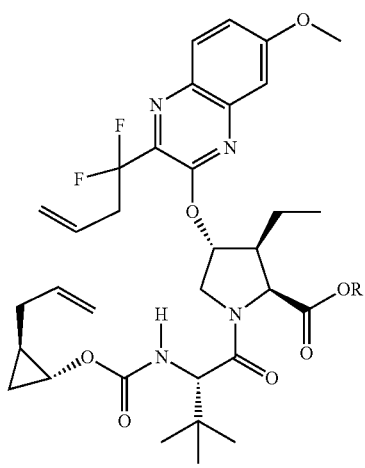

VIII or a co-crystal, or a salt thereof;

to provide the compound of formula IX or a co-crystal, or a salt thereof, wherein R is $C_{1-6}$ alkyl.

In another embodiment, this disclosure provides a process for preparation of a compound of formula I, named (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide:

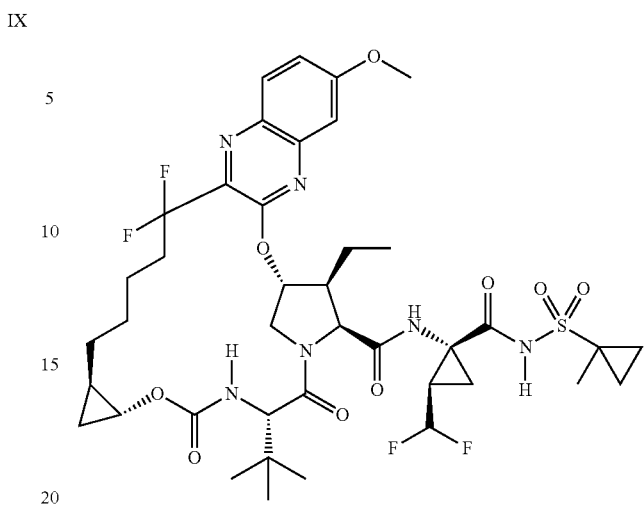

I or a co-crystal, or a salt thereof, comprising:

a) contacting a compound of formula III or a co-crystal, or a salt thereof, with a compound of formula IV:

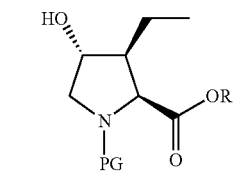

III

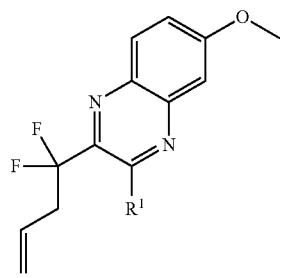

IV under O-arylation conditions to provide a compound of formula V:

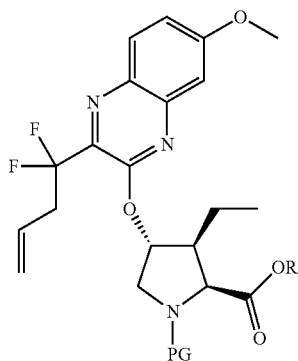

V or a co-crystal, or a salt thereof;

b) subjecting the compound of formula V or a co-crystal, or a salt thereof to N-deprotection conditions to provide a compound of formula VI:

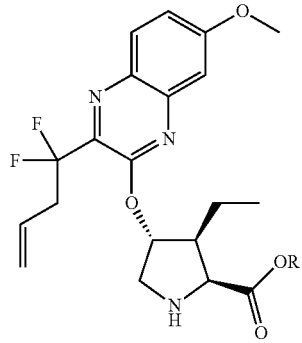

VI or a co-crystal, or a salt thereof;

c) contacting the compound of formula VI or a co-crystal, or a salt thereof with a compound of formula VII:

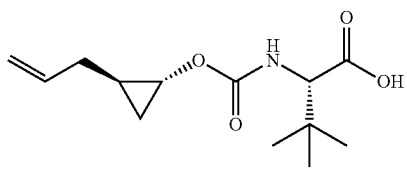

VII or a co-crystal, or a salt thereof, under amide coupling conditions to provide a compound of formula VIII:

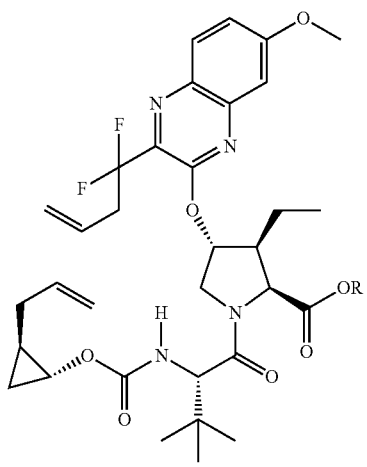

VIII or a co-crystal, or a salt thereof;

d) performing ring closing metathesis of the compound of formula VIII or a co-crystal, or a salt thereof to provide a compound of formula IX:

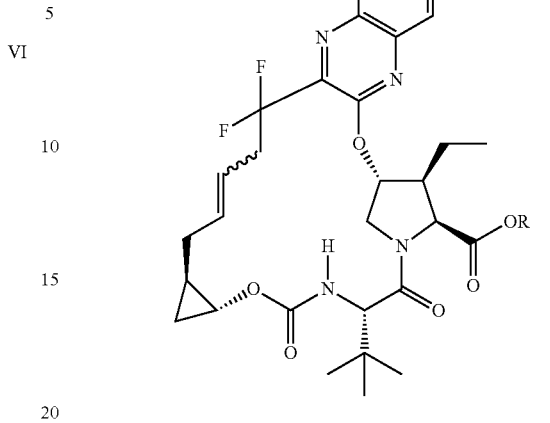

IX or a co-crystal, or a salt thereof;

e) hydrogenating the compound of formula IX or a co-crystal, or a salt thereof in presence of a catalyst to provide a compound of formula X:

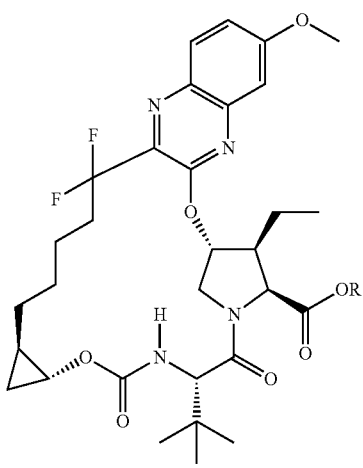

X or a co-crystal, or a salt thereof;

f) hydrolyzing the compound of formula X or a co-crystal, or a salt thereof to provide a compound of formula XI:

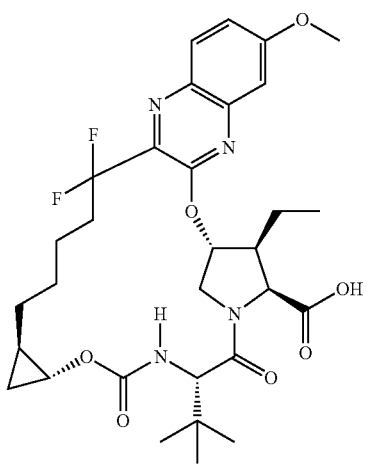

XI or a co-crystal, or a salt thereof;

g) contacting the compound of formula XI or a co-crystal, or a salt thereof with a compound of formula XII:

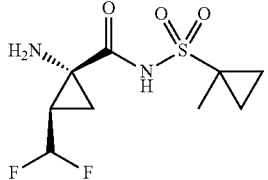

or a co-crystal, or a salt thereof;
under amide coupling conditions to provide the compound formula I:

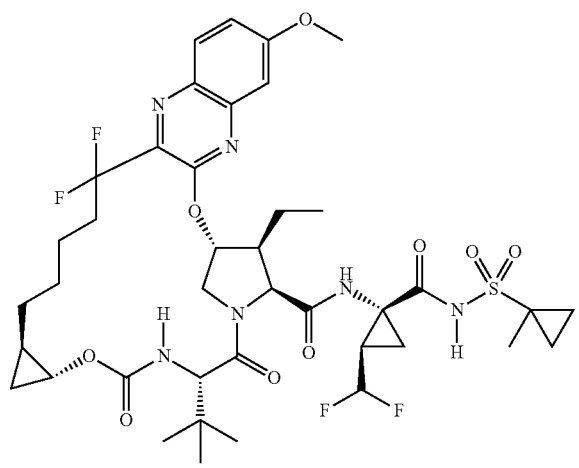

or a co-crystal, or a pharmaceutically acceptable salt thereof, wherein R is $C_{1-6}$ alkyl, PG is a protective group, and $R^1$ is a leaving group.

In another embodiment, this disclosure provides a process for preparation of a compound of formula XVIII:

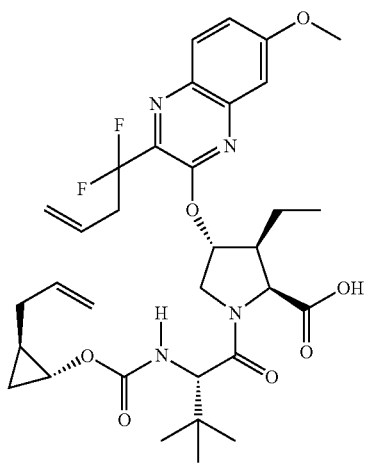

or a co-crystal, or a salt thereof;

comprising hydrolyzing a compound of formula VIII:

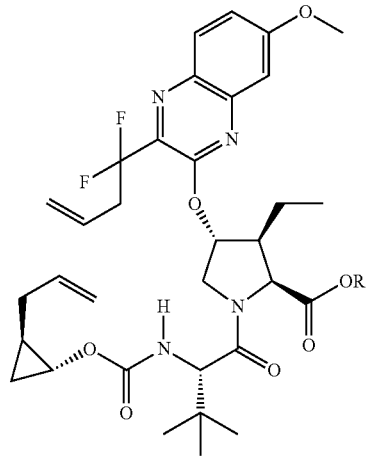

or a co-crystal, or a salt thereof to provide the compound of formula XVIII or a co-crystal, or a salt thereof, wherein R is $C_{1-6}$ alkyl.

In another embodiment, this disclosure provides a process for preparation of a compound of formula XIX:

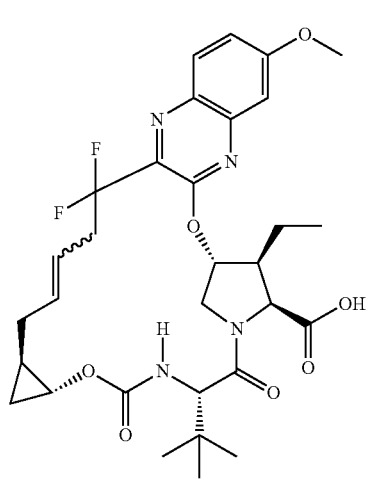

or a co-crystal, or a salt thereof;
comprising performing ring closing metathesis of the compound of formula XVIII or a co-crystal, or a salt thereof in presence of a catalyst to provide the compound of formula XIX.

In another embodiment, this disclosure provides a process for preparation of a compound of formula XI:

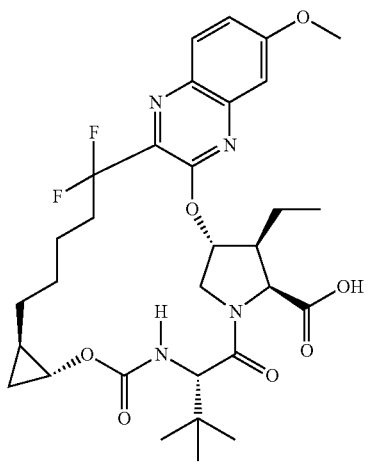

or a co-crystal, or a salt thereof,
comprising hydrogenating a compound of formula XIX:

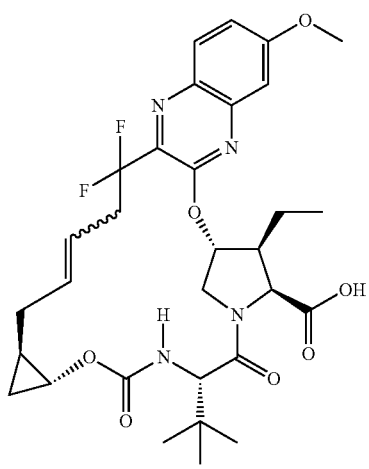

or a co-crystal, or a salt thereof in presence of a catalyst to provide a compound of formula XI:

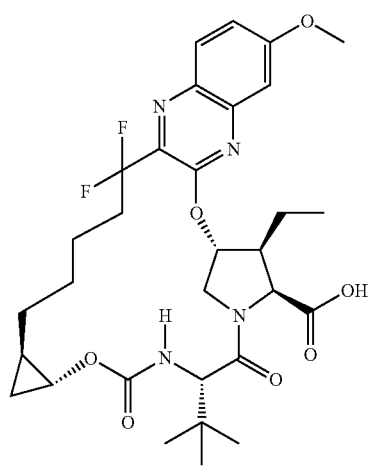

or a co-crystal, or a salt thereof.

In another embodiment, this disclosure provides a process for preparation of a compound of formula I, named (1aR, 5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide:

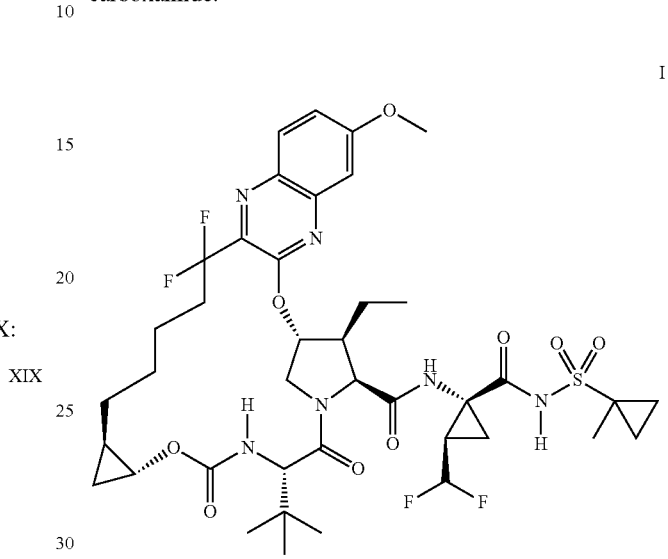

or a co-crystal, or a pharmaceutically acceptable salt thereof, comprising:

a) contacting a compound of formula III or a co-crystal, or a salt thereof, with a compound of formula IV:

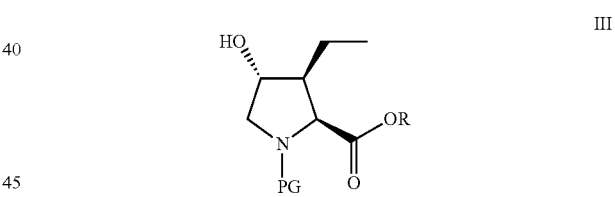

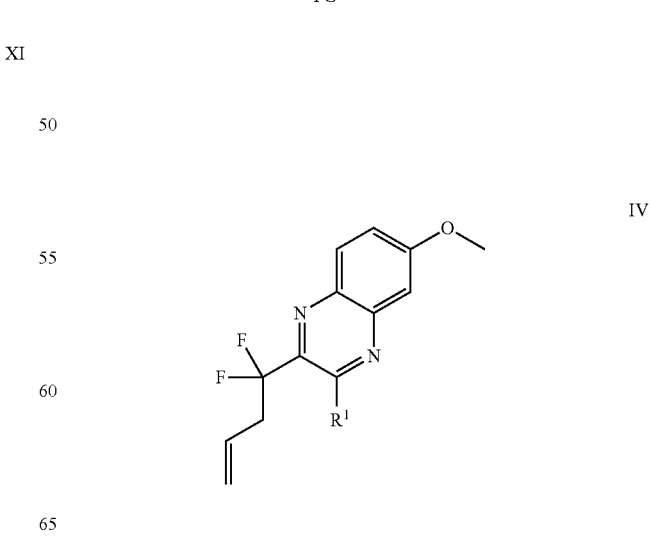

under O-arylation conditions to provide a compound of formula V:

V

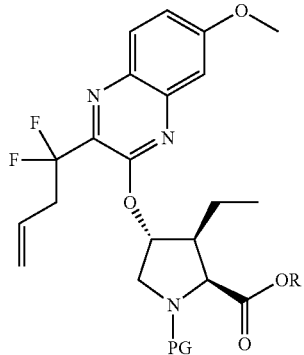

or a co-crystal, or a salt thereof;

b) subjecting the compound of formula V or a co-crystal, or a salt thereof to N-deprotection conditions to provide a compound of formula VI:

VI

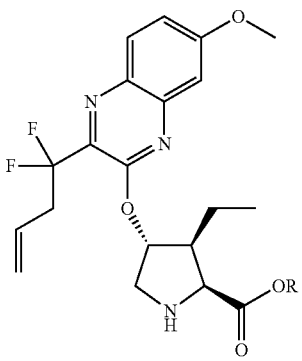

or a co-crystal, or a salt thereof;

c) contacting the compound of formula VI or a co-crystal, or a salt thereof with a compound of formula VII:

VII

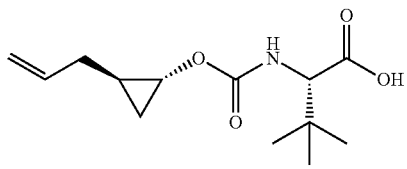

or a co-crystal, or a salt thereof, under amide coupling conditions to provide a compound of formula VIII:

VIII

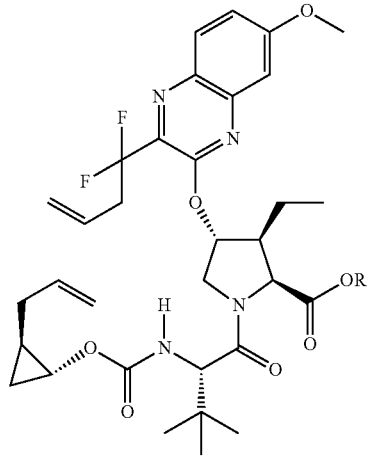

or a co-crystal, or a salt thereof;

d) hydrolyzing the compound of formula VIII or a co-crystal, or a salt thereof to provide a compound of formula XVIII:

XVIII

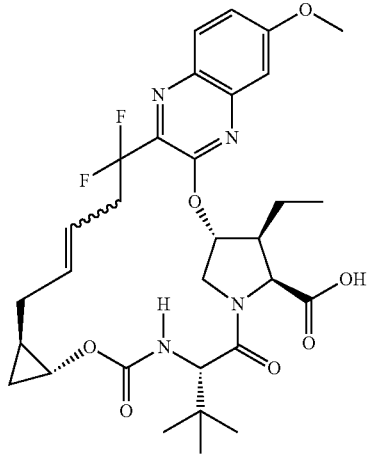

or a co-crystal, or a salt thereof;

e) performing ring closing metathesis of the compound of formula XVIII or a co-crystal, or a salt thereof in presence of a catalyst to provide a compound of formula XIX:

XIX or a co-crystal, or a salt thereof;

f) hydrogenating the compound of formula XIX in presence of a catalyst to provide a compound of formula XI:

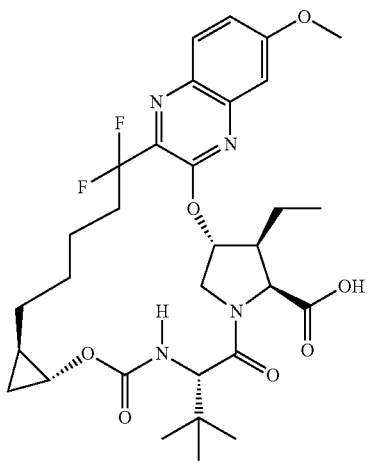

XI or a co-crystal, or a salt thereof;

g) contacting the compound of formula XI or a co-crystal, or a salt thereof with a compound of formula XII:

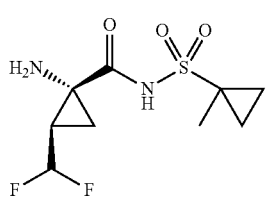

XII or a co-crystal, or a salt thereof;

under amide coupling conditions to provide the compound formula I:

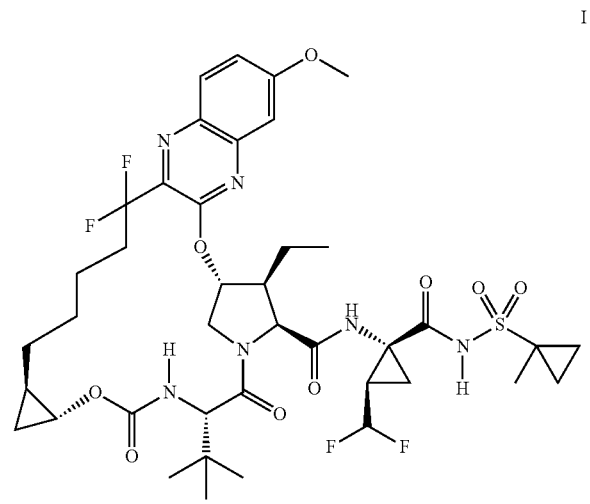 [SMILES: CC[C@@H]1[C@@H]2CN(C(=O)[C@H](C(C)(C)C)NC(=O)O[C@@H]3C[C@H]3CCCCC(F)(F)c3nc4ccc(OC)cc4nc3O2)[C@@H]1C(=O)N[C@]1(C(=O)NS(=O)(=O)C2(C)CC2)C[C@H]1C(F)F]

I or a co-crystal, or a salt thereof, wherein R is $C_{1-6}$ alkyl, PG is a protective group, and $R^1$ is a leaving group.

In another embodiment, this disclosure provides a process for preparation of a compound of formula XV:

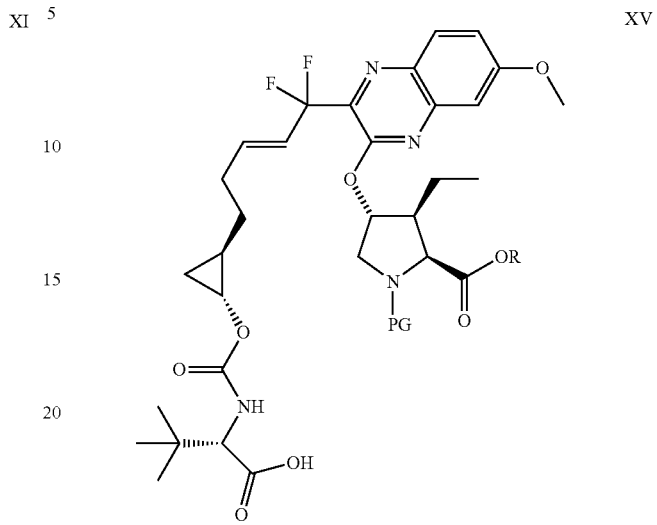

XV or a co-crystal, or a salt thereof, comprising contacting a compound of formula XIII:

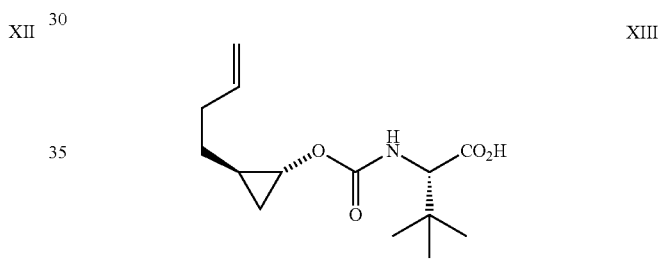

XIII or a co-crystal, or a salt thereof, with a compound of formula XIV:

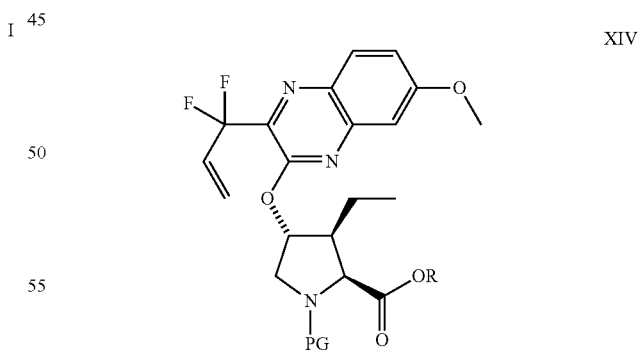

XIV or a co-crystal, or a salt thereof, under cross-metathesis conditions to provide the compound of formula XV or a co-crystal, or a salt thereof, wherein R is $C_{1-6}$ alkyl and PG is a protective group.

In another embodiment, this disclosure provides a process for preparation of a compound of formula XVI:

XVI

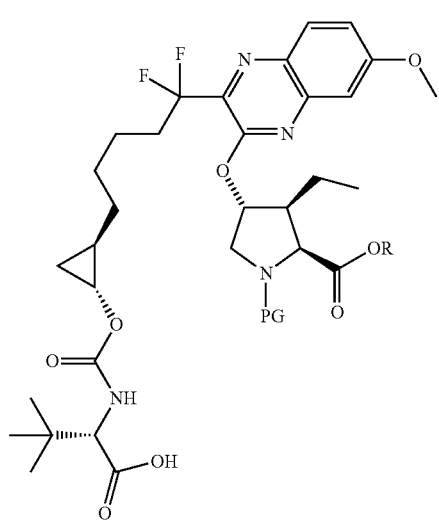

XVII

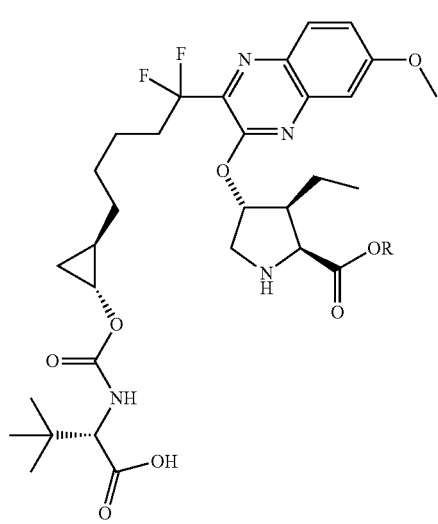

or a co-crystal, or a salt thereof;

comprising hydrogenating the compound of formula XV:

or a co-crystal, or a salt thereof;

comprising subjecting a compound of formula XVI:

XV

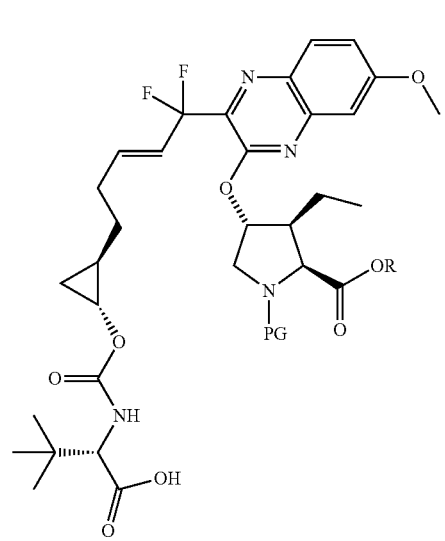

XVI

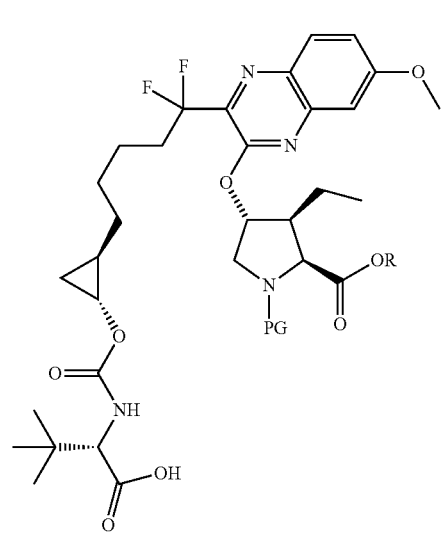

or a co-crystal, or a salt thereof in presence of a catalyst to provide the compound of formula XVI or a co-crystal, or a salt thereof, wherein R is $C_{1-6}$ alkyl and PG is a protective group.

In another embodiment, this disclosure provides a process for preparation of a compound of formula XVII:

or a co-crystal, or a salt thereof;

to N-deprotection conditions to provide the compound of formula XVII or a co-crystal, or a salt thereof, wherein R is $C_{1-6}$ alkyl and PG is a protective group.

In another embodiment, this disclosure provides a process for preparation of a compound of formula X:

X

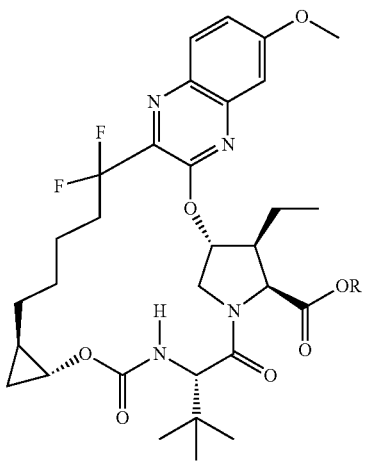

or a co-crystal, or a salt thereof;
comprising contacting the compound of formula XVII with an amide coupling agent under lactamization conditions to give the compound of formula X or a co-crystal, or a salt thereof, wherein R is $C_{1-6}$ alkyl.

In another embodiment, this disclosure provides a process for preparation of a compound of formula I, named (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide:

I

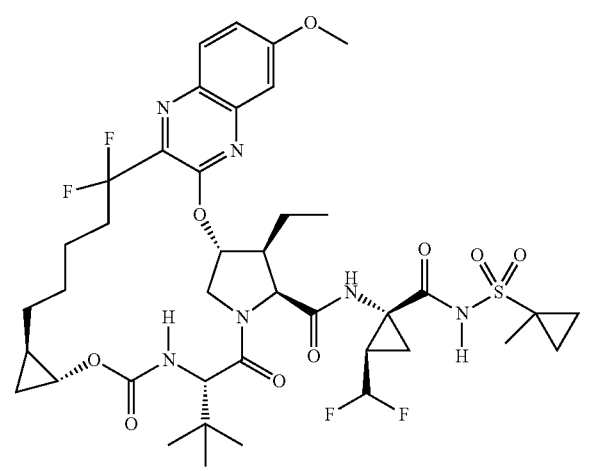

or a co-crystal, or a salt thereof, comprising:
a) contacting a compound of formula XIII:

XIII

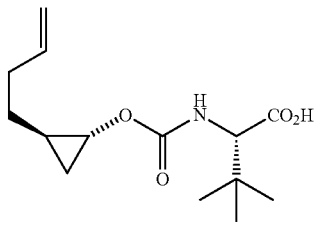

or a co-crystal, or a salt thereof,
with a compound of formula XIV:

XIV

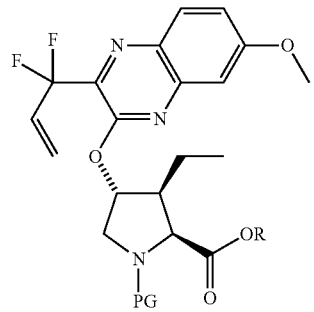

or a co-crystal, or a salt thereof,
under cross-metathesis conditions to provide a compound of formula XV:

XV

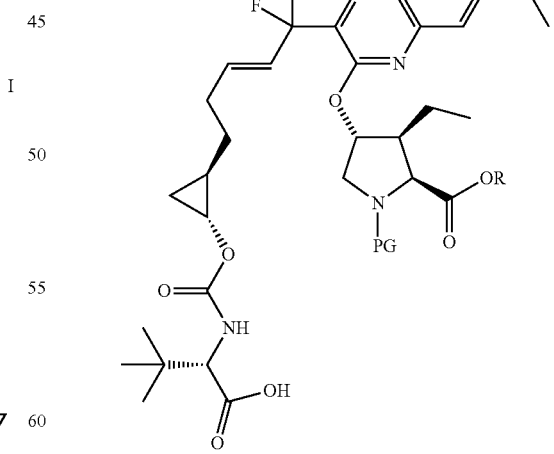

or a co-crystal, or a salt thereof,
b) hydrogenating the compound of formula XV or a co-crystal, or a salt thereof in presence of a catalyst to provide a compound of formula XVI:

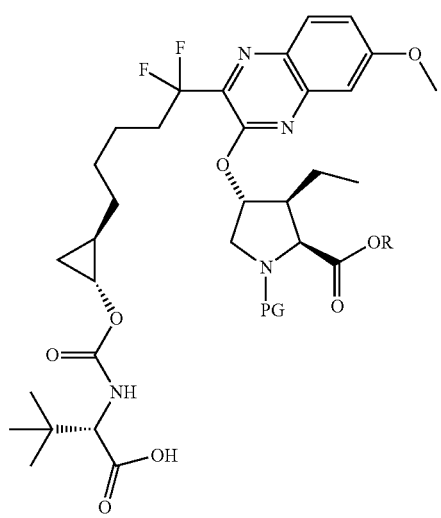

or a co-crystal, or a salt thereof;

c) subjecting the compound of formula XVI or a co-crystal, or a salt thereof to N-deprotection conditions to provide a compound of formula XVII:

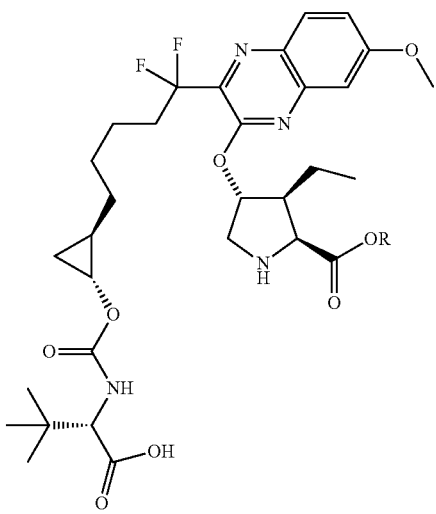

or a co-crystal, or a salt thereof;

d) contacting the compound of formula XVII with an amide coupling agent under lactamization conditions to give a compound of formula X:

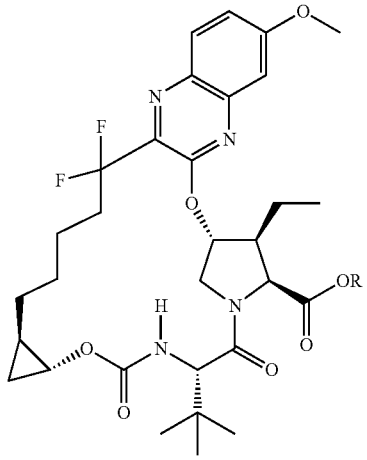

or a co-crystal, or a salt thereof;

e) hydrolyzing the compound of formula X or a co-crystal, or a salt thereof to provide a compound of formula XI:

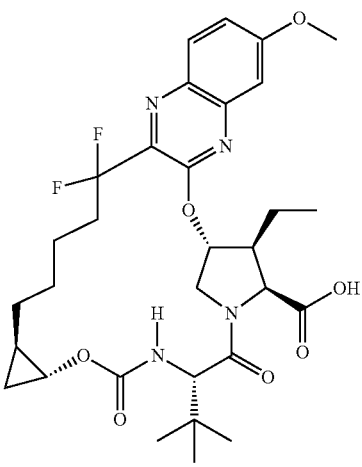

or a co-crystal, or a salt thereof; and f) contacting the compound of formula XI or a co-crystal, or a salt thereof with a compound of formula XII:

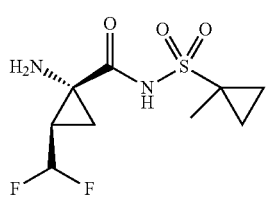

or a co-crystal, or a salt thereof under amide coupling conditions to provide the compound formula I:

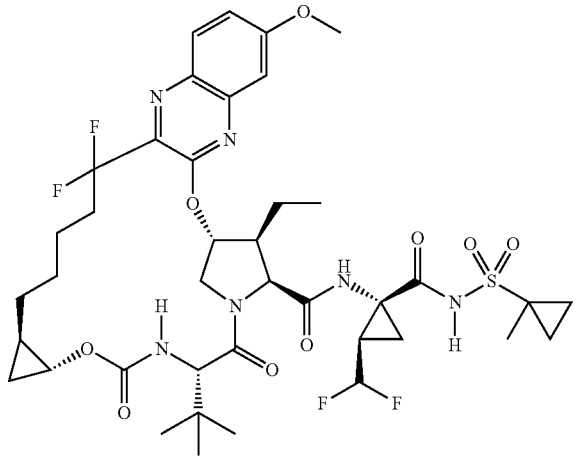

or a co-crystal, or a salt thereof, wherein R is $C_{1-6}$ alkyl and PG is a protective group.

In another embodiment, this disclosure provides a process for preparation of a compound of formula V-v:

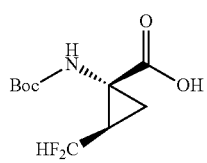

or a co-crystal, or a salt thereof, comprising:

a) hydrolyzing the compound of formula A-b:

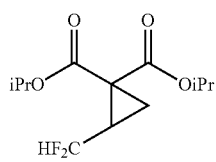

or a co-crystal, or a salt thereof to provide a compound of formula A-c:

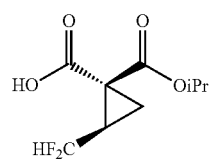

or a co-crystal, or a salt thereof;

b) contacting the compound of formula A-c or a co-crystal, or a salt thereof with dicyclohexylamine to provide a compound of formula A-g:

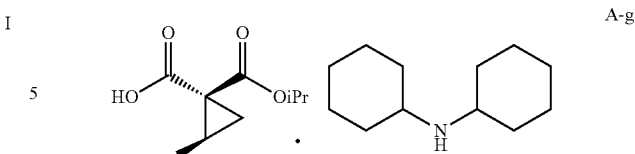

or a co-crystal, or a salt thereof;

c) contacting A-g or a co-crystal, or a salt thereof with cinchonidine to provide a compound of formula A-h:

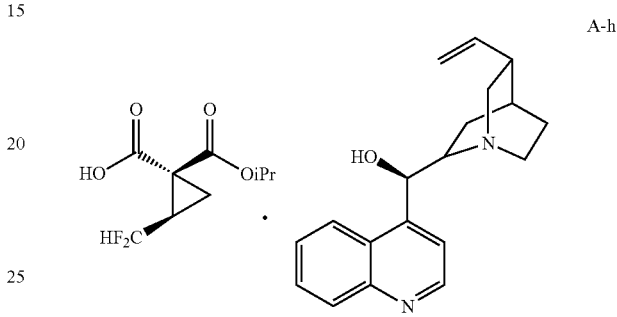

or a co-crystal, or a salt thereof;

d) subjecting A-h or a co-crystal, or a salt thereof to Curtius rearrangement in presence of tert-butanol to provide a compound of formula A-i:

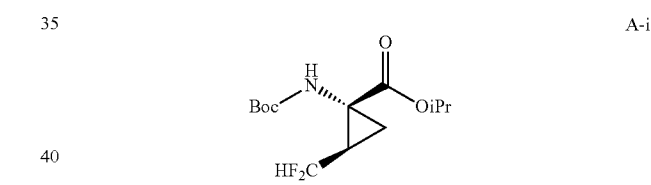

or a co-crystal, or a salt thereof; and e) hydrolysis of A-i or a co-crystal, or a salt thereof to provide V-v or or a co-crystal, or a salt thereof.

In another embodiment, this disclosure provides a compound of formula IV:

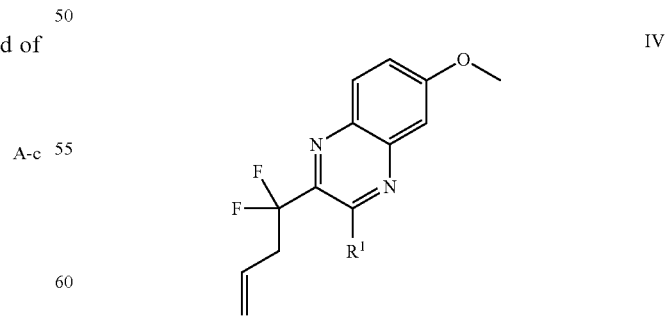

or a co-crystal, or a salt thereof, wherein $R^1$ is a leaving group.

In another embodiment, this disclosure provides a compound of formula V:

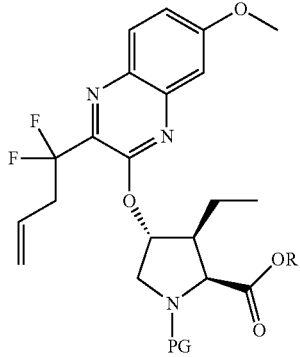

V or a co-crystal, or a salt thereof, wherein R is $C_{1-6}$ alkyl and PG is a protective group.

In another embodiment, this disclosure provides a compound of formula VI:

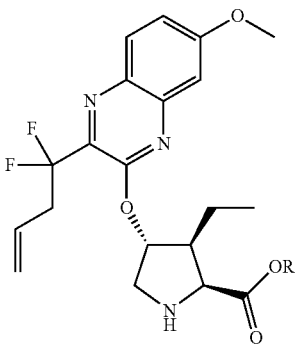

VI or a co-crystal, or a salt thereof, wherein R is $C_{1-6}$ alkyl.

In another embodiment, this disclosure provides a compound of formula VII:

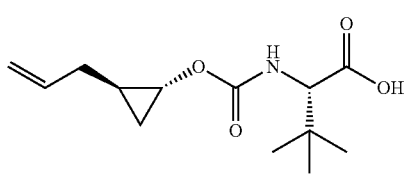

VII or a co-crystal, or a salt thereof.

In another embodiment, this disclosure provides a compound of formula VIII:

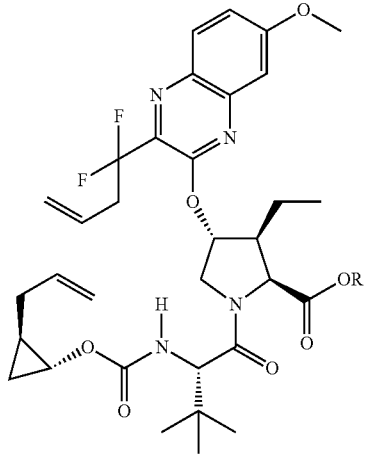

VIII or a co-crystal, or a salt thereof, wherein R is $C_{1-6}$ alkyl.

In another embodiment, this disclosure provides a compound of formula XIII:

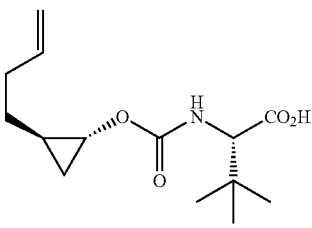

XIII or a co-crystal, or a salt thereof.

In another embodiment, this disclosure provides a compound of formula XIV:

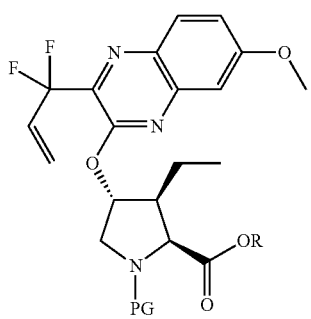

XIV or a co-crystal, or a salt thereof, wherein R is $C_{1-6}$ alkyl and PG is a protective group.

In another embodiment, this disclosure provides a compound of formula XV:

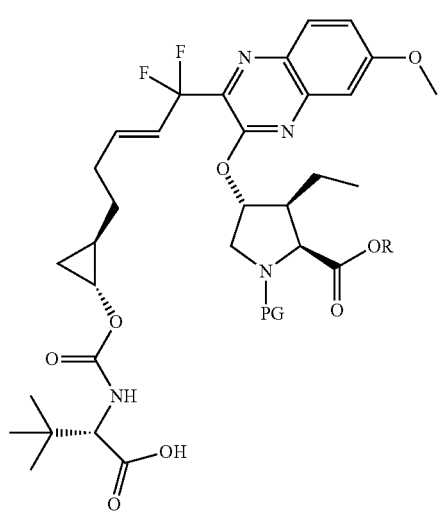

XV or a co-crystal, or a salt thereof, wherein R is $C_{1-6}$ alkyl and PG is a protective group.

In another embodiment, this disclosure provides a compound of formula XVI:

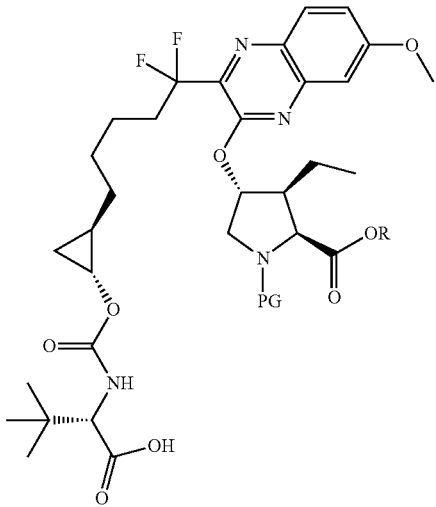

XVI or a co-crystal, or a salt thereof, wherein R is $C_{1-6}$ alkyl and PG is a protective group.

In another embodiment, this disclosure provides a compound of formula XVII:

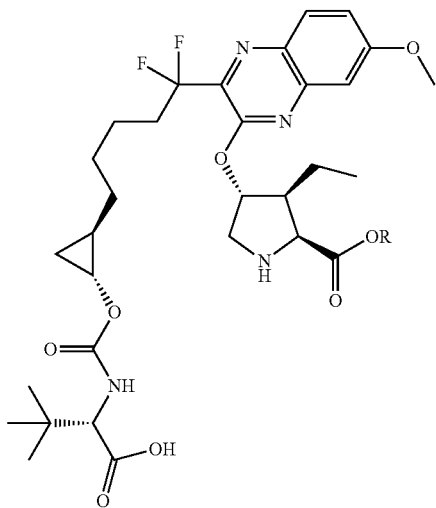

XVII or a co-crystal, or a salt thereof, wherein R is $C_{1-6}$ alkyl.

In another embodiment, this disclosure provides a compound of formula XVIII:

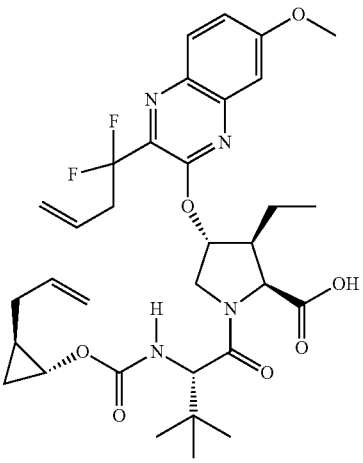

XVIII or a co-crystal, or a salt thereof.

In another embodiment, this disclosure provides a compound of formula XIX:

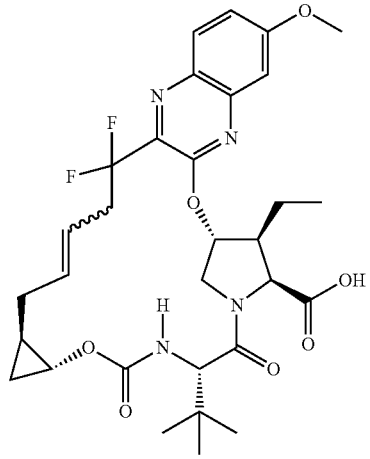

XIX or a co-crystal, or a salt thereof.

In another embodiment, this disclosure provides a compound of formula IV-d:

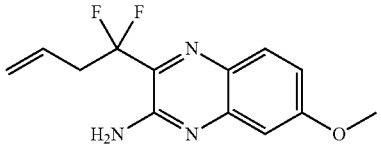

or a co-crystal, or a salt thereof.

In another embodiment, this disclosure provides a compound of formula M3:

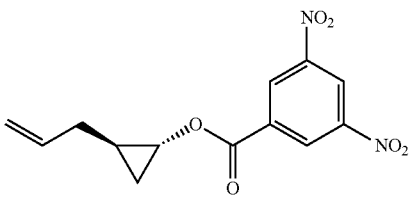

or a co-crystal, or a salt thereof.

In another embodiment, this disclosure provides a compound of formula IV-a:

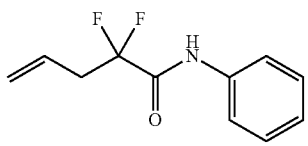

or a co-crystal, or a salt thereof.

In another embodiment, this disclosure provides a compound of formula IV-b:

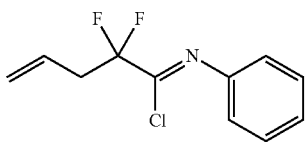

or a co-crystal, or a salt thereof.

In another embodiment, this disclosure provides a compound of formula IV-c:

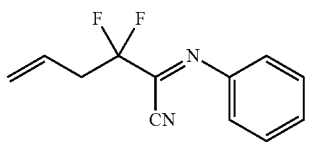

or a co-crystal, or a salt thereof.

More specific embodiments are described below.

DETAILED DESCRIPTION

Definitions

As used in the present specification, the following words and phrases are generally intended to have the meanings as set forth below, except to the extent that the context in which they are used indicates otherwise.

The term "alkyl" as used herein refers to a straight or branched chain, saturated hydrocarbon having the indicated number of carbon atoms. For example, (C1-C8)alkyl is meant to include, but is not limited to methyl, ethyl, propyl, isopropyl, butyl, sec-butyl, tert-butyl, pentyl, isopentyl, neopentyl, hexyl, isohexyl, and neohexyl. In particular embodiments, an alkyl group has 1-20 carbon atoms. An alkyl group can be unsubstituted or optionally substituted with one or more substituents as described herein throughout.

The term "substituted alkyl" refers to:

1) an alkyl group as defined above, having 1, 2, 3, 4 or 5 substituents, (in some embodiments, 1, 2 or 3 substituents) selected from the group consisting of alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO—cycloalkyl, —SO-heterocyclyl, —SO-aryl, —SO-heteroaryl, —SO$_2$-alkyl, —SO$_2$-cycloalkyl, —SO$_2$-heterocyclyl, —SO$_2$-aryl and —SO$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)nR$^a$, in which R$^a$ is alkyl, aryl or heteroaryl and n is 0, 1 or 2; or 2) an alkyl group as defined above that is interrupted by 1-10 atoms (e.g. 1, 2, 3, 4 or 5 atoms) independently chosen from oxygen, sulfur and NRa, where Ra is chosen from hydrogen, alkyl, cycloalkyl, alkenyl, cycloalkenyl, alkynyl, aryl, heteroaryl and heterocyclyl. All substituents may be optionally further substituted by alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)nR$^a$, in which R$^a$ is alkyl, aryl or heteroaryl and n is 0, 1 or 2, or 3) an alkyl group as defined above that has both 1, 2, 3, 4 or 5 substituents as defined above and is also interrupted by 1-10 atoms (e.g. 1, 2, 3, 4 or 5 atoms) as defined below.

As used herein, the term "interrupted by" means a carbon atom of a group (e.g. an alkyl group) is replaced by a heteroatom.

The term "alkylene" refers to a diradical of a branched or unbranched saturated hydrocarbon chain, having from 1 to 20 carbon atoms (e.g. 1-10 carbon atoms or 1, 2, 3, 4, 5 or 6 carbon atoms). This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—), and the like.

The term "aralkyl" refers to an aryl group covalently linked to an alkylene group, where aryl and alkylene are defined herein. "Optionally substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "aralkyloxy" refers to the group —O-aralkyl. "Optionally substituted aralkyloxy" refers to an optionally substituted aralkyl group covalently linked to an optionally substituted alkylene group. Such aralkyl groups are exemplified by benzyloxy, phenylethyloxy, and the like.

The term "alkenyl" refers to a monoradical of a branched or unbranched unsaturated hydrocarbon group having from 2 to 20 carbon atoms (in some embodiments, from 2 to 10 carbon atoms, e.g. 2 to 6 carbon atoms) and having from 1 to 6 carbon-carbon double bonds, e.g. 1, 2 or 3 carbon-carbon double bonds. In some embodiments, alkenyl groups include ethenyl (or vinyl, i.e. —CH=CH$_2$), 1-propylene (or allyl, i.e. —CH$_2$CH=CH$_2$), isopropylene (—C(CH$_3$)=CH$_2$), and the like.

The term "lower alkenyl" refers to alkenyl as defined above having from 2 to 6 carbon atoms.

The term "substituted alkenyl" refers to an alkenyl group as defined above having 1 to 5 substituents (in some embodiments, 1, 2 or 3 substituents) as defined for substituted alkyl.

The term "alkynyl" refers to a monoradical of an unsaturated hydrocarbon, in some embodiments, having from 2 to 20 carbon atoms (in some embodiments, from 2 to 10 carbon atoms, e.g. 2 to 6 carbon atoms) and having from 1 to 6 carbon-carbon triple bonds e.g. 1, 2 or 3 carbon-carbon triple bonds. In some embodiments, alkynyl groups include ethynyl (—C≡CH), propargyl (or propynyl, i.e. —C≡CCH$_3$), and the like.

The term "substituted alkynyl" refers to an alkynyl group as defined above having 1 to 5 substituents (in some embodiments, 1, 2 or 3 substituents) as defined for substituted alkyl.

The term "hydroxy" or "hydroxyl" refers to a group —OH.

The term "alkoxy" refers to the group —O—R, where R is alkyl or —Y—Z, in which Y is alkylene and Z is alkenyl or alkynyl, where alkyl, alkenyl and alkynyl are as defined herein. In some embodiments, alkoxy groups are alkyl-O— and includes, by way of example, methoxy, ethoxy, n-propoxy, iso-propoxy, n-butoxy, tert-butoxy, sec-butoxy, n-pentoxy, n-hexyloxy, 1,2-dimethylbutoxy, and the like.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl and the like or multiple ring structures such as adamantanyl and bicyclo[2.2.1]heptanyl or cyclic alkyl groups to which is fused an aryl group, for example indanyl, and the like, provided that the point of attachment is through the cyclic alkyl group.

The term "cycloalkenyl" refers to cyclic alkyl groups of from 3 to 20 carbon atoms having a single cyclic ring or multiple condensed rings and having at least one double bond and in some embodiments, from 1 to 2 double bonds.

The terms "substituted cycloalkyl" and "substituted cycloalkenyl" refer to cycloalkyl or cycloalkenyl groups having 1, 2, 3, 4 or 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-cycloalkyl, —SO-heterocyclyl, —SO-aryl, —SO-heteroaryl, —SO$_2$-alkyl, —SO$_2$-cycloalkyl, —SO$_2$-heterocyclyl, —SO$_2$-aryl and —SO$_2$-heteroaryl. The term "substituted cycloalkyl" also includes cycloalkyl groups wherein one or more of the annular carbon atoms of the cycloalkyl group has an oxo group bonded thereto. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)nR$^a$, in which R$^a$ is alkyl, aryl or heteroaryl and n is 0, 1 or 2.

The term "cycloalkoxy" refers to the group —O-cycloalkyl

The term "cycloalkenyloxy" refers to the group —O-cycloalkenyl.

The term "aryl" refers to an aromatic carbocyclic group of 6 to 20 carbon atoms having a single ring (e.g., phenyl) or multiple rings (e.g., biphenyl) or multiple condensed (fused) rings (e.g., naphthyl, fluorenyl and anthryl). In some embodiments, aryls include phenyl, fluorenyl, naphthyl, anthryl, and the like.

Unless otherwise constrained by the definition for the aryl substituent, such aryl groups can optionally be substituted with 1, 2, 3, 4 or 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, —SO-alkyl, —SO-cycloalkyl, —SO-heterocyclyl, —SO-aryl, —SO-heteroaryl, —SO$_2$-alkyl, —SO$_2$-cycloalkyl, —SO$_2$-heterocyclyl, —SO$_2$-aryl and —SO$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)nR$^a$, in which R$^a$ is alkyl, aryl or heteroaryl and n is 0, 1 or 2.

The term "aryloxy" refers to the group —O-aryl wherein the aryl group is as defined above, and includes optionally substituted aryl groups as also defined above. The term "arylthio" refers to the group R—S—, where R is as defined for aryl.

The term "arylene" herein refers to a diradical of "aryl" as defined above that is divalent by virtue of formal removal of a hydrogen atom from the aryl.

The term "heterocyclyl," "heterocycle," or "heterocyclic" refers to a monoradical saturated group having a single ring or multiple condensed rings, having from 1 to 40 carbon atoms and from 1 to 10 hetero atoms (in some embodiments from 1 to 4 heteroatoms), selected from nitrogen, sulfur, phosphorus, and/or oxygen within the ring. In some embodiments, the "heterocyclyl," "heterocycle," or "heterocyclic" group is linked to the remainder of the molecule through one of the heteroatoms within the ring.

Unless otherwise constrained by the definition for the heterocyclic substituent, such heterocyclic groups can be optionally substituted with 1 to 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, SO-alkyl, —SO-cycloalkyl, —SO-heterocyclyl, —SO-aryl, —SO-heteroaryl, —SO$_2$-alkyl, —SO$_2$-cycloalkyl, —SO$_2$-heterocyclyl, —SO$_2$-aryl and —SO$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF3, amino, substituted amino, cyano, cycloalkyl, heterocyclyl, aryl, heteroaryl, —S(O)nR$^a$, in which R$^a$ is alkyl, aryl or heteroaryl and n is 0, 1 or 2. Examples of heterocyclics include tetrahydrofuranyl, morpholino, piperidinyl, and the like.

The term "heterocyclooxy" refers to the group —O-heterocyclyl.

The term "heteroaryl" refers to a group comprising single or multiple rings comprising 1 to 15 carbon atoms and 1 to 4 heteroatoms selected from oxygen, nitrogen and sulfur within at least one ring. The term "heteroaryl" is generic to the terms "aromatic heteroaryl" and "partially saturated heteroaryl". The term "aromatic heteroaryl" refers to a heteroaryl in which at least one ring is aromatic, regardless of the point of attachment. Examples of aromatic heteroaryls include pyrrole, thiophene, pyridine, quinoline, pteridine. The term "partially saturated heteroaryl" refers to a heteroaryl having a structure equivalent to an underlying aromatic heteroaryl which has had one or more double bonds in an aromatic ring of the underlying aromatic heteroaryl saturated. Examples of partially saturated heteroaryls include dihydropyrrole, dihydropyridine, chroman, 2-oxo-1,2-dihydropyridin-4-yl, and the like.

Unless otherwise constrained by the definition for the heteroaryl substituent, such heteroaryl groups can be optionally substituted with 1 to 5 substituents (in some embodiments, 1, 2 or 3 substituents) selected from the group consisting alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, SO-alkyl, —SO-cycloalkyl, —SO-heterocyclyl, —SO-aryl, —SO— heteroaryl, —SO$_2$-alkyl, —SO$_2$-cycloalkyl, —SO$_2$-heterocyclyl, —SO$_2$-aryl and —SO$_2$-heteroaryl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, —S(O)$_n$R$^a$, in which R$^a$ is alkyl, aryl or heteroaryl and n is 0, 1 or 2. Such heteroaryl groups can have a single ring (e.g., pyridyl or furyl) or multiple condensed rings (e.g., indolizinyl, benzothiazole or benzothienyl). Examples of nitrogen heterocyclyls and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxynitrogen containing heteroaryl compounds.

The term "heteroaryloxy" refers to the group —O-heteroaryl.

The term "amino" refers to the group —NH$_2$.

The term "substituted amino" refers to the group —NRR where each R is independently selected from the group consisting of hydrogen, alkyl, cycloalkyl, aryl, heteroaryl and heterocyclyl provided that both R groups are not hydrogen or a group —Y—Z, in which Y is optionally substituted alkylene and Z is alkenyl, cycloalkenyl or alkynyl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)—R$^a$, in which R$^a$ is alkyl, aryl or heteroaryl and n is 0, 1 or 2.

The term "alkyl amine" refers to R—NH$_2$ in which R is optionally substituted alkyl.

The term "dialkyl amine" refers to R—NHR in which each R is independently an optionally substituted alkyl.

The term "trialkyl amine" refers to NR$_3$ in which each R is independently an optionally substituted alkyl.

The term "cyano" refers to the group —CN.

The term "azido" refers to a group

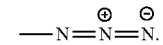

The term "keto" or "oxo" refers to a group =O.

The term "carboxy" refers to a group —C(O)—OH.

The term "ester" or "carboxyester" refers to the group —C(O)OR, where R is alkyl, cycloalkyl, aryl, heteroaryl or heterocyclyl, which may be optionally further substituted by alkyl, alkoxy, halogen, CF3, amino, substituted amino, cyano or, —S(O)nR$^a$, in which R$^a$ is alkyl, aryl or heteroaryl and n is 0, 1 or 2.

The term "acyl" denotes a group —C(O)R, in which R is hydrogen, optionally substituted alkyl, optionally substituted cycloalkyl, optionally substituted cycloalkenyl, optionally substituted heterocyclyl, optionally substituted aryl or optionally substituted heteroaryl.

The term "carboxyalkyl" refers to the groups —C(O)O-alkyl or —C(O)O-cycloalkyl, where alkyl and cycloalkyl are as defined herein, and may be optionally further substituted by alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, —S(O)nR$^a$, in which R$^a$ is alkyl, aryl or heteroaryl and n is 0, 1 or 2.

The term "aminocarbonyl" refers to the group —C(O)NRR where each R is independently hydrogen, alkyl, cycloalkyl, aryl, heteroaryl, heterocyclyl or where both R groups are joined to form a heterocyclic group (e.g., morpholino). Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF3, amino, substituted amino, cyano, cycloalkyl, heterocyclyl, aryl, heteroaryl, —S(O)nR$^a$, in which R$^a$ is alkyl, aryl or heteroaryl and n is 0, 1 or 2.

The term "acyloxy" refers to the groups —OC(O)-alkyl, —OC(O)-cycloalkyl, —OC(O)-aryl, —OC(O)-heteroaryl and —OC(O)-heterocyclyl. Unless otherwise constrained by the definition, all substituents may optionally be further substituted by 1, 2 or 3 substituents chosen from alkyl, alkenyl, alkynyl, carboxy, carboxyalkyl, aminocarbonyl, hydroxy, alkoxy, halogen, CF3, amino, substituted amino, cyano, cycloalkyl, heterocyclyl, aryl, heteroaryl, —S(O)nR$^a$, in which R$^a$ is alkyl, aryl or heteroaryl and n is 0, 1 or 2.

The term "acylamino" refers to the group —NRC(O)R where each R is independently hydrogen, alkyl, cycloalkyl, aryl, heteroaryl or heterocyclyl. All substituents may be optionally further substituted by alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, —S(O)nR$^a$, in which R$^a$ is alkyl, aryl or heteroaryl and n is 0, 1 or 2.

The term "alkoxycarbonylamino" refers to a group —N(R$^c$)C(O)OR in which R is optionally substituted alkyl and R$^c$ is hydrogen or optionally substituted alkyl.

The term "aminocarbonylamino" refers to the group —NR$^d$C(O)NRR, wherein R$^d$ is hydrogen or optionally substituted alkyl and each R is independently selected from the group consisting of hydrogen, alkyl, cycloalkyl, aryl, heteroaryl and heterocyclyl. Unless otherwise constrained by the definition, all substituents may optionally be further substituted by 1, 2 or 3 substituents selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, SO-alkyl, —SO-cycloalkyl, —SO-heterocyclyl, —SO-aryl, —SO— heteroaryl, —SO$_2$-alkyl, —SO$_2$-cycloalkyl, —SO$_2$-heterocyclyl, —SO$_2$-aryl and —SO$_2$-heteroaryl.

The term "thiol" refers to the group —SH.

The term "thiocarbonyl" refers to a group =S.

The term "alkylthio" refers to the group —S-alkyl.

The term "substituted alkylthio" refers to the group —S-substituted alkyl.

The term "heterocyclylthio" refers to the group —S-heterocyclyl.

The term "arylthio" refers to the group —S-aryl.

The term "heteroarylthiol" refers to the group —S-heteroaryl wherein the heteroaryl group is as defined above including optionally substituted heteroaryl groups as also defined above.

The term "sulfoxide" refers to a group —S(O)R, in which R is alkyl, cycloalkyl, heterocyclyl, aryl or heteroaryl. "Substituted sulfoxide" refers to a group —S(O)R, in which R is substituted alkyl, substituted cycloalkyl, substituted heterocyclyl, substituted aryl or substituted heteroaryl, as defined herein.

The term "sulfone" refers to a group —S(O)$_2$R, in which R is alkyl, cycloalkyl, heterocyclyl, aryl or heteroaryl. "Substituted sulfone" refers to a group —S(O)$_2$R, in which R is substituted alkyl, substituted cycloalkyl, substituted heterocyclyl, substituted aryl or substituted heteroaryl, as defined herein.

The term "aminosulfonyl" refers to the group —S(O)$_2$NRR, wherein each R is independently selected from the group consisting of hydrogen, alkyl, cycloalkyl, aryl, heteroaryl and heterocyclyl. Unless otherwise constrained by the definition, all substituents may optionally be further substituted by 1, 2 or 3 substituents selected from the group consisting of alkyl, alkenyl, alkynyl, alkoxy, cycloalkyl, cycloalkenyl, cycloalkoxy, cycloalkenyloxy, acyl, acylamino, acyloxy, amino, substituted amino, aminocarbonyl, alkoxycarbonylamino, azido, cyano, halogen, hydroxy, keto, thiocarbonyl, carboxy, carboxyalkyl, arylthio, heteroarylthio, heterocyclylthio, thiol, alkylthio, aryl, aryloxy, heteroaryl, aminosulfonyl, aminocarbonylamino, heteroaryloxy, heterocyclyl, heterocyclooxy, hydroxyamino, alkoxyamino, nitro, SO-alkyl, —SO— cycloalkyl, —SO-heterocyclyl, —SO-aryl, —SO-heteroaryl, —SO$_2$-alkyl, —SO$_2$-cycloalkyl, —SO$_2$-heterocyclyl, —SO$_2$-aryl and —SO$_2$-heteroaryl.

The term "hydroxyamino" refers to the group —NHOH.

The term "alkoxyamino" refers to the group —NHOR in which R is optionally substituted alkyl.

The term "halogen" or "halo" refers to fluoro, bromo, chloro and iodo.

The term "triflate" refers to the trifluoromethanesulfonategroup (—OSO$_2$—CF$_3$).

"Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g. forming a branch), and also includes embodiments in which the substituent may be a diradical bridging group bound to two adjacent atoms of the substituted group, thereby forming a fused ring on the substituted group.

Where a given group (moiety) is described herein as being attached to a second group and the site of attachment is not explicit, the given group may be attached at any available site of the given group to any available site of the second group. For example, a "alkyl-substituted phenyl", where the attachment sites are not explicit, may have any available site of the alkyl group attached to any available site of the phenyl group. In this regard, an "available site" is a site of the group at which a hydrogen of the group may be replaced with a substituent.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. Also not included are infinite numbers of substituents, whether the substituents are the same or different. In such cases, the maximum number of such substituents is three. Each of the above definitions is thus constrained by a limitation that, for example, substituted aryl groups are limited to -substituted aryl-(substituted aryl)-substituted aryl.

A compound of a given Formula (e.g. the compound of Formula I) is intended to encompass the compounds of the disclosure, and the salts (e.g. pharmaceutically acceptable salts), esters, isomers, tautomers, solvates, isotopes, hydrates, co-crystals, co-formers and/or prodrugs of such compounds. Additionally, the compounds of the disclosure may possess one or more asymmetric centers, and can be produced as a racemic mixture or as individual enantiomers or diastereoisomers. The number of stereoisomers present in any given compound of a given Formula depends upon the number of asymmetric centers present (there are 2n stereoisomers possible where n is the number of asymmetric centers). The individual stereoisomers may be obtained by resolving a racemic or non-racemic mixture of an intermediate at some appropriate stage of the synthesis or by resolution of the compound by conventional means. The individual stereoisomers (including individual enantiomers and diastereoisomers) as well as racemic and non-racemic mixtures of stereoisomers are encompassed within the scope of the present disclosure, all of which are intended to be depicted by the structures of this specification unless otherwise specifically indicated.

"Isomers" are different compounds that have the same molecular formula. Isomers include stereoisomers, enantiomers and diastereomers.

"Stereoisomers" are isomers that contain stereogenic atoms which contain the same connectivity, but which differ only in the way the atoms are arranged in space. The term "stereoisomers" as used herein includes both "enantiomers" and "diastereomers."

"Enantiomers" are a pair of stereoisomers that are non-superimposable mirror images of each other and do not contain a plane of symmetry. A 1:1 mixture of a pair of enantiomers is a "racemic" mixture. The term "(±)" is used to designate a racemic mixture where appropriate.

"Diastereoisomers" are stereoisomers that have at least two stereogenic atoms and may contain a plane of symmetry, but which are not mirror-images of each other in the absence of a plane of symmetry.

The absolute stereochemistry is specified according to the Cahn Ingold Prelog R S system. When the compound is a pure enantiomer the stereochemistry at each chiral carbon may be specified by either R or S. Resolved compounds whose absolute configuration is unknown are designated (+) or (−) depending on the direction (dextro- or laevorotary) that they rotate the plane of polarized light at the wavelength of the sodium D line.

If there is a discrepancy between a depicted structure and a name given to that structure, the depicted structure controls. In addition, if the stereochemistry of a structure or a portion of a structure is not indicated with, for example, bold, wedged, or dashed lines, the structure or portion of the structure is to be interpreted as encompassing all stereoisomers of it.

The term "solvate" refers to a complex formed by the combining of a compound of Formula I, or any other Formula as disclosed herein, and a solvent. As used herein, the term "solvate" includes a hydrate (i.e., a solvate when the solvent is water).

The term "hydrate" refers to the complex formed by the combining of a compound of Formula I, or any Formula disclosed herein, and water.

The term "co-crystal" refers to a crystalline material formed by combining a compound of Formula I, or any Formula disclosed herein and one or more co-crystal formers (i.e., a molecule, ion or atom). In certain instances, co-crystals may have improved properties as compared to the parent form (i.e., the free molecule, zwitter ion, etc.) or a salt of the parent compound. Improved properties can be increased solubility, increased dissolution, increased bioavailability, increased dose response, decreased hygroscopicity, a crystalline form of a normally amorphous compound, a crystalline form of a difficult to salt or unsaltable compound, decreased form diversity, more desired morphology, and the like. Methods for making and characterizing co-crystals are known to those of skill in the art.

The terms "co-former" or "co-crystal former" refer to the non-ionic association of a compound of Formula I, or any Formula disclosed herein with one or more molecules, ions or atoms. Exemplary co-formers are inorganic or organic bases and/or acids.

Any formula or structure given herein, including Formula I, or any Formula disclosed herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorus, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also included compounds of Formula I, or any Formula disclosed herein, in which from 1 to "n" hydrogens attached to a carbon atom is/are replaced by deuterium, in which n is the number of hydrogens in the molecule. Such compounds exhibit increased resistance to metabolism and are thus useful for increasing the half life of any compound of Formula I when administered to a mammal. See, for example, Foster, "Deuterium Isotope Effects in Studies of Drug Metabolism", Trends Pharmacol. Sci. 5(12): 524-527 (1984). Such compounds are synthesized by means well known in the art, for example by employing starting materials in which one or more hydrogen atoms have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life or reduced dosage requirements. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the Formula I, or any Formula disclosed herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Salts of the compounds disclosed herein can be base addition salts or acid addition salts depending on the reactivity of the functional groups present on the specific compound. Base addition salts can be derived from inorganic or organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group. Amines are of general structure $N(R^{30})(R^{31})(R^{32})$, wherein mono-substituted amines have 2 of the three substituents on nitrogen ($R^{30}$, $R^{31}$ and $R^{32}$) as hydrogen, di-substituted amines have 1 of the three substituents on nitrogen ($R^{30}$, $R^{31}$ and $R^{32}$) as hydrogen, whereas tri-substituted amines have none of the three substituents on nitrogen ($R^{30}$, $R^{31}$ and $R^{32}$) as hydrogen. $R^{30}$, $R^{31}$ and $R^{32}$ are selected from a variety of substituents such as hydrogen, optionally substituted alkyl, aryl, heteroaryl, cycloalkyl, cycloalkenyl, heterocyclyl and the like. The above-mentioned amines refer to the compounds wherein either one, two or three substituents on the nitrogen are as listed in the name. For example, the term "cycloalkenyl amine" refers to cycloalkenyl-$NH_2$, wherein "cycloalkenyl" is as defined herein. The term "diheteroarylamine" refers to $NH(heteroaryl)_2$, wherein "heteroaryl" is as defined herein and so on.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Acid addition salts can be derived from inorganic or organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

Any of the salts disclosed herein may be optionally pharmaceutically acceptable. The term "pharmaceutically acceptable salt" of a given compound refers to salts that retain the biological effectiveness and properties of the given compound, and which are not biologically or otherwise undesirable. See: P. Heinrich Stahl and Camille G. Wermuth (Eds.) Pharmaceutical Salts: Properties, Selection, and Use (International Union of Pure and Applied Chemistry), Wiley-VCH; 2nd Revised Edition (May 16, 2011). Pharmaceutically acceptable base addition salts can be prepared from inorganic and organic bases.

Pharmaceutically acceptable base addition salts may be salts prepared from inorganic and organic bases and pharmaceutically acceptable acid addition salts may be salts prepared from inorganic and organic acids.

The term "leaving group" refers to an atom or a group of atoms that is displaced in a chemical reaction as stable species taking with it the bonding electrons. The non-limiting examples of a leaving group include, halo, methanesulfonyloxy, p-toluenesulfonyloxy, trifluoromethanesulfonyloxy, nonafluorobutanesulfonyloxy, (4-bromo-benzene)sulfonyloxy, (4-nitro-benzene)sulfonyloxy, (2-nitro-benzene)-sulfonyloxy, (4-isopropyl-benzene)sulfonyloxy, (2,4,6-tri-isopropyl-benzene)-sulfonyloxy, (2,4,6-trimethyl-benzene)sulfonyloxy, (4-tert-butyl-benzene)sulfonyloxy, benzenesulfonyloxy, (4-methoxy-benzene)sulfonyloxy, and the like.

The term "O-arylation reaction conditions" refers to the reaction conditions under which an —O—R' moiety is installed onto a suitable aromatic substrate. The "O-arylation reaction conditions" as disclosed herein typically comprise a base. The non-limiting examples of the base include sodium carbonate ($Na_2CO_3$) and potassium carbonate ($K_2CO_3$), potassium-tert-butoxide (KOtBu), lithium-tert-butoxide (LiOtBu), magnesium-tert-butoxide (Mg(OtBu)$_2$), sodium-tert-butoxide (NaOtBu), sodium hydride (NaH), potassium hexamethyldisilizide (KHMDS), potassium phosphate ($K_3PO_4$), potassium hydroxide (KOH), lithium hydroxide (LiOH) as well as organic bases such as 1,4-diazabicyclo[2.2.2]octane (DABCO), 1,8-diazabicyclo[5.4.0]undec-7-ene (DBU), and the like.

The term "protective group" refers to a moiety of a compound that masks or alters the properties of a functional group or the properties of the compound as a whole. The chemical substructure of a protective group varies widely. One function of a protective group is to serve as an intermediate in the synthesis of the parental drug substance. Chemical protective groups and strategies for protection/deprotection are well known in the art. See: "Protective Groups in Organic Chemistry", Theodora W. Greene (John Wiley & Sons, Inc., New York, 1991. Protective groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive. The non-limiting examples of protective groups for an amine include t-butyloxycarbonyl (Boc), benzyloxycarbonyl (Cbz), 9-fluorenylmethoxycarbonyl (Fmoc), and the like.

The term "N-deprotection conditions" refers to the reaction conditions under which a protective group from an amine is removed. The non-limiting examples of protective groups for an amine include tert-butyloxycarbonyl (Boc), benzyloxycarbonyl (Cbz), 9-fluorenylmethoxycarbonyl (Fmoc), and the like. The N-deprotection conditions for Boc include using an acid such as HCl, methanesulfonic acid, para-toluenesulfonic acid, and the like. The N-deprotection conditions for Cbz include hydrogenation using hydrogen and a catalyst such as Pd and the like. The N-deprotection conditions for Fmoc include using a base such as 1,8-diazabicyclo[5.4.0]undec-7-ene (DBU), piperidine, and the like.

The term "amide coupling conditions" refers to the reaction conditions under which an amine and a carboxylic acid couple to form an amide using a coupling reagent in presence of a base. The non-limiting examples of coupling reagents include 1-Ethyl-3-(3-dimethylaminopropyl) carbodiimide (EDC) with hydroxybenzotriazole monohydrate (HOBt), O-(7-Azabenzotriazole-1-yl)-N,N,N',N'-tetramethyluronium hexafluorophosphate (HATU), 1-hydroxy-7-azabenzotriazole, and the like. The non-limiting examples of the base include N-methylmorpholine, pyridine, morpholine, imidazole, and the like.

The term "ring closing metathesis" refers to the reaction conditions under which two alkenes in the same molecule react in presence of a catalyst yielding a cycloalkane and a volatile alkene.

The term "Curtius rearrangement" refers to a reaction in which a carboxylic acid (R—COOH) is converted into an amine ($RNH_2$) by first reacting with diphenylphoisphoryl azide to provide an acyl azide ($RCON_3$), which then rearranges to form an isocyanate (RNCO), which on hydrolysis in presence of an alcohol, for example, tert-butanol, provides a boc-protected amine (R—NHBoc).

The term "cross metathesis conditions" refers to the reaction conditions under which two alkenes in separate molecules react in presence of a catalyst yielding a cycloalkane and a volatile alkene.

The non-limiting examples of the catalyst for "ring closing metathesis" and "cross metathesis conditions" include Zhan 1B, Ruthenium-based Grubbs, Grubbs-Hoveyda, saturated and unsaturated imidazole and phosphine-based catalysts as well as Molybdenum-based catalysts, and variants thereof. For a representative, non-exhaustive list, see below, wherein Cy is cyclohexyl, Me is methyl, Ph is phenyl, and iPr is isopropyl.

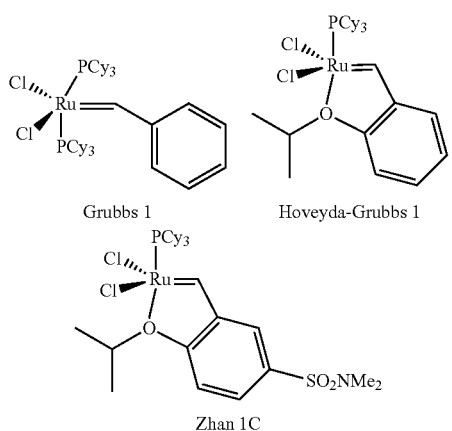

Grubbs 1

Hoveyda-Grubbs 1

Zhan 1C

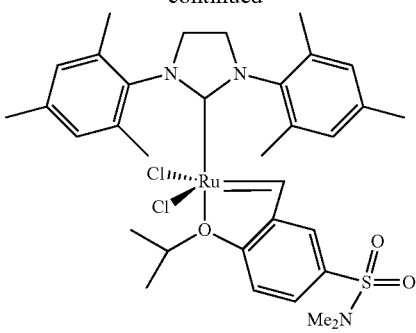

Zhan 1B

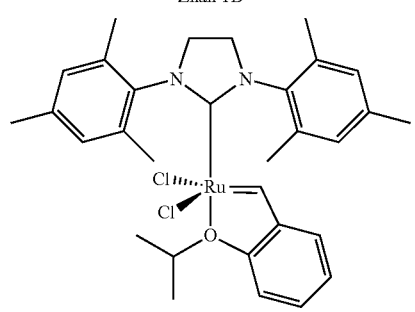

Hoveyda-Grubbs 2

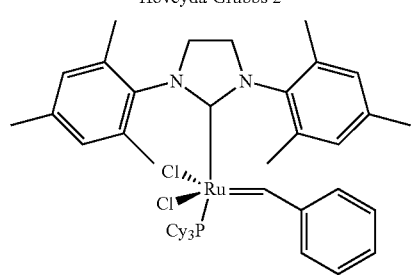

Grubbs 2

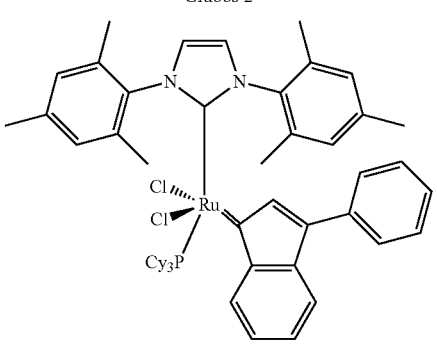

NolanII (IMes)

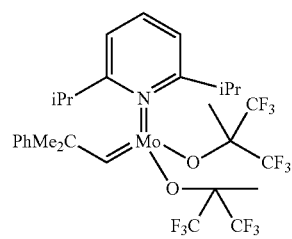

Schrock

In addition, abbreviations as used herein have respective meanings as follows:

| | |
|---|---|
| δ | Chemical shift |
| 9-BBN | 9-borabicyclo[3.3.1]nonane |
| Ac | Acetate |
| Ac$_2$O | Acetic anhydride |
| amu | Atomic mass unit |
| aq. | aqueous |
| atm | Standard atmosphere |
| br | broad |
| Boc | t-butyloxycarbonyl |
| Boc$_2$O | di-tert-butyl dicarbonate |
| calc'd | calculated |
| Cbz | benzyloxycarbonyl |
| CDI | 1,1'-carbonyl-diimidazole |
| CPME | Cyclopentyl methyl ether |
| d | doublet |
| dd | doublet of doublets |
| ddd | doublet of doublet of doublets |
| DCM | dichloromethane |
| DIPEA | Diiopropylethyl amine |
| DMAc or DMA | dimethylacetamide |
| DMAP | 4-(dimethylamino)pyridine |
| DMF | dimethylformamide |
| DMSO | dimethylsulfoxide |
| DPPA | diphenylphosphoryl azide |
| dq | doublet of quartets |
| dt | doublet of triplets |
| EDC | 1-ethyl-3-(3-dimethylaminopropyl) carbodiimide |
| equiv or eq. | equivalents |
| Et | ethyl |
| EtOAc | ethyl acetate |
| EtOH | ethanol |
| Fmoc | 9-fluorenylmethoxycarbonyl |
| GCMS | gas chromatography mass spectrometry |
| g | grams |
| h | hour(s) |
| HATU | O-(7-Azabenzotriazole-1-yl)-N,N,N,N'- |
| HOBt | hydroxybenzotriazole monohydrate |
| HPLC | high pressure liquid chromatography |
| HRMS | High resolution mass spectrometry |
| Hz | hertz |
| iPr | Isopropyl |
| IPA | Isopropanol or 2-propanol |
| IPAC or IPAc | Isopropyl acetate |
| J | Coupling constant |
| L | liter |
| LCMS | liquid chromatography mass spectroscopy |
| M | Molar |
| m | multiplet |
| Me | methyl |
| MeCN | acetonitrile |
| MeTHF | 2-methyltetrahydrofuran |
| MHz | megahertz |
| MIBK | methylisobutyl ketone |
| mmol | millimole |
| mL | milliliter |
| mol | mole |
| MP | Melting point |
| MS | mass spectroscopy |
| MTBE | methyl tert-butyl ether |
| m/z | Mass to charge |
| N | Normal |
| NBS | N-bromosuccinimide |
| NCS | N-chlorosuccinimide |
| NMM | N-methylmorpholine |
| NMP | N-methyl-2-pyrrolidinone |
| NMR | nuclear magnetic resonance |
| ppm | parts per million |
| psig | pounds per square inch |
| rel. | relative |
| s | singlet |
| T3P | Propylphosphonic anhydride |
| t | triplet |
| TBAB | tetra-n-butyl ammonium bromide |
| TBACl | tetra-n-butylammonium chloride |
| TBAI | tetra-n-butylammonium iodide |
| TBPB | tetra-n-butylphosphonium bromide |
| t-BuOAc | tert-butyl acetate |
| TCCA | trichloroisocyanuric acid |
| td | Triplet of doublets |
| tdd | triplet of doublet of doublets |
| tdt | triplet of doublet of triplets |

-continued

| | |
|---|---|
| THF | tetrahydrofuran |
| Ts | Tosyl |
| tt | Triplet of triplets |
| tBu or tBu | tert-butyl |
| tBuOH | t-butanol |
| UPLC | ultra performance liquid chromatography |
| v/v | Volume to volume |
| vol | volume |
| wt | weight |
| wt/wt | Weight to weight |

Processes

As described generally above, the disclosure provides in some embodiments processes for making a compound of formula I. In another embodiment, the disclosure provides processes for making intermediates for the compound of formula I. The processes can also be applied to the synthesis of a stereoisomer or a mixture of stereoisomers of compound of formula I.

Route I

The present disclosure provides in one embodiment a process for making a compound of formula I, named (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide:

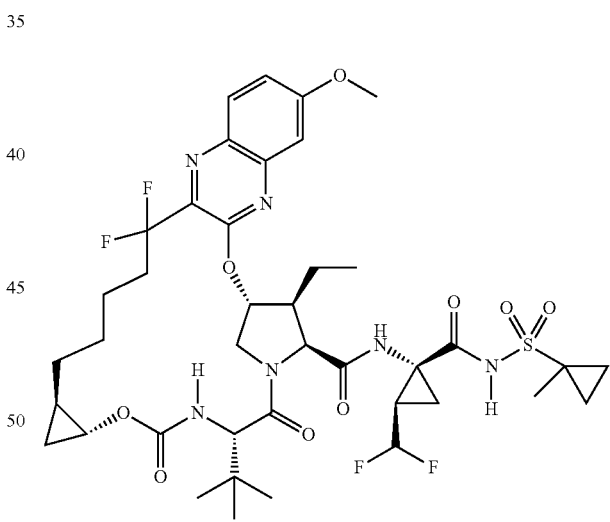

I or a stereoisomer, mixture of stereoisomers, a co-crystal, or a pharmaceutically acceptable salt thereof.

In another embodiment, this disclosure provides a process for preparation of a compound of formula I, named (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide:

I

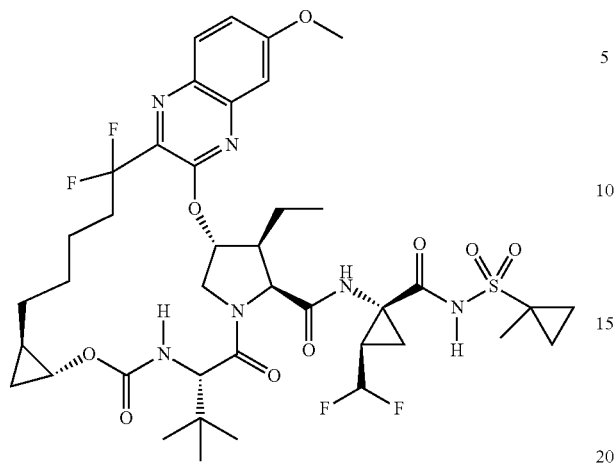

or a co-crystal, or a salt thereof, comprising:
a) contacting a compound of formula III or a co-crystal, or a salt thereof, with a compound of formula IV:

III

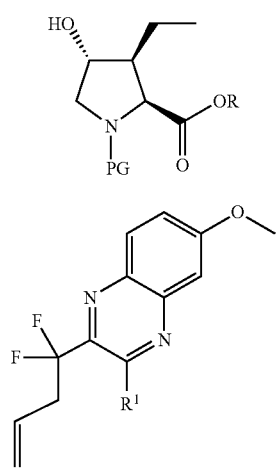

IV

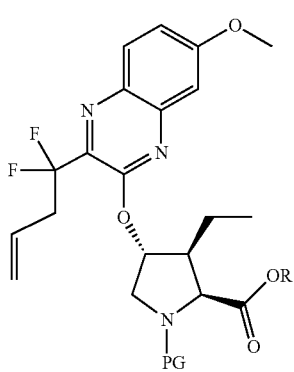

under O-arylation conditions to provide a compound of formula V:

V

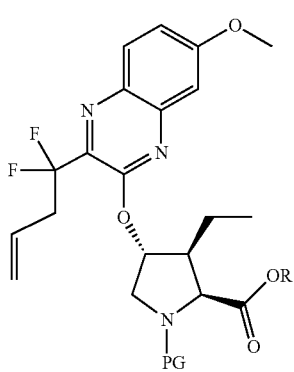

or a co-crystal, or a salt thereof;

b) subjecting the compound of formula V or a co-crystal, or a salt thereof to N-deprotection conditions to provide a compound of formula VI:

VI

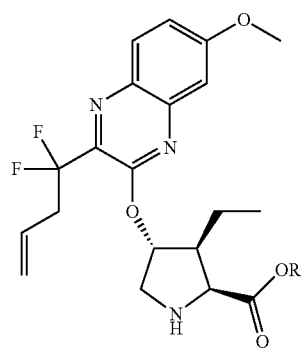

or a co-crystal, or a salt thereof;

c) contacting the compound of formula VI or a co-crystal, or a salt thereof with a compound of formula VII:

VII

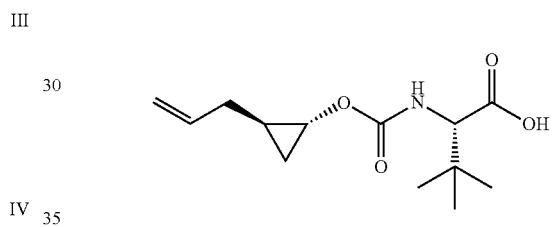

or a co-crystal, or a salt thereof, under amide coupling conditions to provide a compound of formula VIII:

VIII

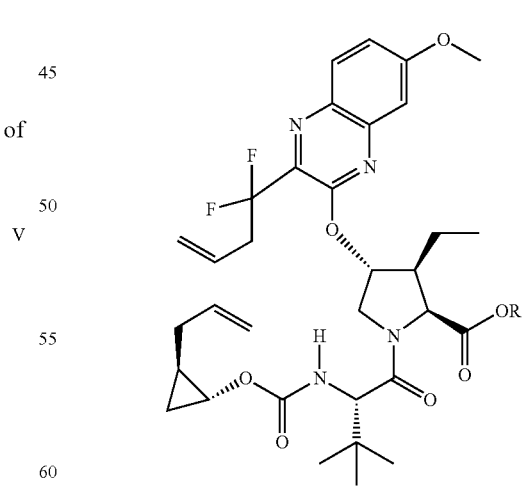

or a co-crystal, or a salt thereof;

d) performing ring closing metathesis of the compound of formula VIII or a co-crystal, or a salt thereof to provide a compound of formula IX:

IX

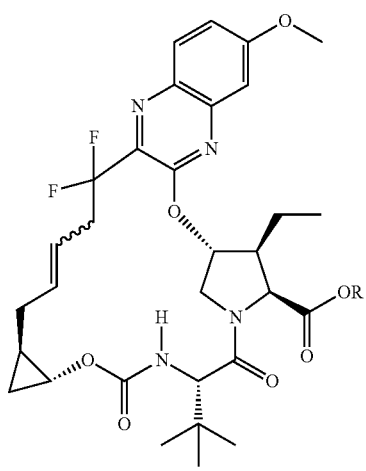

or a co-crystal, or a salt thereof;

e) hydrogenating the compound of formula IX or a co-crystal, or a salt thereof in presence of a catalyst to provide a compound of formula X:

X

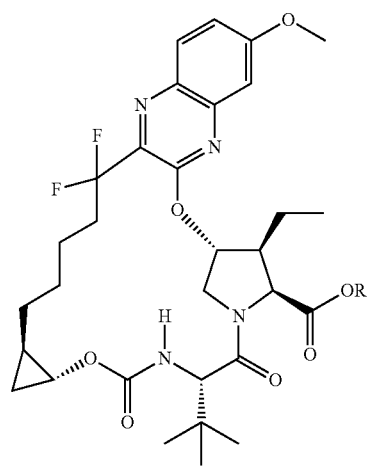

or a co-crystal, or a salt thereof;

f) hydrolyzing the compound of formula X or a co-crystal, or a salt thereof to provide a compound of formula XI:

XI

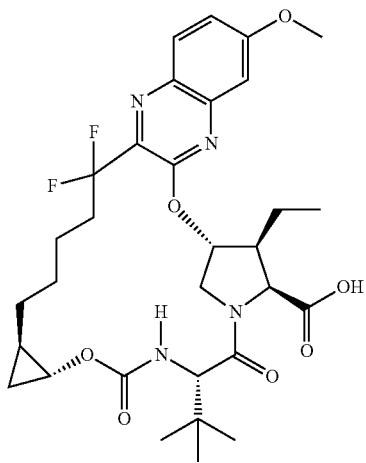

or a co-crystal, or a salt thereof;

g) contacting the compound of formula XI or a co-crystal, or a salt thereof with a compound of formula XII:

XII

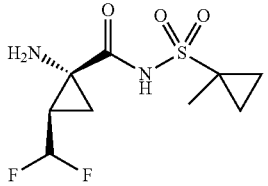

or a co-crystal, or a salt thereof;
under amide coupling conditions to provide the compound formula I:

I

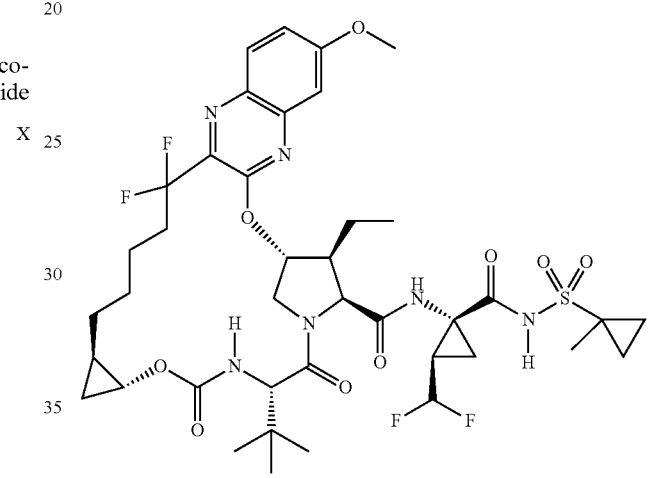

or a co-crystal, or a pharmaceutically acceptable salt thereof, wherein R is $C_{1-6}$ alkyl, PG is a protective group, and $R^1$ is a leaving group.

The O-arylation conditions of step a) comprise a base. The non-limiting examples of the base include sodium carbonate ($Na_2CO_3$) and potassium carbonate ($K_2CO_3$), potassium-tert-butoxide (KOtBu), cesium carbonate ($Cs_2CO_3$), lithium-tert-butoxide (LiOtBu), magnesium-tert-butoxide (Mg(OtBu)$_2$), sodium-tert-butoxide (NaOtBu), sodium hydride (NaH), potassium hexamethyldisilizide (KHMDS), potassium phosphate ($K_3PO_4$), potassium hydroxide (KOH), lithium hydroxide (LiOH) as well as organic bases such as DABCO, DBU, and the like. In one embodiment, the base is cesium carbonate ($Cs_2CO_3$).

The non-limiting examples of leaving group include halo, methanesulfonyloxy, p-toluenesulfonyloxy, trifluoromethanesulfonyloxy, nonafluorobutanesulfonyloxy, (4-bromo-benzene)sulfonyloxy, (4-nitro-benzene)sulfonyloxy, (2-nitro-benzene)-sulfonyloxy, (4-isopropyl-benzene) sulfonyloxy, (2,4,6-tri-isopropyl-benzene)-sulfonyloxy, (2,4,6-trimethyl-benzene)sulfonyloxy, (4-tertbutyl-benzene) sulfonyloxy, benzenesulfonyloxy, (4-methoxy-benzene)sulfonyloxy.

The O-arylation conditions of step a) further comprise a solvent. The non-limiting examples of the solvent include N,N-dimethylformamide (DMF), N-methyl-2-pyrrolidinone (NMP), dimethylsulfoxide (DMSO), acetonitrile (MeCN), acetone; aprotic solvents with small amounts of added water ($H_2O$), ethers such as tetrahydrofuran (THF) and 1,4-dioxane, toluene (in the presence of phase-transfer catalyst), and the like. In one embodiment, the solvent is N,N-Dimethylacetamide (DMAc). In another embodiment, the O-arylation conditions of step a) comprise a temperature of about 100 to 110° C.

A variety of protective groups, PG, can be used in compound of formula III. The non-limiting examples of protective groups for amines include t-butyloxycarbonyl (Boc), benzyloxycarbonyl (Cbz), 9-fluorenylmethoxycarbonyl (Fmoc), and the like. In one embodiment, PG is Boc. The N-deprotection conditions of step b) refer to conditions under which the protective group, P, is removed. In one embodiment, PG is Boc and the N-deprotecting conditions comprise an acid such as HCl, methanesulfonic acid, toluenesulfonic acids, and the like. In one embodiment, the acid is para-toluenesulfonic acid.

The N-deprotection conditions of step b) further comprise a solvent. The non-limiting examples of the solvent include methyl tetrahydrofuran, MTBE, dioxane, isopropyl acetate, a combination thereof, and the like. In one embodiment, the solvent is a mixture of methyl tetrahydrofuran and MTBE. In another embodiment, the N-deprotection conditions of step b) comprise a temperature of about 50 to 55° C.

The amide coupling conditions of step c) comprise a coupling reagent in presence of a base. The non-limiting examples of coupling reagents include 1-ethyl-3-(3-dimethylaminopropyl) carbodiimide (EDC) with hydroxybenzotriazole (HOBt), 1-hydroxy-7-azabenzotriazole, O-(7-azabenzotriazol-1-yl)-N,N,N',N'-tetramethyluronium hexafluorophosphate (HATU), and the like. The non-limiting examples of the base include N-methylmorpholine, pyridine, morpholine, triethylamine, N,N-diisopropylethylamine, imidazole, and the like. In one embodiment, the coupling conditions of step c) comprise 1-ethyl-3-(3-dimethylaminopropyl) carbodiimide and hydroxybenzotriazole using N-methylmorpholine. The amide coupling conditions of step c) comprise a solvent. The non-limiting examples of the solvent include dimethylacetamide, acetonitrile, N,N-dimethylformamide, and the like. In one embodiment, the solvent is N,N-dimethylformamide. In another embodiment, the amide coupling conditions of step c) comprise a temperature of about 0 to 20° C.

The ring closing metathesis of step d) comprise a catalyst. The non-limiting examples of the catalyst for "ring closing metathesis" include Zhan 1B, ruthenium-based Grubbs, Grubbs-Hoveyda, saturated and unsaturated imidazole and phosphine-based catalysts as well as molybdenum-based catalysts, and variants thereof. For a representative, non-exhaustive list, see below, wherein Cy is cyclohexyl, Me is methyl, Ph is phenyl, and iPr is isopropyl.

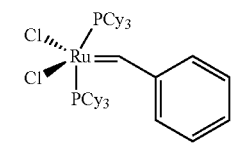

Grubbs 1

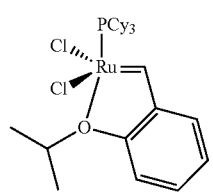

Hoveyda-Grubbs 1

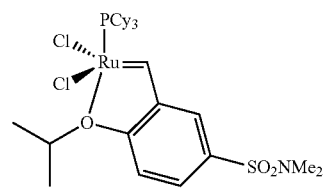

Zhan 1C

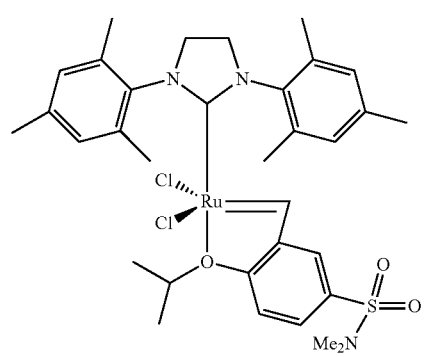

Zhan 1B

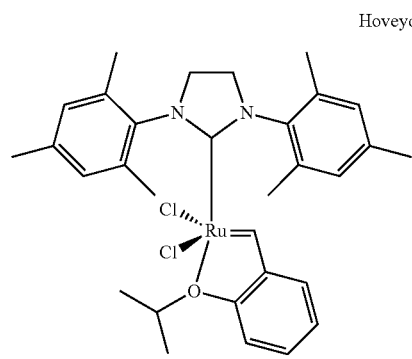

Hoveyda-Grubbs 2

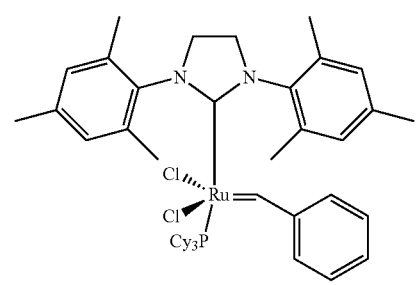

Grubbs 2

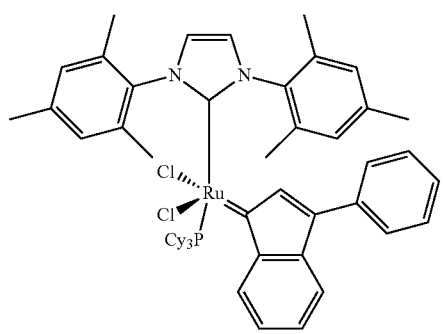

NolanII (IMes)

-continued

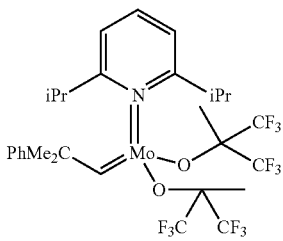
Schrock

In one embodiment, ring closing metathesis of step d) comprise the catalyst Zhan 1B.

The ring closing metathesis of step d) further comprise a solvent. The non-limiting examples of the solvent include dichloromethane, 1,2-dichloroethane, chlorobenzene, hexafluorobenzene, benzene, toluene, THF, methyl-tert-butyl ether, cyclopentyl methyl ether, ethyl acetate, methanol, isopropanol, n-heptane, dimethyl carbonate, dimethyl formamide, acetonitrile, and the like. In one embodiment, the solvent is toluene. In another embodiment, the ring closing metathesis of step d) comprise a temperature of about 40 to 110° C. In another embodiment, the temperature is about 105 to 110° C.

The ring closing metathesis of step d) optionally comprises a promoter. The non-limiting examples of the promoter include acetic acid, benzoquinones, CuI, CsCl, Ti(O-i-Pr)$_4$, microwave irradiation, ethylene, and the like.

The hydrogenation conditions of step e) comprise hydrogen in presence of a catalyst. The non-limiting examples of the catalyst include platinum, palladium, ruthenium, nickel, and other metals on carbon, alumina, silica, and other heterogeneous supports; metal nanoparticles; frustrated Lewis pairs such as hydrogen [4-[bis(2,4,6-trimethylphenyl)phosphino]-2,3,5,6-tetrafluorophenyl]hydrobis(2,3,4,5,6-pentafluorophenyl)borate; homogeneous metal catalysts such as chlorotris(triphenylphosphine)rhodium(I) or (1,5-cyclooctadiene)(pyridine)(tricyclohexylphosphine)-iridium (I) hexafluorophosphate, and the like. In one embodiment, the catalyst is platinum on carbon.

The hydrogenation conditions of step e) further comprise a solvent. The non-limiting examples of the solvent include water, protic solvents such as methanol, ethanol, or acetic acid; aprotic solvents such as dimethyl sulfoxide, tetrahydrofuran, ethyl acetate, iso-propyl acetate, acetonitrile, toluene, dichloromethane or acetone; combinations thereof, and the like. In one embodiment, the solvent is iso-propyl acetate. In another embodiment, the hydrogenation conditions of step e) comprise a temperature of about 20 to 150° C. In another embodiment, the temperature is about 20 to 25° C.

The hydrogenation conditions of step e) comprise hydrogen gas or formates such as ammonium formate or formic acid as a source of hydrogen.

The hydrolysis conditions of step f) comprise either acid hydrolysis or base hydrolysis. The non-limiting examples of acids for acid hydrolysis include protic acids such as sulfuric acid, hydrochloric acid, p-toluene sulfonic acid, or solid-supported acids; Lewis acids such as boron trifluoride, metal salts, metal complexes, or hydrogen-bond donors, and the like. The non-limiting examples of bases for base hydrolysis include carbonates such as lithium, sodium, and cesium carbonates, metal hydrides such as sodium hydride, potassium hydride; alkoxides such as sodium methoxide, sodium tert-butoxide, lithium tert-butoxide, potassium tert-butoxide, or tetraalkylammonium alkoxides; hydroxides such as sodium hydroxide, potassium hydroxide, tin hydroxides, or tetraalkylammonium hydroxides; amine bases, such as 1,8-diazabicycloundec-7-ene, and the like. In one embodiment hydrolysis of step f) comprises a base. In another embodiment, the base is lithium hydroxide.

The hydrolysis conditions of step f) further comprise a solvent. The non-limiting examples of the solvent include polar protic solvents, including water, alcohols such as methanol, ethanol, IPA, tert-butanol, neopentyl alcohols, glycols, and combinations of these with water; polar aprotic solvents, including dimethyl sulfoxide, dimethyl formamide, tetrahydrofuran, 1,4-dioxane, and combinations of these with water; ionic liquids, such as 3-methylimidazolium hexafluorophosphate, and the like. In one embodiment, the solvent is a mixture of iso-propanol and water.

The amide coupling conditions of step g) comprise a coupling reagent in presence of a base and are similar to those described for step c). In one embodiment, the coupling agent is O-(7-azabenzotriazole-1-yl)-N,N,N',N'-tetramethyluronium hexafluorophosphate (HATU). In another embodiment the base is N,N-diisipropylethylamine. In another embodiment, the solvent is DMF.

In one embodiment R is $C_{1-6}$ alkyl. In another embodiment, R is methyl. In another embodiment, R is tert-butyl.

In one embodiment, $R^1$ is selected from the group consisting halo, methanesulfonyloxy, p-toluenesulfonyloxy, trifluoromethanesulfonyloxy, nonafluorobutanesulfonyloxy, (4-bromo-benzene)sulfonyloxy, (4-nitro-benzene)sulfonyloxy, (2-nitro-benzene)-sulfonyloxy, (4-isopropyl-benzene)sulfonyloxy, (2,4,6-tri-isopropyl-benzene)-sulfonyloxy, (2,4,6-trimethyl-benzene)sulfonyloxy, (4-tert-butyl-benzene)sulfonyloxy, benzenesulfonyloxy, (4-methoxy-benzene)sulfonyloxy. In another embodiment, $R^1$ is halo. In another embodiment, $R^1$ is chloro.

In another embodiment, this disclosure provides a process for preparation of a compound of formula V:

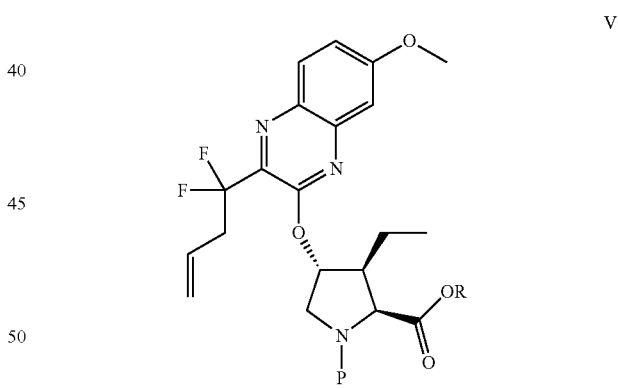
V or a stereoisomer, a mixture of stereoisomers, or a co-crystal, or a salt thereof;
comprising contacting a compound of formula III or a co-crystal, or a salt thereof, with a compound of formula IV:

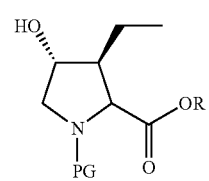
III

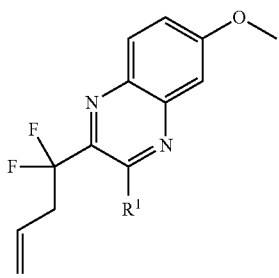

IV under O-arylation conditions to provide the compound of formula V or a co-crystal, or a salt thereof, wherein R is C$_{1-6}$ alkyl, PG is a protective group, and R$^1$ is a leaving group.

In another embodiment, this disclosure provides a process for preparation of a compound of formula VI:

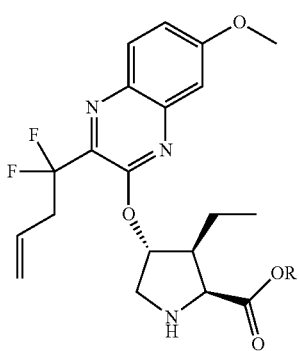

VI or a co-crystal, or a salt thereof;
comprising subjecting a compound of formula V:

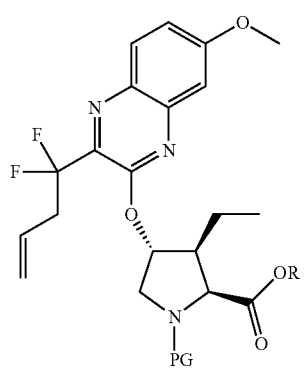

V or a co-crystal, or a salt thereof to N-deprotection conditions to provide the compound of formula VI or a co-crystal, or a salt thereof, wherein R is C$_{1-6}$ alkyl and PG is a protective group.

In another embodiment, this disclosure provides a process for preparation of a compound of formula VIII:

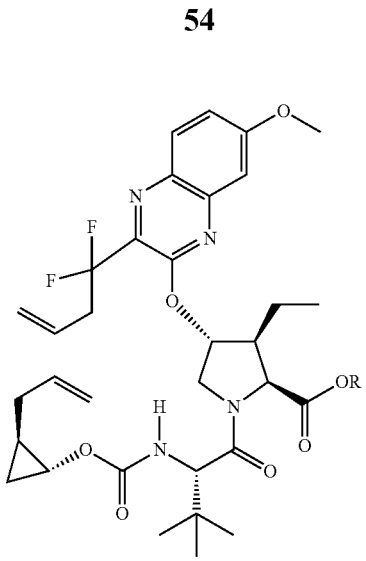

VIII or a co-crystal, or a salt thereof;
comprising contacting a compound of formula VI:

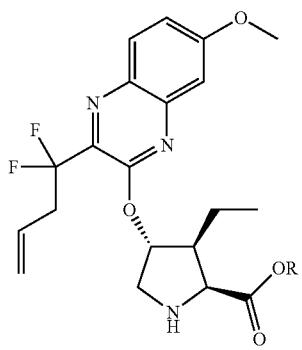

VI or a co-crystal, or a salt thereof;
with a compound of formula VII:

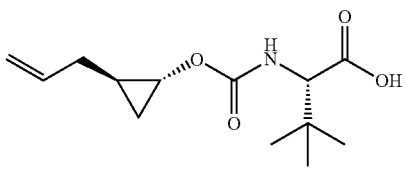

VII or a co-crystal, or a salt thereof,
under amide coupling conditions to provide the compound of formula VIII or a co-crystal, or a salt thereof, wherein R is C$_{1-6}$ alkyl.

In another embodiment, this disclosure provides a process for preparation of a compound of formula IX:

IX

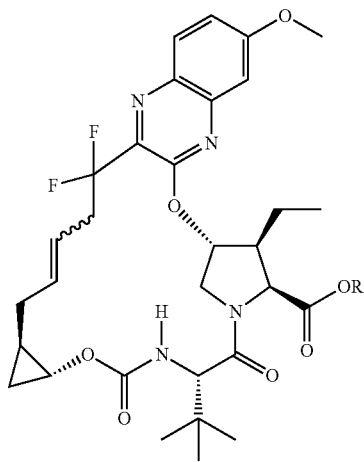

or a co-crystal, or a salt thereof;

comprising performing ring closing metathesis of a compound of formula VIII:

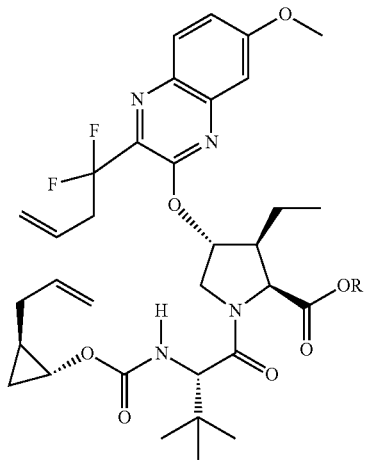

VIII or a co-crystal, or a salt thereof;

to provide the compound of formula IX or a co-crystal, or a salt thereof, wherein R is $C_{1-6}$ alkyl.

Route II

In another embodiment, this disclosure provides a process for preparation of a compound of formula I, named (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide:

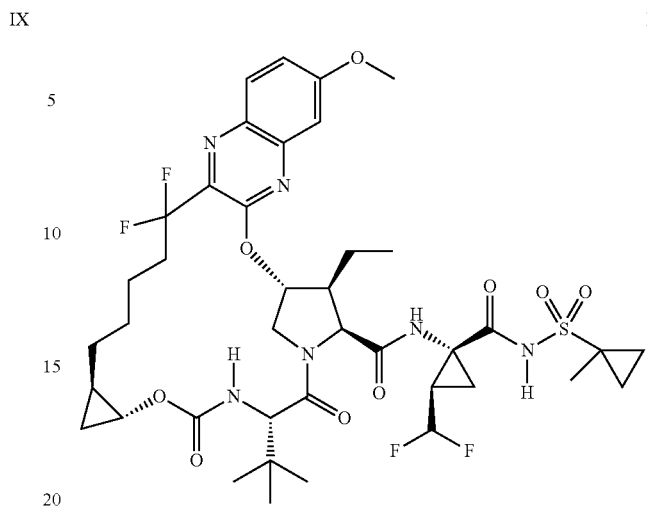

I or a co-crystal, or a pharmaceutically acceptable salt thereof, comprising:

a) contacting a compound of formula III or a co-crystal, or a salt thereof, with a compound of formula IV:

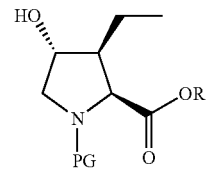

III

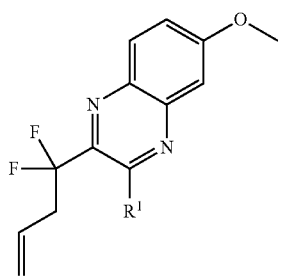

IV under O-arylation conditions to provide a compound of formula V:

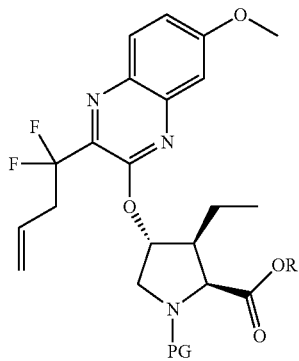

V or a co-crystal, or a salt thereof;

b) subjecting the compound of formula V or a co-crystal, or a salt thereof to N-deprotection conditions to provide a compound of formula VI:

VI

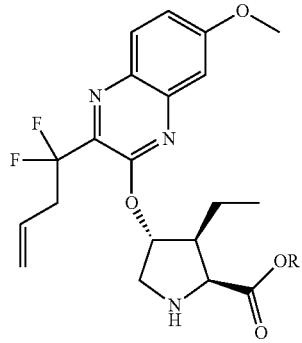

or a co-crystal, or a salt thereof;

c) contacting the compound of formula VI or a co-crystal, or a salt thereof with a compound of formula VII:

VII

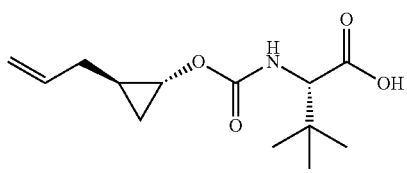

or a co-crystal, or a salt thereof, under amide coupling conditions to provide a compound of formula VIII:

VIII

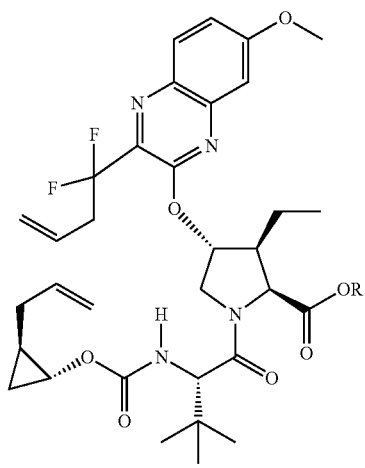

or a co-crystal, or a salt thereof;

d) hydrolyzing the compound of formula VIII or a co-crystal, or a salt thereof to provide a compound of formula XVIII:

XVIII

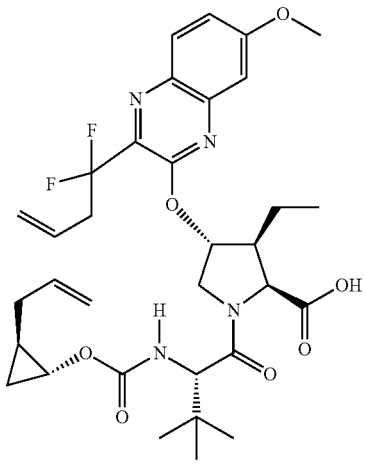

or a co-crystal, or a salt thereof;

e) performing ring closing metathesis of the compound of formula XVIII or a co-crystal, or a salt thereof in presence of a catalyst to provide a compound of formula XIX:

XIX

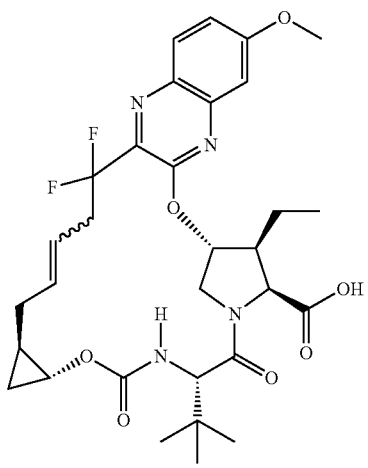

or a co-crystal, or a salt thereof;

f) hydrogenating the compound of formula XIX in presence of a catalyst to provide a compound of formula XI:

XI

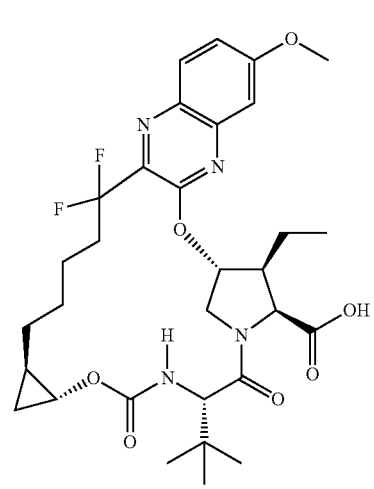

or a co-crystal, or a salt thereof;

g) contacting the compound of formula XI or a co-crystal, or a salt thereof with a compound of formula XII:

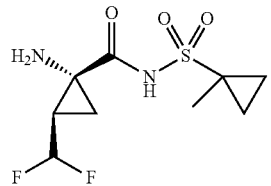

XII or a co-crystal, or a salt thereof;
under amide coupling conditions to provide the compound formula I:

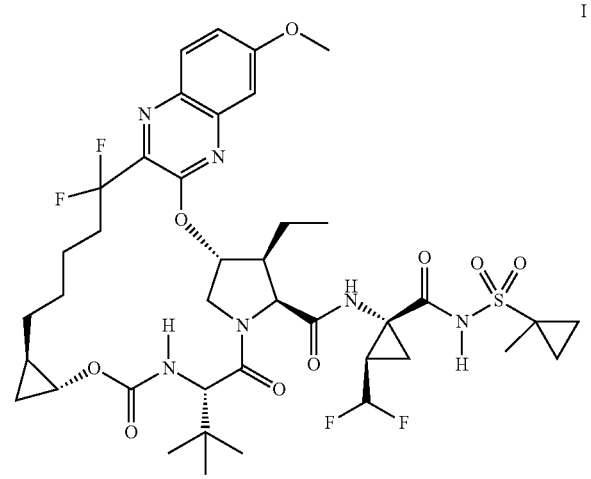 [SMILES: CC[C@@H]1[C@@H]2CN(C(=O)[C@H](C(C)(C)C)NC(=O)O[C@@H]3C[C@H]3CCCCC(F)(F)c3nc4ccc(OC)cc4nc3O2)[C@@H]1C(=O)N[C@]1(C(=O)NS(=O)(=O)C2(C)CC2)C[C@H]1C(F)F]

I or a co-crystal, or a pharmaceutically acceptable salt thereof, wherein R is $C_{1-6}$ alkyl, PG is a protective group, and $R^1$ is a leaving group.

In route II, there is a variation in the order of assembly in that the compound of formula VIII is first hydrolyzed to provide the compound of formula XVIII which is then subjected to ring closing metathesis to give the compound of formula XIX which is hydrogenated to give the compound of formula XI.

In one embodiment R is $C_{1-6}$ alkyl. In another embodiment, R is methyl. In another embodiment, R is tert-butyl.

In one embodiment, $R^1$ is selected from the group consisting of halo, methanesulfonyloxy, p-toluenesulfonyloxy, trifluoromethanesulfonyloxy, nonafluorobutanesulfonyloxy, (4-bromo-benzene)sulfonyloxy, (4-nitro-benzene)sulfonyloxy, (2-nitro-benzene)-sulfonyloxy, (4-isopropyl-benzene) sulfonyloxy, (2,4,6-tri-isopropyl-benzene)-sulfonyloxy, (2,4,6-trimethyl-benzene)sulfonyloxy, (4-tert-butyl-benzene)sulfonyloxy, benzenesulfonyloxy, (4-methoxy-benzene)sulfonyloxy. In another embodiment, $R^1$ is halo. In another embodiment, $R^1$ is chloro.

In another embodiment, this disclosure provides a process for preparation of a compound of formula XVIII:

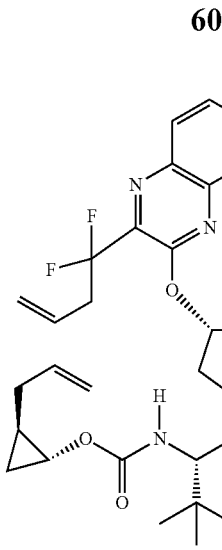

XVIII or a co-crystal, or a salt thereof;
comprising hydrolyzing a compound of formula VIII:

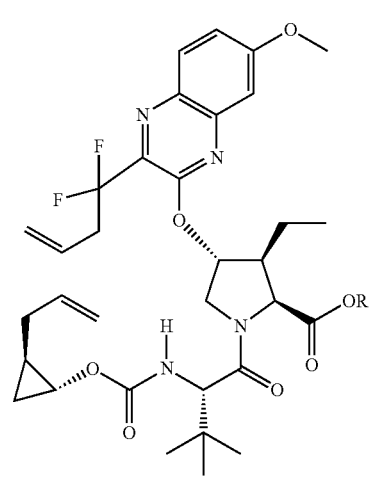

VIII or a co-crystal, or a salt thereof to provide the compound of formula XVIII or a co-crystal, or a salt thereof, wherein R is $C_{1-6}$ alkyl.

In another embodiment, this disclosure provides a process for preparation of a compound of formula XIX:

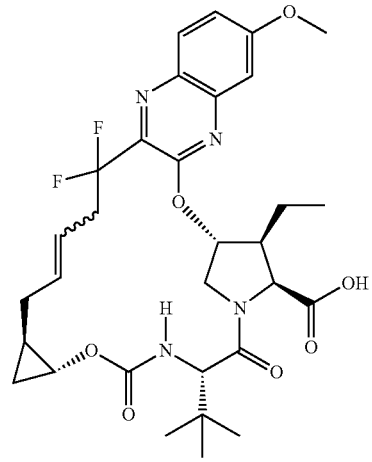

XIX or a co-crystal, or a salt thereof;

comprising performing ring closing metathesis of the compound of formula XVIII or a co-crystal, or a salt thereof in presence of a catalyst to provide the compound of formula XIX.

In another embodiment, this disclosure provides a process for preparation of a compound of formula XI:

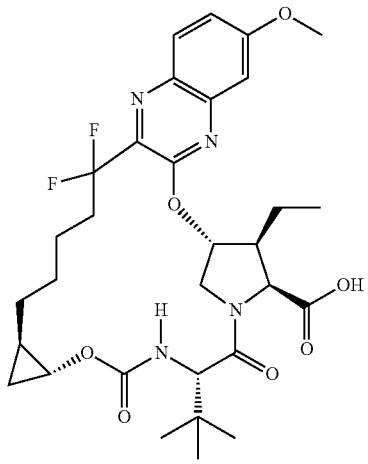

XI or a co-crystal, or a salt thereof,
comprising hydrogenating a compound of formula XIX:

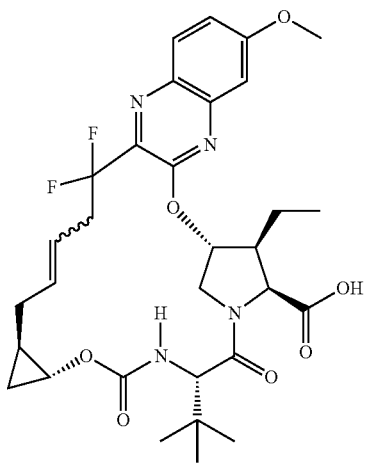

XIX or a co-crystal, or a salt thereof in presence of a catalyst to provide the compound of formula XI or a co-crystal, or a salt thereof.

Route III

In another embodiment, this disclosure provides a process for preparation of a compound of formula I, named (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide:

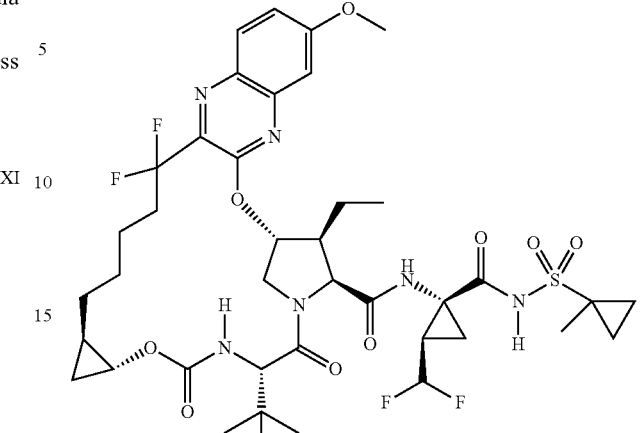

I or a co-crystal, or a pharmaceutically acceptable salt thereof, comprising:

a) contacting a compound of formula XIII:

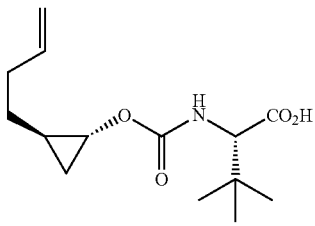

XIII or a co-crystal, or a salt thereof,
with a compound of formula XIV:

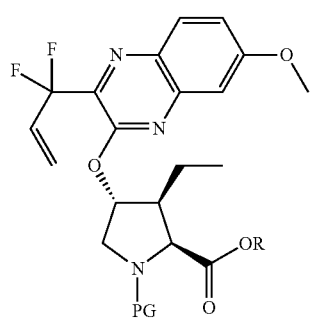

XIV or a co-crystal, or a salt thereof,
under cross-metathesis conditions to provide a compound of formula XV:

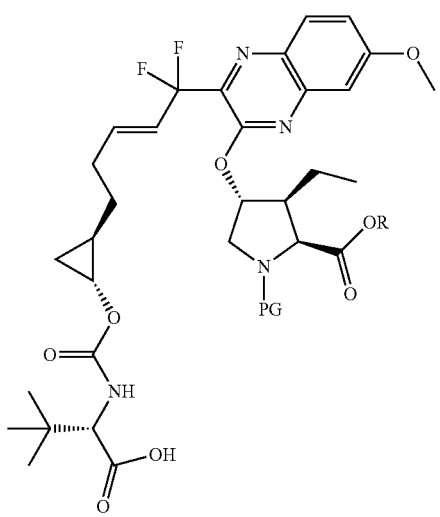

or a co-crystal, or a salt thereof, b) hydrogenating the compound of formula XV or a co-crystal, or a salt thereof in presence of a catalyst to provide a compound of formula XVI:

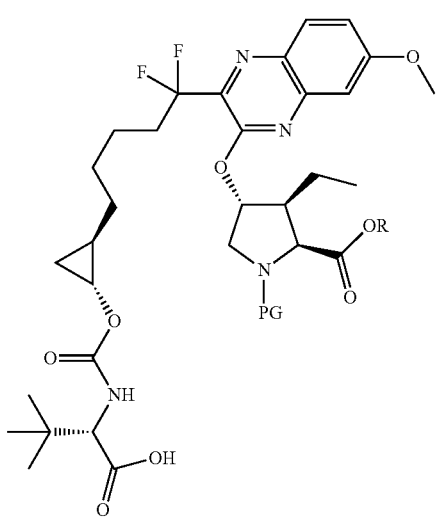

or a co-crystal, or a salt thereof;

c) subjecting the compound of formula XVI or a co-crystal, or a salt thereof to N-deprotection conditions to provide a compound of formula XVII:

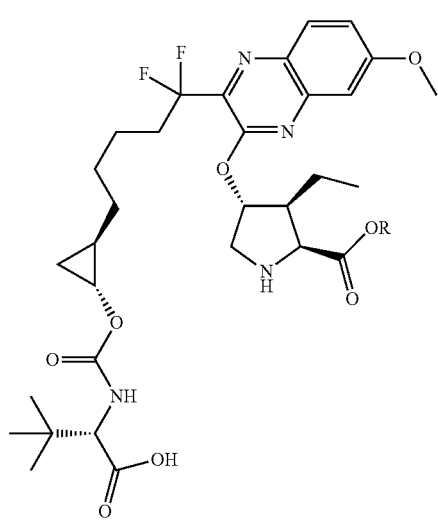

or a co-crystal, or a salt thereof;

d) contacting the compound of formula XVII with an amide coupling agent under lactamization conditions to give a compound of formula X:

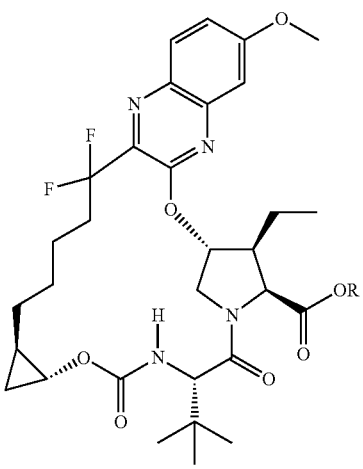

or a co-crystal, or a salt thereof;

e) hydrolyzing the compound of formula X or a co-crystal, or a salt thereof to provide a compound of formula XI:

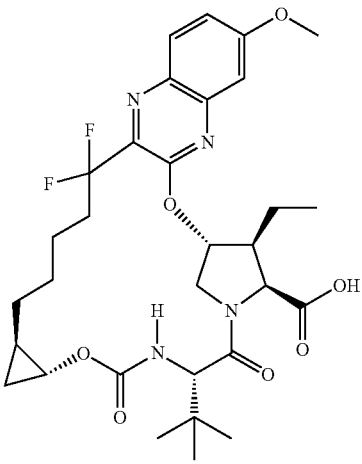

or a co-crystal, or a salt thereof; and f) contacting the compound of formula XI or a co-crystal, or a salt thereof with a compound of formula XII:

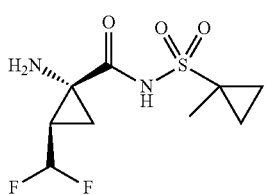

XII or a co-crystal, or a salt thereof under amide coupling conditions to provide the compound formula I:

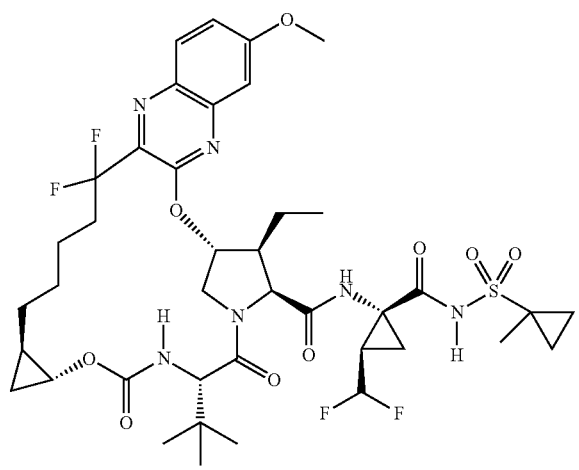

I or a co-crystal, or a pharmaceutically acceptable salt thereof, wherein R is $C_{1-6}$ alkyl and PG is a protective group.

The cross-metathesis conditions comprise a catalyst and a solvent. In one embodiment, the catalyst is Zhan B. In another embodiment, the solvent is toluene. In another embodiment, the cross-metathesis conditions comprise a temperature of about 90-100° C.

The hydrogenation conditions of step b) comprise a catalyst and a solvent. In one embodiment, the catalyst is platinum on carbon. In another embodiment, the solvent is isopropyl acetate.

The N-deprotection conditions for step c) comprise an acid and a solvent. In one embodiment, PG is Boc. In another embodiment, the acid is HCl. In another embodiment, the solvent is dioxane.

The lactamization conditions of step d) comprise a coupling reagent in presence of a base and a solvent. In one embodiment, the coupling agent is 1-ethyl-3-(3-dimethylaminopropyl) carbodiimide (EDC) with hydroxybenzotriazole monohydrate (HOBt). In another embodiment, the base is triethylamine. In another embodiment, the solvent is N,N-dimethylformamide (DMF).

In one embodiment R is $C_{1-6}$ alkyl. In another embodiment, R is methyl. In another embodiment, R is tert-butyl.

In another embodiment, this disclosure provides a process for preparation of a compound of formula XV:

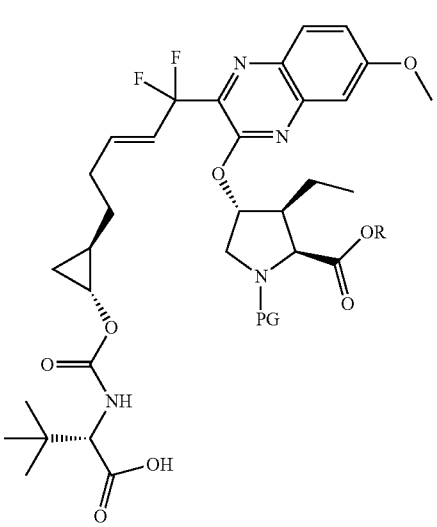

XV or a co-crystal, or a salt thereof, comprising contacting a compound of formula XIII:

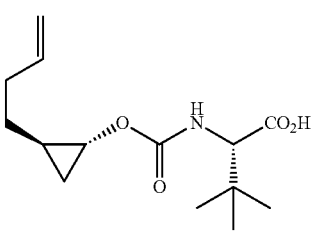

XIII or a co-crystal, or a salt thereof, with a compound of formula XIV:

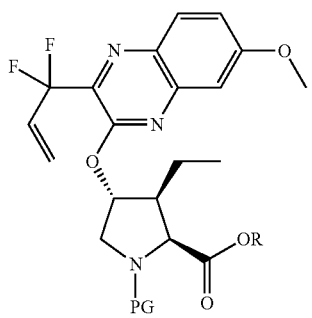

XIV or a co-crystal, or a salt thereof, under cross-metathesis conditions to provide the compound of formula XV or a co-crystal, or a salt thereof, wherein R is $C_{1-6}$ alkyl and PG is a protective group.

In another embodiment, this disclosure provides a process for preparation of a compound of formula XVI:

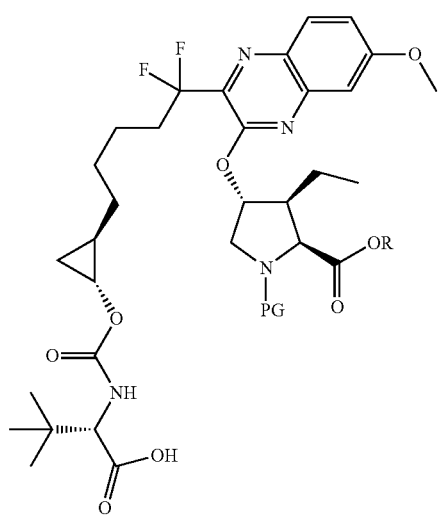

XVI

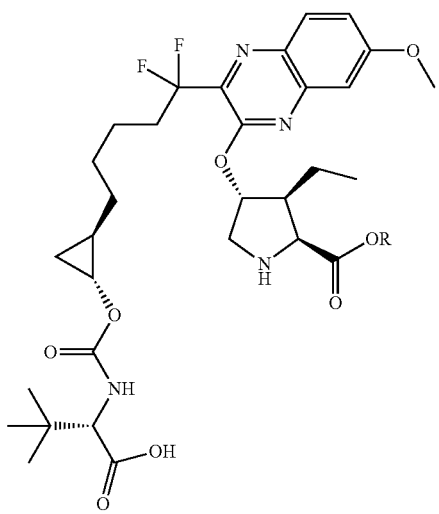

XVII or a co-crystal, or a salt thereof;

comprising hydrogenating the compound of formula XV:

or a co-crystal, or a salt thereof;

comprising subjecting a compound of formula XVI:

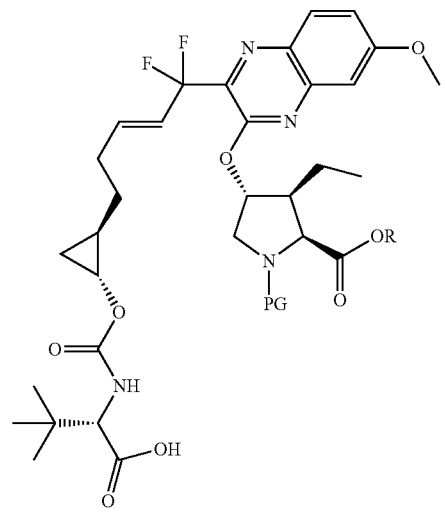

XV

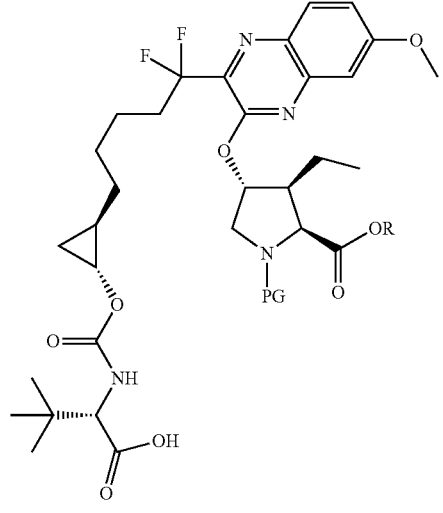

XVI or a co-crystal, or a salt thereof in presence of a catalyst to provide the compound of formula XVI or a co-crystal, or a salt thereof, wherein R is $C_{1-6}$ alkyl and PG is a protective group.

In another embodiment, this disclosure provides a process for preparation of a compound of formula XVII:

or a co-crystal, or a salt thereof;

to N-deprotection conditions to provide the compound of formula XVII or a co-crystal, or a salt thereof, wherein R is $C_{1-6}$ alkyl and PG is a protective group.

In another embodiment, this disclosure provides a process for preparation of a compound of formula X:

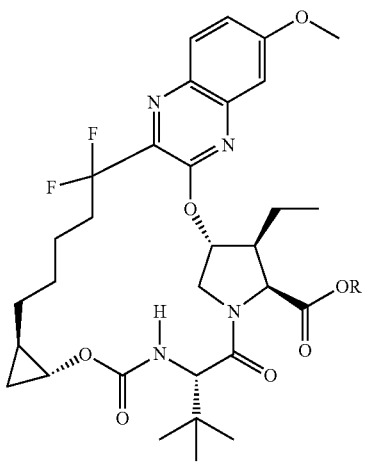

X or a co-crystal, or a salt thereof;

comprising contacting the compound of formula XVII with an amide coupling agent under lactamization conditions to give the compound of formula X or a co-crystal, or a salt thereof, wherein R is $C_{1-6}$ alkyl.

Compounds

In another embodiment, this disclosure provides a compound of formula IV:

IV or a co-crystal, or a salt thereof, wherein $R^1$ is a leaving group. In one embodiment, $R^1$ is selected from the group consisting of halo, —O-(toluenesulfonyl), —O-(trifluoromethanesulfonyl), —O-(4-nitrophenyl), and —B(OY)$_2$, wherein each Y is independently H or $C_{1-4}$ alkyl, or two Y groups together with the atoms to which they are attached form a 5- to 6-membered ring. In another embodiment, $R^1$ is halo. In another embodiment, $R^1$ is chloro.

In another embodiment, $R^1$ is NH$_2$.

In another embodiment, this disclosure provides a compound of formula V:

V or a co-crystal, or a salt thereof, wherein R is $C_{1-6}$ alkyl and PG is a protective group. In one embodiment, PG is selected from the group consisting of Boc, Cbz, and Fmoc. In another embodiment, PG is Boc. In another embodiment, R is methyl. In another embodiment, R is tert-butyl.

In another embodiment, this disclosure provides a compound of formula VI:

VI or a co-crystal, or a salt thereof, wherein R is $C_{1-6}$ alkyl. In another embodiment, R is methyl. In another embodiment, R is tert-butyl.

In another embodiment, this disclosure provides a compound of formula VII:

VII

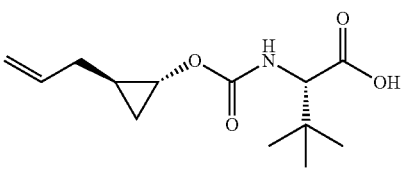

or a co-crystal, or a salt thereof.

In another embodiment, this disclosure provides a compound of formula VIII:

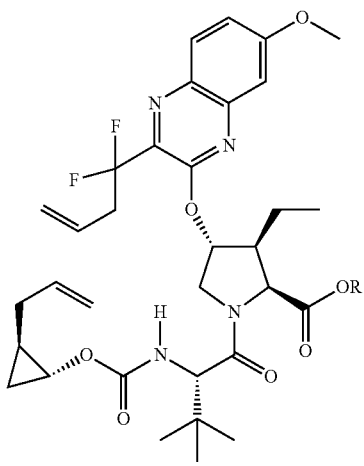

VIII or a co-crystal, or a salt thereof, wherein R is $C_{1-6}$ alkyl. In another embodiment, R is methyl. In another embodiment, R is tert-butyl.

In another embodiment, this disclosure provides a compound of formula XIII:

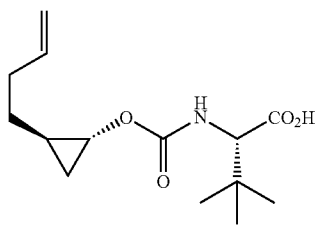

XIII or a co-crystal, or a salt thereof.

In another embodiment, this disclosure provides a compound of formula XIV:

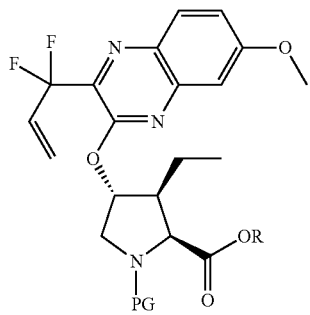

XIV or a co-crystal, or a salt thereof, wherein R is $C_{1-6}$ alkyl and PG is a protective group. In one embodiment, PG is selected from the group consisting of Boc, Cbz, and Fmoc. In another embodiment, PG is Boc. In another embodiment, R is methyl. In another embodiment, R is tert-butyl.

In another embodiment, this disclosure provides a compound of formula XV:

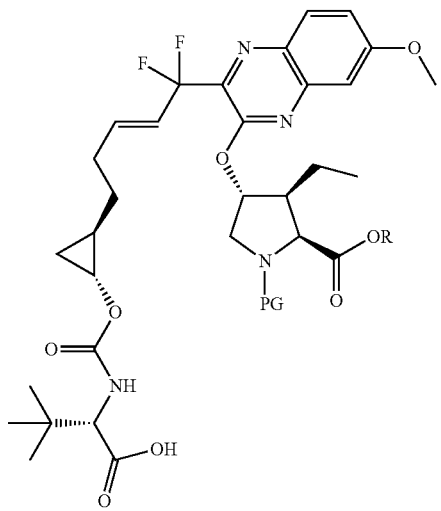

XV or a co-crystal, or a salt thereof, wherein R is $C_{1-6}$ alkyl and PG is a protective group. In one embodiment, PG is selected from the group consisting of Boc, Cbz, and Fmoc. In another embodiment, PG is Boc. In another embodiment, R is methyl. In another embodiment, R is tert-butyl.

In another embodiment, this disclosure provides a compound of formula XVI:

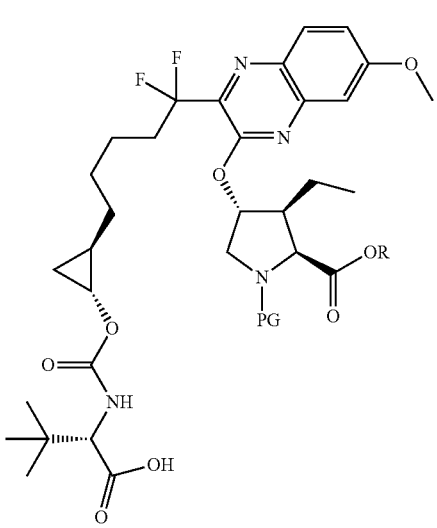

XVI or a co-crystal, or a salt thereof, wherein R is $C_{1-6}$ alkyl and PG is a protective group. In one embodiment, PG is selected from the group consisting of Boc, Cbz, and Fmoc. In another embodiment, PG is Boc. In another embodiment, R is methyl. In another embodiment, R is tert-butyl.

In another embodiment, this disclosure provides a compound of formula XVII:

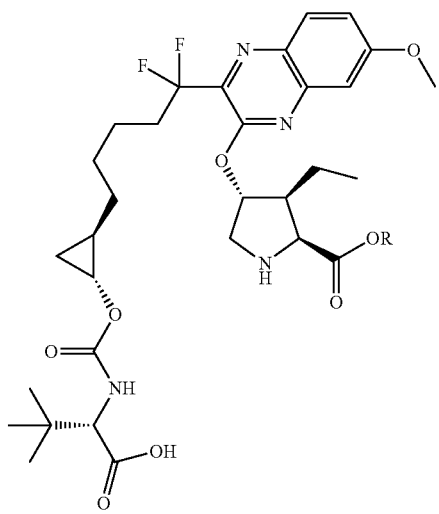

XVII or a co-crystal, or a salt thereof, wherein R is $C_{1-6}$ alkyl. In one embodiment, R is methyl. In another embodiment, R is tert-butyl.

In another embodiment, this disclosure provides a compound of formula XVIII:

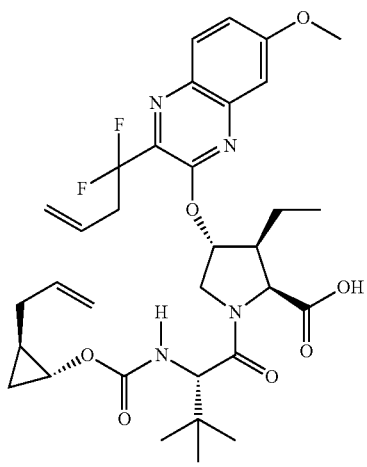

XVIII or a co-crystal, or a salt thereof.

In another embodiment, this disclosure provides a compound of formula XIX:

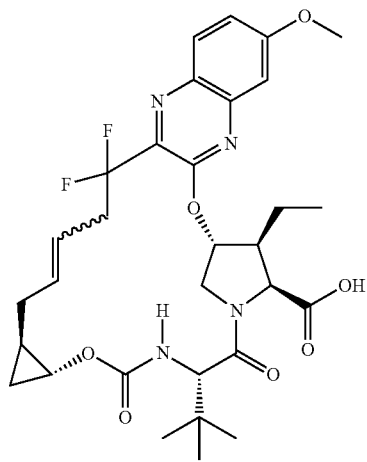

XIX or a co-crystal, or a salt thereof.

The intermediates in the process for the synthesis of formula I can be used in the next step with or without purification. The conventional means of purification include recrystallization, chromatography (e.g. adsorbent, ion exchange, and HPLC), and the like.

In some embodiments, the means of purification can include chiral resolution of one or more intermediates in the process for the synthesis of formula I and/or formula I. Non-limiting examples of such methods include, crystallization, a chiral resolving agent, and/or chiral chromatography. For example, in some embodiments, compounds of formula I can be further purified via crystallization with cinchonine alkaloids.

EXAMPLES

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of compounds described herein, may be accomplished as described in the following examples. If available, reagents may be purchased commercially, e.g. from Sigma Aldrich or other chemical suppliers. Unless otherwise noted, the starting materials for the following reactions may be obtained from commercial sources.

Example 1

Synthesis of (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide (I) by route I Compound of formula I was synthesized via route I as shown below:

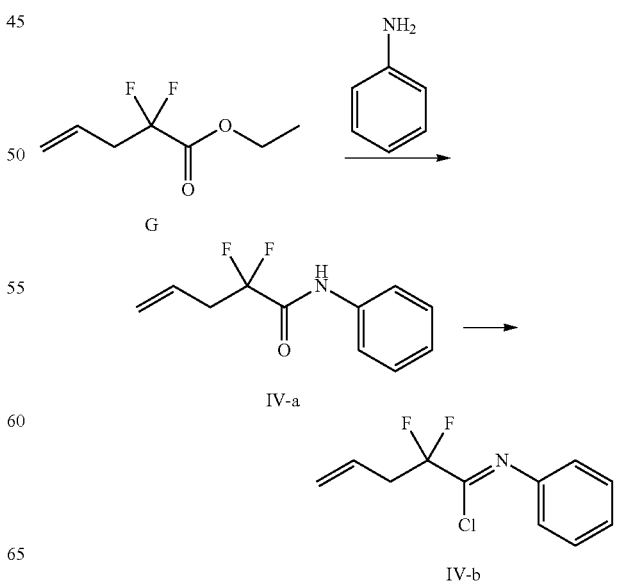

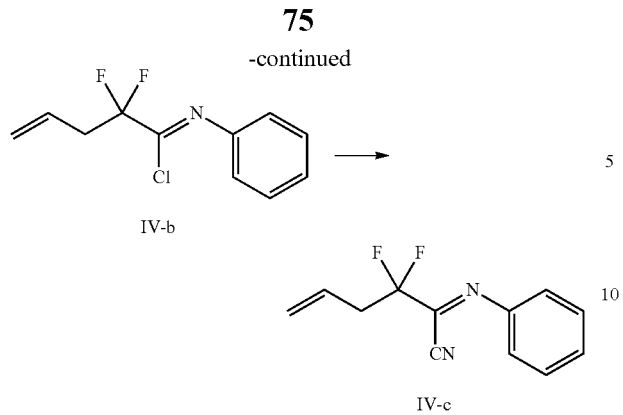

IV-b

IV-c

Synthesis of Intermediates for Compound of Formula I

A. Synthesis of Methyl(2S,3S,4R)-3-ethyl-4-hydroxypyrrolidine-2-carboxylate Tosylate Salt (II)

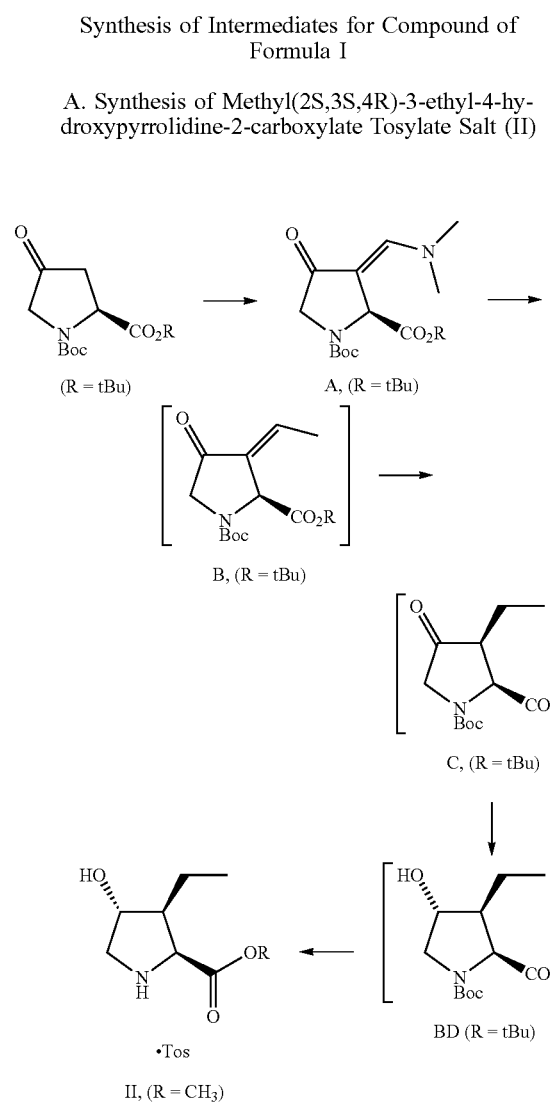

The order of reduction of the double bond and ketone was reversed so new intermediates were formed, B (R=tert-butyl) and C (R=tert-butyl). The tert-butyl ester was used to make D in U.S. Publication No. 2014-0017198; however, it was converted directly to the methyl ester tosylate salt without chromatography and crystallized to remove diastereomeric impurities. A single crystal X-Ray of the tosylate salt II was obtained.

Step 1: Synthesis of A

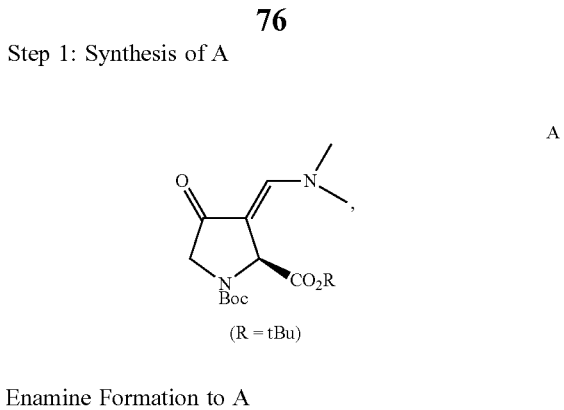

I. Enamine Formation to A

DMF-DMA (125.3 g, 2.0 eq.) and DCM (300 mL) were combined in a reaction vessel and heated to 45° C. In a separate container the commercially available di-tert-butyl (S)-4-oxopyrrolidine-1,2-dicarboxylate (150 g) was dissolved in DCM (300 mL) under $N_2$. This solution was charged over about 3 hours to the reaction vessel containing the DMF-DMA solution. Upon reaction completion, the solution was cooled to about room temperature. 5% LiCl (750 mL) was added to the reactor and the mixture was stirred. The layers were separated and the aqueous layer was removed. The organic layer was washed with water (750 mL) and dried with $Na_2SO_4$ and the mixture was filtered.

The filtrate was concentrated to ~200 mL and heptane (600 mL) was charged to obtain a murky solution. The mixture was further concentrated to remove residual DCM. Additional heptane (600 mL) was added and the mixture was heated to about 50 to 60° C. and aged for about 1 h to obtain a slurry. The slurry was cooled to about 15° C. over about 4 hours before aging at about 15° C. overnight (~18 h). Intermediate A (R=tert-butyl) was isolated via vacuum filtration and rinsed with 2× heptane. The resulting solid was dried at about 45° C. to obtain A (R=tert-butyl). $^1$H NMR (400 MHz, $CDCl_3$) (mixture of E/Z isomer): δ 7.4 (s, 1H), 5.2-5.3 (s, 1H), 3.8 (d, 2H) 3.2 (broad s, 6H), 1.5 (s, 9H), 1.4 (s, 9H). UPLC/MS M+1=341 amu.

Alternative reagents and reaction conditions to those disclosed above may also be employed. For example, alternative solvents may be used, such as other polar aprotic solvents (e.g. dimethylformamide, methyl t-butyl ether, and isopropyl acetate) or nonpolar solvents (e.g. toluene, cyclohexane, heptane) may be used. The reaction could also be performed without solvent or a mixture of the aforementioned solvents. Further, temperatures ranging from about 25 to about 50° C. may employed. Alternative crystallization solvent systems (e.g. DCM:heptane, Toluene:heptane, cyclohexane:heptane, and cyclohexane) may also be used.

Step 2: Synthesis of B (R=tert-butyl)

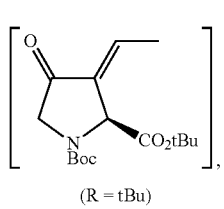

(R = tBu)

I. Methylation of A (R=tert-butyl) to B (R=tert-butyl):

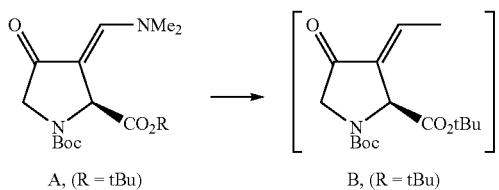

To a reaction vessel was added A (151 g, 0.44 mol, 1.0 equiv). The vessel was evacuated, purged with nitrogen, and the substrate was dissolved in MeTHF (450 mL, 3 vol). The reaction mixture was cooled to an internal temperature of about −12° C. and treated dropwise with methylmagnesium bromide (155 mL of a 3.0 M solution in diethyl ether, 0.55 mol, 1.25 equiv) over about 1 h. Upon reaction completion (about 2 h), a reverse quench was performed by adding the reaction to cold saturated aqueous ammonium chloride (400 mL). If an emulsion was observed, more aqueous ammonium chloride or 2 M HCl was added. The aqueous layer was extracted with toluene (1×200 mL). The organic layers were combined, washed with 1 M HCl (150 mL), then brine (150 mL), and concentrated in vacuo to provide B. $^1$H NMR (400 MHz, CDCl$_3$): δ 6.90-6.92 (1H, m), 5.08-5.16 (1H, m), 3.94-4.00 (2H, m), 2.02-2.04 (3H, m), 1.44-1.49 (18H, m).

Alternative reagents and reactions conditions to those disclosed above may also be employed. For example, other nucleophiles, such as methyl magnesium reagents, methyl lithium, methyl lithium-lithium chloride, methyl cuprates, and other methyl metal reagents may be employed. In addition, alternative solvents may also be used, such as other polar or nonpolar aprotic solvents.

Step 3: Synthesis of C (R=tert-butyl)

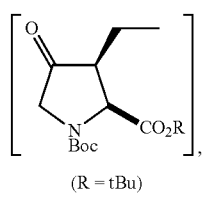

(R = tBu)

I. Hydrogenation of B (R=tert-butyl) to C (R=tert-butyl):

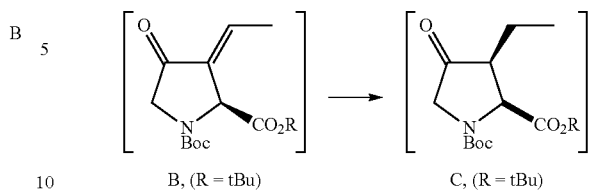

Enone B (R=tert-butyl) (32.0 g, 0.10 mol) was dissolved in toluene (3 vol) under an atmosphere of N$_2$. Pd/C was subsequently added (1.1 g, 0.5 mol %) and the reaction was flushed with N$_2$, followed by H$_2$, and stirred vigorously at room temperature under 1 atm of H$_2$. After completion of the reaction, diatomaceous earth (0.1 S, 13.2 g) was added and the mixture was stirred for 5 minutes. The heterogeneous mixture was filtered through diatomaceous earth and rinsed with additional toluene (0.5-1 vol) and concentrated to dryness to provide C. $^1$H NMR (400 MHz, CD$_3$OD): δ 4.68 (dd, J=36.9, 9.3 Hz, 1H), 3.99-3.75 (m, 2H), 2.63 (tdd, J=13.7, 9.2, 4.6 Hz, 1H), 1.89 (dt, J=13.8, 6.7 Hz, 1H), 1.46 (s, 9H), 1.43 (s, 9H), 1.30-1.16 (m, 1H), 1.07 (t, J=7.4 Hz, 3H).

Alternative reagents and reactions conditions to those disclosed above may also be employed. For example, other heterogeneous metal catalysts, such as platinum, palladium, ruthenium, nickel, and other metals on carbon, alumina, silica, and other heterogeneous supports, or metal nanoparticles may be used. In addition, Lewis pairs such as hydrogen [4-[bis(2,4,6-trimethylphenyl)phosphino]-2,3,5,6-tetrafluorophenyl]hydrobis(2,3,4,5,6-pentafluorophenyl)borate or homogeneous metal catalysts such as chlorotris(triphenylphosphine)rhodium(I) or (1,5-cyclooctadiene)(pyridine)(tricyclohexylphosphine)-iridium(I) hexafluorophosphate may also be employed. Other solvents (e.g., water, protic solvents such as methanol, ethanol, or acetic acid), aprotic solvents (e.g., dimethyl sulfoxide, tetrahydrofuran, ethyl acetate, acetonitrile, toluene, dichloromethane or acetone) or combinations of the above may be used. Further, temperatures can range from about −20° C. to about 150° C. In addition, alternative hydrogen gas at a range of pressures can be used or formates such as ammonium formate or formic acid can be employed. Alternatively, diimide reduction conditions may be employed.

Step 4: Synthesis of D (R=tert-butyl)

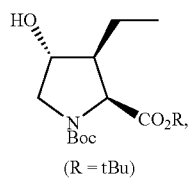

(R = tBu)

I. Reduction of C (R=tert-butyl) to provide D (R=tert-butyl)

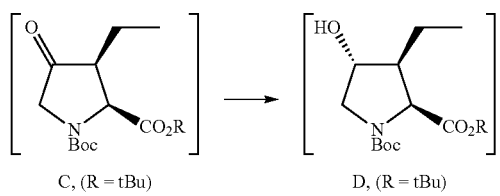

C, (R = tBu)    D, (R = tBu)

ZnCl$_2$ (27.3 g, 200 mmol, 2 equiv) and CPME (7 vol relative to C, 220 mL) were combined and the heterogeneous mixture was warmed to an internal temperature of about 95° C. and stirred for about 1.5 hours at that temperature. The resulting slurry was cooled to about 25° C. NaBH$_4$ (7.56 g, 200 mmol, 2 equiv) was added and the mixture was stirred overnight (~18 hrs).

The slurry was cooled to about 0° C., and the solution of C (R=tert-butyl) (~100 mmol) in toluene (3 total vol) was added slowly while maintaining the temperature to about below +3° C. After addition, the mixture was stirred at about 0° C. until complete consumption of the starting material. The reaction was quenched by reverse addition into a solution of citric acid (2.5 equiv, 48 g) in ice water (200 mL). The layers were separated and the organic layer was washed with brine (60 mL, 2 vol), dried over MgSO$_4$ (0.05 S, 1.5 g), and filtered. The crude organic solution was concentrated, diluted with 2 volumes of hexanes and filtered through silica gel, eluting with 1:1 acetone:hexanes. Concentration in vacuo provided compound of formula D (R=tert-butyl).

$^1$H NMR (400 MHz, CDCl$_3$): δ 4.30 (dd, J=26.4, 8.4 Hz, 1H), 4.24-4.14 (m, 1H), 3.89 (ddd, J=14.6, 10.6, 7.5 Hz, 1H), 3.15 (ddd, J=17.7, 10.6, 7.1 Hz, 1H), 2.20-2.05 (m, 2H), 1.70-1.59 (m, 1H), 1.48 (s, 9H), 1.44 (s, 9H), 1.35-1.23 (m, 1H), 1.07 (t, J=7.4 Hz, 3H).

Alternative reagents and reactions conditions to those disclosed above may also be employed. For example, other reducing regents may be employed, such as borohydrides (e.g., sodium, lithium, or calcium borohyride), boroacyloxyhydrides (e.g., sodium acetoxyborohyride, or lithium trifluoroacetoxyborohydride), borane, or complexes of borane, hydrogen, aluminum hydride reagents (e.g., lithium aluminum hydride or di-isobutylaluminum hydride), diborane, diazene, sodium cyanoborohydride, 9-BBN, tributyltin hydride, silanes (e.g., triethylsilane), aluminumisopropylates in combination with isopropanol. Further, alternative catalysts or promoters may be employed, such as Lewis or Bronsted acids, or combinations of the two; bases; heterogeneous metal catalysts (e.g., platinum, palladium, ruthenium, nickel, and other metals on carbon, alumina, silica, and other heterogeneous supports); metal nanoparticles; frustrated Lewis pairs (e.g., hydrogen [4-[bis(2,4,6-trimethylphenyl)phosphino]-2,3,5,6-tetrafluorophenyl]hydrobis(2,3,4,5,6-pentafluorophenyl)borate); homogeneous metal catalysts (e.g., such as chlorotris(triphenylphosphine)rhodium(I) or (1,5-Cyclooctadiene)(pyridine)(tricyclohexylphosphine)-iridium(I) hexafluorophosphate). In addition, other solvents such as water, protic solvents (e.g., methanol, ethanol, or acetic acid), aprotic solvents (e.g., dimethyl sulfoxide, tetrahydrofuran, ethyl acetate, acetonitrile, toluene, dichloromethane or acetone), combinations of the above may be employed.

Synthesis of Compound of Formula II (R=CH$_3$)

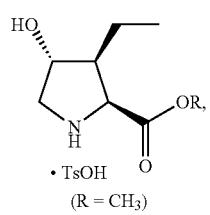

II (R = CH$_3$)

Deprotection and Transesterification of D (R=tert-butyl) to II (R=CH$_3$):

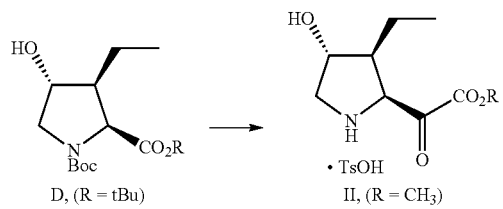

D, (R = tBu)    II, (R = CH$_3$)

D (R=tBu) (5.55 g, 17.6 mmol) and methanol (55.5 mL) were combined in a reaction vessel. p-Toluenesulfonic acid (10.7 g, 3.2 eq.) was charged to the solution and the mixture is stirred for about 1 hour at room temperature. The mixture was then heated to about 60° C. The reaction was stirred until reaction completion. The reaction mixture was concentrated to about 4 volumes and cooled to about 45° C. MTBE (4 volumes) were added slowly followed by II seed (0.05%). The mixture was then aged for about 30 minutes. Additional MTBE (5 volumes) were charged over about 90 minutes and the resulting mixture was stirred overnight.

The mixture was filtered and rinsed with 2 volumes of MTBE. The resulting wet cake was dried under vacuum at about 40° C. to obtain compound II (R=CH$_3$) as a tosylate salt. $^1$H NMR (400 MHz, MeOD) δ 7.7 (d, 2H), 7.2 (d, 2H), 4.7 (d, 1H), 4.3 (m, 1H), 3.8 (s, 3H), 3.6 (m, 1H), 3.2 (m, 1H), 2.4 (m, 1H), 2.3 (s, 3H), 1.3 (m, 2H), 1.0 (t, 3H). LC/MS M+1=174.1

Alternative reagents and reactions conditions to those disclosed above may also be employed. For example, methanol with co-solvents, MTBE, toluene or other non-alcoholic solvents may be used and temperatures ranging from about 0 to 60° C. may be employed. In addition, alternative crystallization solvent systems may include methanol: MTBE; ethanol:MTBE; or acetone:MTBE. Further, alternative salts (e.g., HCl, HBr, mesylate, brosylate, triflate, benzenesulfonate) may be employed.

B. Synthesis of 3-Chloro-2-(1,1-difluorobut-3-en-1-yl)-6-methoxyquinoxaline (IV)

Compound IV was synthesized via two different routes as discussed below.

Route I

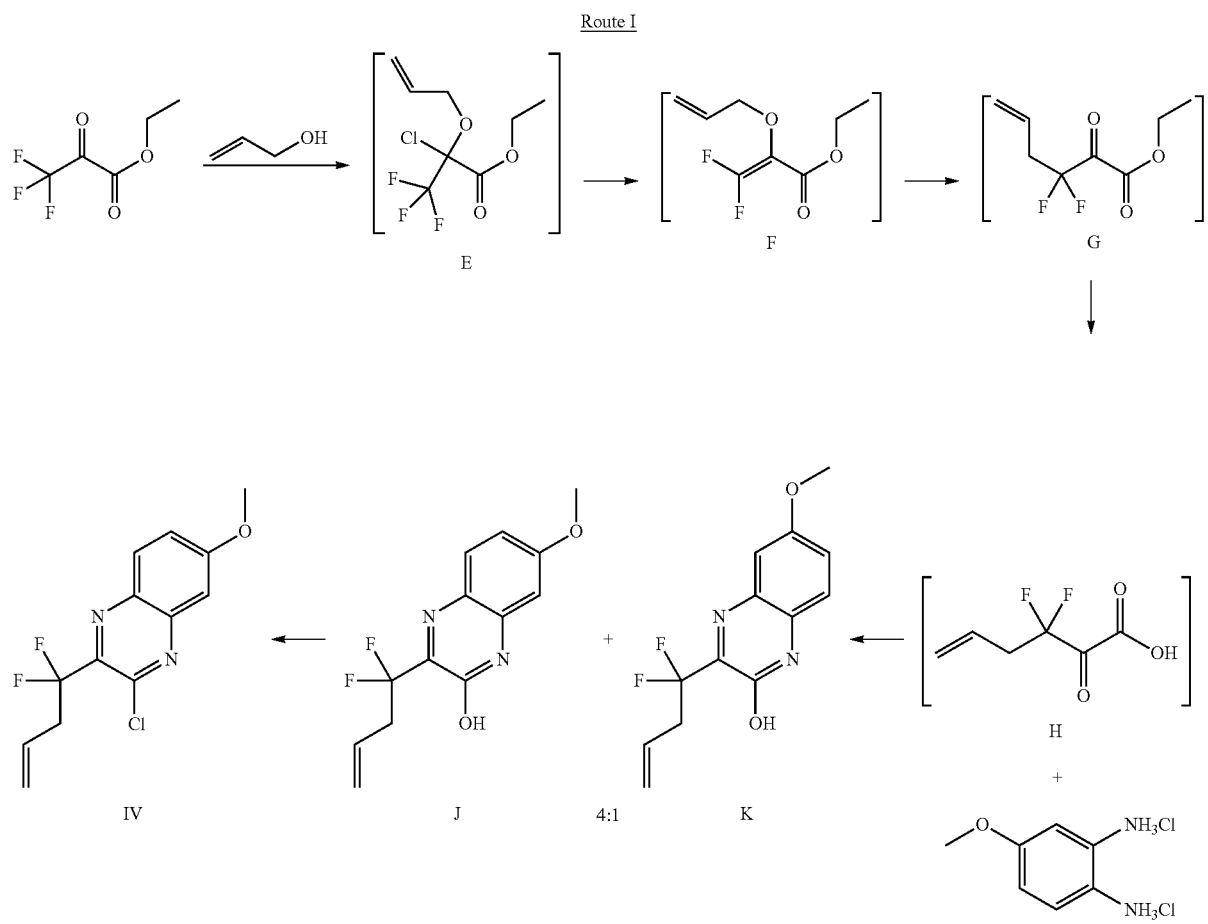

Compound IV contains one more methylene group than the analog used in U.S. Publication No. 2014-0017198 and so requires a different starting material. Ethyl trifluoropyruvate was converted to intermediate G in three steps. Intermediate G was telescoped through to a 4:1 regioisomeric mixture of J and K. In the U.S. Publication No. 2014-0017198, a nitro, amino-anisole was used for the ring formation in a two-step process of reacting the amine first and then reducing the nitro group to allow cyclization. Two regioisomers were formed. In this route, the starting material was instead the diamino analog and similar mixture was obtained. The mixture was chlorinated and the desired isomer IV was purified by conventional methods.

Step 1: Synthesis of G

I. Synthesis of Intermediate of Formula G from Ethyl Trifluoropyruvate:

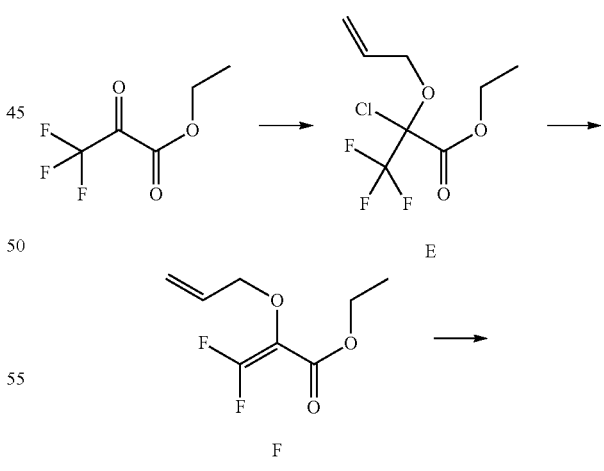

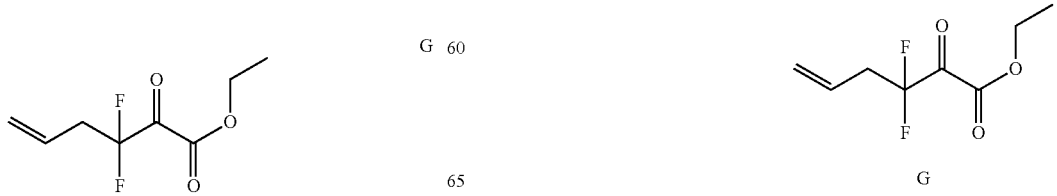

a. Allylation of Ethyl Trifluoropyruvate to Provide E:

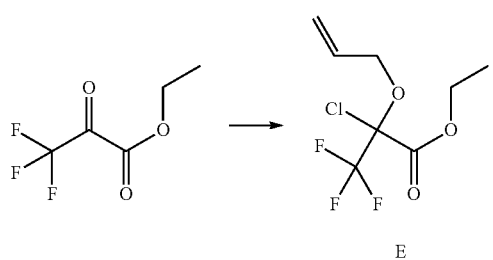

To a reaction vessel was charged ethyl trifluoropyruvate (86 g, 0.5056 mol, 1.0 equivalent) and dichloromethane (260 mL). Allyl alcohol (31 g, 0.5337 mol, 1.1 equivalent) was added dropwise over about 30 minutes while maintaining the reaction temperature less than about 27° C. The reaction was cooled to about 5° C. and pyridine (123 mL, 1.52 mol, 3.0 equivalents) was added over about 50 minutes, maintaining a reaction temperature below about 8° C., followed by charging thionyl chloride (90 g, 0.76 mol, 1.5 equivalents) over about 90 minutes while maintaining the reaction temperature below about 12° C. The reaction was stirred for about 30 minutes at 5 to 10° C., warmed to about 22° C. over about 30 minutes and held at about 22° C. until the reaction was deemed complete. The reaction mixture was poured into 860 mL of chilled (about 8° C.) water and the phases separated. The aqueous phase was back-extracted with 200 mL dichloromethane. The combined dichloromethane phases were washed successively with water (860 mL), 5 wt % NaHCO$_3$ solution (2×250 mL), and a final water wash (250 mL) and dried over Na$_2$SO$_4$. After the removal of the solvents, the crude product E was isolated and used directly for the next step. $^1$H NMR (300 MHz, CDCl$_3$): δ 5.92 (m, 1H), 5.38 (dq, J=14.1, 1.4 Hz, 1H), 5.27 (dq, J=10.3, 1.2 Hz, 1H), 4.40 (d, J=7.1 Hz, 2H), 4.34 (m, 2H), 1.30 (t, J=7.1 Hz, 3H).

II. Zn-Mediated Elimination of ClF from E to Provide F Followed by Claisen to Provide G:

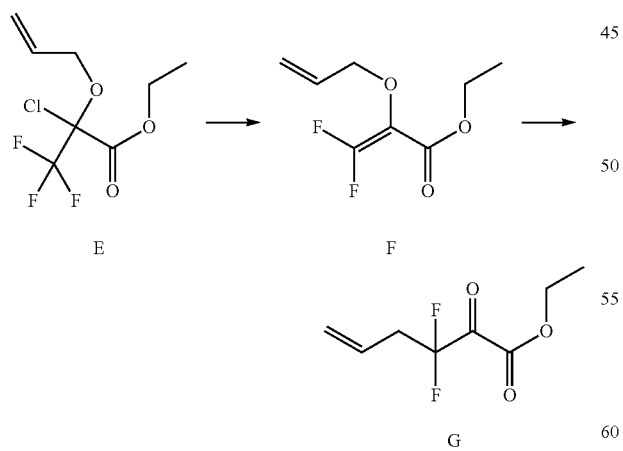

To a reaction vessel was charged zinc powder (324 g, 4.95 mol, 2.0 equivalents), CuI (6 g, 0.032 mmol, 0.013 equivalents) and N,N-dimethylformamide (DMF) (3.0 L). The mixture was stirred vigorously as Me$_3$SiCl (309 mL, 2.43 mmol, 1.0 equivalents) was charged dropwise via addition funnel over about 10 minutes, maintaining the reaction temperature at about <25° C. The reaction was stirred for about 30 minutes at about 25° C. The reaction was then cooled to 0 to 5° C. over 20 minutes and a solution of compound E (600 g, 2.43 mol, 1.0 equivalents) in DMF (3.0 L) was added slowly over about 60 minutes, maintaining the reaction temperature about <10° C. The reaction was stirred for about 30 minutes at 5 to 10° C., warmed to about 22° C. over about 30 minutes and then held at about 22° C. until the reaction was deemed complete by $^{19}$F NMR (typically 1-2 hours).

III. Claisen Rearrangement of F to Provide G

The above reaction mixture was filtered and washed with ethyl acetate (2×3 L). Water (1.5 L) was added to the organic phase and the layers were separated. The organic layer was washed two additional portions of water (2×1.5 L). The organic solution was concentrated to obtain crude F. This was dissolved in 3.0 L (5 volumes) of toluene and heated to about 80° C. until the reaction was deemed complete (typically 1-3 h). The reaction was cooled to about 22° C. and the solvent removed via rotary evaporation to obtain the crude product G (~70 wt %)). $^1$H NMR (300 MHz, CDCl$_3$): δ 5.90 (m, 1H), 5.28 (m, 2H), 4.40 (q, J=7.1 Hz, 2H), 2.83 (dt, J=18.5, 7.0 Hz, 2H), 1.32 (t, J=7.0 Hz, 3H); $^{19}$F NMR (CDCl$_3$) δ −112.8 (t).

Alternative reagents and reactions conditions to those disclosed above may also be employed. For example, other amine bases (e.g., 4-dimethylaminopyridine, imidazole, or triethylamine) may be used. In addition, alternate allylating agent (e.g., allyl chloride, allyl bromide), halogenating agent (e.g., thionyl bromide), olefinating agent (e.g., magnesium), or zinc activator (e.g., methanesulfonic acid, hydrochloric acid, di-isobutylaluminum hydride, diethylaluminum chloride) may be employed. Further, other solvents (e.g., dichloromethane, benzene, toluene, methyl-t-butyl ether, tetrahydrofuran, or 2-methyl tetrahydrofuran) can be used.

Step 2: Synthesis of H

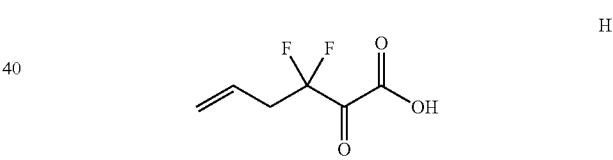

I. Synthesis of H from G

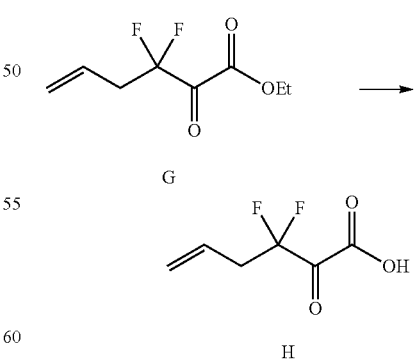

To a reaction flask was charged G (26.2 g, 136.6 mmol, 1.0 equivalent) and THF (236 mL, 9 vol.). Water (52 mL, 2 vol.) was charged followed by LiOH.H$_2$O (14.9 g, 354.5 mmol, 2.6 equiv.) maintaining a reaction temperature below about 33° C. The reaction was held at about 22° C. for about 3 hours followed by quenching with 250 mL of 1M HCl. The pH was then adjusted to 3 by addition of concentrated HCl (20 mL). The phases were separated and the aqueous phase was back-extracted with methyl-t-butyl ether (260 mL). The layers were split and NaCl (52 grams) was added to the aqueous phase which was extracted with MTBE (2×130 mL) followed by EtOAc (50 mL). All the organic phases were combined and dried over Na$_2$SO$_4$, filtered, concentrated and dried under vacuum to obtain H. $^1$H-NMR (400 MHz, DMSO-d$_6$) δ 13.2 (br s, 1H), 6.92 (br s, 2H), 5.83-5.70 (m, 1H), 5.20-5.13 (m, 2H), 2.83-2.65 (m, 2H). $^{19}$F-NMR (DMSO-d$_6$) δ −88.20 (t, J=20.8 Hz).

Alternative reagents and reactions conditions to those disclosed above may also be employed. For example, other bases may be used, such as potassium/sodium hydroxide, potassium-tert-butoxide, or sodium/potassium trimethylsiloxide. In addition, alternate catalysts (e.g. tetrabutylammonium chloride) may be employed. Further, other solvents may be used, such as methyl-t-butyl ether/water, 2-methyl tetrahydrofuran/water, tetrahydrofuran/water, methyl-t-butyl ether/water/heptane.

Step 3: Synthesis of J

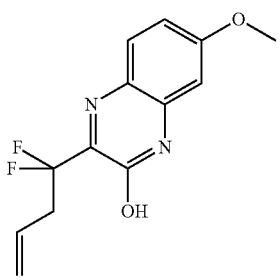

I. Condensation Followed by Cyclization to Provide J from H:

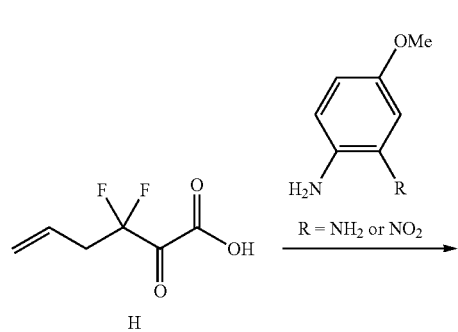

To a reaction vessel was charged diamine (6.06 g, 28.7 mmol, 1.0 equivalent) and ethanol (130 mL). Triethylamine (8.8 mL, 63.1 mol, 2.2 equivalents) was charged over about 5 minutes maintaining the reaction temperature about <25° C. The reaction was agitated for about 10 minutes to afford a solution. Acetic acid (16.4 mL, 287 mmol, 10 equiv.) followed by a solution of H (5.75 g, 31.6 mmol, 1.1 equiv.) in ethanol (40 mL) was charged and the reaction was held at about 22° C. until the reaction was complete. The reaction mixture was solvent exchanged into about 80 mL of dichloromethane and washed successively with 0.1 N HCl (60 mL), saturated NaHCO$_3$ solution (60 mL) and a final brine wash (60 mL). The organic layer was dried over Na$_2$SO$_4$ and filtered. After the removal of the solvents, crude mixture of J/K was obtained. This crude mixture was dissolved in dichloromethane, washed twice with 0.1N HCl, once with water and once with brine followed by drying over sodium sulfate, filtered and concentrated to obtain J/K). $^1$H NMR (300 MHz, CDCl$_3$): δ 7.82 (d, J=9.0 Hz, 1H), 7.38 (m, 1H), 6.97 (dd, J=9.0, 3.0 Hz, 1H), 6.82 (d, J=3.0 Hz, 1H), 5.88 (m, 1H), 5.22 (m, 2H), 3.91 (s, 3H), 3.28 (td, J=12.0, 3.0 Hz, 2H). $^{19}$F NMR (282.2 MHz, CDCl$_3$): δ −100.3 ppm (J) and −100.8 ppm (K). LCMS: m/z=266.93.

Alternative reagents and reactions conditions to those disclosed above may also be employed. For example, when R=NH$_2$, other bases (e.g., potassium/sodium hydroxide, potassium-tert-butoxide, sodium/potassium trimethylsiloxide) may be used. Other additives and alternative solvents (e.g., ethanol, ethanol/isopropyl acetate or toluene) may be employed.

In addition, alternative reagents and reactions conditions to those disclosed above may also be employed when R=NO$_2$. For example, iron, BHT, and AcOH may be used in combination with ethanol as solvent and temperatures ranging from about 60° C. to about 70° C.

Step 4: Synthesis of IV

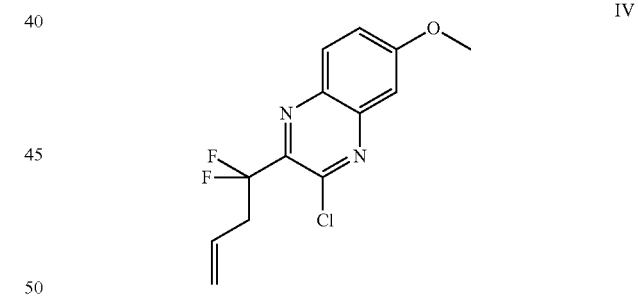

I. Chlorination of J to Provide Compound of Formula IV:

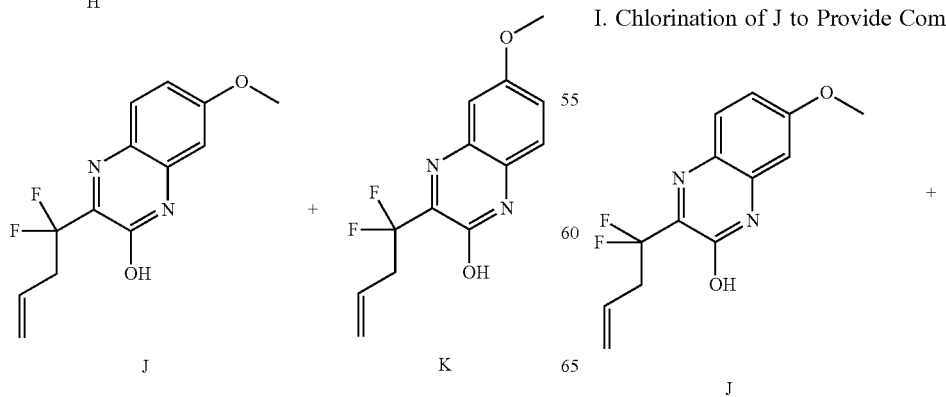

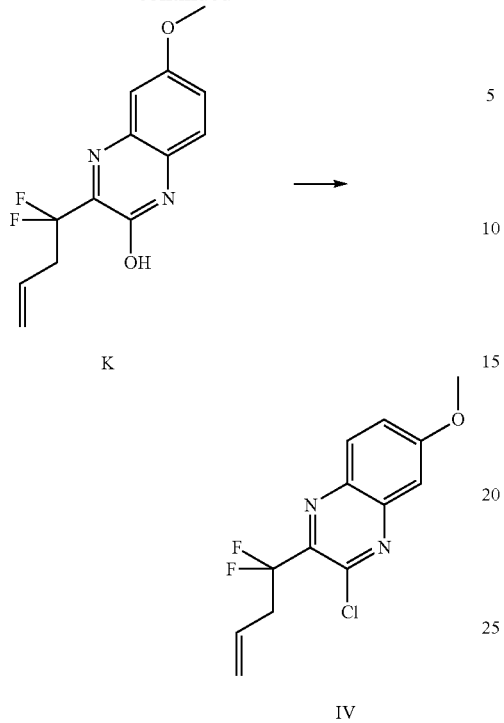

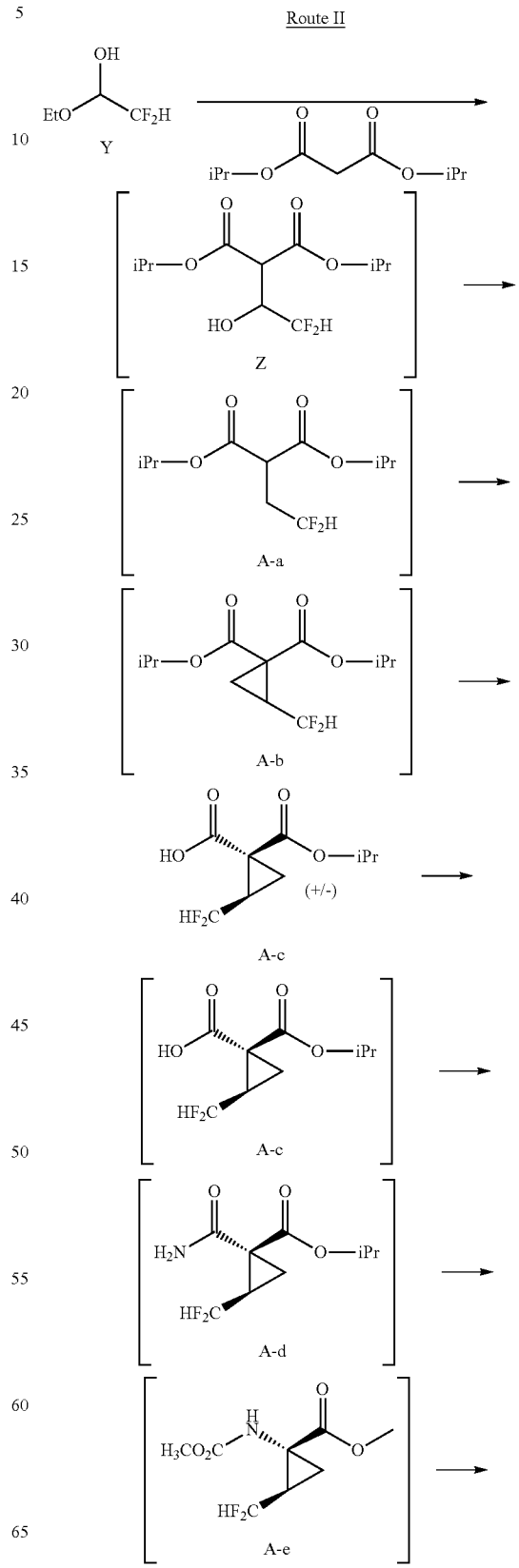

Route II

To a reaction vessel was charged J (7.4 g, 27.79 mmol, 1.0 equivalent) and DMF (148 mL). Phosphorus oxychloride (POCl₃) (4.2 mL, 44.47 m mol, 1.6 equivalent) was charged over about 3 minutes maintaining the reaction temperature was kept below about 30° C. The reaction was heated to about 75° C. until reaction completion. The reaction mixture was slowly poured into 150 mL of water while maintaining the temperature below about 25° C. Methyl-t-butyl ether (MTBE) (75 mL) was charged and the phases separated. The aqueous phase was back-extracted with 4×75 mL of MTBE. The combined MTBE phases were washed successively with saturated NaHCO₃ solution (200 mL) and saturated NaCl solution (150 mL) and dried over Na₂SO₄. After the removal of the solvents, the crude product IV was isolated. The crude material was suspended in hexanes (4.3 volumes), heated to dissolution and slowly cooled to about 20° C. resulting in slurry formation of the desired regioisomer IV which was then isolated by filtration and dried. $^1$H NMR (300 MHz, CDCl₃): δ 8.02 (d, J=9.0 Hz, 1H), 7.48 (dd, J=9.0, 3.0 Hz, 1H), 7.34 (d, J=3.0 Hz, 1H), 5.97 (m, 1H), 5.31 (m, 2H), 4.0 (s, 3H), 3.35 (td, J=12.0, 3.0 Hz, 2H). $^{19}$F NMR (282.2 MHz, CDCl₃): δ −96.3 ppm (IV) and −97.1 ppm (regioisomer). LCMS: m/z=285.27.

Alternative reagents and reactions conditions to those disclosed above may also be employed. For example, other chlorinating agents (e.g., trichloroisocyanuric acid, chlorine gas, 1,3-dichloro-5,5-dimethylhydantoin, N-chlorosuccinimide, thionyl chloride/DMF, oxalyl chloride/DMF) may be used. In addition, other solvents, such as acetonitrile or acetic acid, as well hydrocarbon solvents (e.g., toluene or heptane), ethers (e.g., methyl-t-butyl ether or THF), or chlorinated solvents (e.g., dichloromethane or chloroform) may be employed. Other amine additives (e.g., DABCO, triethylamine, or N-methylmorpholine) or phase transfer catalysts (e.g., benzyl trimethylammonium chloride) may also be employed. Further, temperatures ranging from about 20° C. to about 80° C. may be used.

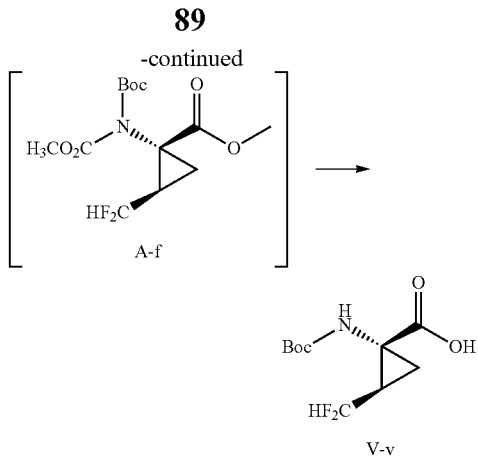

δ 5.82-5.96 (m, 1H), δ 5.35 (d, J=8.4 Hz, 1H), δ 5.30 (s, 1H), δ 3.07 (tdt, J=15.9, 7.2, 1.2 Hz, 2H); $^{13}$C NMR (75 Hz, CDCl$_3$): δ 144.8, 139.7 (t, J=36.7 Hz), 129.0, 127.7 (t, J=5.8 Hz), 126.4, 124.2 (t, J=282.8 Hz), 121.7, 120.2, 39.5 (t, J=24.0 Hz).

Alternative reagents and reactions conditions to those disclosed above may also be employed. For example, other bases (e.g. diisopropylethyl amine (DIPEA), pyridine, tributylamine, DBU, N-methylmorpholine (NMM)) may be used. In addition, alternate halogenating agent (e.g. N-chlorosuccinimide, chlorine(g), chloramine-T) may be employed. Further, other solvents (e.g. dichloromethane, chloroform, chlorobenzene) can be used.

II. Synthesis of IV-b from G

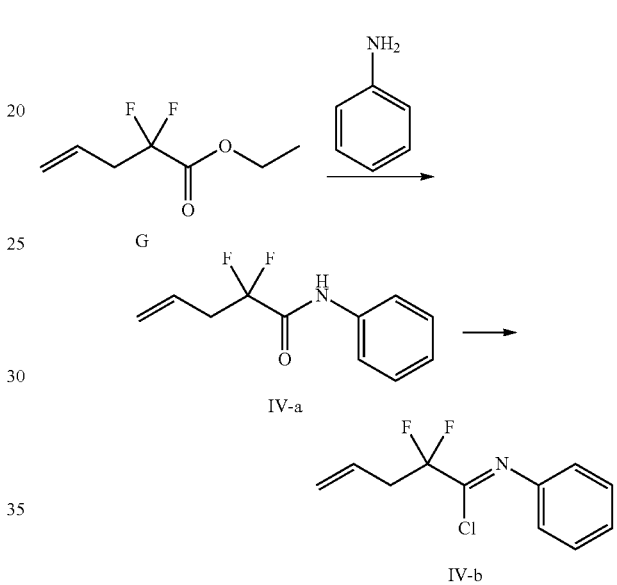

Compounds G and H were synthesized as discussed above in route I.

Step 1: Synthesis of IV-b
I. Synthesis of IV-b from H

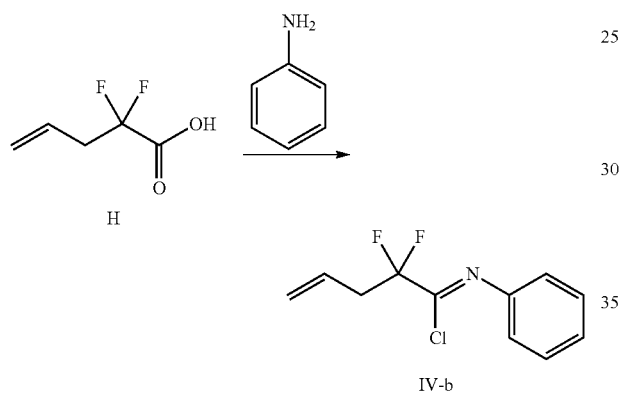

In a reaction vessel, triphenylphosphine (235.2 g, 896.3 mmol) was dissolved in tetrachloride (300 mL) at ambient temperature. The solution was cooled to below about 5° C. followed by addition of triethylamine (73 mL, 523.7 mmol) and H (41.8 g active, 295.4 mmol). Aniline (32 mL, 351.2 mmol) was then slowly added in about 30 minutes. The mixture was agitated at below about 5° C. for about one hour, and allowed to warm to ambient temperature. The solution was then heated to 50 to 55° C., at which point the reaction became exothermic. The reaction temperature quickly rose up to about 92° C. without heating, with rigorous refluxing and gas evolution. The temperature was cooled to about 75° C., and the mixture was agitated for about ten hours. To the reaction mixture was added heptane (700 mL) followed by concentration to remove about 700 mL of distillate. The second portion of heptane (700 mL) was added, and the mixture was heated to reflux at about 100° C. for about 30 minutes before cooling to about 20° C. The mixture was agitated at about 20° C. for about 30 minutes, and then filtered. The filtered cake was mixed with additional heptane (700 mL), heated to reflux for about 30 minutes, cooled to about 20° C., and agitated for about 30 minutes. The mixture was filtered, and the two filtrates were combined, and concentrated to provide crude IV-b The crude IV-b was used directly in the next step without further processing. $^1$H NMR (300 Hz, CDCl$_3$): δ 7.37-7.45 (m, 2H), δ 7.25 (tt, J=7.8, 0.9 Hz, 1H), δ 6.98 (dd, J=8.7, 1.2 Hz, 2H), a. Synthesis of IV-a from G

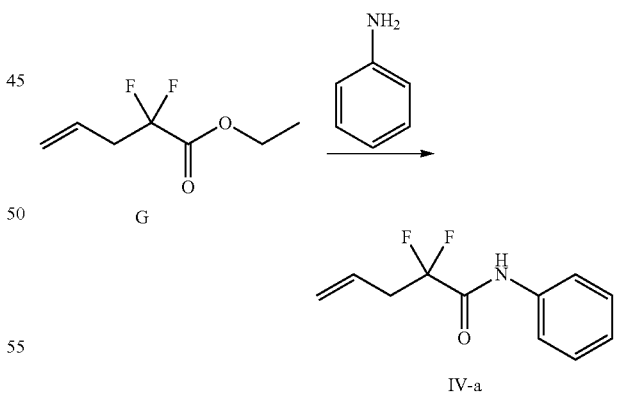

In a reaction vessel, G (10.0 g, 60.9 mmol) was dissolved in aniline (50 mL, 548.7 mmol) at ambient temperature. The solution was heated to reflux at about 150° C. for about 24 hours under nitrogen. The mixture was cooled to below about 5° C. followed by diluting with MTBE (100 mL). The pH was then adjusted to acidic by adding about 100 mL of 6N HCl aqueous solution at below about 5° C. The mixture was allowed warming up to ambient temperature, settled, and separated. The aqueous phase was extracted with MTBE (2×100 mL). The organic phases were combined, washed with 1N HCl aqueous solution and 5% NaHCO₃ aqueous solution in sequence. The organic phase was filtered through a pad of Na₂SO₄, and concentrated to provide crude IV-a. $^1$H NMR (300 Hz, CDCl₃): δ 7.95 (bs, 1H), δ 7.57 (d, J=7.5 Hz, 1H), δ 7.37 (tt, J=8.7, 2.4 Hz, 1H), δ 7.19 (tt, J=7.8, 1.2 Hz, 1H), δ 5.72-5.86 (m, 1H), δ 5.27-5.35 (m, 2H), δ 2.96 (tdt, J=17.1, 7.5, 1.2 Hz, 2H); $^{13}$C NMR (75 Hz, CDCl₃): δ 161.6 (t, J=28.7 Hz), 135.9, 129.2, 127.0 (t, J=5.7 Hz), 125.6, 122.2, 120.2, 117.1 (t, J=254.3 Hz), 38.4 (t, J=24.0 Hz); M.P.: 48.0° C.; GCMS m/z (rel. intensity): 211 (100, M⁺).

Alternative reagents and reactions conditions to those disclosed above may also be employed. For example, other solvents (toluene, xylenes, chlorobenzene, acetonitrile) can be used.

b. Synthesis of IV-b from IV-a

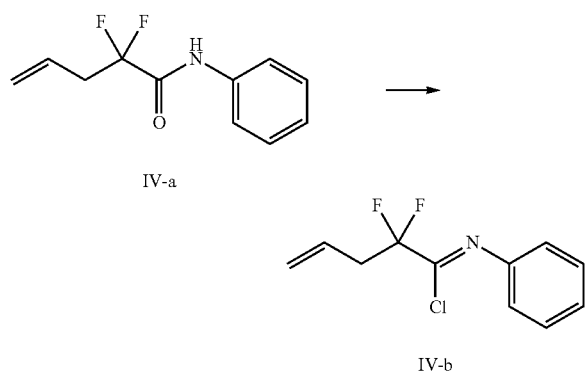

The IV-a (6.1 g, 28.0 mmol) was dissolved in DCM (60 mL) in a reaction vessel at ambient temperature. Phosphorus pentachloride (10.8 g, 51.9 mmol) was added in one portion. The mixture was agitated at ambient temperature for about 16 hours. The reaction mixture was quenched by slowly transferring the mixture into 40% K₃PO₄ aqueous solution while maintaining the temperature below about 20° C. The pH of the aqueous phase was adjusted to about 7.5 by adding additional 40% K₃PO₄ aqueous solution. The phases were separated, and the aqueous phase was extracted with DCM (60 mL). The combined organic phases were filtered through a pad of Na₂SO₄, and concentrated to provide crude IV-b. $^1$H NMR (300 Hz, CDCl₃): δ 7.37-7.45 (m, 2H), δ 7.25 (tt, J=7.8, 0.9 Hz, 1H), δ 6.98 (dd, J=8.7, 1.2 Hz, 2H), δ 5.82-5.96 (m, 1H), δ 5.35 (d, J=8.4 Hz, 1H), δ 5.30 (s, 1H), δ 3.07 (tdt, J=15.9, 7.2, 1.2 Hz, 2H); $^{13}$C NMR (75 Hz, CDCl₃): δ 144.8, 139.7 (t, J=36.7 Hz), 129.0, 127.7 (t, J=5.8 Hz), 126.4, 124.2 (t, J=282.8 Hz), 121.7, 120.2, 39.5 (t, J=24.0 Hz).

Alternative reagents and reactions conditions to those disclosed above may also be employed. For example, other bases (e.g. sodium hydroxide, potassium hydroxide, potassium phosphate dibasic, potassium carbonate, sodium carbonate) may be used. In addition, alternate halogenating agent (e.g. N-chlorosuccinimide, chlorine(g), chloramine-T, phosphorous oxychloride, thionyl chloride) may be employed. Further, other solvents (e.g. dichloromethane, chloroform, chlorobenzene, toluene, acetonitrile) can be used.

Step 2: Synthesis of IV-c from IV-b

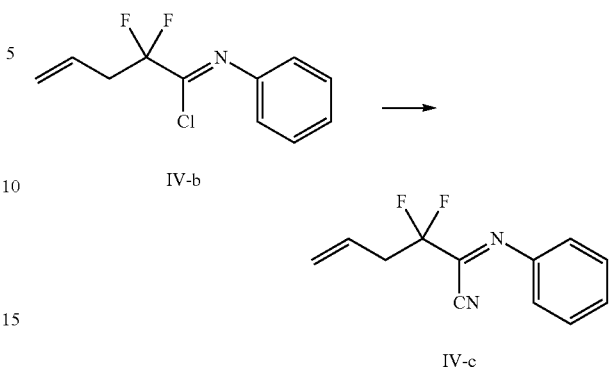

In a reaction vessel, IV-b (29.5 g active or 32 g crude, 128.2 mmol) was dissolved in acetonitrile (500 mL) followed by addition of potassium cyanide (8.5 g, 130.5 mmol). The mixture was vacuum degassed with nitrogen, and agitated at ambient temperature for about 16 hours. The mixture was concentrated under vacuum to remove acetonitrile completely, and then suspended in toluene (500 mL). The 5% NaHCO₃ aqueous solution (250 mL) was added to dissolve the inorganic salt. The mixture was settled, and separated. The aqueous phase was extracted with toluene (250 mL). The organic phases were combined, filtered through a pad of Na₂SO₄, and concentrated to provide crude IV-c. $^1$H NMR (300 Hz, CDCl₃): δ 7.49 (tt, J=7.2, 1.8 Hz, 2H), δ 7.41 (tt, J=7.2, 1.2 Hz, 1H), δ 7.26 (dt, J=7.2, 1.8 Hz, 2H), δ 5.79-5.92 (m, 1H), δ 5.37 (dd, J=5.1, 1.2 Hz, 1H), δ 5.32 (s, 1H), δ 3.07 (tdt, J=16.5, 7.2, 1.2 Hz, 2H); $^{13}$C NMR (75 Hz, CDCl₃): δ 146.0, 135.7 (t, J=35.5 Hz), 129.5, 127.0 (t, J=4.7), 122.4, 120.9, 120.2, 117.3 (t, J=245.0 Hz), 108.9, 38.8 (t, J=24.1 Hz); GCMS m/z (rel. intensity): 220 (70, M⁺).

Alternative reagents and reactions conditions to those disclosed above may also be employed. For example, other bases (e.g. sodium hydroxide, potassium hydroxide, potassium phosphate dibasic, potassium carbonate, sodium carbonate) may be used. In addition, alternate cyanation agent (e.g. trimethylsilylcyanide, sodium cyanide, potassium ferricyanide, lithium cyanide) may be employed. Further, other solvents (e.g. dichloromethane, chloroform, chlorobenzene, toluene) can be used.

Step 3: Synthesis of IV-d from IV-c

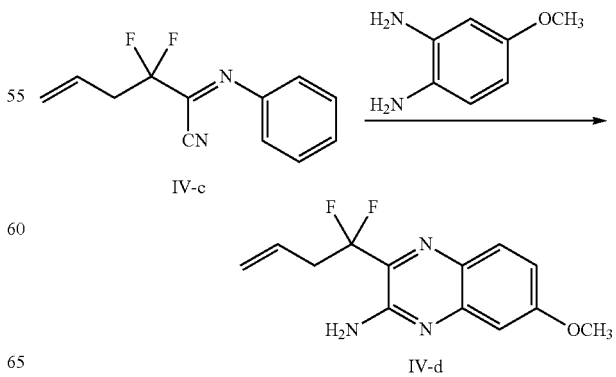

In a reaction vessel, methoxy-o-phenylenediamine was mixed with toluene (41 mL) at ambient temperature followed by addition of acetic acid (14.2 mL, 248 mmol). The black solution was vacuum degassed with nitrogen. At about 20° C., the prepared solution of IV-c (4.89 g active or 6.4 g crude, 22.2 mmol) in toluene (11 mL) was slowly added into above solution in about three hours while maintaining the temperature at about 20° C. The resulting mixture was then heated to about 30° C. for about 64 hours. The reaction mixture was cooled to below about 20° C., and EtOAc (40 mL) was added followed by pH adjustment to about 9-9.5 with about 76.5 mL of 3N NaOH aqueous solution. The mixture was filtered through diatomaceous earth (5 g) before settling and phase separation. The separated aqueous phase was extracted with EtOAc (80 mL). The two organic phases were combined, and activated charcoal (5 g) was added. The mixture was stirred at ambient temperature for about 16 hours, and filtered through diatomaceous earth (5 g). The filtrate was concentrated under vacuum to remove solvent completely, and IPA (20 mL) was added. The mixture was heated to dissolve the crude solid at about 40° C. The solution was heated to reflux for about 30 minutes, and then cooled to about 20° C. The IV-d seed (5 mg) was added to induce the crystallization. The suspension was agitated at about 20° C. for about one hour. Water (30 mL) was slowly added in about five hours while maintaining the temperature at about 20° C. The resulting suspension was agitated at about 20° C. for over about 10 hours before filtering and washing with 33% IPA/H$_2$O (15 mL). The cake was dried to provide IV-d. $^1$H NMR (300 Hz, CDCl$_3$): δ 7.77 (d, J=8.7 Hz, 1H), δ 7.09 (dd, J=9.6, 3.0 Hz, 1H), δ 6.98 (d, J=3.0 Hz, 1H), δ 5.93-6.07 (m, 1H), δ 5.25-5.37 (m, 4H), δ 3.92 (s, 3H), δ 3.32 (tdt, J=17.4, 6.9, 1.2 Hz, 2H); $^{13}$C NMR (75 Hz, CDCl$_3$): δ 162.3, 149.9, 144.1, 134.5 (t, J=30.9 Hz), 131.6, 130.4, 128.9 (t, J=4.6 Hz), 122.6 (t, J=238.2 Hz), 120.9, 118.2, 104.0, 55.7, 39.4 (t, J=24.1 Hz);

MP: 102.4° C.; LCMS m/z (rel. intensity) 265.70 (100, M$^+$).

Alternative reagents and reactions conditions to those disclosed above may also be employed. For example, other solvents (e.g. dichloromethane, chloroform, chlorobenzene, toluene, acetonitrile) can be used and temperatures ranging from 10 to 80° C. may be employed.

Step 4: Synthesis of IV from IV-d

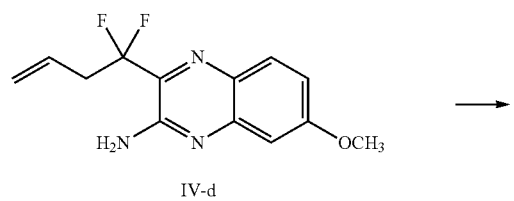

IV-d

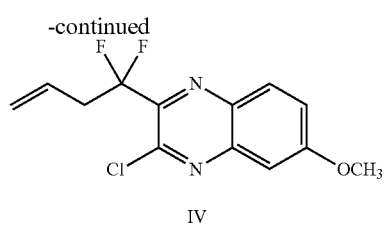

IV

In a reaction vessel, IV-d (5.0 g, 18.8 mmol) was dissolved in 100 mL DCM at ambient temperature. The solution was cooled to below about 5° C. followed by slow addition of 1M BCl3 in DCM (19 mL, 19 mmol) in about 15 minutes. Then t-BuNO$_2$ (9 mL) was slowly added in about two hours while maintaining the temperature at below about 5° C. The mixture was allowed warming up to ambient temperature, and agitated for about 12 hours. Upon reaction reaching completion, the mixture was concentrated under vacuum to remove solvent, and then dissolved in EtOAc (100 mL). The solution was cooled to below about 5° C. followed by slow addition of 5% NaHCO$_3$ aqueous solution. The resulting mixture was allowed warming up to ambient temperature, settled, and separated. The aqueous phase was extracted with EtOAc (2×100 mL). To the combined organic phase was added activated charcoal (2.0 g), and the mixture was agitated for about 16 hours before filtering through diatomaceous earth (5 g). The filtrate was concentrated under vacuum to remove solvent completely, and IPA (25 mL) was added. The mixture was heated to reflux for about 30 minutes, and then slowly cooled down. IV seed (5 mg) was added at 35-40° C. to induce the crystallization. The mixture was cooled to about 20° C., and agitated for about two hours. Water (10 mL) was slowly added in about two hours. The mixture was agitated for about one hour, and then cooled to below about 5° C. The mixture was agitated at below about 5° C. for about one hour, then filtered and washed with 50% IPA/H$_2$O (15 mL). The cake was dried to provide IV. $^1$H NMR (400 Hz, CDCl$_3$): δ 8.00 (d, J=9.2 Hz, 1H), δ 7.45 (dd, J=9.6, 2.8 Hz, 1H), δ 7.32 (d, J=2.8 Hz, 1H), δ 5.91-6.01 (m, 1H), δ 5.23-5.34 (m, 2H), δ 3.98 (s, 3H), δ 3.32 (tdt, J=16.8, 7.2, 1.2 Hz, 2H);

$^{13}$C NMR (400 Hz, CDCl$_3$): δ 162.8, 144.7, 143.9, 142.9 (t, J=29.7 Hz), 134.9, 130.4, 128.6 (t, J=4.6 Hz), 124.3, 122.4, 120.0 (t, J=241.8 Hz), 105.5, 56.0, 40.2 (t, J=24.5 Hz); MP: 82.8° C.; LCMS m/z (rel. intensity): 284.69 (100, M$^+$).

Alternative reagents and reactions conditions to those disclosed above may also be employed. For example, other bases (e.g. sodium hydroxide, potassium hydroxide, potassium phosphate dibasic, potassium carbonate, sodium carbonate) may be used. Further, other solvents (e.g. dichloromethane, chloroform, chlorobenzene, toluene, acetonitrile) can be used.

C. Synthesis of (S)-2-((((1R,2R)-2-allylcyclopropoxy)carbonyl)amino)-3,3-dimethylbutanoic acid (S)-1-Phenylethan-1-amine Salt (VII)

Compound VII was synthesized via two different routes as discussed below.

Route I

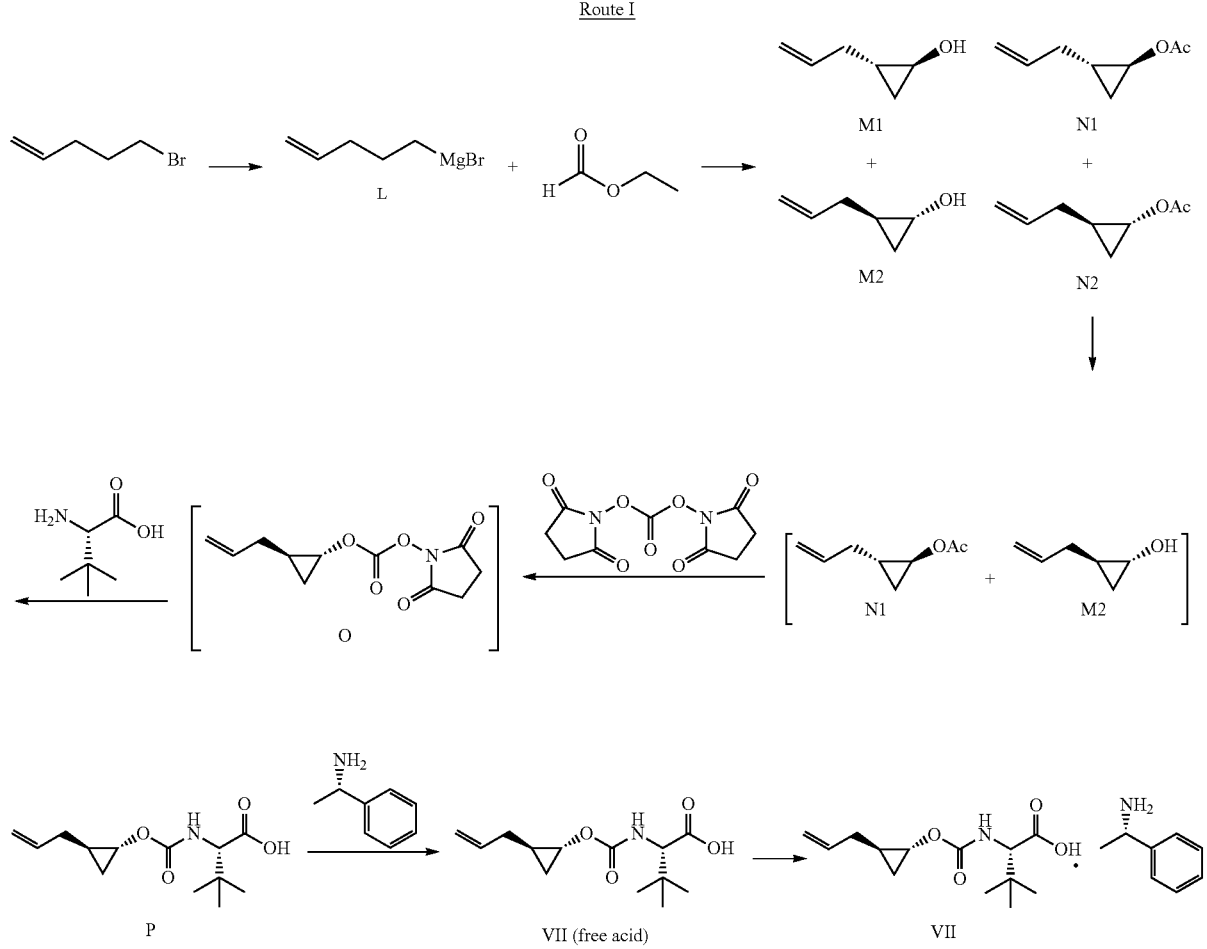

Compound of formula VII was obtained from 5-bromo-pent-1-ene via Kulinkovich cyclopropanation, acylation and enzymatic resolution. The cyclopropanol and then cyclopropyl acetate were distilled but it was not necessary to do so. Acid-base extractions were used to remove still acetylated material. The final product was isolated as a S-1-phenylethanamine salt which improved the diastereomeric and overall purity of the product. Recrystallization may be used to further improve the purity of the product. Other salts may be possible.

Kulinkovich reaction, acetylation and enzymatic resolution:

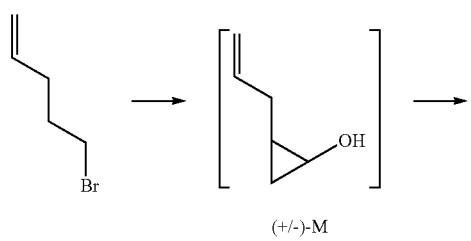

Step 1: Synthesis of
(1R,2R)-2-allylcyclopropan-1-ol (M1)

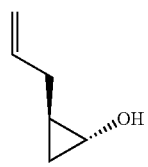

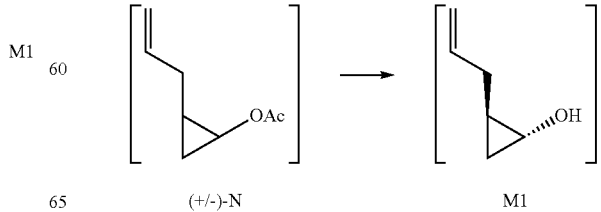

I. Kulinkovich Reaction with Ethyl Formate and 5-bromo-1-pentene

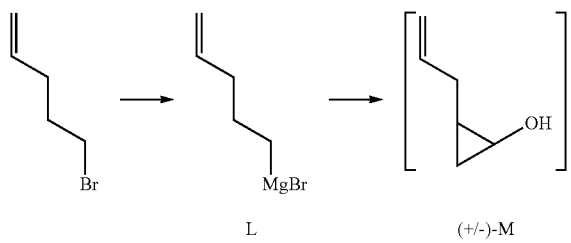

To a reaction vessel was added magnesium turnings (2.45 equivalents) and MeTHF (8 volumes). The flask was then sparged with nitrogen and 5-bromo-1-pentene (2.4 equivalents) was added to the addition funnel. The mixture was heated to about 60° C. and 0.05 volumes of 5-bromo-1-pentene were dripped into the mixture to initiate the reaction. Once the reaction initiated, the remaining portion of 5-bromo-1-pentene was slowly added into the flask over about 3 hours. After the addition, the reaction was allowed to stir at about 60° C. for about 1 hour after which Grignard L was cooled to room temperature. In a separate flask was added ethyl formate (1.0 equivalent) and titanium isopropoxide (0.5 equivalents) in MeTHF (2 volumes) under nitrogen. The mixture was cooled to about 0° C. and slowly the Grignard L was added into the flask over 3 hours. Upon complete addition, the reaction mixture was allowed to warm to room temperature and the reaction was stirred for about 12 hours. The mixture was then cooled to about 0° C. and 4M sulfuric acid (10 volumes) was added slowly. The slurry was stirred for 30 minutes after which the salts were dissolved. The mixture was then polished filtered. The biphasic mixture was separated and the organic layer was then washed twice with 10 wt. % sodium bicarbonate (10 volumes) and once with water (10 volumes). The organic layer is concentrated under reduced pressure at about 0° C. to obtain crude 2-allylcyclopentanol M. $^1$H NMR (400 MHz, CDCl$_3$): δ 5.53-5.43 (m, 1H), 4.76-4.70 (m, 1H), 4.65-4.59 (m, 1H), 2.90-2.86 (m, 1H), 1.75 (br s, 1H), 1.65-1.51 (m, 2H), 0.69-0.59 (m, 1H), 0.40-0.35 (m, 1H), 0.05-0.01 (m, 1H).

Alternative reagents and reactions conditions to those disclosed above may also be employed. For example, other aprotic solvents (e.g., tetrahydrofuran or diethyl ether) may be used. In addition, other titanium catalysts, such as Titanium(IV) alkoxides (e.g., MeTi(OiPr)$_3$, MeTi(OtBu)$_3$, ClTi(OiPr)$_3$, ClTi(OtBu)$_3$, or Ti(OtBu)$_4$) may be employed. Further, temperatures ranging from about −20° C. to about 100° C. may be used.

II. Acetylation of 2-allylcyclopentanol (+/−)-M:

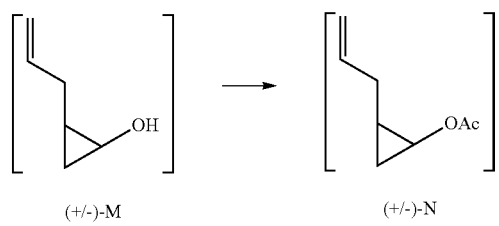

Into a reaction vessel was added 2-allylcyclopentanol M (1 equivalent) in MeTHF (10 volumes). The vessel was purged with nitrogen and the solution was then cooled to 0° C. Triethylamine (3.0 equivalents) was then slowly added to the solution over about 30 minutes. The mixture was allowed to stir for about 30 minutes after which acetyl chloride (2.5 equivalents) was added maintaining the internal temperature about below 20° C. The reaction was then allowed to stir for at least 12 hours at about 21° C. After the allotted time, water (6 volumes) was slowly charged to the reactor and the phases were separated. The organic layer was then washed with 2M hydrochloric acid (6 volumes), 10 wt. % sodium bicarbonate (6 volumes) and then brine (6 volumes). The organic layer is concentrated under reduced pressure at about 0° C. to obtain crude racemic 2-allylcyclopropyl acetate N. $^1$H NMR (400 MHz, CDCl$_3$): δ 5.85-5.73 (m, 1H), 5.10-5.04 (m, 1H), 5.00-4.97 (m, 1H), 3.85-3.82 (m, 1H), 2.13-2.07 (m, 1H), 1.99 (s, 3H), 2.01-1.89 (m, 1H), 1.14-1.03 (m, 1H), 0.87-0.76 (m, 1H), 0.64-0.57 (m, 1H).

Alternative reagents and reactions conditions to those disclosed above may also be employed. For example, other acetylating agents, such as acetic anhydride may be used. In addition, other acyl groups could be used for the enzymatic resolution, such as alkyl homologs (e.g., C1-C10) or aromatic groups (e.g., benzoate, substituted benzoates, or naphthoates). Further, other amine bases (e.g., N,N'-diisopropylethylamine, pyridine or piperidine), metal hydrides (e.g., sodium hydride and potassium hydride), alkoxides (e.g., sodium tert-butoxide, lithium tert-butoxide, or potassium tert-butoxide) can be used. Other halogenated solvents (e.g., dichloromethane or dichloroethane), and combinations of these with 2-methyltetrahydrofuran or tetrahydrofuran can also be employed. In addition, other temperature ranges between about −20° C. to about 80° C. can be employed.

III. Enzymatic Resolution of 2-allylcyclopentanol

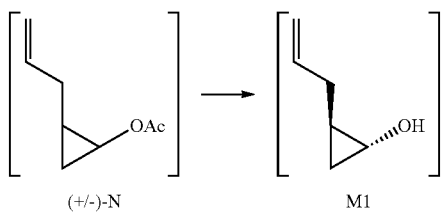

To a reaction vessel was charged 2-allylcyclopropyl acetate N in MeTHF (2 volumes) and MTBE phosphate buffer solution (10 volumes). The MTBE phosphate buffer solution was prepared by first dissolving potassium phosphate dibasic (283 g) and potassium phosphate monobasic (104.8 g) in water (1.6 L). MTBE (800 mL) was added to the solution and the biphasic mixture was stirred at about 21° C. for about 1 hour. The organic layer was then separated and used as the MTBE phosphate buffer solution. The reaction mixture was then cooled to about 0° C. and solid supported Novozyme 435 (1.7 wt. %) was charged. The reaction was allowed to stir at about 0° C. for about 6 hours after which the mixture was filtered. The filtrate was then concentrated under reduced pressure at about 0° C. to obtain the majority as (1R,2R)-2-allylcyclopropan-1-ol M1 and the racemic (1S,2S)-2-allylcyclopropan-1-ol in a 10:1 to 15:1 mixture as a mixture of the corresponding remaining acylated starting materials. The crude mixture was carried forward as is.

Alternative reagents and reactions conditions to those disclosed above may also be employed. For example, ethereal solvents (e.g., tetrahydrofuran (THF), methyl tetrahy- Step 2: Synthesis of VII

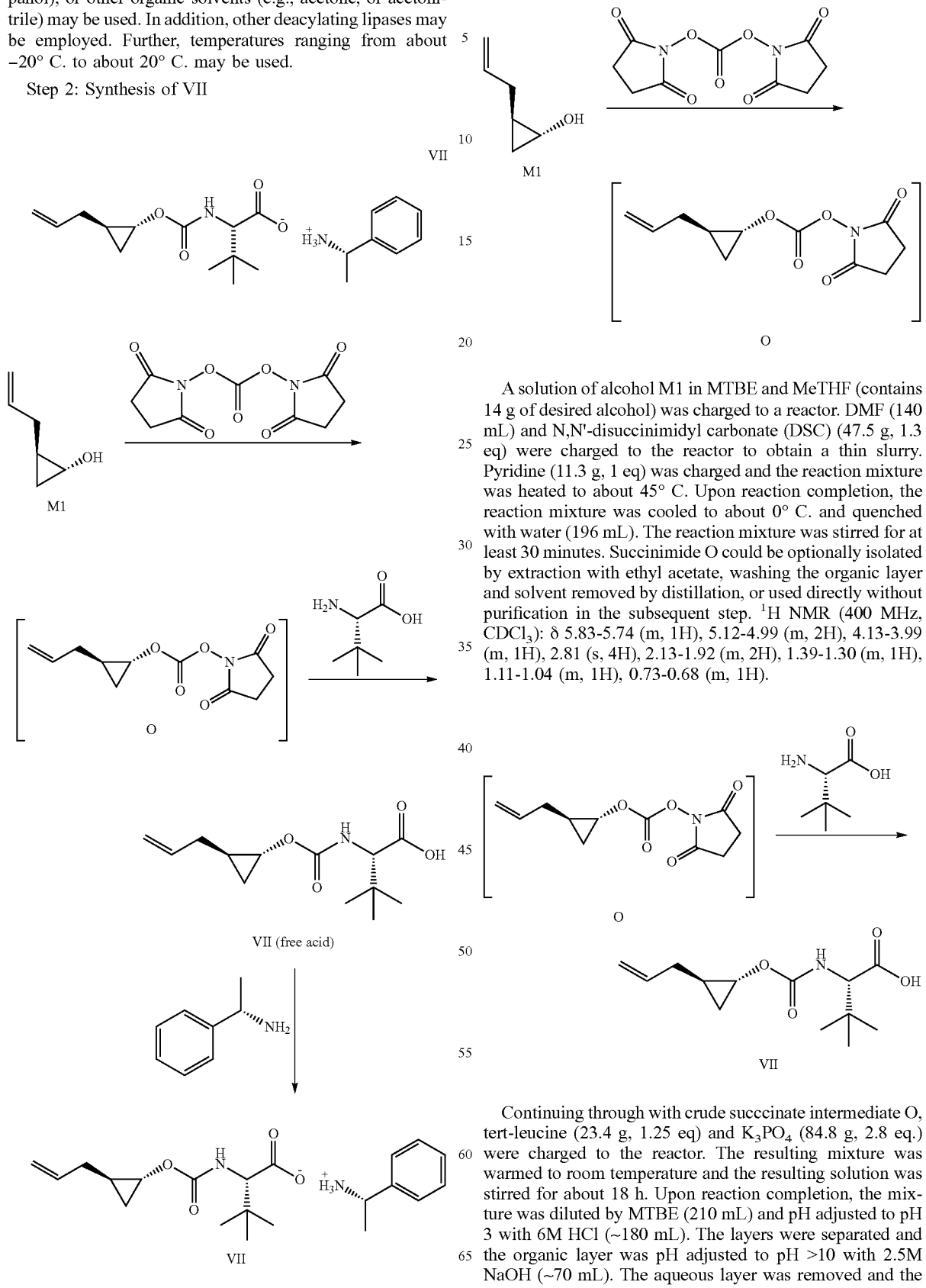

I. Coupling to VII

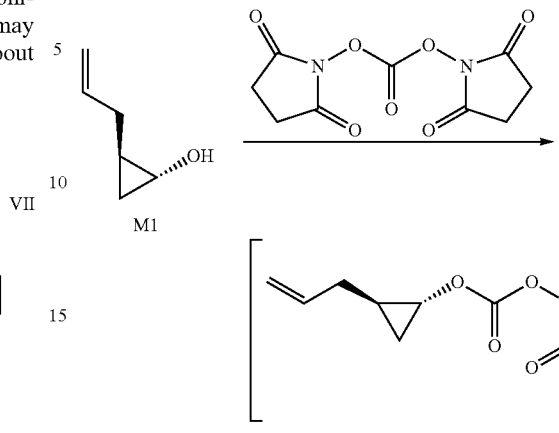

A solution of alcohol M1 in MTBE and MeTHF (contains 14 g of desired alcohol) was charged to a reactor. DMF (140 mL) and N,N'-disuccinimidyl carbonate (DSC) (47.5 g, 1.3 eq) were charged to the reactor to obtain a thin slurry. Pyridine (11.3 g, 1 eq) was charged and the reaction mixture was heated to about 45° C. Upon reaction completion, the reaction mixture was cooled to about 0° C. and quenched with water (196 mL). The reaction mixture was stirred for at least 30 minutes. Succinimide O could be optionally isolated by extraction with ethyl acetate, washing the organic layer and solvent removed by distillation, or used directly without purification in the subsequent step. $^1$H NMR (400 MHz, CDCl$_3$): δ 5.83-5.74 (m, 1H), 5.12-4.99 (m, 2H), 4.13-3.99 (m, 1H), 2.81 (s, 4H), 2.13-1.92 (m, 2H), 1.39-1.30 (m, 1H), 1.11-1.04 (m, 1H), 0.73-0.68 (m, 1H).

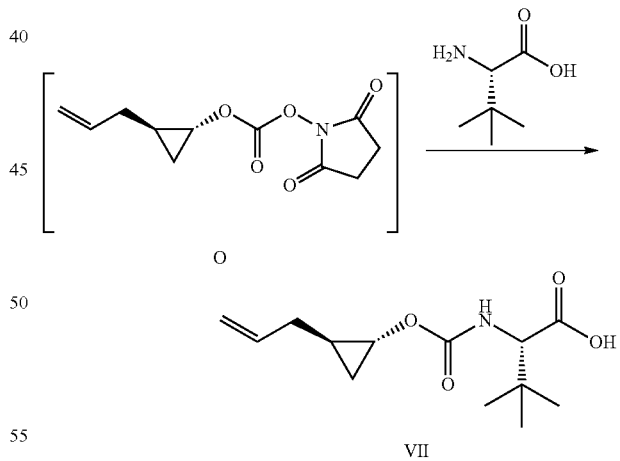

Continuing through with crude succcinate intermediate O, tert-leucine (23.4 g, 1.25 eq) and K$_3$PO$_4$ (84.8 g, 2.8 eq.) were charged to the reactor. The resulting mixture was warmed to room temperature and the resulting solution was stirred for about 18 h. Upon reaction completion, the mixture was diluted by MTBE (210 mL) and pH adjusted to pH 3 with 6M HCl (~180 mL). The layers were separated and the organic layer was pH adjusted to pH >10 with 2.5M NaOH (~70 mL). The aqueous layer was removed and the organic layer was washed with 0.5 M NaOH (100 mL). The combined basic aqueous layers was readjusted to pH <3 with 6M HCl (~50 mL) and washed twice with MTBE (100 mL×2).

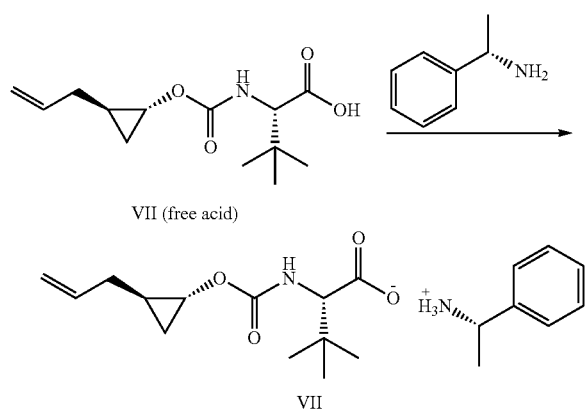

The combined organic layers were solvent swapped to MTBE (107 mL). In a separate container, S(−) 1-phenylethylamine (10.9 g, 1 eq.) was dissolved in MTBE (32.7 mL). The solution of the amine was charged slowly to the solution containing the succinimide intermediate. A small amount of VII (S)-1-phenylethan-1-amine salt (0.055 g, 0.5%) was charged followed by the rest of the amine solution. The slurry was aged overnight to obtain a thick slurry. The resulting slurry was filtered and rinsed with MTBE (50 mL). The solids were dried in the vacuum oven until constant weight was reached to obtain VII as the (S)-1-phenylethan-1-amine salt. NMRs of the free acid: $^1$H NMR (400 MHz, CDCl$_3$) δ 7.4 (m, 5H), 6.3 (broad s, 3H), 5.8 (m, 1H), 5.3 (d, 1H), 5.1 (d, 1H), 4.2 (q, 1H), 3.8 (d, 1H), 3.7 (m, 1H), 2.1 (m, 1H), 1.9 (m, 1H), 1.5 (d, 3H), 1.1 (m, 1H), 0.9 (d, 9H), 0.8 (m, 1H), 0.5 (q, 1H). $^{13}$C-NMR (CDCl$_3$) δ 173.1, 157.0, 115.7, 63.3, 53.9, 36.2, 34.9, 33.7, 27.1, 17.3, 11.7.

Alternative reagents and reactions conditions to those disclosed above may also be employed. For example, polar aprotic solvents (e.g., dimethylacetamide) and temperatures ranging from about 25° C. to about 65° C. may be employed. In addition, alternative crystallization solvent systems (e.g., acetonitrile) can be used.

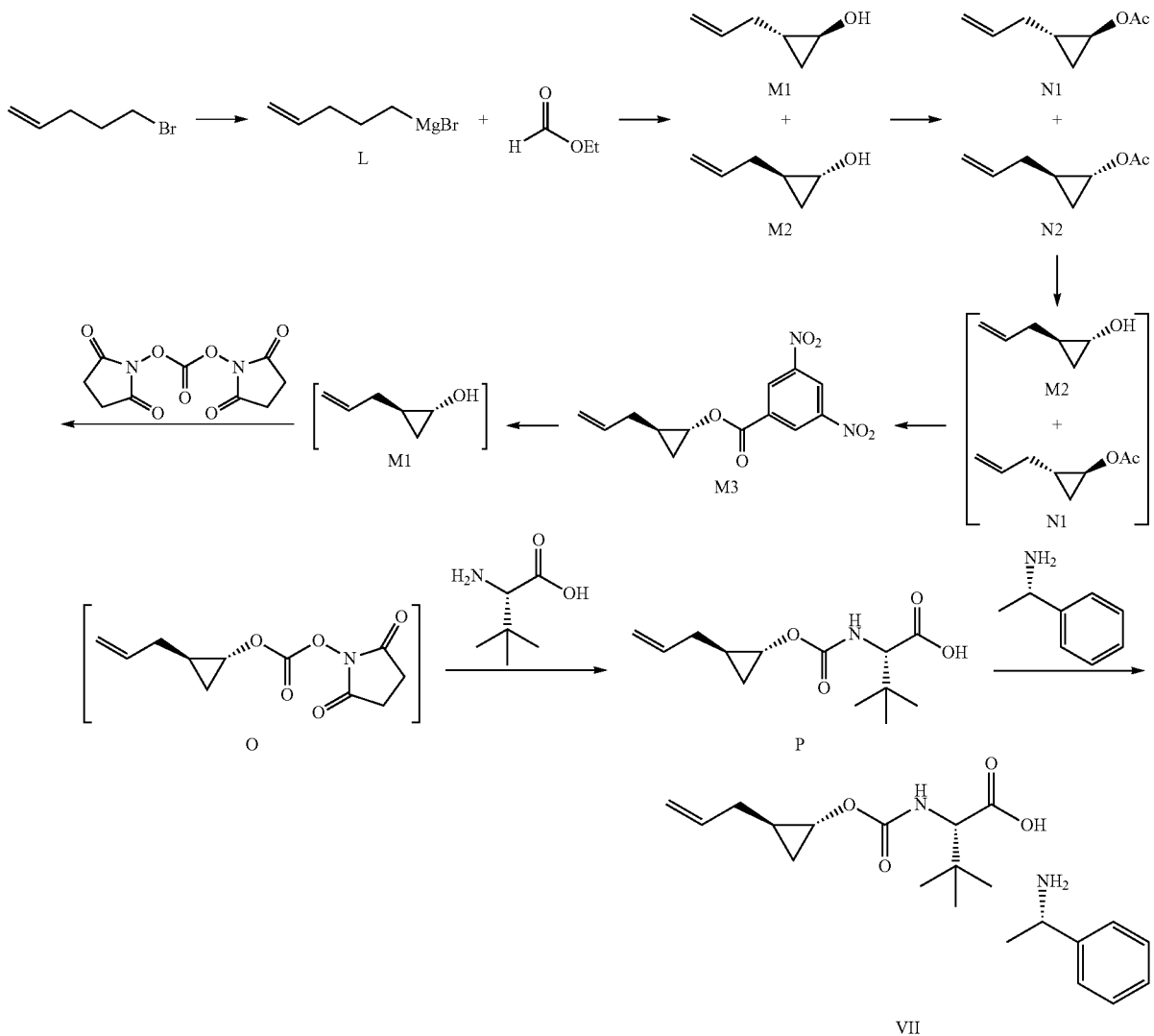

Route II

The route II shown above differs from route I in the formation of intermediate M3 and its conversion to M1. The synthesis of M3 and its conversion to VII are discussed below.

Synthesis of M3 from M2

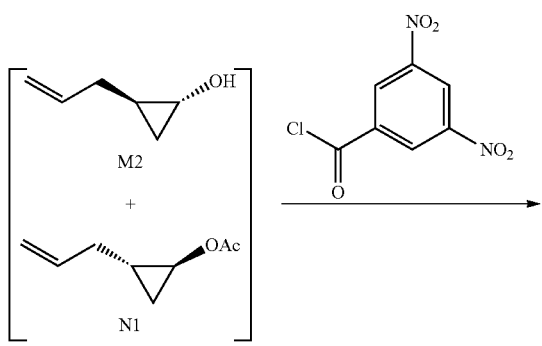

To a reaction vessel was charged alcohol M2 (100.0 g, 1019.0 mmol, alcohol M2 comes as a solution in MTBE along with an acetate impurity N1 from the previous enzymatic resolution step. The actual amount of solution that was charged was calculated after determining the wt % of the enzymatic resolution solution and then adjusting the charge to ensure that 100.0 g of alcohol was present within that charge.). To this was charged dichloromethane (300 mL) and triethylamine (134.0 g, 1324.6 mmol). The reaction was cooled to an internal temperature of about 0° C. In a separate flask, 3,5-dinitrobenzoyl chloride (305.4 g, 1324.6 mmol) was dissolved in dichloromethane (300 mL). The dinitrobenzoyl chloride stream was then charged to the alcohol stream over approximately 15 minutes maintaining an internal temperature below about 5° C. The combined mixture was aged for approximately 4 h. The reaction mixture was allowed to warm to room temperature and then water (600 mL) was added and the phases were vigorously agitated to ensure good mixing of the phases. The phases were allowed to settle and the bottom phase was separated and washed an additional two times with water (600 mL). To the final organic phase was charged silica gel (200 g), and the slurry was allowed to age at room temperature for approximately 30 minutes. The slurry was filtered and the silica gel cake was washed with 20 vol % isopropyl alcohol in heptane (amount of wash solution is determined by eluting with 4× the volume of the silica pad.) The combined filtrate and washes were concentrated by rotary evaporation to an approximate volume of 200 mL. Isopropyl alcohol (600 mL) was charged to the concentrated stream and distilled back down by rotary evaporation to an approximate volume of 200 mL. This process was repeated until less than 5% dichloromethane in comparison to isopropyl alcohol was observed by $^1$H NMR. Heptane was then charged to the reaction mixture to reach a final volume of approximately 500 mL. The mixture was then heated to an internal temperature of about 45° C. The crystallization was then seeded with 0.5 wt % (500 mg) of ester M3 seeds. The reaction was then cooled to about 0° C. over about 5 h and aged at that temperature for at least about 12 h. The resulting slurry was filtered and the cake was washed with hepatane (100 mL). The isolated solids were then dried under vacuum at about 21° C. to afford M3. $^1$H NMR (400 MHz, CDCl$_3$): δ 9.22-9.21 (m, 1H), 9.11-9.10 (m, 2H), 5.95-5.85 (m, 1H), 5.17-5.05 (m, 2H), 4.27-4.24 (m, 1H), 2.22-2.07 (m, 2H), 1.41-1.33 (m, 1H), 1.14-1.09 (m, 1H), 0.85-0.80 (m, 1H); HRMS calc'd C$_{13}$H$_{13}$N$_2$O$_6$ [M+H]$^+$: 293.0774 found: 293.0777.

Alternative reagents and reactions conditions to those disclosed above may also be employed. For example, other bases (e.g., di-isopropyl ethyl amine, N-methyl morpholine) and other solvents (e.g. chloroform, tetrahydrofuran, MTBE, 2-methyl tetrahydrofuran, cyclopentyl methyl ether) can be used.

Hydrolysis of M3 to M1

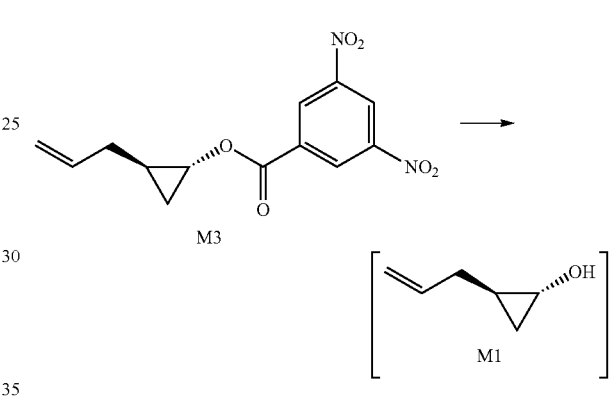

To a reaction vessel was charged M3 (100.0 g, 342.2 mmol) and this was dissolved in tetrahydrofuran (300 mL). To this was charged sodium hydroxide (300 mL of a 1.0 M aqueous solution) and the resulting mixture was stirred at room temperature for about 1 h. Toluene (200 mL) was charged to the reaction followed by HCl (120 mL of a 1.0 M aqueous solution.) The phases of the resulting biphasic mixture were split and the organic phase was washed with sodium bicarbonate (120 mL of a 5 wt % aqueous solution.) The phases were split again and the organic layer was washed twice with water (200 mL). The final organic phase was washed with brine (200 mL of 10 wt % aqueous solution), dried over MgSO$_4$, and then filtered. The final solution of alcohol M1 was used in the subsequent step without further purification.

Alternative reagents and reactions conditions to those disclosed above may also be employed. For example, other bases (e.g., potassium hydroxide, tetrabutyl ammonium hydroxide) and other solvents (e.g. 2-Methyl tetrahydrofuran, MTBE, toluene) can be used.

Synthesis of O from M1

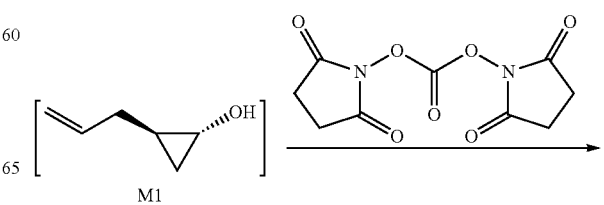

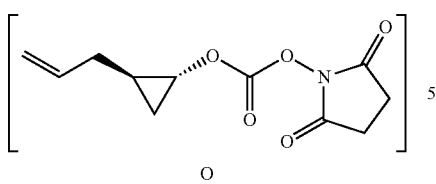

To a reaction vessel was charged the toluene solution of alcohol M1 (the amount of solution charged was determined by obtaining a wt % by $^1$H NMR of the alcohol in solution and then charging the amount necessary to have 28.0 g, 285.3 mmol of alcohol M1 in the reaction.) To this was charged pyridine (29.3 g, 370.9 mmol) followed by N,N'-Disuccinimidyl carbonate (116.9 g, 456.5 mmol). The resulting heterogeneous reaction mixture was heated to 45° C. and stirred at this temperature for 4 h. The reaction was then cooled to room temperature and water (170 mL) was charged. The mixture was agitated at room temperature for 30 min and then the phases were split. The final toluene solution is used without further purification in the subsequent step. In this fashion, O (52.9 g determined by $^1$H NMR wt % assay, 221.3 mmol, 77.6%) was synthesized.

Alternative reagents and reactions conditions to those disclosed above may also be employed. For example, other bases (e.g., di-isopropyl amine, triethylamine, di-isopropyl ethyl amine) and other solvents (e.g. xylenes, chlorobenzene, MTBE) can be used. Also, temperatures ranging from about 0° C. to about 110° C. may be employed.

Synthesis of VII from O

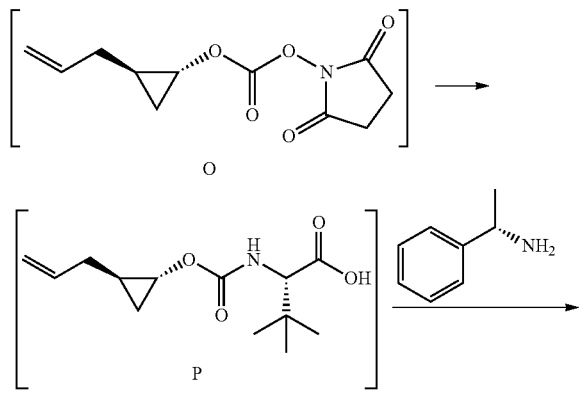

To a reaction vessel was charged a toluene solution of carbonate O (the amount of solution charged was determined by obtaining a wt % by $^1$H NMR of the carbonate in solution and then charging the amount necessary to have 9.9 g, 41.4 mmol of carbonate O in the reaction.). Additional toluene was charged to the reaction to bring the final reaction volume up to 60 mL. To this solution was charged di-isopropyl ethyl amine (10.7 g, 82.8 mmol) and L-tert-leucine (6.0 g, 45.52 mmol). The reaction mixture was heated to about 45° C. and agitated at this temperature for about 6 h. The reaction was then cooled to room temperature and hydrochloric acid (60 mL of a 3N aqueous solution) was charged. The biphasic mixture was agitated for about 30 min at room temperature and then the phases were split. The organic rich stream was then concentrated to approximately 20 mL by rotary evaporation and then 80 mL of acetonitrile was added. Concentration down to 20 mL and then recharging of acetonitrile was continued until the amount of toluene is about <5% v/v. The final stream is adjusted to a volume of 80 mL using acetonitrile and heated to about 50° C. The mixture is then heated to about 50° C. and (S)-phenethylamine (6.0 g, 49.7 mmol as a solution in 30 mL of acetonitrile at 50° C.) was charged. The reaction mixture was seeded with 0.5 wt % seeds of VII (0.05 g) and the thin slurry was aged for 1 h at 50° C. The mixture was then cooled down to room temperature over about 3 h and the resulting slurry was aged for at least about 12 h. The solids were collected by filtration and the cake was washed with about 20 mL of acetonitrile. The final wet cake was dried in the oven at about 40° C. under vacuum to afford VII.

Alternative reagents and reactions conditions to those disclosed above may also be employed. For example, other bases (e.g., potassium carbonate, sodium carbonate, potassium phosphate tribasic) and other solvents (e.g. dimethylformamide, dimethylacetamide) can be used. Also, other salt form in h amines (e.g. (R)-phenethylamine, D-phenylalaninol, (1S,2S)-(+)-2-amino-1-(4-nitrophenyl)-1,3-propanediol, (S)-(+)-2-phenylglycinol) may be employed.

D. Synthesis of (1R,2R)-1-Amino-2-(difluoromethyl)-N-((1-methylcyclopropyl)sulfonyl)cyclopropane-1-carboxamide Hydrochloride Salt (XII)

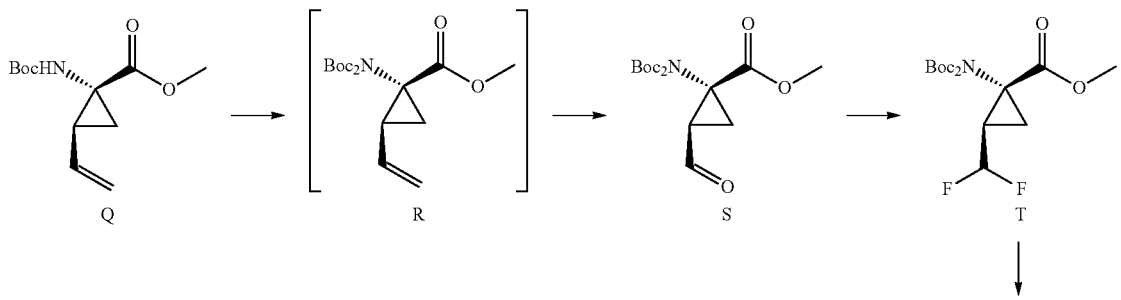

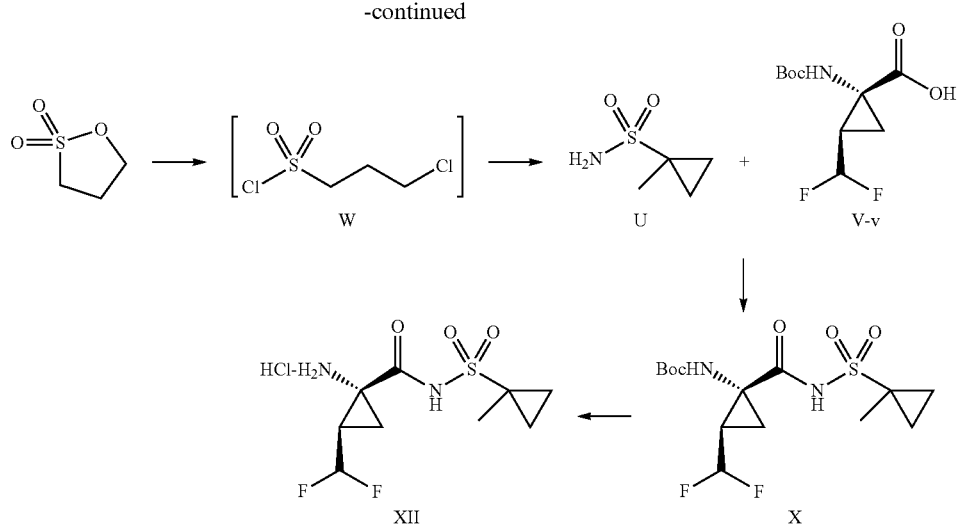
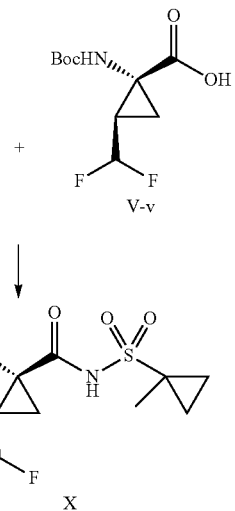

The existing process route shown above was disclosed is in the U.S. Publication No. 2014-0017198. The route shown below proceeds through a common known intermediate V-v. This intermediate V-v was synthesized using two alternative schemes. In the first scheme, racemic A-b was selectively hydrolyzed to racemic (±)-A-c with an approximate 10:1 ratio of cis/trans diastereomers. This mono acid is subjected to a classical resolution with a chiral amine to form chiral A-c as a salt. A recrystallization can be performed to enhance enantiomeric excess. The carboxylic acid was next converted to the amide A-d and isolated. In telescoping steps, the amide was subjected to a Hoffman rearrangement, hydrolysis to the amine, protection of the amine with Boc and hydrolysis of the methyl ester to form the desired amino acid, V-v. V-v was then converted to XII as shown in the above scheme.

First Alternative Scheme for Intermediate V-v Used to Synthesize XII

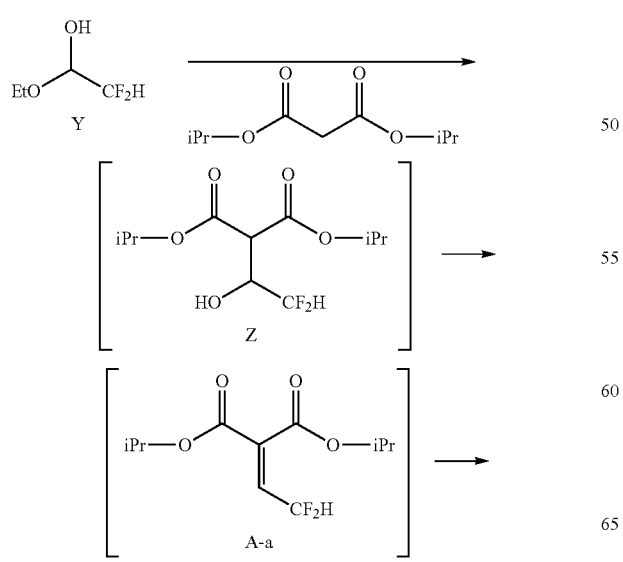

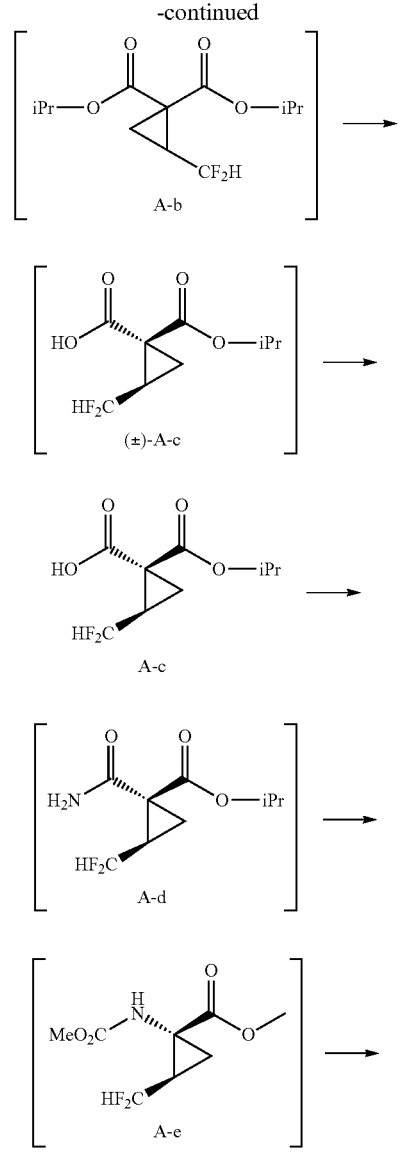

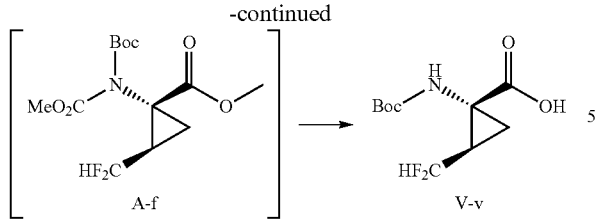

Synthesis of (1S,2R)-2-(Difluoromethyl)-1-(iso-propoxycarbonyl)cyclopropane-1-carboxylic acid (A-c)

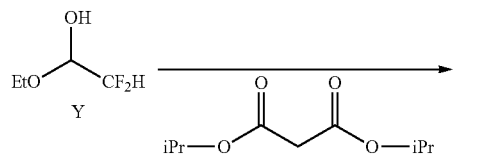

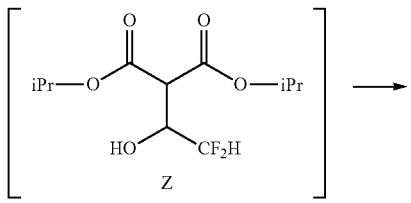

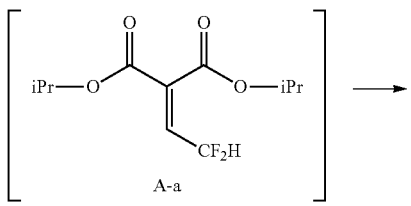

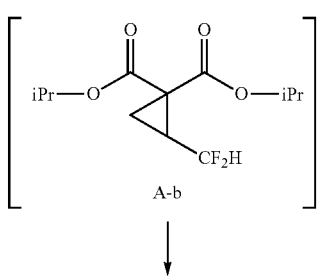

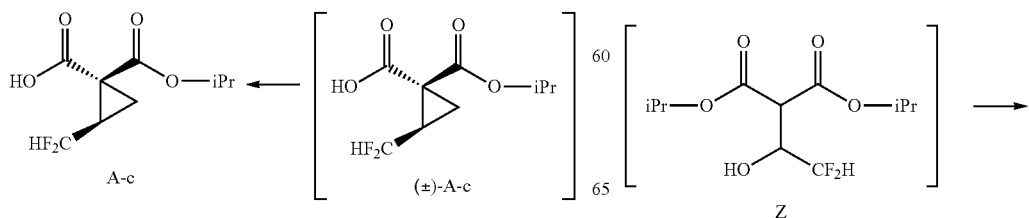

Synthesis of (1S,2R)-2-(difluoromethyl)-1-(iso-propoxycarbonyl)cyclopropane-1-carboxylic acid (B)

Step 1: Synthesis of Intermediate Z

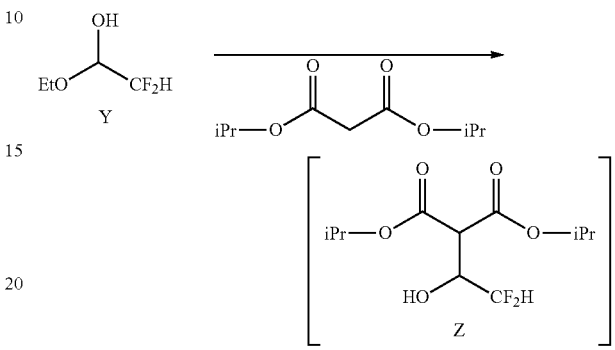

To a reactor was charged difluoroacetaldehyde ethyl hemiacetal Y (100 g, 0.79 mole), cyclopentyl methyl ether (CPME, 500 mL, 5 mL/g) and diisopropyl malonate (150 mL, 1 eq.). To the resulting solution, held at about 20° C., was added triethylamine ($Et_3N$, 100 mL, 1 mL/g). The mixture was warmed to about 35° C. and stirring was continued for about 20 hours. Upon reaction completion, a small sample was taken from this CPME solution of alcohol Z and washed with 1M aq. $KH_2PO_4$ until the pH was decreased to ~7 followed by brine. The organic layer was dried over $MgSO_4$ and concentration to dryness under vacuum. The residue was purified via column chromatography on silica gel using a gradient of 0% to 25% MTBE in hexanes to afford a clean sample of alcohol Z. $^1H$ NMR (300 MHz, $CDCl_3$): δ 1.275-1.30 (m, 12H), 3.63 (d, J=4.5 Hz, 1H), 3.95 (d, J=7.8 Hz, 1H), 4.32-4.45 (m, 1H), 5.06-5.20 (m, 2H) and 5.93 (dt, J=55.4 Hz and 4.2 Hz). $^{19}F$ NMR (282 MHz, $CDCl_3$): δ -129.0 (m). LCMS: (m/z) 291.1 (M+Na), 269.1 (M+H).

Alternative reagents and reactions conditions to those disclosed above may also be employed. For example, other ethereal solvents (e.g., THF, MeTHF, or MTBE) may be employed. In addition, temperatures ranging from about 0° C. to about 60° C. may be used. In addition, other organic amines (e.g., DIPEA) and malonate ester analogs (e.g., methyl, ethyl, benzyl, and a variety of other esters) may be employed.

Step 2: Synthesis of Intermediate A-a from Z

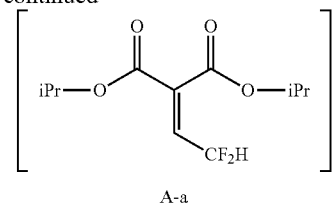

A-a

The bulk of the CPME solution of alcohol Z was cooled to about 20° C. followed by addition of acetic anhydride (Ac₂O, 200 mL, 2 mL/g) and 4-(dimethylamino)pyridine (DMAP, 4.83 g, 0.05 eq.) which resulted in an exotherm up to about 50° C. The resulting solution was stirred for about 20 hours at about 20° C. Upon reaction completion, 1M aq. K₂HPO₄ (1.0 L, 10 mL/g) was added which resulted in an exotherm. After 15 minutes the layers were separated. The CPME layer was washed with 1M aq. K₂HPO₄ (500 mL, 5 mL/g), a mixture of 1:1 (100 mL) 1M aq. K₂HPO₄ and 1M aq. KH₂PO₄ and brine (500 mL, 5 mL/g). To the CPME solution was added CPME (500 mL, 5 mL/g) and the volume was reduced to ~400 mL (4 mL/g) via distillation under vacuum. A small sample was taken, from this CPME solution of olefin A-a and this solution was concentrated to dryness under vacuum. The residue was purified via column chromatography on silica gel using a gradient of 0% to 15% MTBE in hexanes to afford a clean sample of olefin A-a. $^1$H NMR (300 MHz, CDCl₃): δ 1.25-1.29 (m, 12H), 5.06-5.21 (m, 2H), 6.50 (dt, J=54.6 Hz and 5.72 Hz) and 6.67-6.75 (m, 1H). $^{19}$F NMR (282 MHz, CDCl₃): δ -114.4 (m). GCMS: (m/z) 251 (M+H).

Alternative reagents and reactions conditions to those disclosed above may also be employed. For example, other ethereal solvents (e.g., THF, MeTHF, or MTBE) or non-ethereal solvents (e.g. toluene) may be employed. In addition, strong organic bases (e.g., DBU) may also be used. Further, other activating groups (e.g., triflic anhydride, mesyl chloride, or toluene sulfonyl chloride) and temperatures ranging from about 0° C. to about 60° C. may be employed.

Step 3: Synthesis of A-b from A-a

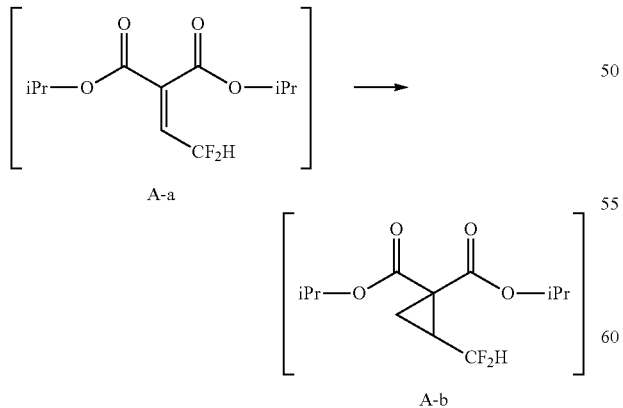

To a reactor was charged trimethylsulfoxonium iodide (Me₃SOI, 200 g, 1.15 eq.), potassium tert-butoxide (KOtBu, 97.5 g, 1.0 eq.) and dimethylsulfoxide (DMSO, 500 mL, 5 mL/g). The resulting suspension was stirred at about 25° C. for about 4 hours after which a clear solution was formed. To this DMSO solution was slowly added the CPME solution of olefin C in such a rate so not to exceed about 55° C. The resulting suspension was stirred overnight at about 25° C. The temperature was decreased to about 20° C. followed by addition of 1M aq. H₂SO₄ (1.0 L, 10 mL/g) which resulted in an exotherm. After 15 minutes the layers were separated. To the organic layer was added CPME (400 mL, 4 mL/g) and 10% aq. K₂CO₃ (500 mL, 5 mL/g). The layers were separated. The organic layer was washed with water (250 mL, 2.5 mL/g) followed by addition of CPME (200 mL, 2 mL/g) and reduction of volume to ~500 mL (~5 mL/g) via distillation under vacuum. To the resulting suspension was added charcoal (5.0 g, 0.05 g/g). The resulting suspension was filtered through diatomaceous earth followed by a rinse with CPME (200 mL, 2 mL/g). A small sample was taken from the CPME solution of cyclopropane A-b and was concentrated to dryness under vacuum and analyzed. The residue was purified via column chromatography on silica gel using a gradient of 0% to 15% MTBE in hexanes to afford a clean sample of cyclopropane A-b. $^1$H NMR (300 MHz, CDCl₃): δ 1.24-1.30 (m, 12H), 1.46-1.51 (m, 1H), 1.69-1.74 (m, 1H), 2.26-2.40 (m, 1H), 5.01-5.14 (m, 2H) and 5.68 (dt, J=56.0 Hz and 5.1 Hz). $^{19}$F NMR (282 MHz, CDCl₃): δ -114.1 (m). GCMS: (m/z) 223 (M+H). LCMS: (m/z) 287.1 (M+Na), 265.1 (M+H).

Alternative reagents and reactions conditions to those disclosed above may also be employed. For example, DMSO mixtures with other non-protic solvents (e.g., THF, MeTHF, or MTBE) and temperatures ranging from about 0° C. to about 60° C. may be employed. Further, strong base, such as NaH may be used.

Step 4: Synthesis of Intermediate A-c from A-b

Synthesis of (1S,2R)-2-(Difluoromethyl)-1-(iso-propoxycarbonyl)cyclopropane-1-carboxylic acid (A-c)

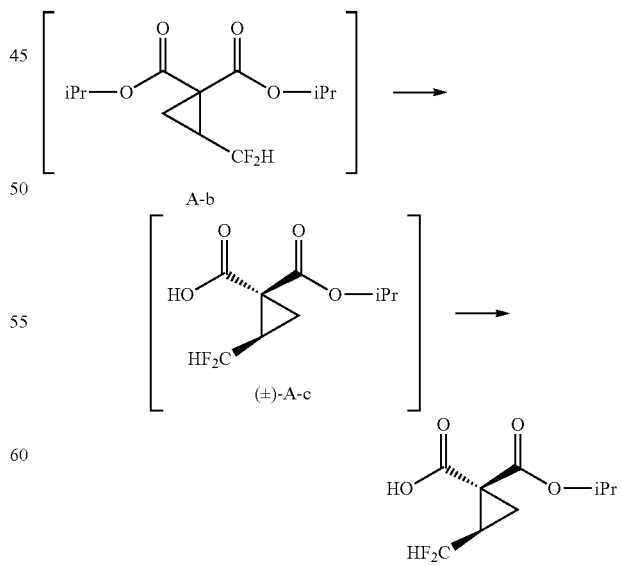

The CPME solution of cyclopropane A-b was diluted with isopropanol (IPA, 800 mL) and the volume was reduced to ~400 mL via distillation under vacuum. The resulting solution was cooled to about −3° C. followed by addition of 35% aq. tetraethylammonium hydroxide (Et$_4$NOH, 266 mL, 0.80 eq.) was added in such a rate not to exceed about 0° C. The reaction mixture was stirred overnight. 1M aq. HCl (200 mL) was slowly added in such a rate not to exceed about 5° C. followed by water (400 mL). The temperature was increased to about 15° C. and CPME (200 mL) was added. The layers were separated. The pH of the aqueous layer was checked and proved to be ~6.5. The CPME layer was extracted with 0.5M aq. K$_2$CO$_3$ (100 mL). Both aqueous layers were combined followed by addition of conc. H$_2$SO$_4$ (20 mL) which lowers the pH to ~2. Next CPME (400 mL) was added and the layers were separated. The CPME layer was extracted twice with 0.5M aq. K$_2$CO$_3$]. Both aqueous layers were combined and acidified to pH ~2 with H$_2$SO$_4$ (20 mL). Next CPME (500 mL) was added. Layers were separated. The CPME layer was washed with water (250 mL) followed by addition of CPME (400 mL). The volume was reduced to ~500 mL via distillation under vacuum. At this point activated charcoal (5.0 g) was added and the resulting suspension was filtered through diatomaceous earth followed by a rinse with CPME (100 mL). The volume was again reduced to ~500 mL via distillation under vacuum. A small sample was taken from this CPME solution of half ester/acid (±)-A-c and the CPA salt was formed. The solids were obtained via filtration. The solids were suspended in CPME and 1M aq. NaOH. After all the solids were dissolved the layers were separated. The aq. layer was acidified with conc. H$_2$SO$_4$ to pH ~2 and half ester/acid (±)-A-c was extracted into CPME. This solution was concentrated to dryness under vacuum to afford a clean sample of half ester/acid (±)-A-c. $^1$H NMR (300 MHz, CDCl$_3$): δ 1.31 (d, J=6.3 Hz, 5H), 1.91-1.98 (m, 2H), 2.52-2.59 (m, 1H), 5.15-5.24 (m, 2H) and 5.80 (dt, J=55.7 Hz and 6.3 Hz). $^{19}$F NMR (282 MHz, CDCl$_3$): δ −111.9 (m). LCMS: (m/z) 443.0 (2M−H), 220.9 (M−H).

To the solution of half ester/acid (±)-A-c in CPME was added (R)-(+)-1-(4-methylphenyl)ethylamine (62.5 mL, 0.55 eq.) which resulted in an exotherm. Next, seeds of A-c (100 mg) in heptane (20 mL) were added followed by heptane (500 mL, 5 ml/g). After the suspension thickened the temperature was increased to about 50° C. After stirring overnight the temperature was decreased to about 25° C. over about 5 hours. Next the temperature was decreased to 0° C. to 5° C. and held at that temperature for about 1 hour. The solids were collected via filtration and rinsed with 33% CPME in heptane (250 mL, 2.5 mL/g). The solids were dried in a vacuum oven at about 40° C. to constant weight to afford the salt of half ester/acid A-c. This material was suspended in CPME (500 m, 10 mL/g) and heated to about 70° C. at which point a clear solution was obtained. This solution was cooled to about 65° C. followed by addition of seeds. The resulting suspension was cooled to about 50° C. over about 3 hours. The resulting thick suspension was held at about 50° C. overnight. The temperature was decreased to about 30° C. over about 4 hours followed by decreasing the temperature to 0° C. to 5° C. and holding at that temperature for about 1 hour. The solids were obtained via filtration followed by a rinse with 50% CPME in heptane (100 mL). The solids were dried at about 40° C. in a vacuum oven to constant weight to afford the salt of half ester/acid A-c. $^1$H NMR (300 MHz, DMSO-d$_6$): δ 1.08-1.17 (m, 7H), 1.44 (d, J=6.3 Hz, 3H), 1.86-1.90 (m, 1H), 2.30 (s, 3H), 4.23-4.30 (m, 1H), 4.81-4.89 (m, 1H), 5.70 (dt, J=56.3 Hz and 6.0 Hz, 1H), 7.20 (d, J=7.5 Hz, 2H) and 7.35 (d, J=7.5 Hz, 2H. $^{19}$F NMR (282 MHz, DMSO-d$_6$): δ −111.4 (m).

Both mother liquors were combined and extracted twice with 0.5M aq. K$_2$CO$_3$ (500 mL). Both aqueous layers were combined and acidified with H$_2$SO$_4$ (30 mL, 0.3 mL/g) to pH ~2 in such a rate not to exceed about 30° C. Next CPME (500 mL) was added and the layers were separated. The CPME layer was washed with water (250 mL). Next CPME (600 mL) was added and the volume was reduced to ~500 mL via distillation under vacuum. Next charcoal (5.0 g) was added and the resulting suspension was filtered through diatomaceous earth followed by a rinse with CPME (100 mL). The volume of the filtrate was reduced to ~500 mL via distillation under vacuum. Next (S)-(−)-1-(4-methylphenyl)ethylamine (51 mL, 0.45 eq.) was added which resulted in an exotherm. To the resulting solution were added seeds (100 mg) followed by heptanes (500 mL). After about 1 hour the resulting suspension was heated to about 60° C. After about 1.5 hours the temperature was decreased to about 50° C. over about 1 hour. The resulting suspension was held at about 50° C. overnight.

The temperature was decreased to about 25° C. over about 5 hours. The temperature was further decreased to about 0° C. to about 5° C. and held at that temperature for about 1 hour. The solids were collected via filtration and rinsed with 33% CPME in heptane (200 mL). The solids were dried in a vacuum oven at about 40° C. to constant weight to afford the salt of half ester/acid A-c. This material was suspended in CPME (500 mL) and heated to about 75° C. at which point a clear solution was obtained. This solution was cooled to about 65° C. followed by addition of seeds. The resulting suspension was cooled to about 50° C. over about 5 hours. The resulting thick suspension was held at about 50° C. overnight. The temperature was then decreased to about 30° C. over about 4 hours followed by decreasing the temperature to 0° C. to 5° C. and holding at that temperature for about 1 hour. The solids were obtained via filtration followed by a rinse with 50% CPME in heptane (110 mL). The solids were dried at about 40° C. in a vacuum oven to constant weight to afford the salt of half ester/acid A-c. $^1$H NMR (300 MHz, DMSO-d$_6$): δ 1.08-1.17 (m, 7H), 1.44 (d, J=6.3 Hz, 3H), 1.86-1.90 (m, 1H), 2.30 (s, 3H), 4.23-4.30 (m, 1H), 4.81-4.89 (m, 1H), 5.70 (dt, J=56.3 Hz and 6.0 Hz, 1H), 7.20 (d, J=7.5 Hz, 2H) and 7.35 (d, J=7.5 Hz, 2H. $^{19}$F NMR (282 MHz, DMSO-d$_6$): δ −111.4 (m).

Alternative reagents and reactions conditions to those disclosed above may also be employed. For example, other alcoholic solvents matching the remaining ester may be used. In addition, other soluble hydroxides in IPA (e.g., KOH) and additional phase transfer catalysts (e.g., tetrabutylammonium hydroxide) may be employed. Further, other chiral amines that lead to crystalline salts of the correct product stereoisomer and temperatures ranging from about −20° C. to about 60° C. may be used.

Synthesis of V-v from A-c

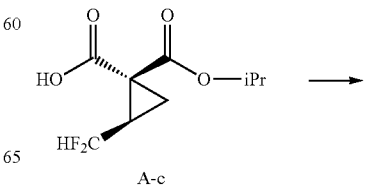

A-c

-continued

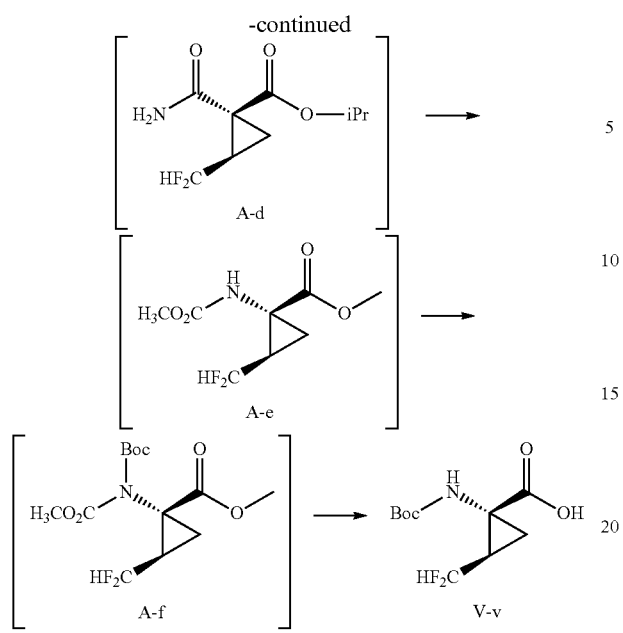

Synthesis of A-d from A-c

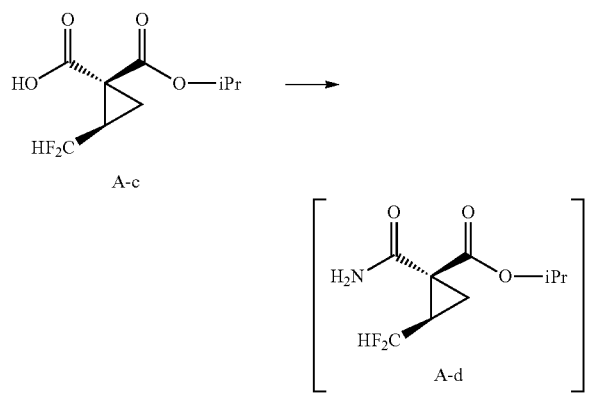

The salt of half ester/acid A-c (35 g, 97.9 mmol) was suspended in CPME (105 mL) and 1M aq. HCl (105 mL). The resulting suspension was stirred to the point that all solids were dissolved. The layers were separated and the CPME layer was washed with 1M aq. HCl (35 mL) and brine (70 mL) followed by drying over $Na_2SO_4$ and concentration under vacuum. To the resulting solution was slowly added 1,1'-carbonyl-diimidazole (CDI, 19.9 g, 1.25 eq.) in such a rate as to control off-gassing. The reaction mixture was stirred for 1 hour during which a precipitate forms. Next 28% aq. ammonium hydroxide ($NH_4OH$, 35 mL, 2.86 eq.) was added. The reaction mixture was stirred overnight. The next morning the layers were separated and the CPME layer was washed with 0.5M aq. $H_2SO_4$ (105 mL, 0.5M aq. $K_2CO_3$ (105 mL) and brine (70 mL), respectively. The CPME solution was dried over $MgSO_4$ and concentrated to dryness under vacuum to afford crude amide A-d. GCMS: 221 (M+).

Alternative reagents and reactions conditions to those disclosed above may also be employed. For example, ethereal solvents (e.g., THF, MeTHF, or MTBE) and temperatures ranging from about 0° C. to about 60° C. may be used. In addition, other ammonia sources (e.g., liquid ammonia) may be used. Further, other activating agents, such as any peptide coupling agent (e.g., T3P), or chlorinating reagent (e.g., thionyl chloride) may be employed.

Synthesis of A-e from A-d

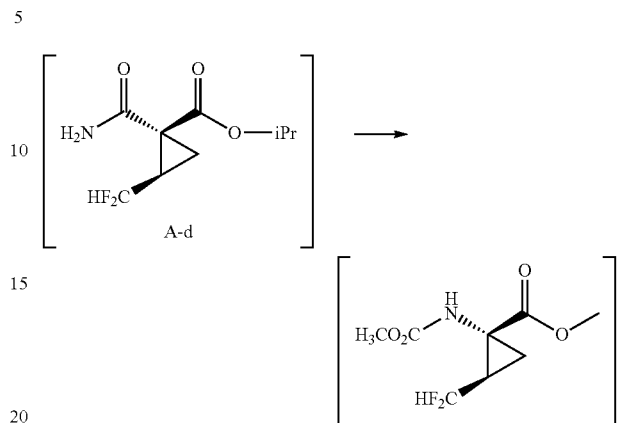

Crude amide A-d was taken up in methanol (MeOH, 262 mL, 7.5 mL/g) and trichloroisocyanuric acid (TCCA, 8.65 g, 0.38 eq.) was added followed by slow addition of 1,8-diazabicyclo[5.4.0]undec-7-ene (DBU, 35 mL, 2.4 eq.) in such a rate so as to not exceed 40° C. After about 1 hour the temperature was increased to about 65° C. and the reaction mixture was held at this temperature for 20 hours. Next, MeOH was removed via distillation under vacuum. The residue was diluted with isopropyl acetate (IPAC, 175 mL) and 1M aq. $KH_2PO_4$ (175 mL). After vigorously stirring for 15 minutes the solids were removed via filtration through diatomaceous earth followed by a rinse with IPAC (35 mL). The layers of the filtrate were separated. The IPAC layer was washed with brine (70 mL, 2 mL/g) followed by drying over $MgSO_4$ and concentrated to dryness under vacuum to afford carbamate A-e. GCMS: 223 (M+).

Alternative reagents and reactions conditions to those disclosed above may also be employed. For example, other methanolic mixtures with non-protic solvents (e.g., THF, MeTHF, or MTBE) and temperatures ranging from about 0° C. to about 60° C. may be used. In addition, other halogenating reagents (e.g., chlorine, bromine, NBS, or NCS) and strong hindered organic bases (e.g. DIPEA) may be used.

Synthesis of A-f from A-e:

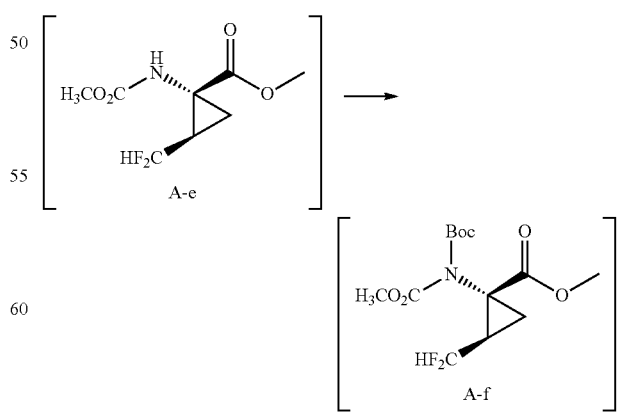

The residue containing crude carbamate A-e was taken up in isopropyl acetate (70 mL) followed by addition of di-tertbutyl dicarbonate (Boc$_2$O, 21.4 g, 1.0 eq.) and DMAP (598 mg, 0.05 eq.). The reaction mixture was stirred for about 20 hours. The reaction mixture was concentrated to dryness under vacuum to afford bis-carbamate A-f. GCMS: 257 (M-tBu), 223 (M-Boc).

Alternative reagents and reactions conditions to those disclosed above may also be employed. For example, non-protic solvents (e.g., THF, MeTHF, MTBE, or toluene) and temperatures ranging from about 0° C. to about 60° C. may be used. In addition, hindered organic bases (e.g., DIPEA) may be employed.

Synthesis of V-v from A-f

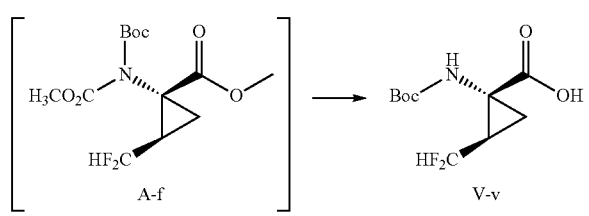

~2. The layers were separated. The IPAC layer was washed with water (25 mL). Next the IPAC layer was dried over Na$_2$SO$_4$ and concentrated to dryness under vacuum. The residue was taken up in IPAC (10 mL) and hexane (200 mL) were added slowly. The resulting suspension was stirred for a few hours. The solids were collected via filtration, rinsed with hexane and dried at about 40° C. in a vacuum oven to afford V-v (6.8 g).

Alternative reagents and reactions conditions to those disclosed above may also be employed. For example, other alcohol solvents (e.g., methanol, or ethanol) and temperatures ranging from about 0° C. to about 60° C. may be used. In addition, other hydroxide sources (e.g., LiOH, or tetra-butylammonium hydroxide) may be employed.

In the second alternative scheme, racemic A-b was selectively hydrolyzed to racemic (±)-A-c. This mono acid (±)-A-c was subjected to form a salt A-g with dicyclohexylamine. This salt was then freebased and subjected to a classical resolution by converting to the cinchonidine salt A-h. Curtius rearrangement of A-h followed by hydrolysis afforded intermediate V-v which was then converted to XII as shown in the above scheme.

Second Alternative Scheme for Intermediate V-v Used to Synthesize XII

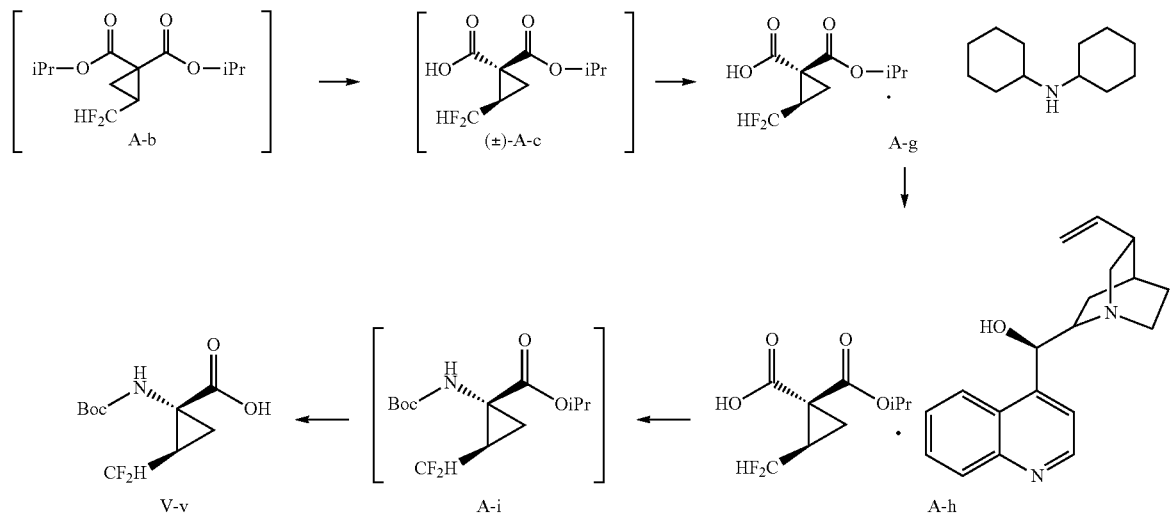

The residue containing bis-carbamate A-f was taken up in IPA (100 mL, 2.5 mL/g) followed by addition of 2M aq. KOH (100 mL). After stirring overnight, 2M aq. HCl (100 mL) was added followed by CPME (100 mL). The layers were separated. The CPME layer was extracted twice with 1M aq. NaOH (35 mL). Both aqueous layers were combined followed addition of IPA (70 mL) and 1M aq. HCl (70 mL). After stirring overnight the resulting suspension was filtered and the solids (racemic V-v) were washed with 50% aq. IPA (35 mL). The filtrate was extracted with IPAC (100 mL). The IPAC layer was dried over Na$_2$SO$_4$ and concentrated to dryness under vacuum. The residue was taken up in heptane and concentrated to dryness under vacuum. The residue was taken up in THF (25 mL) and 1M aq. NaOH (25 mL) followed by addition of Boc$_2$O (21.4 g, 1.0 eq.). The reaction mixture was stirred overnight. Next morning IPAC (25 mL) and water (25 mL) was added. The layers were separated. The IPAC layer was extracted with 0.5M aq. K$_2$CO$_3$ (12.5 mL). Both aqueous layers were combined and IPAC (25 mL) was added followed by acidification with 1M aq. HCl to pH Hydrolysis of A-b to (±)-A-c

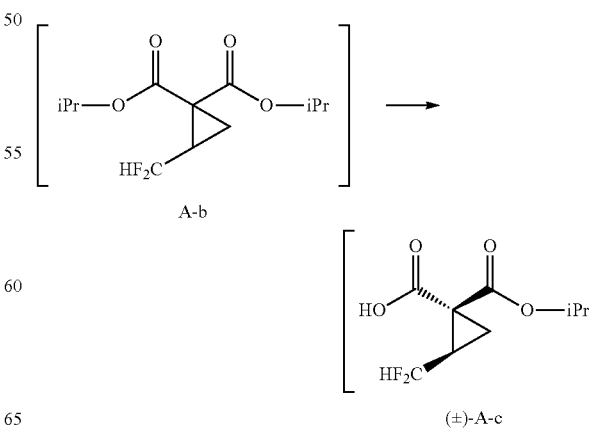

To the solution of A-b was charged isopropanol (250 mL), and the solution was cooled to between about −15 and about −10° C. To this was added tetraethylammonium hydroxide (35 wt % in H$_2$O, 365.2 g, 0.88 moles, 2.2 equiv) over at least about two hours, maintaining a temperature below about −10° C. After stirring between about −15 and about −10° C. for about 12 hours until reaction completion, toluene (250 mL) and water (200 mL) were added, maintaining the temperature below about 0° C. This mixture was stirred at about −5-0° C. for about 15 minutes, then warmed to about 20° C. to about 25° C. This mixture was stirred at about 20° C. to about 25° C. for about 15 minutes, and the phases were allowed to separate for 30 minutes.

The aqueous layer was transferred to a second reactor and toluene (150 mL) was added. This mixture was stirred at about 20° C. to about 25° C. for about 15 minutes, and the phases were allowed to separate for about 30 minutes. The phases were split, and toluene (400 mL) was added to the aqueous layer. The mixture was cooled to about 10° C., and 50% aq. H$_2$SO$_4$ (ca. 20 mL) was added, maintaining the temperature below about 15° C. until about pH 2-3 achieved. This mixture was stirred at about 10° C. for about 15 minutes, and the phases were allowed to separate for about 30 minutes. The organic layer was assayed, and the volume reduced from approximately 550 mL to 80 mL by vacuum distillation at about 40° C. to about 45° C. to provide A-c.

Alternative reagents and reactions conditions to those disclosed above may also be employed. For example, other bases (e.g. sodium hydroxide, potassium hydroxide, lithium hydroxide, tetrabutylammonium hydroxide, tetramethylammonium hydroxide, tetrapropylammonium hydroxide, potassium phosphate dibasic, potassium carbonate, sodium carbonate) may be used. In addition, other solvents (e.g. cyclopentyl methyl ether, methyl tert-butyl ether, dichloromethane, chloroform, chlorobenzene, tetrahydrofuran, 2-methyltetrahydrofuran, acetonitrile, methanol, ethanol, tert-butanol) may be employed. Also, temperatures ranging from about −15° C. to about −10° C. may be used.

Synthesis of A-g from (±)-A-c

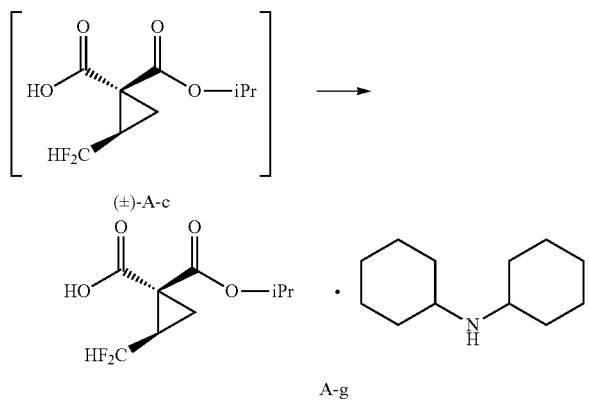

To the toluene solution from above was added toluene (54 mL). Then, maintaining the temperature below about 40° C., dicyclohexylamine (26.2 g, 140 mmol, 0.36 equiv) was added. The mixture was heated to 75° C. until dissolution achieved. The mixture was cooled to about 65° C. to allow crystallization, then stirred at about 65° C. for about 30 minutes, then cooled to about 0° C. over three hours. The slurry was stirred at about 0° C. for about two hours, then filtered. The filter cake was washed three times with 10:1 heptane:toluene (20 mL), and the solids dried at about 40° C. under vacuum to provide A-g. $^1$H NMR (400 MHz, CDCl$_3$): δ 1.18-1.26 (m, 12H), 1.28-1.33 (m, 1H), 1.39-1.48 (m, 5H), 1.65 (d, J=8 Hz, 2H), 1.79 (d, J=12 Hz, 4H), 1.99 (d, J=11.6 Hz, 4H), 2.1-2.2 (m, 1H), 2.95 (tt, J=8 Hz and 3.6, 2H), 5.03 (septet, J=6 Hz, 1H), 5.63 (td, J=56.4 and 5.6, 1H). $^{19}$F NMR (376 MHz, CDCl$_3$): δ −113 (ddd, J=2326 Hz, 285 Hz and 8.3 Hz).

Alternative reagents and reactions conditions to those disclosed above may also be employed. For example, other solvents (e.g. dichloromethane, chloroform, chlorobenzene, methyl tert-butyl ether, cyclopentyl methyl ether, 2-methyltetrahydrofuran, hexanes, cyclohexane) may be employed.

Alternative reagents and reactions conditions to those disclosed above may also be employed. For example, other solvents (e.g. dichloromethane, chloroform, chlorobenzene, MTBE, cyclopentyl methyl ether, 2-methyltetrahydrofuran, hexanes, cyclohexane) may be employed.

Synthesis of A-h from A-g

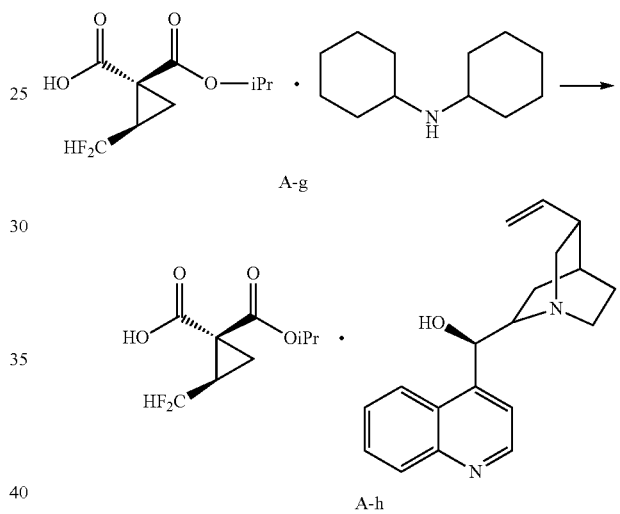

Solid A-g (444.8 g, 1.10 moles) was charged to a 5-L reactor under N$_2$. To this was added methylisobutyl ketone (MIBK, 2200 L) followed by 1 M H$_3$PO$_4$ (2200 ml), and the layers were agitated for about 15 minutes and separated. The organic layer was washed with water (1 L). Concentrate the reaction contents by distilling ~500 ml of solvent (including H$_2$O). The solution was filtered through diatomaceous earth.

Cinchonidine (304.5 g, 1.03 moles, 1.0 equiv.) was added to the reactor, along with MIBK (2500 ml). To this suspension was added the MIBK solution of (±)-A-c (in 2000 ml MIBK). The reaction mixture was heated to about 50° C. A-h (534 mg, 0.1 wt %) was added as seed, then the mixture was treated with the following temperature program: about 50° C. for about 1 hr, heated to about 60° C. over about 30 minutes, aged at about 60° C. for about 3 hrs, cooled to about 58° C. over about 4 hrs, cooled to about 50° C. over about 4 hrs, cooled to about 40° C. over about 2 hrs, cooled to about 20° C. over about 2 hrs, held at about 20° C. for about 2 hrs. The slurry was filtered. The cake was washed with MIBK (400 ml). The material was dried in a vacuum oven.

The resulting solids were added to a 5-L reactor under N$_2$, followed by MIBK (1438 ml, 7V) and methanol (144 ml, 0.7V) The resulting slurry was heated to about 60° C. to achieve a solution, then seeded with 0.1 wt % A-h. The light suspension was maintained at about 60° C. for about three hours, then underwent parabolic cooling to about 20° C. and held at about 20° C. for about five hours. Next, MIBK (200 mL, 1V) was added, and the slurry distilled under vacuum to about 6.5-7V to remove MeOH. Once the MeOH content was below 0.5%, the slurry was cooled to about 5° C. over about 2.5 hours and held at about 5° C. for about one hour. The slurry was filtered and the cake washed three times with MIBK (150 mL, 0.7V). The material was dried in a vacuum oven to afford A-h. $^1$H NMR (400 MHz, CDCl$_3$): δ 1.24 (t, J=6 Hz, 7H), 1.41-1.45 (m, 1H), 1.52 (t, J=5.6 Hz, 1H), 1.70-1.80 (m, 1H), 2.02 (m, 1H), 2.10 (m, 1H), 2.20-2.30 (m, 1H), 2.60 (bs, 1H), 3.03 (td, J=13.6 Hz and 4.4 Hz 1H), 3.10-3.16 (m, 1H), 3.33 (dt, J=10.4 Hz and 3.2 Hz, 2H), 4.30 (m, 1H), 4.98-5.00 (m, 1H), 5.08 (septet, J=6.4 Hz, 1H), 5.48-5.55 (m, 1H), 5.69 (td, J=56.8 Hz and 5.2 Hz, 1H), 6.26 (s, 1H), 7.46 (t, J=8 Hz, 1H), 7.63 (t, J=8 Hz, 1H), 7.69 (d, 4.4 Hz, 1H), 7.92 (d, 8.4 Hz, 1H), 8.03 (d, J=8 Hz, 1H), 8.86 (d, J=4.4 Hz, 1H). $^{19}$F NMR (376 MHz, CDCl$_3$): δ -113 (ddd, J=2435 Hz, 286 Hz and 7.1 Hz).

Alternative reagents and reactions conditions to those disclosed above may also be employed. For example, other acids (e.g. sulfuric acid) may be employed and other solvents (e.g. isopropyl acetate, MTBE) may be employed.

Curtius Rearrangement of A-h to A-i

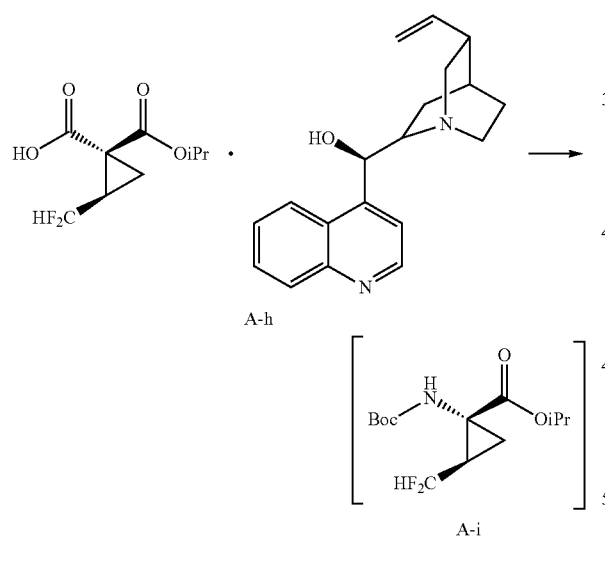

In a reaction vessel, was charged A-h (200 g, 387 mmole) and 15% aq. H$_3$PO$_4$ (800 mL, 4 mug). To the resulting suspension was added MTBE (400 mL, 2 ml/g) and an exotherm from about 22° C. to about 25° C. was observed. Within about 5 minutes all the solids were dissolved. After about 15 minutes stirring was discontinued and the layers were allowed to separate for about 10 minutes. The bottom layer (~880 mL; pH ~2.5; aq. layer 1) was removed. Stirring was resumed followed by addition of water (400 mL, 2 ml/g). Stirring was discontinued after about 15 minutes and the layers were allowed to separate for about 10 minutes. The bottom layer (~400 mL; ph ~2.5; aq. layer 2) was removed. Stirring was resumed followed by addition of toluene (400 mL, 2 mL/g). The volume was reduced under vacuum to 300 mL (1.5 mL/g; 40 torr, jacketed temperature up to about 50° C. ~575 mL distillate; distillate 1). The KF was checked and deemed acceptable (32 ppm; <100 ppm).

To a reaction vessel, was charged DMAP (94.5 g, 774 mmol, 2 equiv.) and toluene (300 mL, 1.5 mL/g) followed by DPPA (125 mL, 581 mmol, 1.5 eq.). The resulting suspension was heated to about 85° C. The hazy product in toluene solution was polish filtered into the hot DMAP/DPPA suspension in such a rate to maintain the temperature between about 80° C. and about 100° C. This was followed by a rinse with toluene (100 mL, 0.5 mL/g). Upon completion of the addition, the reaction contents were cooled to about 80° C. to about 83° C. tBuOH (65.5 mL, 774 mmol, 2 equiv) was added. The reaction mixture was aged for about 6 hours at about 75° C. to about 80° C. The reaction mixture was cooled to about 20° C. followed by addition of water (400 mL, 2 mL/g) which resulted in an exotherm up to about 23° C. Stirring was discontinued after about 15 minutes and the layers were allowed to separate for about 15 minutes. The bottom layer (~600 mL, pH ~9; aq. layer 3) was removed. Stirring was resumed and water (200 mL, 1 mL/g) was added. After about 10 minutes stirring was discontinued and the layers were allowed to settle for about 10 minutes. The bottom layer (~200 mL, pH ~9; aq. layer 4) was removed. Stirring was resumed and the volume was reduced to 300 mL (1.5 mL/g) via distillation. The resulting solution was cooled to about 20° C.

Alternative reagents and reactions conditions to those disclosed above may also be employed. For example, other acids (e.g. sulfuric acid) may be employed and other bases (e.g. diisopropylethylamine, triethylamine) may be employed. Also, temperatures ranging from about 70° C. to 100° C. may be used.

Hydrolysis of A-i to V-v

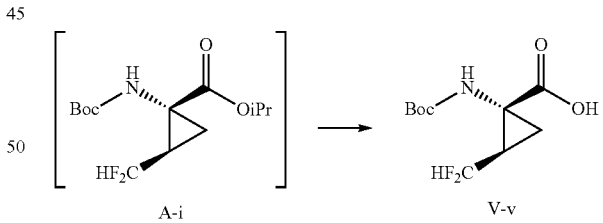

To a reaction vessel were charged MeOH (300 mL, 1.5 mL/g) and powdered KOH (43.4 g, 774 mmol, 2 equiv). After the exotherm subsided the resulting hazy solution was added into the two liter reactor which resulted in an exotherm up about 40° C. After about 3 hours the reaction was deemed complete.

At this point, 15% aq. H$_3$PO$_4$ (600 mL, 3 mL/g) was added which resulted in an exotherm up to about 32° C. and a pH of about 2.5. After about 10 minutes the resulting suspension was filtered followed by a rinse with MTBE (200 mL, 1 mL/g). The filtrate was stirred for about five minutes followed by discontinuation of stirring. The layers were allowed to separate for about five minutes. The bottom layer (~900 mL, pH ~2.5; aq. layer 5) was removed. Stirring was resumed and water (200 mL, 1 mL/g) was added. After about five minutes stirring was discontinued and the layers were allowed to separate for about 5 minutes. The bottom layer (~250 mL, pH ~2.5; aq. layer 6) was removed. Stirring was resumed and toluene (400 mL, 2 mL/g) was added. The volume was reduced to 300 mL (1.5 mL/g) via distillation. The resulting solution was stirred at about 20° C. and within about 1 hour a suspension is formed. After about 3 hours heptane (300 mL, 1.5 mL/g) was slowly added over about 30 minutes. The resulting suspension was stirred overnight followed by cooling to about 5° C. The solids were obtained via filtration. The mother liquor was used for rinsing and the rinse was added the filter cake. After the filter cake was pulled dry a rinse with 40% toluene in heptanes (100 mL, 0.5 mL/g) was added to the filter cake followed by pulling this rinse through the filter cake. The solids were dried at about 40° C. in a vacuum oven afford V-v. $^1$H NMR (400 MHz, CD$_3$OD): δ 1.43 (s, 10H), 1.64-1.80 (m, 1H), 1.89-2.00 (m, 1H), 5.87 (td, J=53.6 Hz and 7.2 Hz, 1H). $^{19}$F NMR (376 MHz, CDCl$_3$): δ −113 (m).

Assembly Steps of Route I to Compound of Formula I
A. Synthesis of Compound of Formula III (R=CH$_3$)
I. Free-basing and Boc-protection of II (R=CH$_3$) to Provide III (R=CH$_3$):

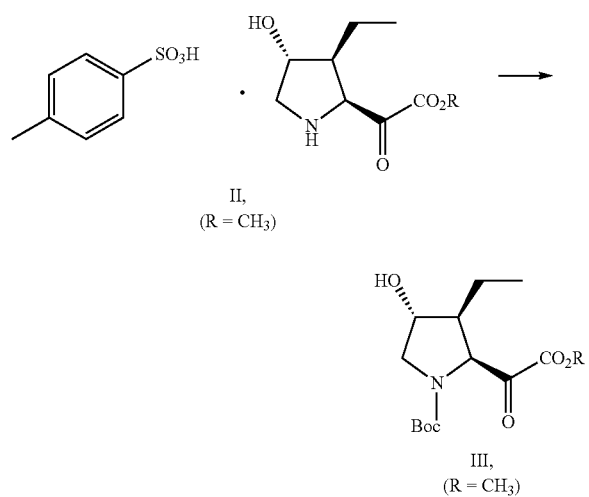

II (10.1 g, 29.3 mmol, 1.00 equivalents) was combined with dichloromethane (40 mL) and the mixture stirred at about 20 to about 25° C. Triethylamine (8.36 g, 82.6 mmol, 3.00 equivalents) was added dropwise via syringe, maintaining a reaction temperature of about 20° C. to about 25° C. To the resultant solution was charged 4-dimethylaminopyridine (360 mg, 2.95 mmol, 0.1 equivalent) followed by a solution of di-tert-butyl dicarbonate (6.52 g, 29.9 mmol, 1.02 equivalent) in dichloromethane (40 mL), while maintaining a reaction temperature of about 20° C. to about 25° C. The mixture was stirred for about 2-4 hours and monitored for completion. Upon reaction completion, 100 mL of 1.0 N HCl was charged dropwise, while maintaining a reaction temperature below about 30° C. The biphasic mixture was vigorously stirred for about 15 minutes followed by allowing the layers to separate. The bottom organic layer was partitioned and washed successively with 5% wt/wt aqueous sodium bicarbonate (100 mL) and water (100 mL). The organic phase was concentrated under reduced pressure and dried under vacuum to afford III (R=CH$_3$). $^1$H NMR (300 MHz, CD$_3$OD): δ 4.41 (d, J=6.0 Hz, 1H), 4.01-4.07 (m, 1H), 3.65-3.79 (m, 4H), 3.05-3.15 (m, 1H), 2.10-2.20 (m, 1H), 1.50-1.60 (m, 1H), 1.39-1.45 (app d, 9H), 1.10-1.20 (m, 2H), 0.99-1.08 (m, 3H). $^{13}$C NMR (75 MHz, CDCl$_3$): δ 12.3, 21.3, 28.2, 50.5, 50.6, 51.4, 52.2, 61.8, 71.9, 80.2, 154.2, 171.9.

Alternative reagents and reactions conditions to those disclosed above may also be employed. For example, amine bases (e.g., diisopropylethylamine, or sodium hexamethyldisilizide), carbonates (e.g., potassium, or cesium carbonate), bicarbonates (e.g., sodium bicarbonate), or inorganic/organic hydroxides (e.g., sodium hydroxide, or tetramethylammonium hydroxide) may be employed. In addition, other Boc-delivery agents (e.g., BOC—ON=C(CN)Ph, BOC—ONH$_2$, 1,2,2,2-tetrachloroethyl tert-butyl carbonate, or 1-(t-butoxylcarbonyl)benzotriazole) and promoters (e.g., imidazole, or ultrasound) can be used. Further, other organic solvents (toluene, acetonitrile, or acetone), water, polar aprotics (e.g., N,N-Dimethylformamide (DMF) or dimethyl sulfoxide (DMSO), or combinations of these with water), alcohols (e.g., methanol or ethanol), ethers (e.g., tetrahydrofuran, dioxane or methyl-t-butyl ether), or esters (e.g., ethyl acetate) can be used.

B. Synthesis of Compound of Formula V (R=CH$_3$)

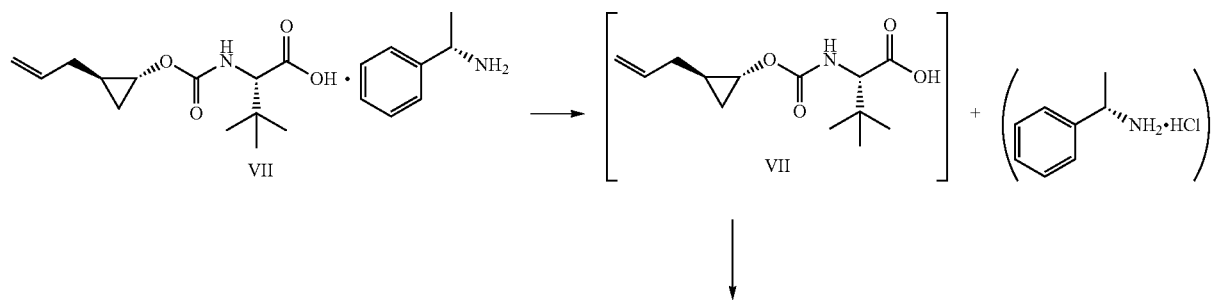

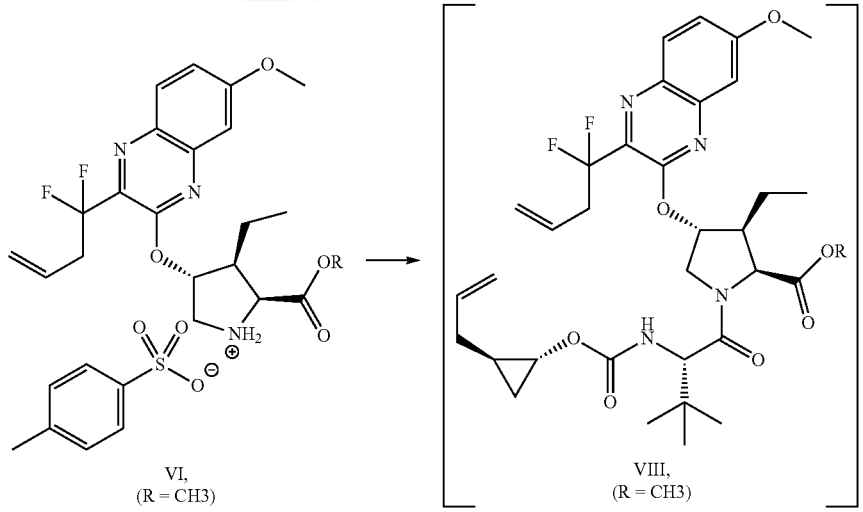

II. S$_N$Ar Reaction of IV with III (R=CH$_3$) to Form V (R=CH$_3$)

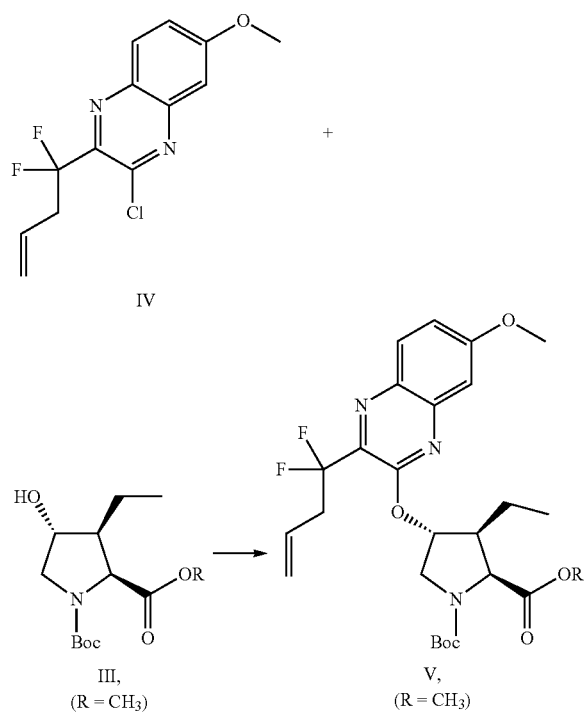

Into a reactor containing III (R=CH$_3$) (1.00 equivalent) in N,N-dimethylacetamide (6 volumes) was charged IV (1.00 equivalent) and cesium carbonate (1.20 equivalents) under nitrogen atmosphere. The heterogeneous reaction was heated to about 100 to 110° C. with stirring. Upon reaction completion, the reaction mixture was then cooled down to about 20° C. and MTBE (10 volumes) was charged. The resulting mixture was washed twice with water (6 volumes) and the MTBE solvent was swapped with isopropanol (6 volumes) via vacuum distillation. The solution was then heated to about 60° C. and water (3 volumes) slowly added over about 1.5 hours. Once the addition was complete, the mixture was held at about 60° C. for about 30 minutes. A small amount of V (R=CH$_3$) (1-2 wt/wt %) were then charged after which the temperature was slowly cooled to room temperature over about 3 hours. The contents were then aged for at least about 12 hours after which the slurry was filtered over the appropriate filter. The wet cake was washed with 2:1 isopropanol/water (3.5 volumes), followed by two water washes (3.5 volumes) and oven dried under vacuum at about 40 to 45° C. $^1$H NMR (400 MHz, CDCl$_3$): δ 7.93-7.90 (m, 1H), 7.25-7.22 (m, 1H), 7.20-7.16 (m, 1H), 5.95-5.85 (m, 1H), 5.44-5.38 (m, 1H), 5.25-5.21 (m, 2H), 4.54-4.52 (m, 1H), 4.47-4.40 (m, 1H), 3.97 (s, 3H), 3.77 (s, 3H), 3.43-3.39 (m, 1H), 3.27-3.17 (m, 2H), 2.79-2.68 (m, 1H), 1.64-1.55 (m, 1H), 1.44-1.43 (m, 9H), 1.44-1.32 (m, 1H), 1.10-1.06 (m, 3H). LCMS (M+1): 521.97.

Alternative reagents and reactions conditions to those disclosed above may also be employed. For example, other inorganic bases (e.g., sodium carbonate (Na$_2$CO$_3$), potassium carbonate (K$_2$CO$_3$), potassium-tert-butoxide (KOtBu), lithium-tert-butoxide (LiOtBu), magnesium-tert-butoxide (Mg(OtBu)$_2$), sodium-tert-butoxide (NaOtBu), sodium hydride (NaH), potassium hexamethyldisilizide (KHMDS), potassium phosphate (K$_3$PO$_4$), potassium hydroxide (KOH), or lithium hydroxide (LiOH)) or organic bases (e.g., DABCO, or DBU) may be used. In addition, aprotic solvents (e.g. N,N-dimethylformamide (DMF), N-methyl-2-pyrrolidinone (NMP), dimethylsulfoxide (DMSO), acetonitrile (MeCN), or acetone), aprotic solvents with small amounts of added water added, ethers (e.g., tetrahydrofuran (THF), or 1,4-dioxane), or toluene in the presence of phase-transfer catalyst may be used. Further, other additives (e.g., tetra-n-butyl ammonium bromide (TBAB), tetra-n-butylammonium iodide (TBAI), tetra-n-butylammonium chloride (TBACl), sodium iodide (NaI), or tetra-n-butylphosphonium bromide (TBPB)) and temperatures ranging from about 20° C. to about 120° C. may be used.

C. Synthesis of Compound of Formula VI (R=CH₃) Tosylate Salt

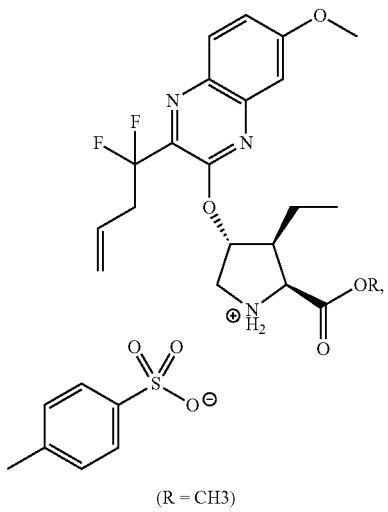

(R = CH3)

I. Boc Deprotection of V (R=CH₃) to Provide VI (R=CH₃)

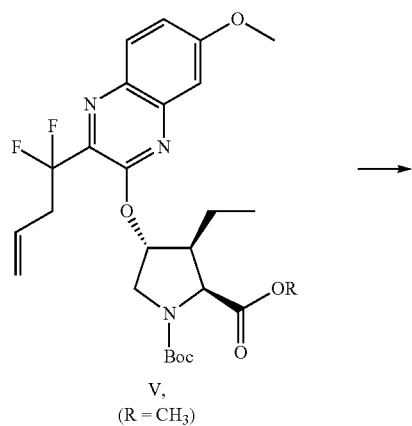

V,
(R = CH₃)

-continued

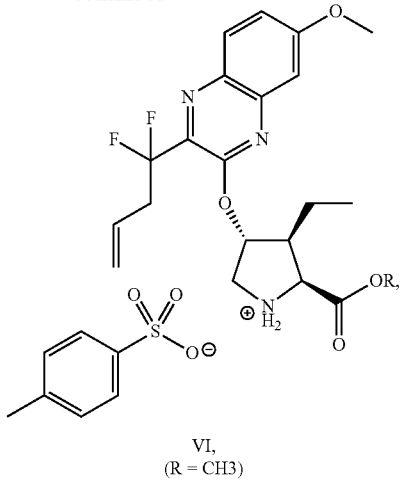

VI,
(R = CH3)

V (R=CH₃) (50.0 g, 95.9 mmol, 1.00 equivalents) is combined with methyl tetrahydrofuran (150 mL, 3.0 volumes) and the mixture was agitated at about 15 to 25° C., preferably about 20° C. Para-toluenesulfonic acid (45.6 g, 240 mmol, 2.50 equivalents) in methyl tetrahydrofuran (100 mL, 2.0 volumes) was charged to the reaction mixture. Once the acid addition was complete, the contents were heated to about 50 to 60° C. and the reaction contents were agitated for about 3 to 5 hours. Upon reaction completion, MTBE (100 mL, 2 volumes) was added slowly to the slurry. The contents were then cooled to about 15 to 25° C., and the slurry was filtered and washed with a mixture of methyl tetrahydrofuran (105 mL, 2.1 volumes) and MTBE (45 mL, 0.9 volumes). The solids were placed in a vacuum oven to dry at about 35 to 45° C. $^1$H NMR (400 MHz, CDCl₃) δ 10.33 (s, 1H), 9.58 (s, 1H), 7.92 (d, J=9.2 Hz, 1H), 7.72 (d, J=8.1 Hz, 2H), 7.31-7.21 (m, 1H), 7.11 (t, J=5.7 Hz, 3H), 5.97-5.77 (m, 1H), 5.49 (t, J=7.1 Hz, 1H), 5.19 (dd, J=27.6, 13.7 Hz, 2H), 4.73 (dd, J=12.1, 5.7 Hz, 1H), 4.49 (dd, J=11.8, 6.4 Hz, 1H), 3.93 (d, J=9.1 Hz, 3H), 3.77 (s, 3H), 3.60 (dd, J=13.2, 3.5 Hz, 1H), 3.17 (td, J=16.8, 7.0 Hz, 2H), 2.84 (dd, J=14.1, 6.9 Hz, 1H), 2.30 (s, 3H), 1.67-1.34 (m, 2H), 1.05 (t, J=7.4 Hz, 3H). LC/MS: M/Z=422.2.

Alternative reagents and reactions conditions to those disclosed above may also be employed. For example, other acids (e.g., hydrochloric acid, or methanesulfonic acid) can be used. In addition, other organic solvents (e.g., isopropyl acetate) may be employed.

D. Synthesis of Compound of Formula VIII (R=CH₃)

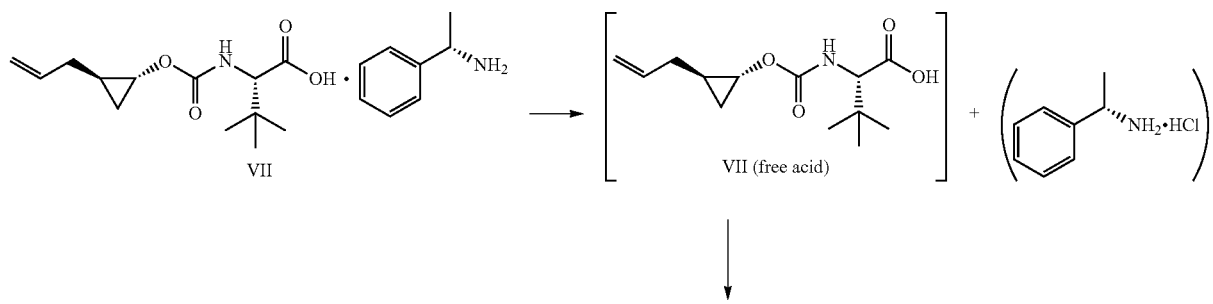

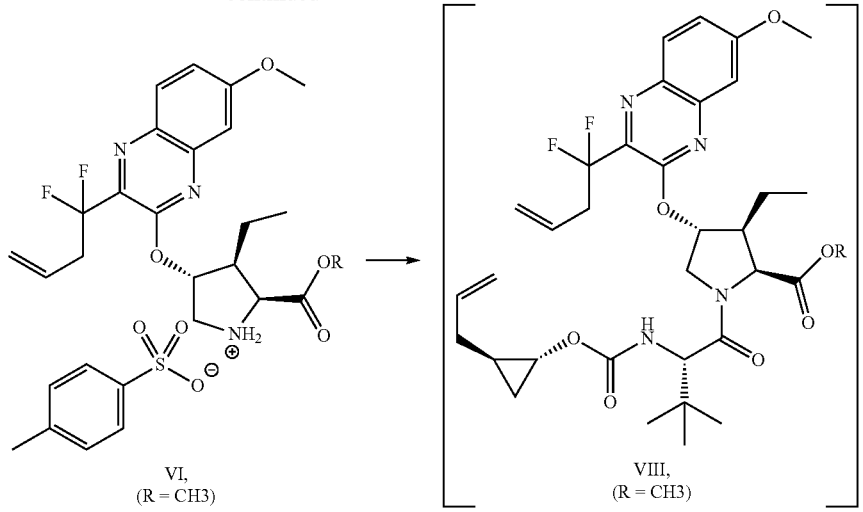

VI,
(R = CH3)

VIII,
(R = CH3)

I. Salt Break of VII to Provide VII Free-Acid

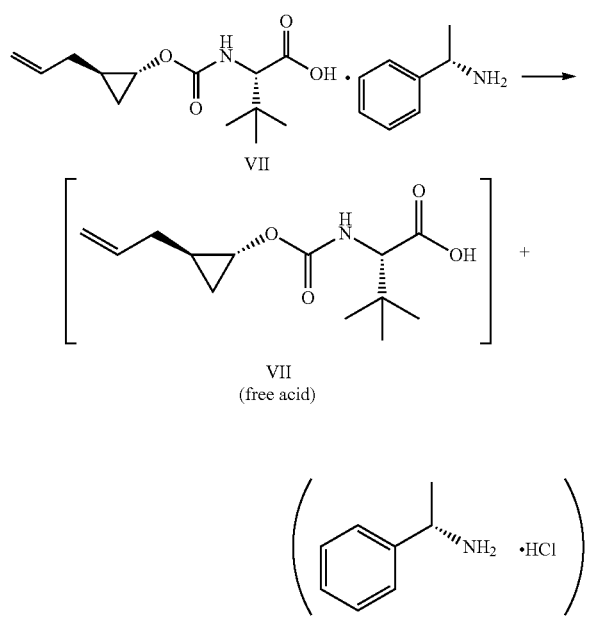

VII (33.0 g, 87.6 mmol, 1.0 equivalents) was combined with MTBE (198 mL, 6.0 volumes) and the resulting suspension was agitated. A solution of concentrated hydrochloric acid (33 mL, 1.0 volume) and water (165 mL, 5.0 volumes) was charged to the suspension at a rate that maintained a reaction temperature of about 15 to 25° C. As the acid was added, the suspension became a biphasic solution. The resulting reaction mixture was agitated for about 1 hour at about 15 to 25° C. Agitation was stopped and the layers separated for about 15 minutes before the aqueous layer was removed. Water (330 mL, 10 volumes) was added to the organic and was agitated for a about 15 min at about 15 to 25° C. Agitation was stopped and the layers separated for about 15 minutes before the aqueous layer was removed. Water (330 mL, 10 volumes) was added to the organic and was agitated for a about 15 min at about 15 to 25° C. Agitation was stopped and the layers separated for about 15 minutes before the aqueous layer was removed. A solution of 10 wt. % sodium chloride in water (300 mL, 9 volumes) was added to the organic and the mixture was agitated for about 15 min at about 15 to 25° C. Agitation was stopped and the layers were separated for about 15 minutes before the aqueous layer was removed. The resulting organic layer was then concentrated to the minimum volume and was diluted with dimethylformamide (297 mL, 9.0 volumes). The final solution was removed and polish filtered.

Alternative reagents and reactions conditions to those disclosed above may also be employed. For example, other acids (e.g., sulfuric acid, or phosphoric acid) may be used. Further, other organic solvents (e.g., methyl-THF, or ethyl acetate) can be used.

II. Amide Coupling of VI (R═CH₃) and VII (Free Acid) to Provide VIII (R═CH₃)

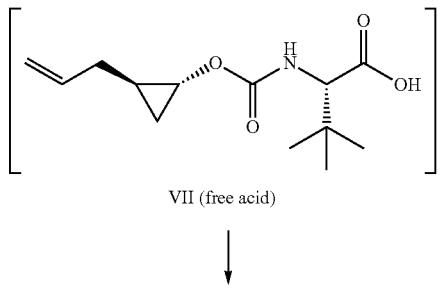

VII (free acid)

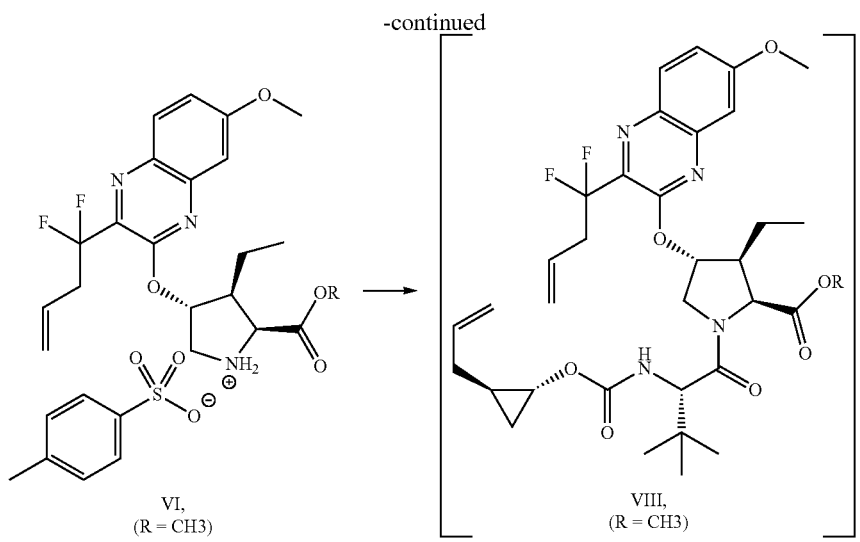

VI,
(R = CH3)

VIII,
(R = CH3)

VII (free acid) (40.0 g; 67.4 mmol; 0.77 eq.), EDC.HCl (16.8 g, 87.6 mmol, 1.0 eq.), and HOBt monohydrate (13.4 g, 87.6 mmol, 1.0 eq) were combined in a reaction vessel. The previously prepared VII (free acid) in DMF solution was charged to the solids, rinsed forward with DMF (39.6 mL, 1.2 vol) and agitated to form a solution. The reaction mixture was cooled to about 0 to 10° C. before NMM was charged (19.3 mL, 175 mmol, 2.0 eq.). The contents are agitated at about 0 to 10° C. for no less than about 1 hour. The reaction mixture was then adjusted to about 15 to 25° C. and agitated until reaction was complete by LC analysis Upon reaction completion, toluene (429 mL, 13 volumes) was charged to the reactor and the temperature adjusted to about −5 to 5° C. Water (198 mL, 6 volumes) was slowly charged to maintain a reaction temperature between about 0 and 25° C. After water addition was complete, the contents were adjusted to about 15 to 25° C. Agitation was stopped and the contents settled for no less than 15 minutes before the aqueous layer was removed. A solution of potassium carbonate (20.6 g, 149 mmol, 1.7 equivalents) in water (181 mL, 5.5 volumes) was charged to the organic phase and the resulting solution permitted to and agitate for about 15 minutes before the agitation was stopped and the contents were allowed to settle for about 15 minutes. The aqueous basic layer was removed. Water (181 mL, 5.5 volumes) was charged to the organic phase and agitated for about 15 minutes before the agitation was stopped and the contents allowed to settle for about 15 minutes. The aqueous basic layer was removed. The organic phase was again partitioned between water (181 mL 5.5 volumes) and agitated for about 15 minutes before agitation was stopped and the contents allowed to settle for about 15 minutes. The aqueous basic layer was removed. A solution of sodium chloride (20.5 g; 350 mmol 4.00 equivalents) in water (181 mL; 5.5 volumes) was charged to the organic and agitated for about 15 minutes before agitation was stopped and the contents settled for about 15 minutes. The aqueous acidic layer was removed. The organic was concentrated to minimum stirring volume and was removed and polish filtered.

$^1$H NMR (400 MHz, CDCl3) δ 8.01 (d, J=9.1 Hz, 1H), 7.19-7.34 (m, 3H), 6.09-5.78 (m, 2H), 5.55-5.21 (m, 3H), 5.06 (dd, J=32.9, 13.4 Hz, 2H), 4.92 (d, J=8.5 Hz, 1H), 4.59 (dd, J=10.7, 6.3 Hz, 1H), 4.35 (d, J=9.7 Hz, 1H), 4.11-3.92 (s, 3H), 3.95-3.87 (m, 1H), 3.85 (d, J=28.1 Hz, 3H), 3.78-3.70 (m, 1H), 3.37-3.17 (m, 2H), 2.81-2.69 (m, 1H), 2.18-2.06 (m, 1H), 1.95 (d, J=7.4 Hz, 1H), 1.63 (dd, J=14.4, 7.3 Hz, 1H), 1.48 (dd, J=14.4, 7.2 Hz, 1H), 1.17 (t, J=7.4 Hz, 3H), 1.12 (s, 9H), 0.84 (s, 1H), 0.54 (d, J=6.4 Hz, 1H). LC/MS: m/z=659.

Alternative reagents and reactions conditions to those disclosed above may also be employed. For example, other coupling agents (e.g. 1-hydroxy-7-azabenzotriazole) and base (e.g. pyridine, morpholine, or imidazole) may be employed. In addition, other organic solvents (e.g., dimethylacetamide or acetonitrile) can be used.

E. Synthesis of compound of Formula IX (R=CH$_3$)

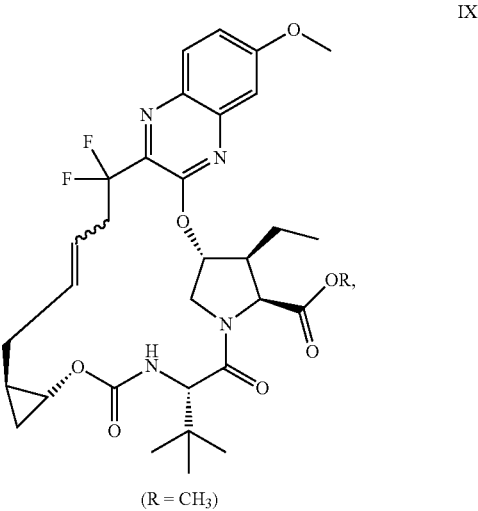

IX (R = CH3)

Ring Closing Metathesis of VIII (R=CH₃) to Provide IX (R=CH₃):

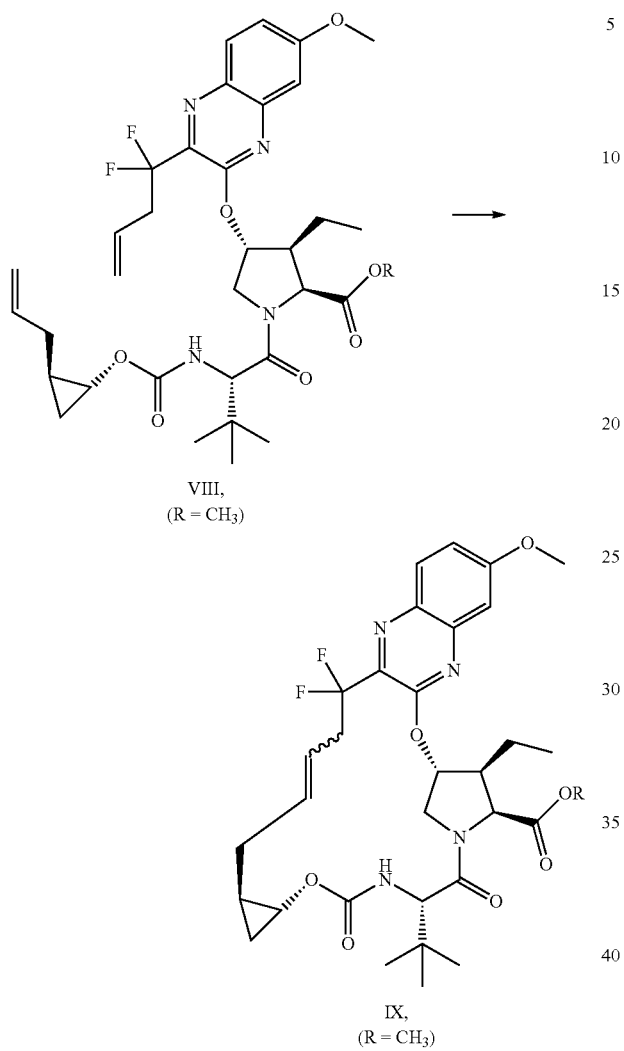

VIII (R=CH₃) (33 g of a 14.3 wt. % solution in toluene, 7.1 mmol, 1.00 equivalents) and toluene (27 mL) were combined and the mixture was agitated and heated to reflux (110° C.) and held at reflux temperature for about 3 to 5 hours. Separately, toluene (20 mL) was charged to a reaction vessel. and degassed vigorously. Zhan 1B catalyst (173 mg, 0.24 mmol, 0.033 equivalents) was charged and the mixture is agitated at about 20 to 25° C. for about 60 minutes to obtain a homogenous solution. The toluene solution of Zhan catalyst was added to the refluxing toluene solution of VIII (R=CH₃) over about 2 hours, maintaining a reaction temperature of about 111° C. Upon reaction completion, the reaction was cooled to about 20° C. and 9.4 grams (2S) of silica gel was charged. The slurry was vigorously agitated for about 4 hours and then filtered. The reactor and filter were washed with isopropyl acetate (2×32 mL) and the filtrate was concentrated to 50% volume (approximately 11 volumes). To this solution was charged 2.4 grams of activated charcoal (0.5 S). The slurry was vigorously agitated for about 4 hours and then filtered. The reactor and filter were washed with isopropyl acetate (2×16 mL) and the filtrate was solvent exchanged to 5 volumes isopropyl acetate and used directly next step. ¹H NMR (300 MHz, CDCl₃): δ 7.95 (d, J=6.0 Hz, 1H), 7.26 (m, 1H), 7.12 (m, 1H), 5.89 (m, 1H), 5.69 (m, 2H), 5.22 (d, J=9.0 Hz, 1H), 4.77 (d, J=6.0 Hz, 1H), 4.40 (d, J=9.0 Hz, 1H), 4.29 (d, J=6.0 Hz, 1H), 4.02-3.95 (m, 1H), 3.96 (s, 3H), 3.85 (m, 1H), 3.73 (s, 3H), 3.21 (s, 2H), 2.90-2.70 (m, 1H), 2.49 (d, J=12.0 Hz, 1H), 1.41 (m, 2H), 1.25-1.18 (m, 4H), 1.06 (s, 9H), 1.00-0.93 (m, 2H), 0.50 (m, 1H). LCMS: m/z=631.02.

Alternative reagents and reactions conditions to those disclosed above may also be employed. For example, other ruthenium-based Grubbs, Grubbs-Hoveyda, saturated and unsaturated imidazole and phosphine-based catalysts as well as Molybdenum-based catalysts, and variants thereof (for a representative, non-exhaustive list, see below, wherein Cy is cyclohexyl, Me is methyl, Ph is phenyl, and iPr is isopropyl) can be used.

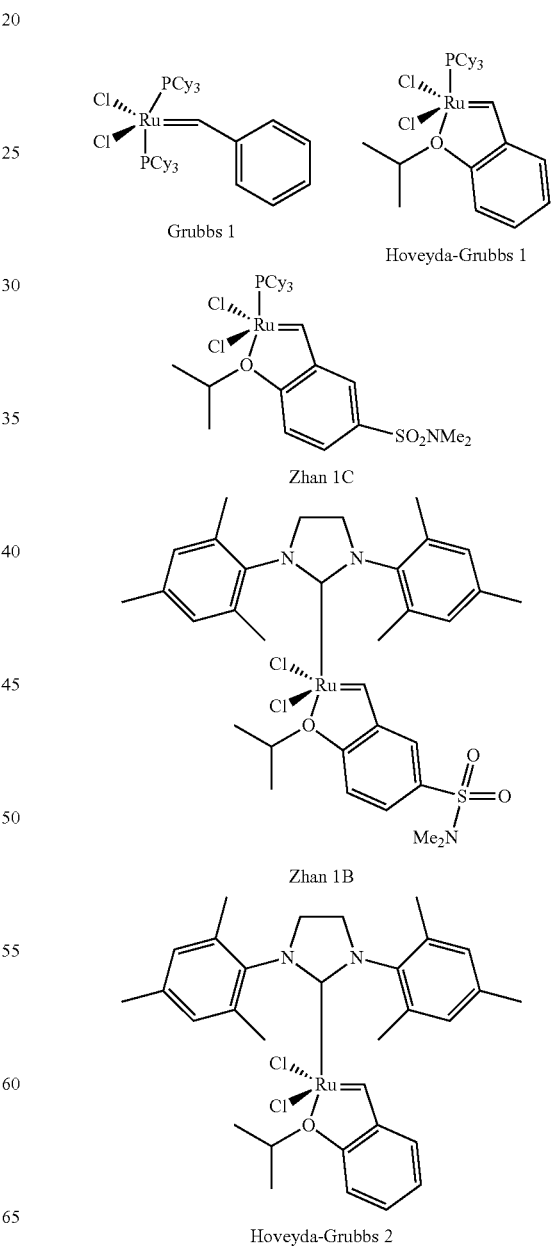

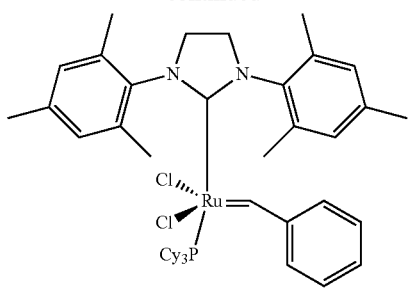

Grubbs 2

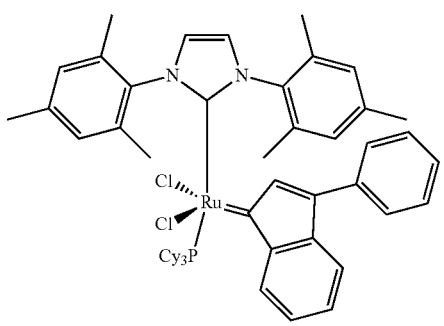

NolanII (IMes)

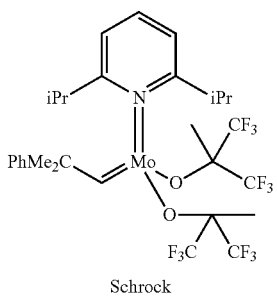

Schrock

In addition, other promoters (e.g., acetic acid, benzoquinones, CuI, CsCl, or Ti(O-i-Pr)₄), ethylene, or promoting conditions (e.g., microwave irradiation) may be employed. Further, temperatures ranging from about 40° C. to 110° C. may be used. Other solvents, such as halogenated (e.g., dichloromethane, 1,2-dichloroethane, chlorobenzene, or hexafluorobenzene), organic (e.g., benzene, THF, methyl-tert-butyl ether, cyclopentyl methyl ether, ethyl acetate, n-heptane, dimethyl carbonate, dimethyl formamide, acetonitrile), or alcohols (e.g., methanol, isopropanol) may be used.

F. Synthesis of Compound of Formula X (R=CH₃)

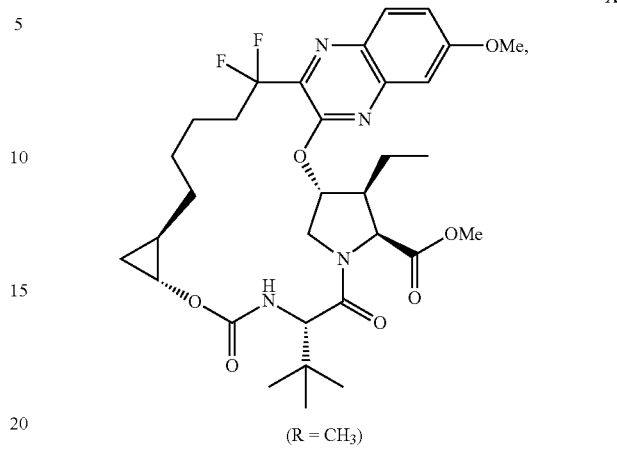

Hydrogenation of IX (R=CH₃) to Provide X (R=CH₃):

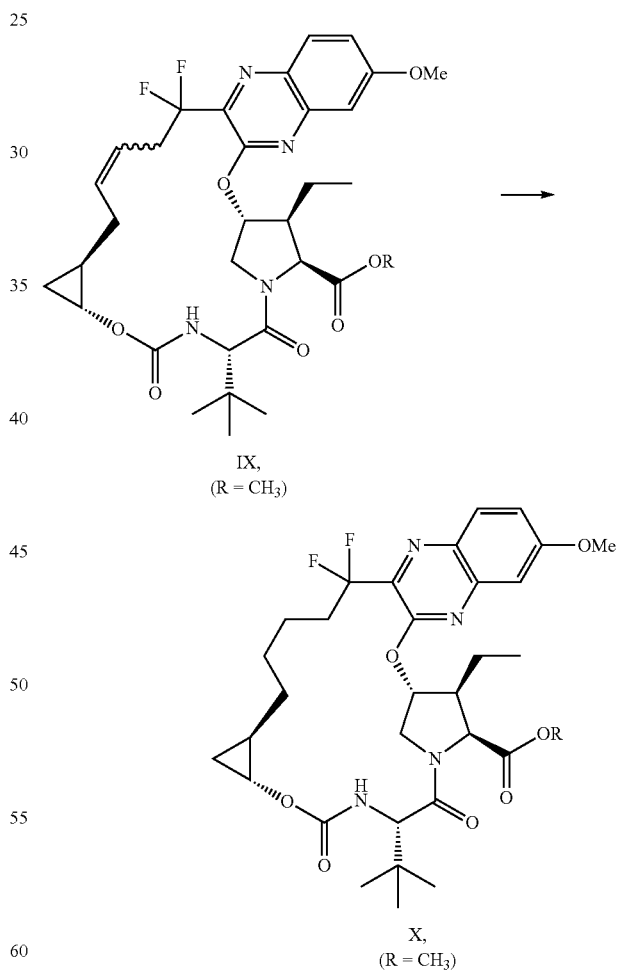

IX (R=CH₃) in 5 volumes of iso-propyl acetate (IPAc) and Pt/C (5 wt % relative to IX (R=CH₃)) were charged to a reaction vessel. The reactor was inerted with N₂, then evacuated and filled with H₂ to 5 psig. The mixture was stirred vigorously for about 12 to 24 hours under 5 psig H₂ at room temperature. After completion of the reaction, diatomaceous earth (5 wt %) was charged, and mixture was filtered to remove the solids, rinsing forward with additional IPAc. The IPAc solution was treated with 6 volumes of 5% aqueous N-acetyl cysteine solution at about 50° C. for overnight under $N_2$ with vigorous agitation. After cooling to room temperature, the aqueous layer was removed and the organic layer was rinse with 6 volumes of 5-10% aqueous $NaHCO_3$ and 6 volumes of 10% aqueous NaCl. Diatomaceous earth (0.5 S) was added, the mixture was stirred for about 5 minutes, and the solids were subsequently removed by filtration. The solution of X ($R=CH_3$) was carried on without further purification.

$^1$H NMR (400 MHz, $CDCl_3$) δ 7.97 (d, J=9.2 Hz, 1H), 7.26 (dd, J=9.2, 2.7 Hz, 1H), 7.09 (d, J=2.7 Hz, 1H), 5.88 (d, J=3.9 Hz, 1H), 5.29 (d, J=9.9 Hz, 1H), 4.74 (d, J=7.2 Hz, 1H), 4.38-4.25 (m, 2H), 4.13-4.07 (m, 1H), 3.94 (s, 3H), 3.78-3.76 (m, 1H), 3.71 (s, 3H) 2.63 (app dd, J=15.0, 7.5 Hz, 1H), 2.54-2.32 (m, 1H), 2.02-1.98 (m, 1H), 1.84-1.63 (m, 4H), 1.53-1.33 (m, 3H), 1.30-1.10 (m, 4H), 1.07 (s, 9H), 0.95-0.80 (m, 2H), 0.77-0.64 (m, 1H), 0.46 (dd, J=12.9, 6.3 Hz, 1H). 19F NMR (376 MHz, CDCl3) δ −102.43 (ddd, J=250.4, 25.4, 8.6 Hz), −103.47 (ddd, J=250.4, 28.7, 11.3 Hz).

Alternative reagents and reactions conditions to those disclosed above may also be employed. For example, other catalysts, such as heterogeneous metal catalysts (e.g., platinum, palladium, ruthenium, or nickel), metals on carbon, alumina, silica, and other heterogeneous supports, metal nanoparticles, frustrated Lewis pairs (e.g., hydrogen [4-[bis (2,4,6-trimethylphenyl)phosphino]-2,3,5,6-tetrafluorophenyl]hydrobis(2,3,4,5,6-pentafluorophenyl)borate), homogeneous metal catalysts (e.g., chlorotris(triphenylphosphine) rhodium(I), or (1,5-cyclooctadiene)(pyridine)(tricyclohexylphosphine)-iridium(I) hexafluorophosphate) can be used. In addition, water, protic solvents (e.g., methanol, ethanol, or acetic acid), aprotic solvents (e.g., dimethyl sulfoxide, tetrahydrofuran, ethyl acetate, acetonitrile, toluene, dichloromethane or acetone), or combinations of the above may be employed. Further, hydrogen gas at a range of pressures or formates (e.g., ammonium formate or formic acid) may be used. In addition, diimide and temperatures ranging from about −20° C. to about 150° C. may be employed.

G. Synthesis of Compound of Formula XI (R=H) from X ($R=CH_3$)

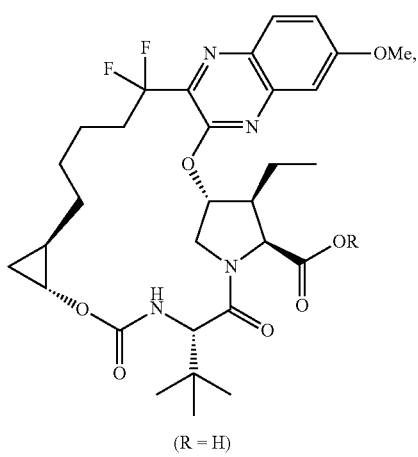

XI
(R = H)

II. Hydrolysis of X to Provide XI:

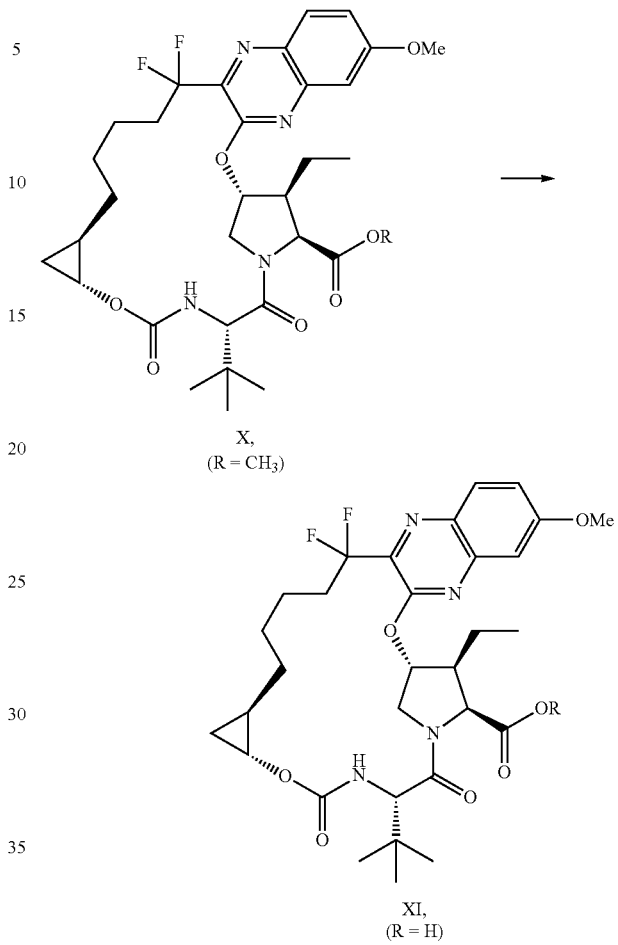

X,
(R = CH$_3$)

XI,
(R = H)

To solution of X ($R=CH_3$) in IPA (7 volumes) at about 30° C. under $N_2$ was added a solution of aqueous LiOH over about 5 to 10 minutes (1M, 2.3 eq). The reaction mixture was warmed to an internal temperature of about 40° C., and stirred. After cooling to room temperature MTBE (8 volumes) was added. The resulting mixture was acidified to pH 3 with 1M HCl. The aqueous layer is removed and the organic layer is rinsed twice with 10% aqueous NaCl. Diatomaceous earth is added (0.1 S), and the resulting slurry is filtered, rinsing forward with additional MTBE. The MTBE is removed via vacuum distillation, and the resulting solids are dissolved in 5 volumes ethanol and 5 volumes heptane at about 60 to 65° C. The solution is then cooled to about 45 to 50° C. and seeded with a slurry of XI in ethanol/heptane (0.005 S). After stirring for about 6 hours at about 45° C., the slurry is cooled to about 15° C. over about 10 hours. An additional 5 volumes heptane are added over about 1 hour. XI was isolated via vacuum filtration and rinsed with 5 volumes 1:9 EtOH:heptane. The resulting solids are dried in a vacuum oven at about 40° C. to constant weight. $^1$H NMR (400 MHz, CDCl$_3$) δ 7.95 (d, J=9.2 Hz, 1H), 7.24 (dd, J=9.2, 2.6 Hz, 1H), 7.07 (d, J=2.6 Hz, 1H), 5.87 (d, J=3.5 Hz, 1H), 5.47 (d, J=9.9 Hz, 1H), 4.72 (d, J=7.2 Hz, 1H), 4.33 (d, J=12.2 Hz, 1H), 4.32 (d, J=9.9 Hz, 1H), 4.04 (dd, J=11.9, 4.0 Hz, 1H), 3.93 (s, 3H), 3.7 (m, 1H), 2.64 (m, 1H), 2.43 (m, 1H), 1.99 (m, 1H), 1.8-1.3 (m, 6H), 1.25-1.15 (m, 3H), 1.0 (m, 1H). $^{13}$C NMR (75 MHz, CDCl₃): δ 172.63, 171.64, 162.06, 157.49, 153.37, 142.42, 139.12 (dd, $J_{CF}$=30.6, 25.8 Hz), 133.06, 130.44, 120.1 (t, $J_{CF}$=245 Hz), 119.93, 105.31, 77.45, 61.66, 59.49, 55.74, 54.98, 51.92, 46.52, 36.42 (t, $J_{CF}$=25.0), 34.91, 30.35, 27.74, 26.19, 21.53, 19.99, 18.34, 12.06, 11.33.

Alternative reagents and reactions conditions to those disclosed above may also be employed. For example, carbonates (e.g., lithium, sodium, or cesium carbonates), metal hydrides (e.g., sodium hydride, or potassium hydride), alkoxides (e.g., sodium methoxide, sodium tert-butoxide, lithium tert-butoxide, potassium tert-butoxide, or tetraalkylammonium alkoxides), hydroxides (e.g., sodium hydroxide, potassium hydroxide, tin hydroxides, or tetraalkylammonium hydroxides), or amine bases, (e.g., DBU) may be employed. In addition, protic acids (e.g., sulfuric acid, hydrochloric acid, p-toluene sulfonic acid, or solid-supported acids), Lewis acids (e.g., boron trifluoride), metal salts, metal complexes, or hydrogen-bond donors can be used. Further, polar protic solvents, including water, alcohols (e.g., methanol, ethanol, iso-propanol, tert-butanol, neopentyl alcohols, glycols, and combinations of these with water), polar aprotic solvents, (e.g., dimethyl sulfoxide, dimethyl formamide, tetrahydrofuran, 1,4-dioxane, or combinations of these with water), or ionic liquids, (e.g., 3-methylimidazolium hexafluorophosphate) may be employed.

H. Synthesis of Compound of Formula I from X (R=CH₃)

Synthesis of compound of formula I from X was similar to that described in U.S. Publication No. 2014-0017198. X (R=CH₃) was hydrolyzed to form XI (R=H) which was coupled with XII to form I.

Alternative Route with t-Butyl Ester on Proline

An alternative scheme employing the t-butyl ester of the proline portion as was used in U.S. Publication No. 2014-0017198, but with the new RCM route homologs of the proline and cyclopropyl-leucine portions. The tert-butyl group can be removed by acid treatment after the hydrogenation stage.

Synthesis of Compound of Formula VI (R=tert-Bu), tert-Butyl(2S,3S,4R)-4-((3-(1,1-difluorobut-3-en-1-yl)-7-methoxyquinoxalin-2-yl)oxy)-3-ethylpyrrolidine-2-carboxylate

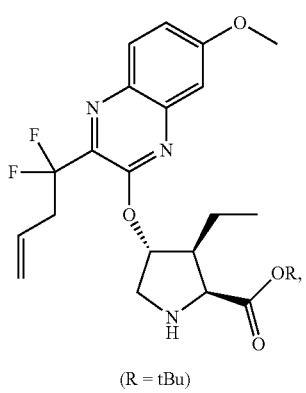

VI
(R = tBu)

I. Boc Deprotection of V (R=tert-Bu) to Provide VI (R=tert-Bu)

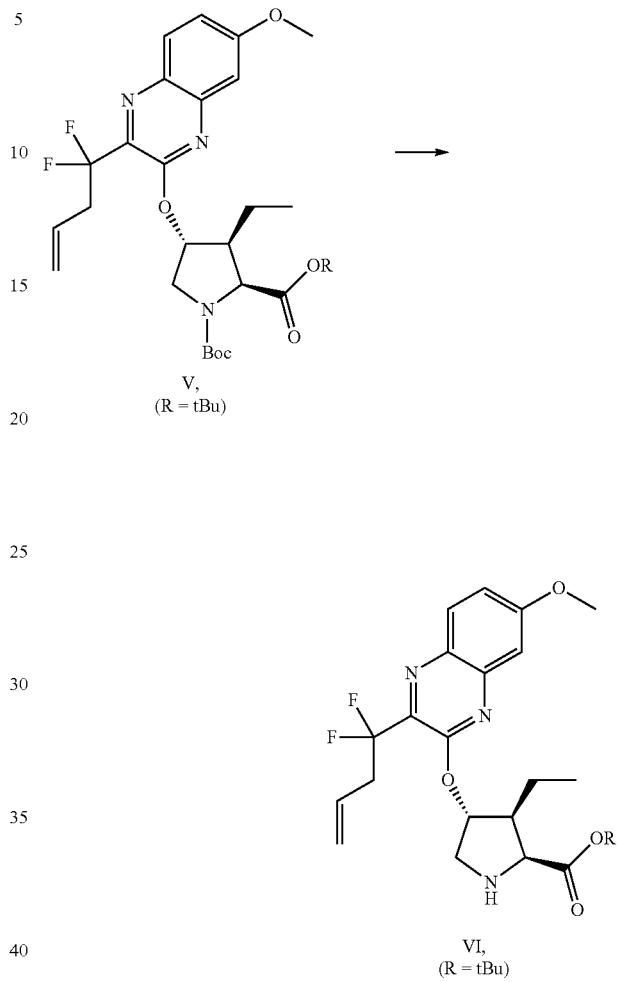

V (R=tert-Bu) (0.88 g, 1.56 mmol, 1.0 eq.), t-BuOAc (9.5 mL, 11 vols.) and CH₂Cl₂ (2.4 mL, 2.7 vols.) were charged to a round bottom flask equipped with a magnetic stir bar. Methanesulfonic acid was charged (0.51 mL, 7.8 mmol, 5.0 eq.) and the reaction mixture was stirred overnight at about 20° C. for about two hours. The reaction solution was then poured into 60 mL of a 1:1 saturated NaHCO₃/EtOAc mixture and the organic layer was separated. The aqueous layer was subsequently back-extracted with EtOAc and the combined organics were washed successively with saturated NaHCO₃ and brine followed by drying with magnesium sulfate, filtering and concentrating to obtain VI (R=tert-Bu). LCMS: m/z=464.4.

Alternative reagents and reactions conditions to those disclosed above may also be employed. For example, other acids, such as inorganic (e.g., hydrochloric acid) or organic (e.g., p-toluenesulfonic acid) may be used. In addition, other organic solvents (e.g., isopropyl acetate, methyl-t-butyl ether, or 2-methyl tetrahydrofuran) and temperatures ranging from about 50° C. to about 60° C. may be employed.

Synthesis of compound of formula VIII (R=tert-Bu), tert-Butyl(2S,3S,4R)-1-((S)-2-((((1R,2R)-2-allylcyclopropoxy)carbonyl)amino)-3,3-dimethylbutanoyl)-4-((3-(1,1-difluorobut-3-en-1-yl)-7-methoxyquinoxalin-2-yl)oxy)-3-ethylpyrrolidine-2-carboxylate I. Amide Coupling of VI (R=Tert-Bu) and VII to Provide VIII (R=Tert-Bu)

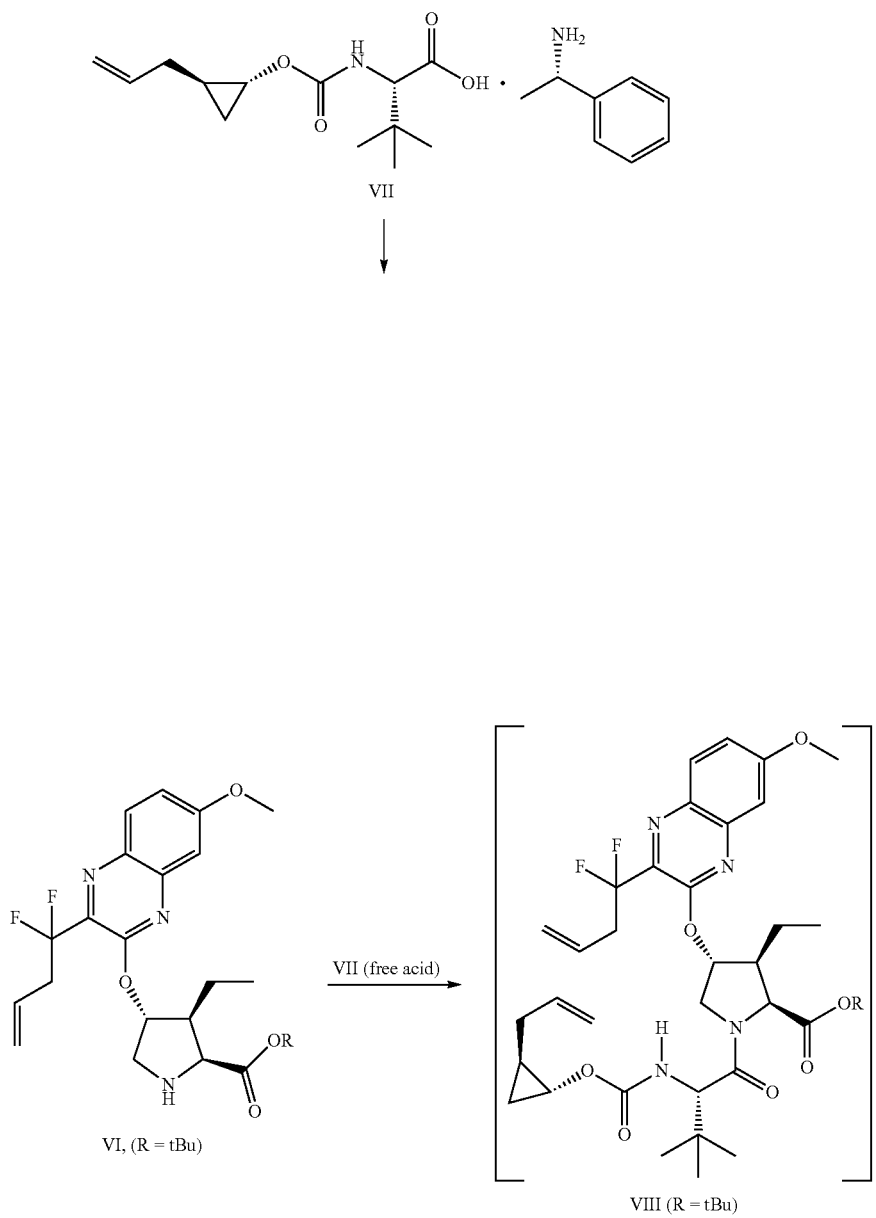

VI (R=tert-Bu) (4.12 g, 8.9 mmol, 1.0 eq.), VII (2.72 g, 10.7 mmol, 1.2 eq.) and acetonitrile (120 mL, 29 vols.) were charged to a flask. HATU (4.4 g, 11.6 mmol, 1.3 eq.) followed by DIPEA (6.2 mL, 35.6 mmol 4 eq.) were then charged. The reaction mixture was stirred overnight at about 20° C. The reaction mixture was then concentrated and purified by silica gel flash column chromatography (eluent gradient of 0% to 18% to 25% ethyl acetate in hexanes) to obtain VIII. LCMS: m/z=701.1.

Alternative reagents and reactions conditions to those disclosed above may also be employed. For example, other coupling reagents (e.g., ethyl-3-(3-dimethylaminopropyl) carbodiimide or hydroxybenzotriazole monohydrate) can be used. In addition, other bases (e.g., pyridine, morpholine, imidazole, or N-methylmorpholine) and organic solvents (e.g., dimethylacetamide, or N,N-dimethylformamide) may be employed.

Synthesis of compound of formula IX (R=tert-Bu) tert-butyl(33R,34S,35S,91R,92R,5S)-5-(tert-butyl)-34-ethyl-14,14-difluoro-17-methoxy-4,7-dioxo-2,8-dioxa-6-aza-1(2,3)-quinoxalina-3(3,1)-pyrrolidina-9(1,2)-cyclopropanacyclotetradecaphan-11-ene-35-carboxylate

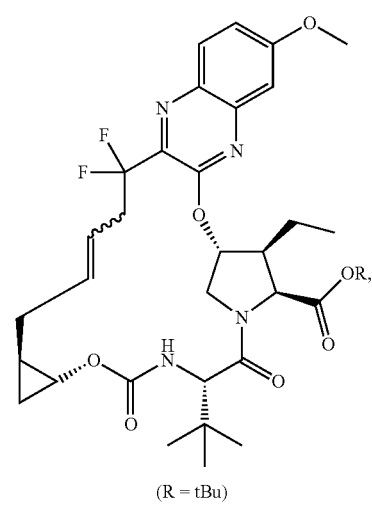

(R = tBu)

II. Ring Closing Metathesis of VIII (R=Tert-Bu) to Provide IX (R=Tert-Bu)

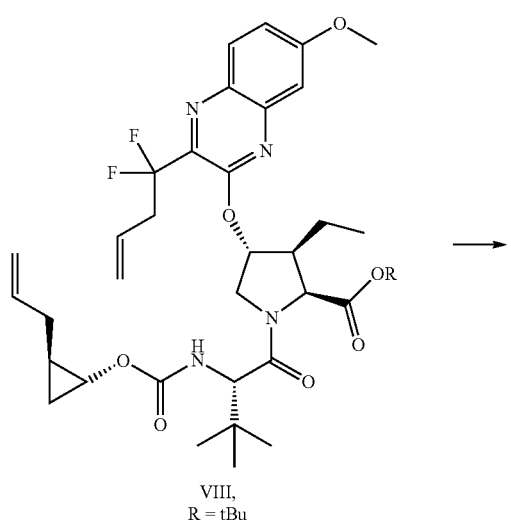

VIII, R = tBu

-continued

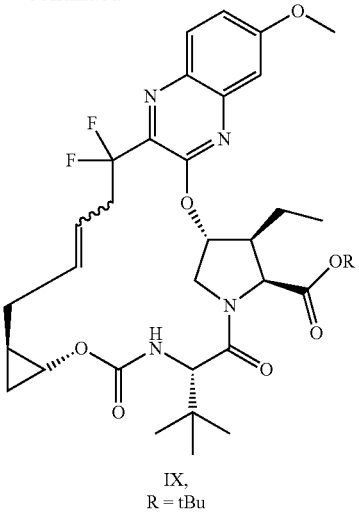

IX, R = tBu

Zhan 1B catalyst (26 mg, 0.036 mmol, 0.025 equiv.) was charged to a flask. The flask was evacuated and back-filled with nitrogen three times. Nitrogen-sparged toluene (25 mL) was charged and the mixture was agitated and heated to reflux (about 110° C.). A solution of compound VIII (R=tert-Bu) (1.0 g, 1.4 mmol, 1.00 equivalents) in 5 mL toluene was added over 30 minutes, maintaining a reaction temperature of about 110° C. Upon reaction completion, the reaction mixture was cooled to about 20° C. and purified by flash column chromatography (54 g silica gel, 20% ethyl acetate in hexane as eluent) to yield IX (R=tert-Bu). $^1$H NMR (300 MHz, CDCl$_3$): δ 7.95 (d, J=6.0 Hz, 1H), 7.26 (m, 1H), 7.12 (m, 1H), 5.89 (m, 1H), 5.69 (m, 2H), 5.27 (d, J=9.0 Hz, 1H), 4.62 (d, J=6.0 Hz, 1H), 4.35 (d, J=9.0 Hz, 1H), 4.29 (d, J=6.0 Hz, 1H), 4.02-3.95 (m, 1H), 3.96 (s, 3H), 3.88 (m, 1H), 3.21 (s, 2H), 2.90-2.70 (m, 1H), 2.49 (d, J=12.0 Hz, 1H), 1.48 (m, 9H), 1.41 (m, 2H), 1.25-1.18 (m, 4H), 1.06 (s, 9H), 1.00-0.93 (m, 2H), 0.50 (m, 1H). $^{19}$F NMR (282.2 MHz, CDCl$_3$): δ −101.0 ppm (m).

Alternative reagents and reactions conditions to those disclosed above may also be employed. For example, other ruthenium-based Grubbs, Grubbs-Hoveyda, saturated and unsaturated imidazole and phosphine-based catalysts as well as Molybdenum-based catalysts, and variants thereof (for a representative, non-exhaustive list, see below, wherein Cy is cyclohexyl, Me is methyl, Ph is phenyl, and iPr is isopropyl) can be used.

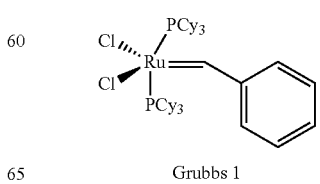

Grubbs 1

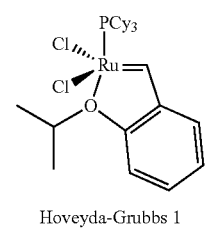

Hoveyda-Grubbs 1

-continued

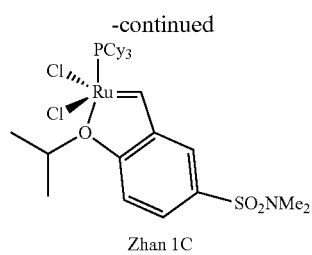

Zhan 1C

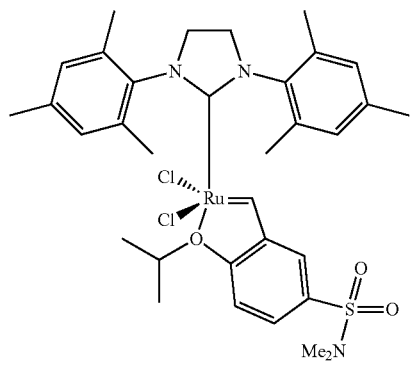

Zhan 1B

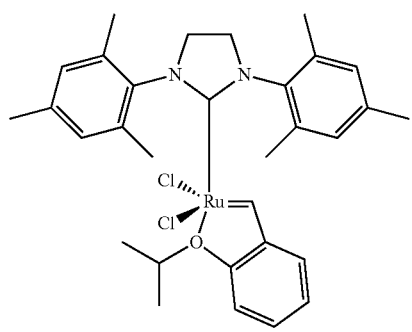

Hoveyda-Grubbs 2

-continued

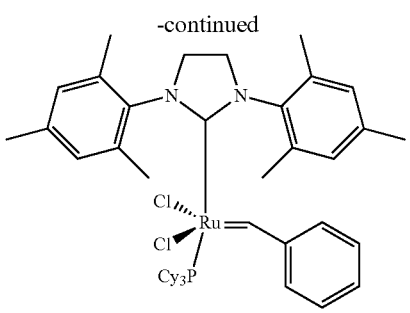

Grubbs 2

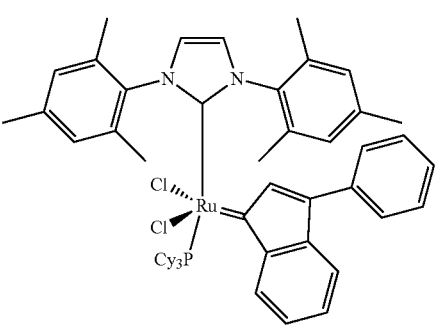

NolanII (IMes)

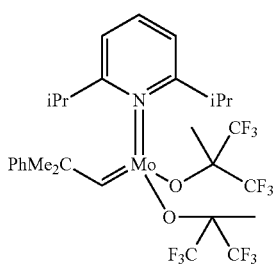

Schrock

In addition, other promoters (e.g., acetic acid, benzoquinones, CuI, CsCl, or Ti(O-i-Pr)), or promoting conditions (e.g., microwave irradiation, or ethylene) may be employed. Further, temperatures ranging from about 40° C. to 110° C. may be used. Other solvents, such as halogenated (e.g., dichloromethane, 1,2-dichloroethane, chlorobenzene, or hexafluorobenzene), organic (e.g., benzene, THF, methyl tert-butyl ether, cyclopentyl methyl ether, ethyl acetate, n-heptane, dimethyl carbonate, dimethyl formamide, or acetonitrile), or alcohols (e.g., methanol, isopropanol) may be used.

Example 2
Synthesis of (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide (I) by route II
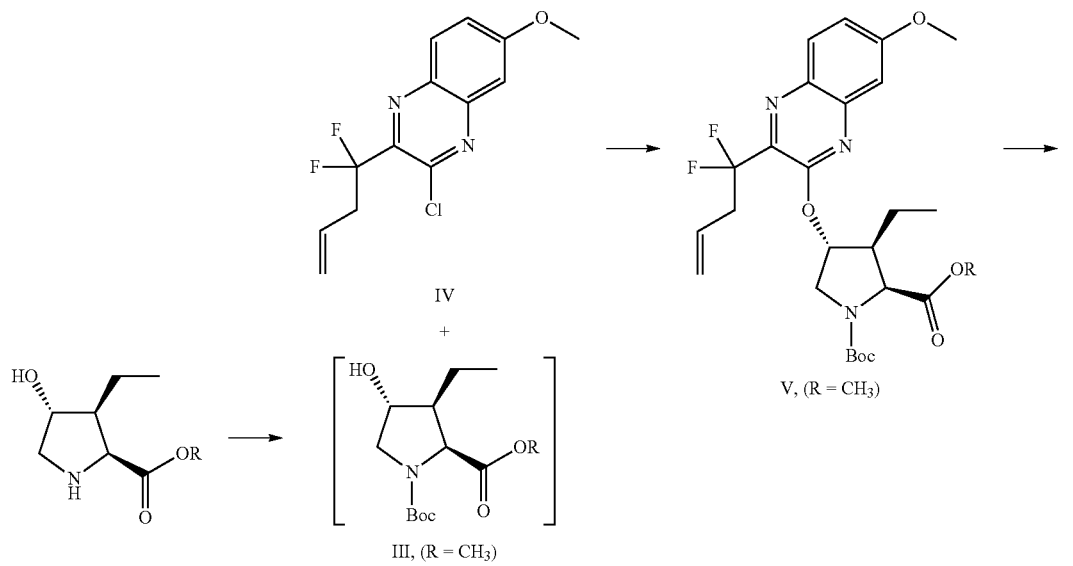
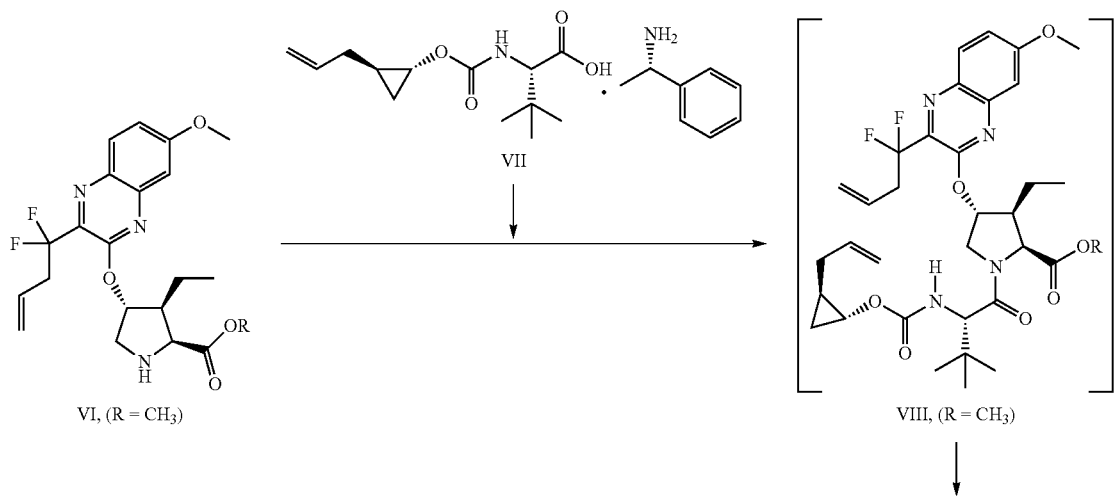

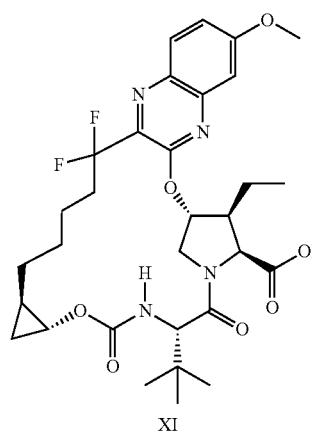
XI
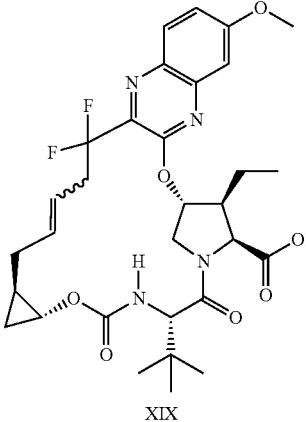
XIX
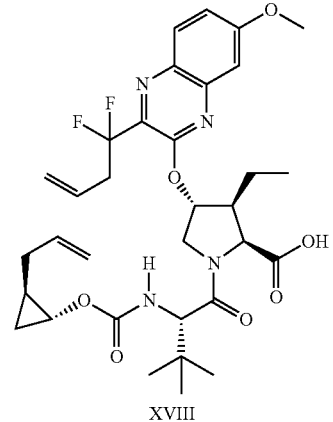
XVIII
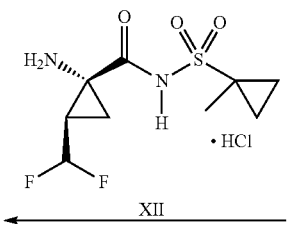
I ← XII
a. Hydrolysis, Ring Closing Metathesis and Hydrogenation:
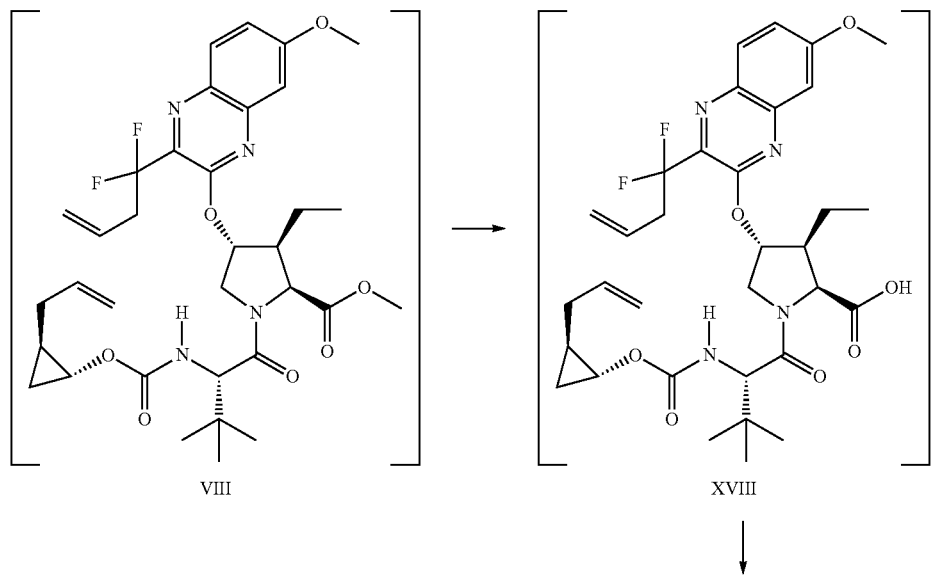

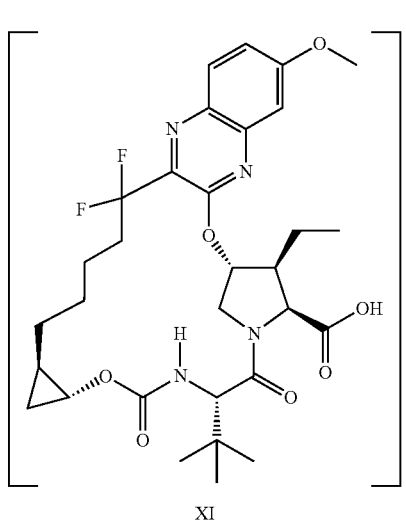

XI

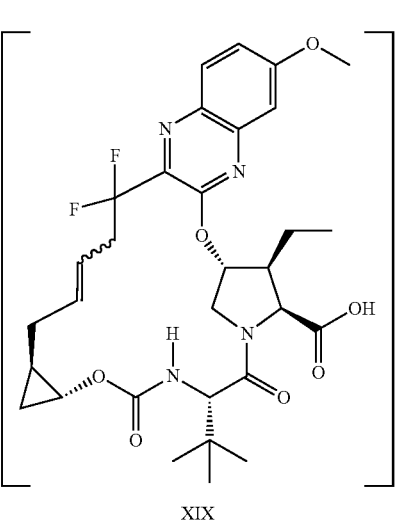

XIX

Route II differs from route I of Example I in the order of assembly. Compound of formula VIII was hydrolyzed first to provide compound of formula XVIII and then subjected to the ring closing metathesis to provide compound of formula XIX which on hydrogenation yielded compound of formula XI. The reaction conditions for hydrolysis, ring closing metathesis, and hydrogenation were similar to those disclosed in route I. Compound of formula XI was converted to compound of formula I as discussed above in Example 1.

Example 3

Synthesis of (1aR,5S,8S,9S,10R,22aR)-5-tert-butyl-N-[(1R,2R)-2-(difluoromethyl)-1-{[(1-methylcyclopropyl)sulfonyl]carbamoyl}cyclopropyl]-9-ethyl-18,18-difluoro-14-methoxy-3,6-dioxo-1,1a,3,4,5,6,9,10,18,19,20,21,22,22a-tetradecahydro-8H-7,10-methanocyclopropa[18,19][1,10,3,6]dioxadiazacyclononadecino[11,12-b]quinoxaline-8-carboxamide (I) by route III Compound of formula I was synthesized via route III as shown below:

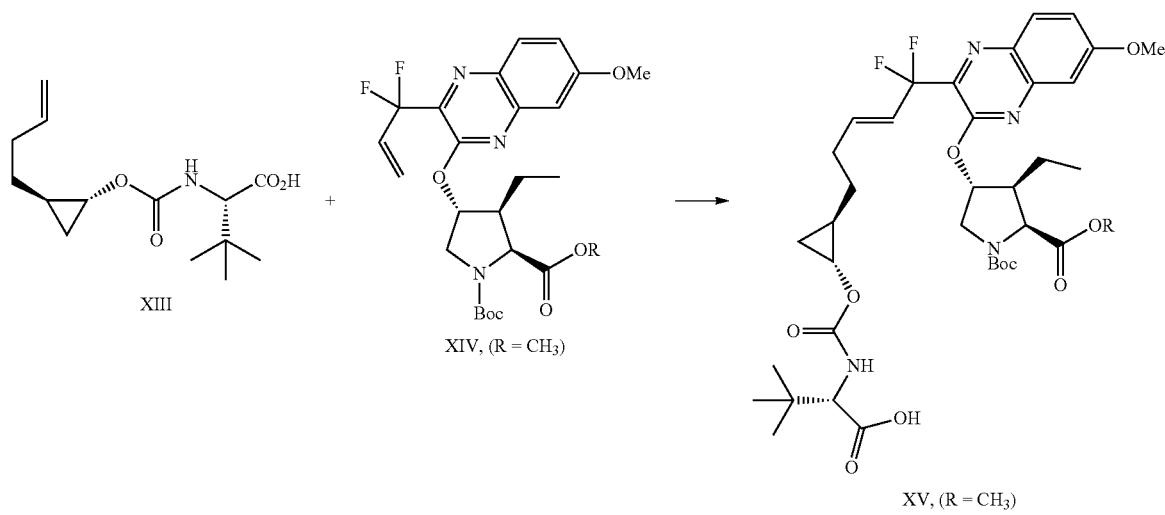

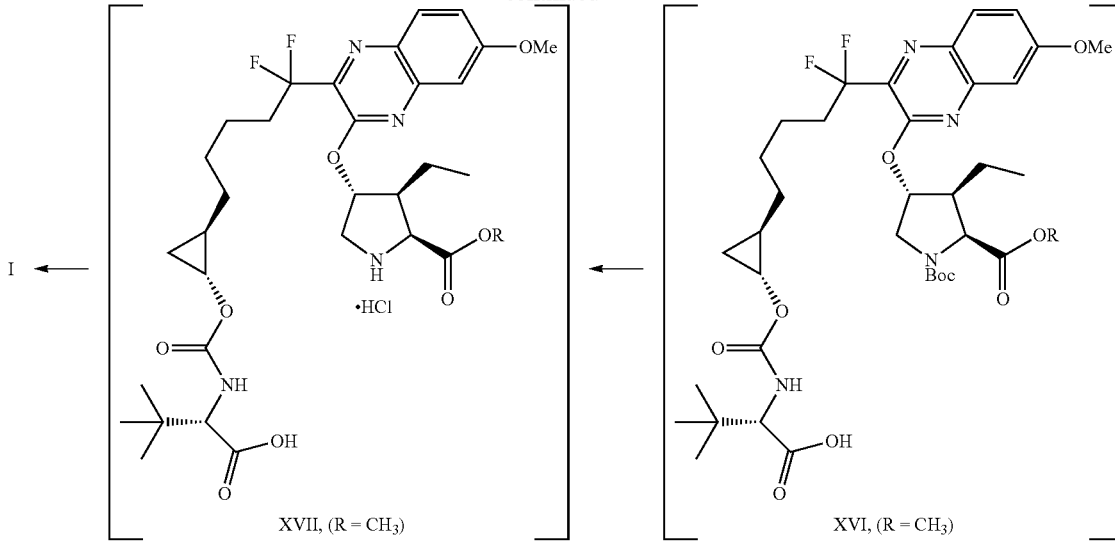

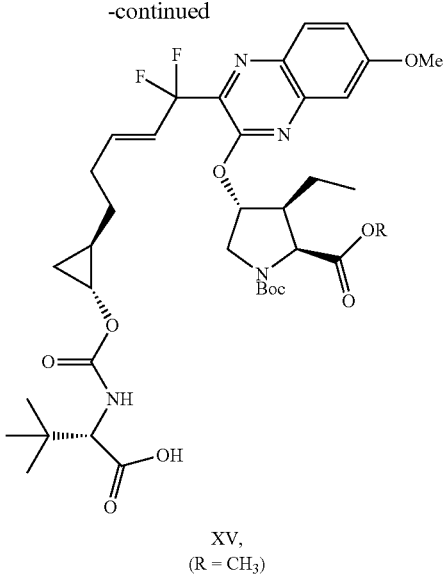

A. Synthesis of XV

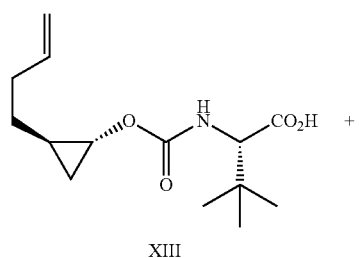

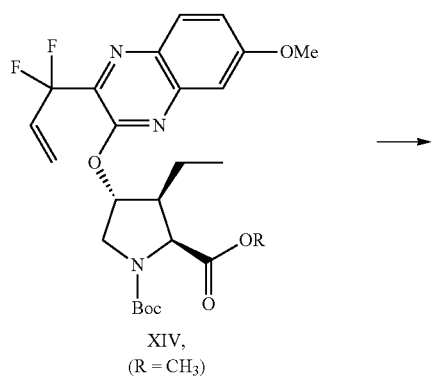

Compound XIV (R=CH₃) (180 mg, 0.35 mmol, 1 equiv) and XIII (180 mg, 0.67 mmol, 1.9 equiv) were dissolved in 15 volumes of degassed toluene (2.7 mL). The system was inerted under nitrogen, and Zhan 1B catalyst (53 mg, 0.073 mmol, 0.20 equiv.) was charged. The mixture was warmed to about 95° C. and stirred for about 45 minutes. The reaction was cooled to about 20° C., and purified by silica gel chromatography to provide intermediate XV (R =CH₃). LCMS (M+1): 749 m/z. $^1$H NMR (400 MHz, CDCl₃): δ 7.98-7.90 (m, 1H), 7.28-7.14 (m, 2H), 6.30-5.95 (m, 1H), 5.58-5.19 (m, 3H), 4.56 (dd, 1H, J=36.8, 8.5 Hz), 4.46-4.24 (m, 1H), 4.22-4.01 (m, 3H), 3.95 (s, 3H), 3.85-3.67 (m, 5H), 3.40-3.27 (m, 1H), 2.50-1.98 (m, 4H), 1.65-1.55 (m, 1H), 1.43-1.41 (m, 9H), 1.1-0.7 (m, 11H), 0.57-0.40 (m, 2H).

B. Hydrogenation of Intermediate XV (R=CH₃) and Hydrolysis of XVI (R=CH₃)

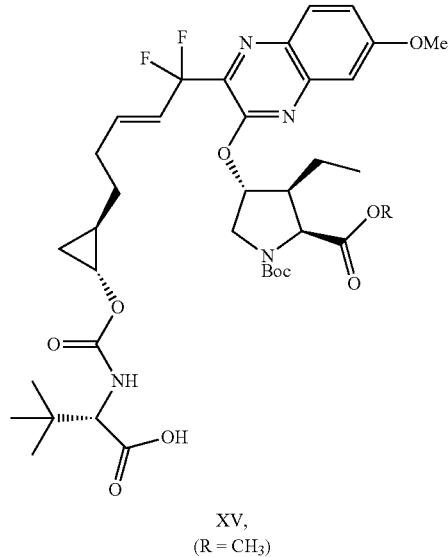

XV, (R = CH₃)

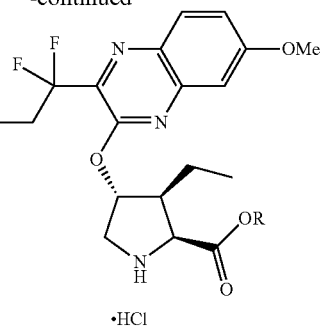

XVII, (R = CH₃)

A mixture of intermediate XV (R=CH₃) (117 mg, 0.156 mmol) and Pt/C (13 mg, 5 wt %) in 14 volumes of IPAc (1.6 mL) was stirred under 5 psig H₂ at room temperature for 20 hours. The mixture was filtered through diatomaceous earth, concentrated in vacuo, and purified by silica gel chromatography to yield ~75 mg of intermediate XVI (64% yield). Intermediate XVI was dissolved in 1 mL CH₂Cl₂, and combined with 0.5 mL 4M HCl in dioxane at rt. After about 40 minutes, the mixture was concentrated to yield intermediate XVII, which was carried forward without further purification.

C. Lactamization of (S)-2-(((((1S,2S)-2-(5-(3-(((3R,4S,5S)-4-ethyl-5-(methoxycarbonyl)pyrrolidin-3-yl)oxy)-6-methoxyquinoxalin-2-yl)-5,5-difluoropentyl)cyclopropoxy)carbonyl)amino)-3,3-dimethylbutanoic acid hydrochloride (XVII (R=CH₃)) to form X (R=CH₃)

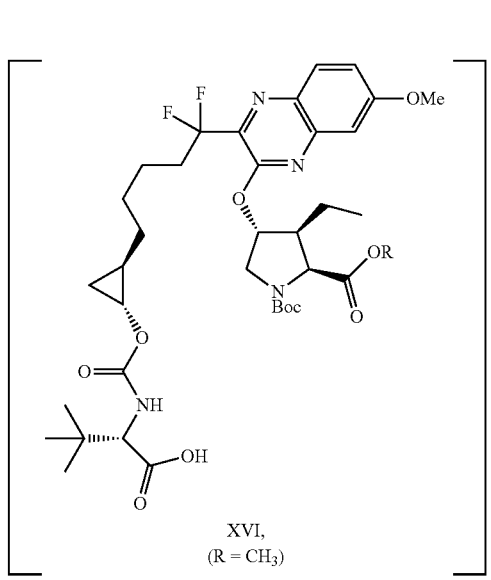

XVI, (R = CH₃)

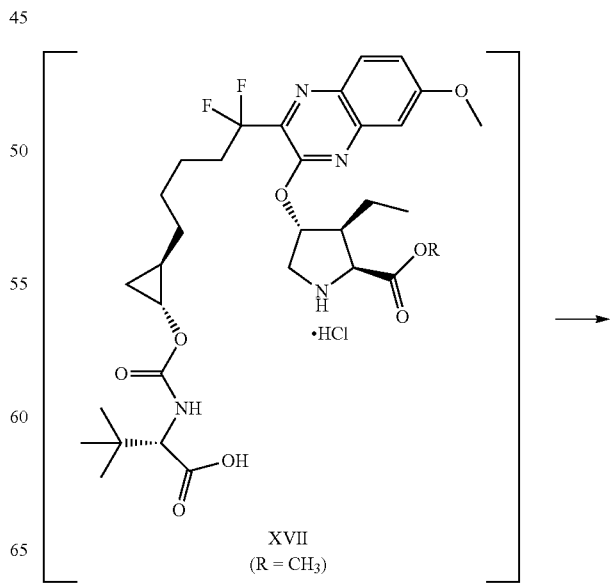

XVII (R = CH₃)

-continued

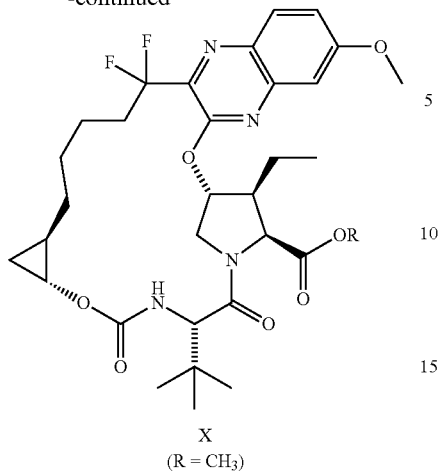

X
(R = CH₃)

To a solution of XVII (20 mg, 0.029 mmol, 1 equiv) in 100V DMF (2 mL) at rt was added HOBt (39.3 mg, 0.29 mmol, 10 equiv), followed by EDC (56 mg, 0.29 mmol, 10 equiv). The mixture was stirred for 5 minutes at which point triethylamine (0.1 mL, 0.72 mmol, 25 equiv) was added. After 4.5 hours, the mixture was diluted with MTBE, rinsed with twice with saturated aqueous NH₄Cl, twice with saturated aqueous NaHCO₃, dried over MgSO₄, filtered, and concentrated in vacuo. The crude product thus obtained was diluted to 25 mL in a volumetric flask. UPLC analysis indicated the presence of X (R=CH₃) (10.6 mg, 59% assay yield).

However, alternative reagents and reactions conditions to those disclosed above may also be employed. For example, other coupling reagents (e.g., carbodiimidazole, N,N'-Dicyclohexylcarbodiimide, N,N'-Diisopropylcarbodiimide, benzotriazol-1-yl-oxytripyrrolidinophosphonium hexafluorophosphate, 1-[Bis(dimethylamino)methylene]-1H-1,2,3-triazolo[4,5-b]pyridinium 3-oxide hexafluorophosphate, or 2,4,6-trichlorobenzoyl chloride) may be used In addition, other bases, such as amine (e.g., diisopropylethylamine, pyridine or sodium hexamethyldisilizide), carbonates (e.g., potassium, or cesium carbonate), bicarbonates (e.g., sodium bicarbonate), or inorganic/organic hydroxides (e.g., sodium hydroxide, or tetramethylammonium hydroxide) may be employed. Other promoters (e.g., 4-dimethylaminopyridine, or 1-Hydroxy-7-azabenzotriazole) can be used. Further, other solvents, such as water, polar aprotics (e.g., N,N-Dimethylformamide (DMF) and dimethyl sulfoxide (DMSO) (or combinations of these with water), organics (e.g., toluene, acetonitrile, or acetone), alcohols (e.g., methanol or ethanol), ethers (e.g., tetrahydrofuran, dioxane or methyl-t-butyl ether), esters (e.g., ethyl acetate), or chlorinated solvents (e.g., dichloromethane) may be employed.

Compound of formula X was converted to compound of formula I as discussed above in Example 1.

What is claimed is:
1. A process for preparation of a compound of formula V:

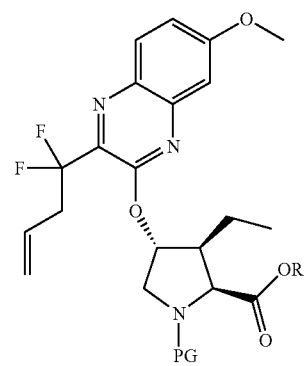

V or a salt thereof;
comprising contacting a compound of formula III or a salt thereof, with a compound of formula IV:

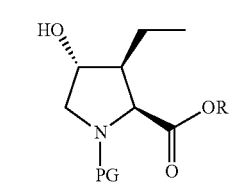

III

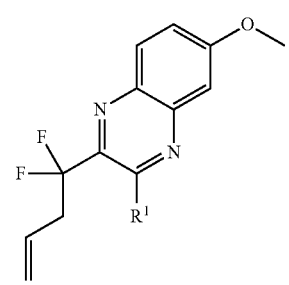

IV under O-arylation conditions to provide the compound of formula V or a salt thereof, wherein R is $C_{1-6}$ alkyl, PG is a protective group, and $R^1$ is a leaving group.

2. A process for preparation of a compound of formula I:

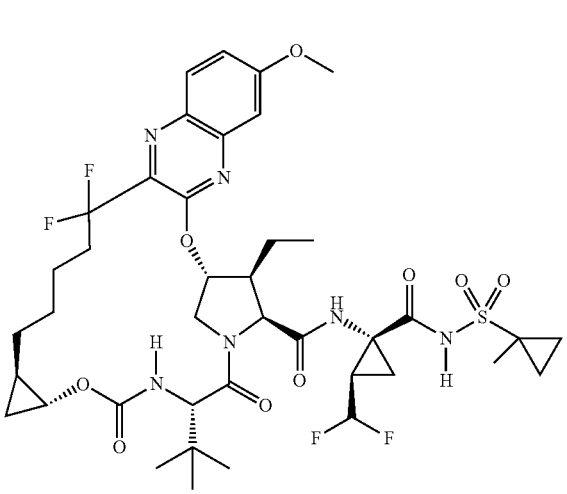

I or a pharmaceutically acceptable salt thereof; comprising:

a) preparing a compound of formula V:

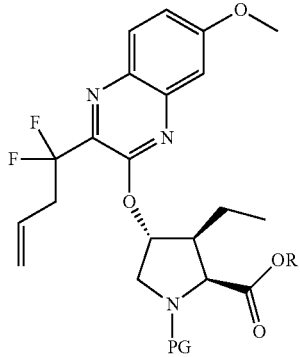

V or a salt thereof according to the process of claim 1;

b) subjecting the compound of formula V or a salt thereof to N-deprotection conditions to provide a compound of formula VI:

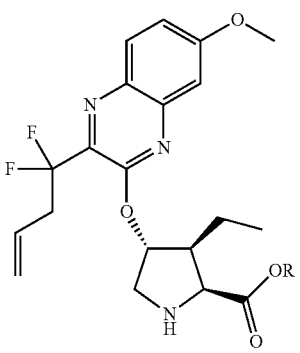

VI or a salt thereof;

c) contacting the compound of formula VI or a salt thereof with a compound of formula VII:

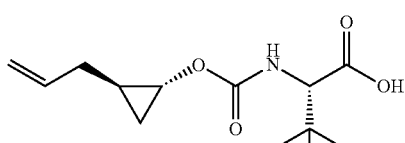

VII or a salt thereof, under amide coupling conditions to provide a compound of formula VIII:

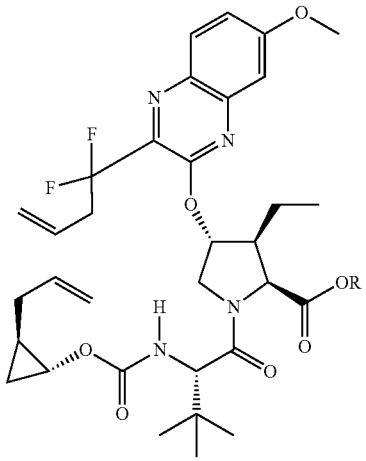

VIII or a salt thereof;

d) performing ring closing metathesis of the compound of formula VIII or a salt thereof to provide a compound of formula IX:

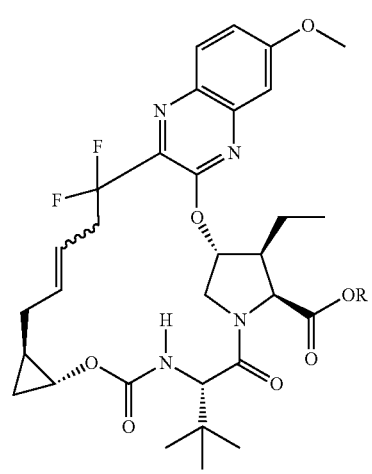

IX or a salt thereof;

e) hydrogenating the compound of formula IX or a co-crystal, or a salt thereof in presence of a catalyst to provide a compound of formula X:

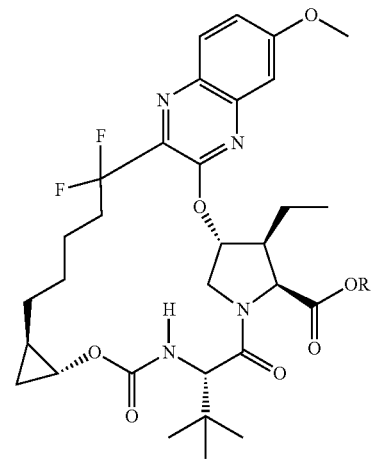

X or a salt thereof;

f) hydrolyzing the compound of formula X or a salt thereof to provide a compound of formula XI:

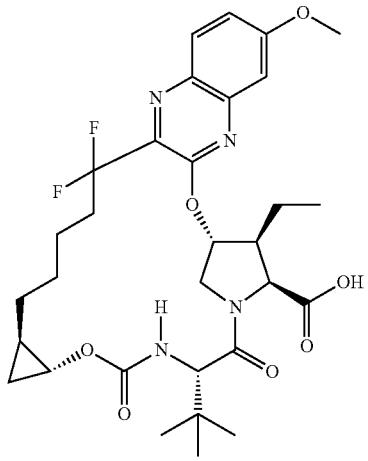

XI or a salt thereof;

g) contacting the compound of formula XI or a salt thereof with a compound of formula

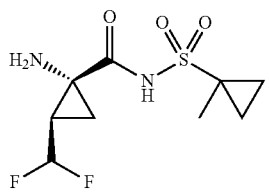

XII or a salt thereof;

under amide coupling conditions to provide the compound formula I:

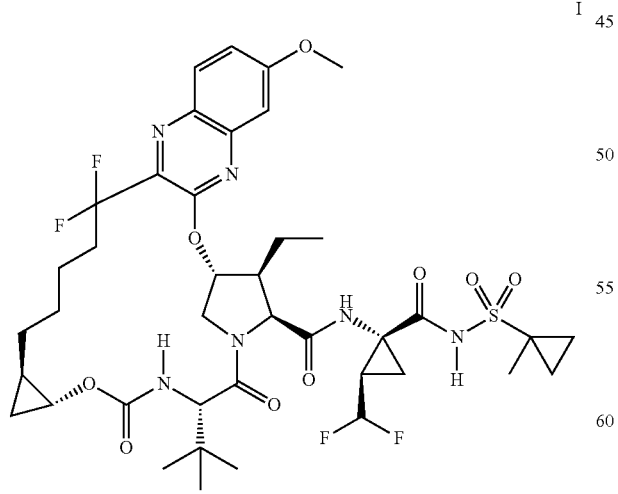

I or a pharmaceutically acceptable salt thereof, wherein R is $C_{1-6}$ alkyl, PG is a protective group, and $R^1$ is a leaving group.

3. A process for preparation of a compound of formula I:

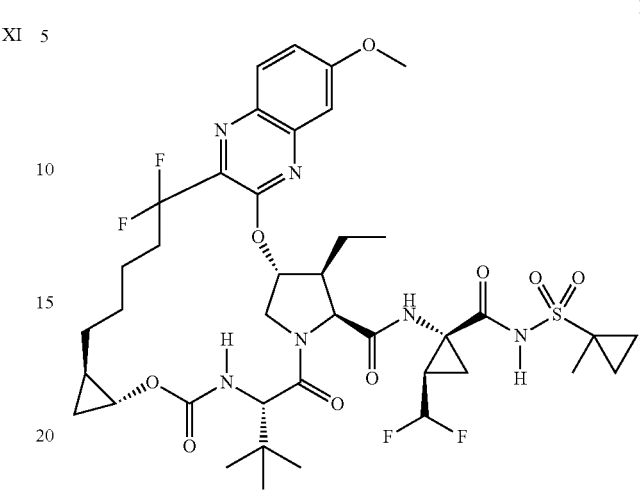

I or a pharmaceutically acceptable salt thereof, comprising:

a) preparing a compound of formula V

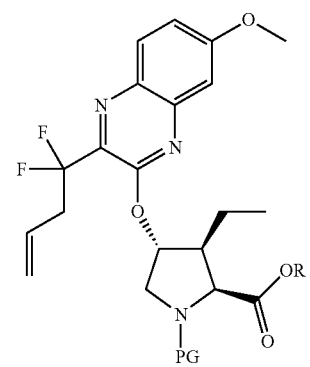

V or a salt thereof according to the process of claim 1;

b) contacting the compound of formula V or a salt thereof with an acid under N-deprotection conditions to provide a compound of formula VI:

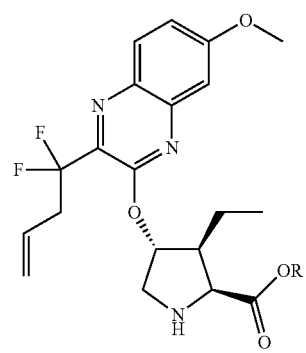

VI or a salt thereof;

c) contacting the compound of formula VI or a salt thereof with a compound of formula VII:

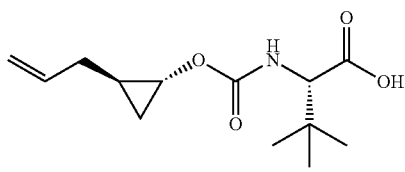
VII or a salt thereof, under amide coupling conditions to provide a compound of formula VIII:

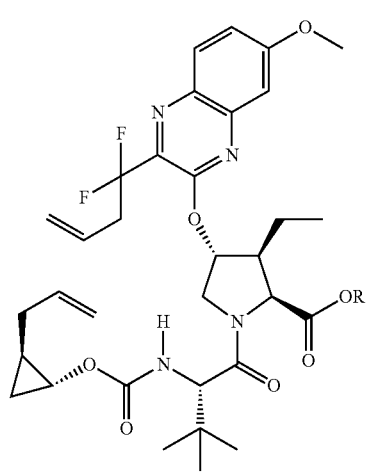
VIII or a salt thereof;

d) hydrolyzing the compound of formula VIII or a salt thereof to provide a compound of formula XVIII:

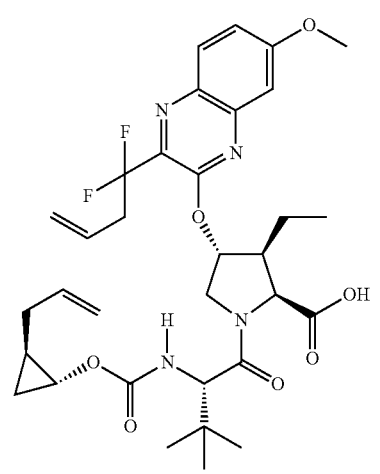
XVIII or a salt thereof;

e) performing ring closing metathesis of the compound of formula XVIII or a salt thereof in presence of a catalyst to provide a compound of formula XIX:

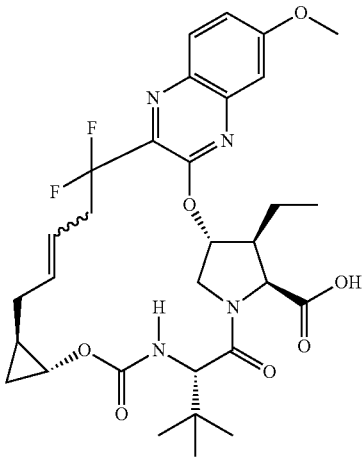
XIX or a salt thereof;

f) hydrogenating the compound of formula XIX in presence of a catalyst to provide a compound of formula XI:

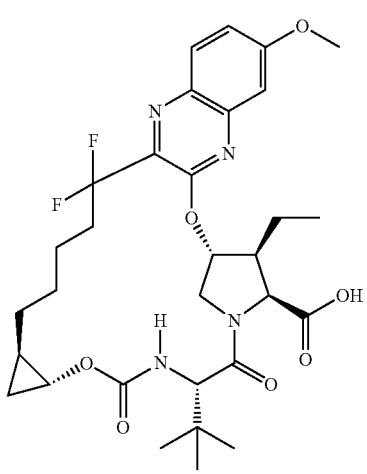
XI or a salt thereof;

g) contacting the compound of formula XI or a salt thereof with a compound of formula XII:

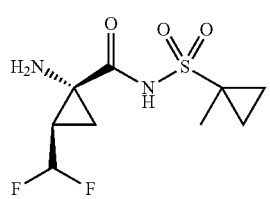
XII or a salt thereof;

under amide coupling conditions to provide the compound formula I:

I

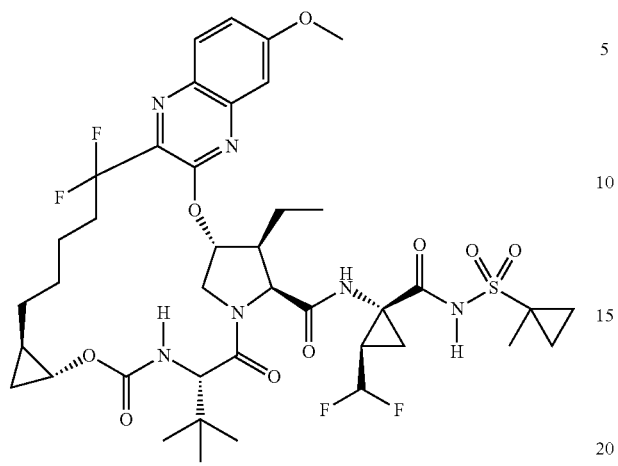

or a pharmaceutically acceptable salt thereof, wherein R is $C_{1-6}$ alkyl, PG is a protective group, and $R^1$ is a leaving group.

4. A process for preparation of a compound of formula XV:

XV

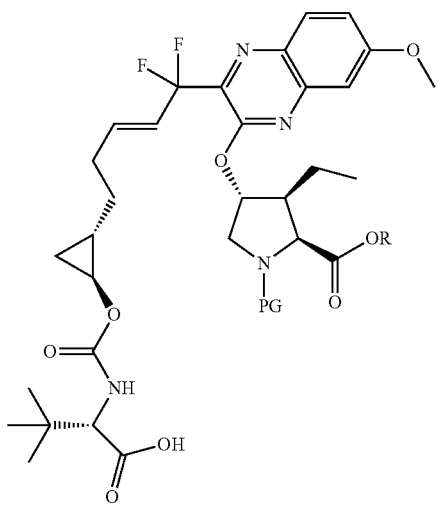

or a salt thereof, comprising contacting a compound of formula XIII:

XIII

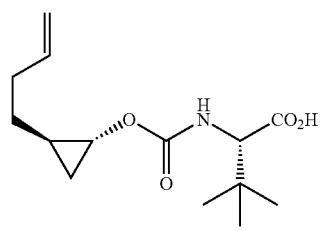

or a salt thereof, with a compound of formula XIV:

XIV

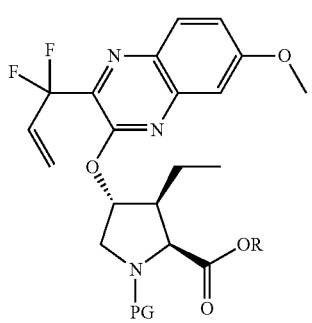

or a salt thereof,
under cross-metathesis conditions to provide the compound of formula XV or a salt thereof, wherein R is $C_{1-6}$ alkyl and PG is a protective group.

5. A process for preparation of a compound of formula I:

I

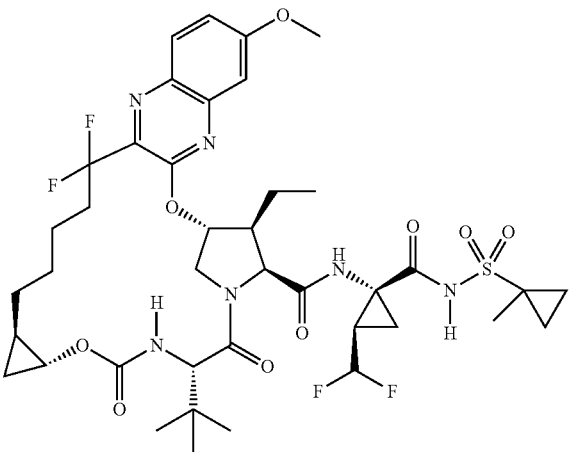

or a pharmaceutically acceptable salt thereof, comprising:
a) preparing a compound of formula XV:

XV

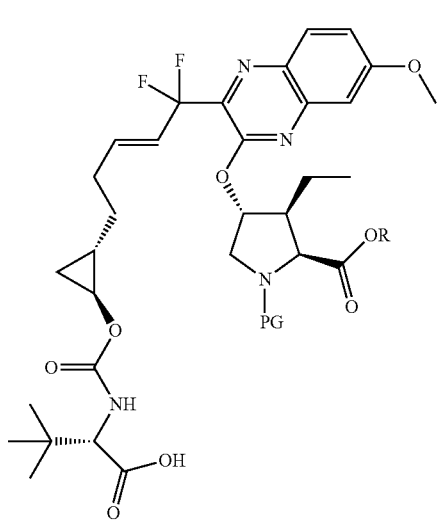

or a salt thereof according to the process of claim 4, b) hydrogenating the compound of formula XV or a salt thereof in presence of a catalyst to provide a compound of formula XVI:

XVI

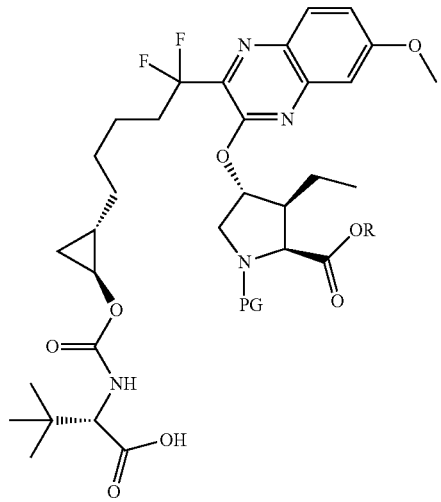

or a salt thereof;

c) subjecting the compound of formula XVI or a salt thereof to N-deprotection conditions to provide a compound of formula XVII:

XVII

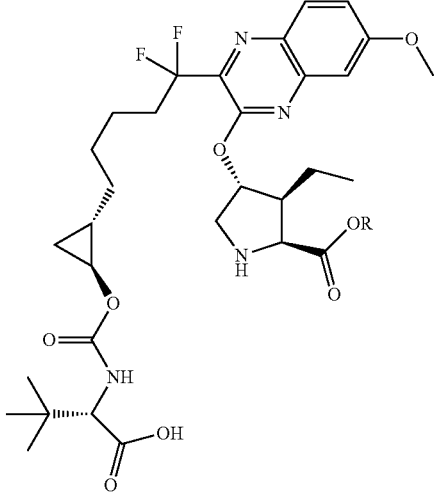

or a salt thereof;

d) contacting the compound of formula XVII with an amide coupling agent under lactamization conditions to give a compound of formula X:

X

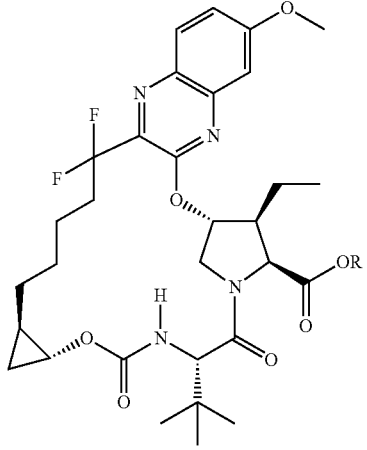

or a salt thereof;

e) hydrolyzing the compound of formula X or a salt thereof to provide a compound of formula XI:

XI

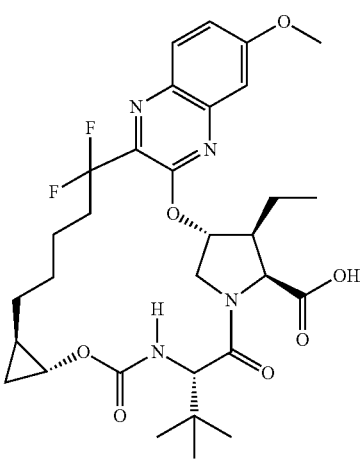

or a salt thereof; and contacting the compound of formula XI or a salt thereof with a compound of formula XII:

XII

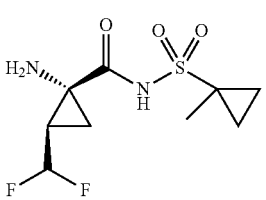

or a salt thereof under amide coupling conditions to provide the compound formula I:

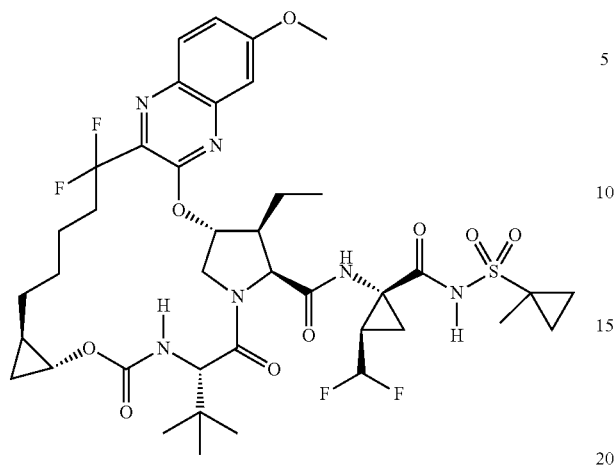

or a salt thereof, wherein R is $C_{1-6}$ alkyl and PG is a protective group.

6. A process for preparation of a compound of formula V-v:

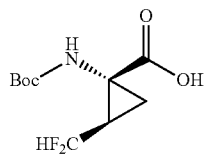

a salt thereof, comprising:
hydrolyzing the compound of formula A-b:

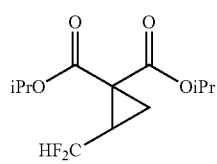

or a salt thereof to provide a compound of formula A-c:

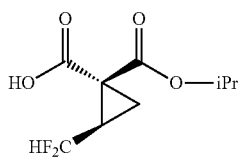

or a salt thereof;

b) contacting the compound of formula A-c or a salt thereof with dicyclohexylamine to provide a compound of formula A-g:

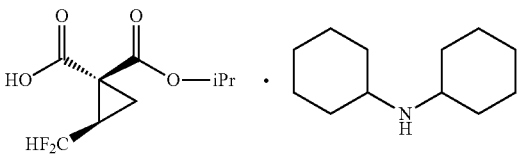

or a salt thereof;

c) contacting A-g or a salt thereof with cinchonidine to provide a compound of formula A-h:

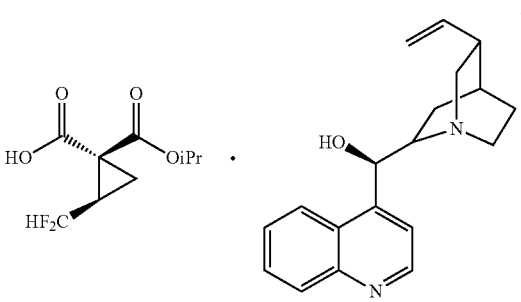

or a salt thereof;

d) subjecting A-h or a salt thereof to Curtius rearrangement in presence of tert-butanol to provide a compound of formula A-i:

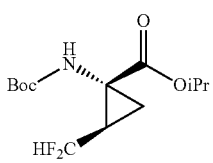

or a salt thereof; and e) hydrolysis of A-i or a salt thereof to provide V-v a salt thereof.

* * * * *

UNITED STATES PATENT AND TRADEMARK OFFICE
CERTIFICATE OF CORRECTION

| | | |
|---|---|---|
| PATENT NO. | : 9,440,991 B2 | Page 1 of 3 |
| APPLICATION NO. | : 14/576143 | |
| DATED | : September 13, 2016 | |
| INVENTOR(S) | : Amy Cagulada et al. | |

It is certified that error appears in the above-identified patent and that said Letters Patent is hereby corrected as shown below:

In the Claims

In Claim 2, Column 161, Lines 26-27, please replace "contacting the compound of formula XI or a salt thereof with a compound of formula" with --contacting the compound of formula XI or a salt thereof with a compound of formula XII:--.

In Claim 4, Column 165, Lines 30-50, please replace the chemical structure:

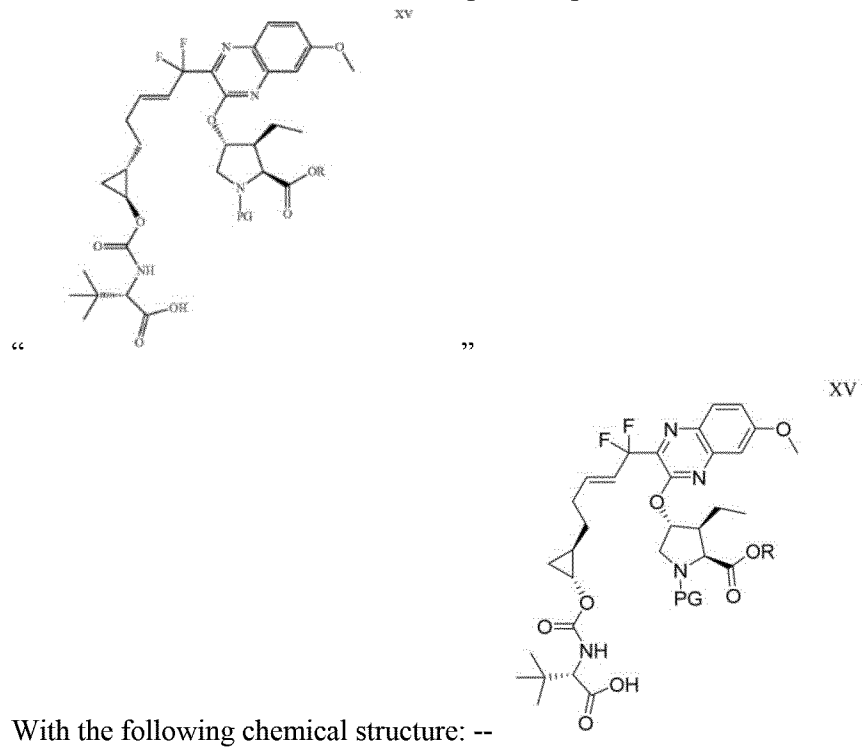

With the following chemical structure: --                              --.

Signed and Sealed this
Sixteenth Day of April, 2019

Andrei Iancu
*Director of the United States Patent and Trademark Office*

In Claim 5, Column 166, Lines 45-65, please replace the chemical structure:
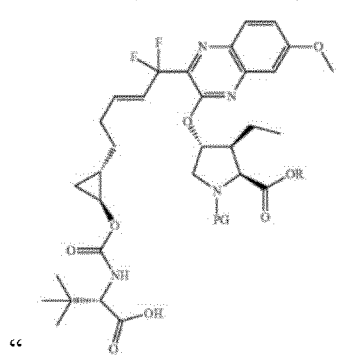
" "
With the following chemical structure: -- 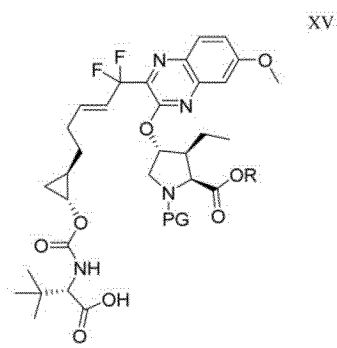 --.
In Claim 5, Column 167, Lines 5-30, please replace the chemical structure:
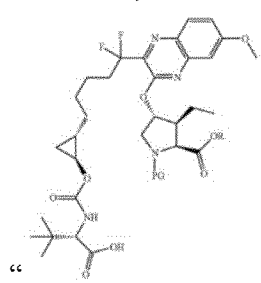
" "
With the following chemical structure: -- 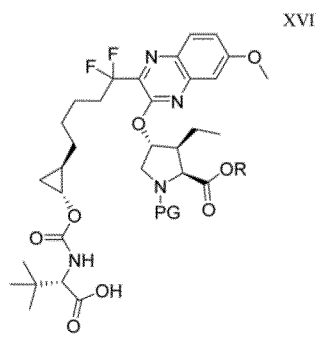 --.

CERTIFICATE OF CORRECTION (continued)
U.S. Pat. No. 9,440,991 B2

Page 3 of 3

In Claim 5, Column 167, Lines 37-60, please replace the chemical structure:

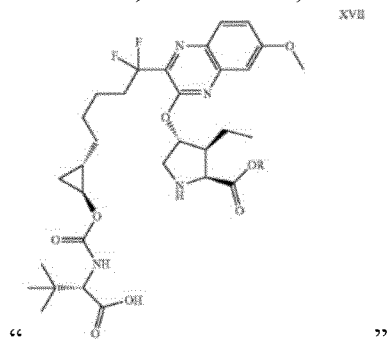

" "

With the following chemical structure: -- 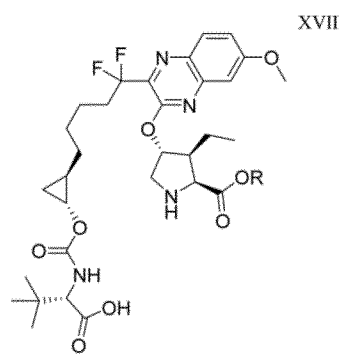 --.